United States Patent
Liu et al.

(10) Patent No.: US 11,918,662 B2
(45) Date of Patent: Mar. 5, 2024

(54) HETEROCYCLIC COMPOUNDS AND IMAGING AGENTS FOR IMAGING HUNTINGTIN PROTEIN

(71) Applicant: CHDI Foundation, Inc., York, NY (US)

(72) Inventors: Longbin Liu, Thousand Oaks, CA (US); Matthew Lee, San Diego, CA (US); Celia Dominguez, Los Angeles, CA (US); Peter David Johnson, Wantage (GB); Catherine Jane Greenaway, Banbury (GB); Kanika Khurana, London (GB); Matthew Robert Mills, Wantage (GB); Filippo Rota, Bristol (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 17/344,582

(22) Filed: Jun. 10, 2021

(65) Prior Publication Data

US 2021/0393812 A1 Dec. 23, 2021

Related U.S. Application Data

(60) Provisional application No. 63/037,751, filed on Jun. 11, 2020.

(51) Int. Cl.
| | | |
|---|---|---|
| *A61K 51/04* | (2006.01) | |
| *C07B 59/00* | (2006.01) | |
| *C07D 231/12* | (2006.01) | |
| *C07D 471/04* | (2006.01) | |
| *C07D 487/04* | (2006.01) | |
| *C07D 487/14* | (2006.01) | |
| *C07D 519/00* | (2006.01) | |

(52) U.S. Cl.
CPC ...... *A61K 51/0459* (2013.01); *A61K 51/0455* (2013.01); *A61K 51/0463* (2013.01); *C07B 59/002* (2013.01); *C07D 231/12* (2013.01); *C07D 471/04* (2013.01); *C07D 487/04* (2013.01); *C07D 487/14* (2013.01); *C07D 519/00* (2013.01); *C07B 2200/05* (2013.01)

(58) Field of Classification Search
CPC ............ A61K 51/0459; A61K 51/0455; A61K 51/0463; C07B 59/002; C07B 2200/05; C07D 231/12; C07D 471/04; C07D 487/04; C07D 487/14; C07D 519/00

USPC ....................................................... 424/1.89
See application file for complete search history.

(56) References Cited

U.S. PATENT DOCUMENTS

| 5,405,847 A | 4/1995 | Dieter et al. |
| 2010/0168084 A1 | 7/2010 | Huber et al. |
| 2011/0257184 A1 | 10/2011 | Qu et al. |

FOREIGN PATENT DOCUMENTS

| EP | 1 798 233 A1 | 6/2007 | |
| WO | WO 96/16644 A1 | 6/1996 | |
| WO | WO 2005/028474 A2 | 3/2005 | |
| WO | WO 2005/041664 A1 | 5/2005 | |
| WO | WO 2006/072608 A2 | 7/2006 | |
| WO | WO 2006/094210 A2 | 9/2006 | |
| WO | WO 2008/017883 A2 | 2/2008 | |
| WO | WO 2008/041264 A1 | 4/2008 | |
| WO | WO 2009/073620 A2 | 6/2009 | |
| WO | WO-2010016005 A1 * | 2/2010 | ........... C07D 401/14 |
| WO | WO 2010/135571 A1 | 11/2010 | |
| WO | WO 2012/078633 A2 | 6/2012 | |
| WO | WO 2013/003383 A2 | 1/2013 | |
| WO | WO 2013/019469 A1 | 2/2013 | |
| WO | WO 2013/040321 A1 | 3/2013 | |
| WO | WO 2017/040336 A1 | 3/2017 | |
| WO | WO 2017/062751 A1 | 4/2017 | |
| WO | WO 2018/204370 A1 | 11/2018 | |
| WO | WO 2019/084271 A1 | 5/2019 | |

OTHER PUBLICATIONS

International Search Report and Written Opinion for PCT/US2021/036830, dated Oct. 22, 2021, 14 pages.
Gennaro Pagano et al., "Current status of PET imaging in Huntington's disease", 2016, vol. 43, No. 6, p. 1171-1182.
Kevin J. Frankowski et al., "Discovery of Small Molecule Kappa Opioid Receptor Agonist and Antagonist Chemotypes through a HTS and Hit Refinement Strategy", ACS Chemical Neuroscience, vol. 3, No. 3, pp. 221-236 (2012).
Giuseppe Campiani et al., "Quinoxalinylethylpyridylthioureas (QXPTs) as potent non-nucleoside HIV-1 reverse transcriptase (RT) inhibitors. Further SAR studies and identification of a novel orally bioavailable hydrazine-based antiviral agent", Journal of Medicinal Chemistry, vol. 44, No. 3, pp. 305-315 (2001).

\* cited by examiner

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided herein are certain compounds and imaging agents useful for detecting a disease or condition associated with protein aggregation, compositions thereof, and methods of their use.

8 Claims, No Drawings

HETEROCYCLIC COMPOUNDS AND IMAGING AGENTS FOR IMAGING HUNTINGTIN PROTEIN

CROSS REFERENCE TO RELATED APPLICATIONS

This application claims priority to U.S. Provisional Application No. 63/037,751, filed Jun. 11, 2020, which is incorporated herein by reference for all purposes.

FIELD

Provided herein are compounds and imaging agents useful for detecting, treating, or preventing a disease or condition associated with protein aggregation, compositions thereof, and methods of their use.

BACKGROUND

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The introduction of high-resolution molecular imaging technology is considered by many experts as a major breakthrough.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Molecular probes labeled with positron-emitting radionuclides and associated PET imaging assays are under development to target, detect, visualize, and quantify various extracellular and intracellular molecules and processes associated with various diseases.

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. HD is caused by the expanded CAG trinucleotide repeat in the exon-1 region of the huntingtin gene (HTT). The resulting polyglutamate domain expansion may induce misfolding and conformational changes in the mutant huntingtin (mHTT) protein, leading to formation of protein aggregates. HD has a prevalence of 5-10 cases per 100,000 worldwide, which makes it the most common inherited and monogenic neurodegenerative disorder.

Consistent with other medical conditions, treatments for HD are ideally initiated at or before early signs of disease. Thus, early indicators of disease onset and reliable pharmacodynamic biomarkers of disease progression are highly desirable.

In view of the central role of the accumulation of aggregated forms of proteins in the pathogenesis of neurodegenerative conditions including HD, there is a need for molecules that bind to such proteins with high sensitivity and specificity and that permit molecular imaging.

SUMMARY

The present disclosure relates to compounds useful for imaging Huntingtin protein.

Some embodiments provide for a compound of Formula I' as described herein, wherein the compound is optionally labeled with one or more radioactive isotopes. In some embodiments, the compound of Formula I' contains one or more positron-emitting radioactive isotopes selected from $^{11}C$, $^{13}N$, $^{15}O$, and $^{18}F$. In some embodiments, an imaging agent comprising the compound of Formula I', or an isotopically enriched analog, pharmaceutically acceptable salt, prodrug, tautomer, stereoisomer, or a mixture of stereoisomers thereof, is provided.

Some embodiments provide for a compound of Formula I as described herein, wherein the compound is optionally labeled with one or more radioactive isotopes. In some embodiments, the compound of Formula I contains one or more positron-emitting radioactive isotopes selected from $^{11}C$, $^{13}N$, $^{15}O$, and $^{18}F$.

In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are imaging agents comprising a compound described herein, wherein the compound is labeled with one or more positron-emitting radionuclides. In some embodiments, the compound contains one or more positron-emitting radionuclides selected from $^{11}C$, $^{13}N$, $^{15}O$, and $^{18}F$.

Also provided is a method of generating diagnostic images, for example positron emission tomography (PET) images, in an individual comprising administering an effective amount of a compound described herein or an imaging agent comprising a compound described herein, and generating an image of a body part or body area of the individual.

In some embodiments, provided is a compound or an imaging agent for use in generating diagnostic images in an individual, wherein the use comprises administering an effective amount of a compound or an imaging agent described herein to an individual, and generating an image of a body part or body area of the individual.

In some embodiments, provided is a compound or an imaging agent for use as described herein, wherein generating an image of a body part or body area of the individual comprises generating an image to detect the presence or absence of a protein susceptible to aggregation in the image. In some embodiments, provided is a compound or an imaging agent for use as described herein, wherein the protein susceptible to aggregation is huntingtin protein (HTT protein). In some embodiments, provided is a compound or an imaging agent for use as described herein, wherein the HTT protein is found in basal ganglia.

In some embodiments, provided is a compound or an imaging agent for use as described herein, wherein the presence or absence of a protein aggregate corresponds to the presence or absence of a neurodegenerative disease.

In some embodiments, provided is a compound or an imaging agent for use as described herein, wherein the neurodegenerative disease is selected from Alzheimer's disease, amyotrophic lateral sclerosis, Huntington's disease, Parkinson's disease, Prion disease and spinocerebellar ataxias. In some embodiments, provided is a compound or an imaging agent for use as described herein, wherein the neurodegenerative disease is Huntington's disease (HD).

In some embodiments, provided is a compound or an imaging agent for use as described herein, wherein the effective amount of the imaging agent comprises from about 0.1 to about 20 mCi. In some embodiments, provided is a compound or an imaging agent for use as described herein, wherein the effective amount of the imaging agent comprises about 10 mCi.

In some embodiments, provided is a compound or an imaging agent for use as described herein, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

In some embodiments, provided is a compound or an imaging agent for use as described herein, wherein generating an image comprises PET imaging.

In some embodiments, provided is a compound or an imaging agent for use as described herein, wherein the HTT protein is present as oligomers or aggregates, or a combination thereof. In some embodiments, provided is a compound or an imaging agent for use as described herein, wherein the HTT protein is mutant.

In some embodiments, provided is a compound or an imaging agent for use as described herein, wherein the body part or body area is head, spinal cord, limb, thorax, or abdomen. In some embodiments, provided is a compound or an imaging agent for use as described herein, wherein the body part or body area is brain.

DETAILED DESCRIPTION

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I', Formula I, Formula Ia, Formula IIa, Formula IIb, Formula IIc, Formula IId, or a compound described any wherein herein including the Examples, or a compound of Table 1A or Table 1B, or a labeled isomer of such compound as defined herein, or an imaging agent or pharmaceutical composition comprising such compound or labeled compound.

A dash ("-") that is not between two letters or symbols is used to indicate a point of attachment to a parent structure for a substituent. For example, —C(O)NH$_2$ is attached to a parent structure through the carbon atom. A dash at the front or end of a chemical group is a matter of convenience; chemical groups may be depicted with or without one or more dashes without losing their ordinary meaning. A wavy line or a dashed line drawn through a bond in a structure indicates a specified point of attachment. Unless chemically or structurally required, no directionality or stereochemistry is indicated or implied by the order in which a chemical group is written or named.

The prefix "C$_{u-v}$" indicates that the following group has from u to v carbon atoms, exclusive of further substitution. For example, "C$_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 9 carbon atoms (i.e., C$_{1-9}$ alkyl), 1 to 8 carbon atoms (i.e., C$_{1-8}$ alkyl), 1 to 6 carbon atoms (i.e., C$_{1-6}$ alkyl) or 1 to 4 carbon atoms (i.e., C$_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Alternative chemical names known to those of skill in the art may be used in lieu of the terms provided herein. For example, a divalent group such as a divalent "alkyl" group, a divalent "aryl" group, etc., may also be referred to as an "alkylene" or an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl) or 2 to 4 carbon atoms (i.e., C$_{2-4}$ alkenyl). Examples of alkenyl groups include, e.g., ethenyl, propenyl, butadienyl (including 1,2-butadienyl and 1,3-butadienyl), and isoprenyl.

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl) or 2 to 4 carbon atoms (i.e., C$_{2-4}$ alkynyl). The term "alkynyl" also includes those groups having one triple bond and one double bond.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "(alkyl)$_2$N—". Examples of dialkylamino groups include, e.g., dimethylamino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to the group "alkyl-S(O)—". "Alkylsulfonyl" refers to a group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to a group —C(O)NR$^y$R$^z$ and an "N-amido" group which refers to a group —NR$^y$C(O)R$^z$, wherein R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to a group —NR$^y$R$^z$ wherein R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein. In some embodiments, "amino" refers to a group NH$_2$.

"Amidino" refers to a group —C(NR$^y$)(NR$^z$$_2$), wherein R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl) or 6 to 10 carbon ring atoms (i.e., C$_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group which refers to a group —O—C(O)NR$^y$R$^z$ and an "N-carbamoyl" group which refers to a group —NR$^y$C(O)OR$^z$, wherein R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, haloalkyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ ring carbon atom (i.e., at least one non-aromatic ring). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —NR$^y$C(=NR$^z$)(NR$^y$R$^z$), wherein each R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Imino" refers to a group —C(NR$^y$)R$^z$, wherein R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Halogen" or "halo" refers to a substituent atom of group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms, up to and including all hydrogen atoms, are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2 or 3 carbon atoms may be independently replaced with the same or different heteroatomic group. Heteroatomic groups include, but are not limited to, —NR$^y$—, —C(O)NR$^y$—, —NR$^y$C(O)—, —O—, —S—, —S(O)—, —S(O)$_2$—, and the like, wherein R$^y$ is hydrogen, alkyl, alkenyl, alkynyl, haloalkyl, cycloalkyl, heterocyclyl, aryl, heteroalkyl or heteroaryl; each of which may be optionally substituted, as defined herein.

Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and aminoalkyls (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3) N-oxide (—O—) moieties. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen and sulfur, wherein the nitrogen or sulfur atoms are optionally oxidized to form an N-oxide, a sulfinyl (—S(O)—), or a sulfoxide (—S(O)$_2$—). The term "heterocyclyl" includes heterocycloalkenyl groups (i.e., a heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro. Regardless of substituent groups listed, a heterocyclyl may comprise one or more (e.g., 1 to 3) oxo (=O) or N-oxide (—O—) moieties unless stated otherwise. A heterocyclyl can be bound through a carbon atom or a heteroatom as valency permits. Further, the term heterocyclyl encompasses any ring system including a non-aromatic ring containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl." Examples of the spiroheterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. When there are two positions for substitution on a carbon atom in a parent structure, heterocyclyl as a substituent group may include spiroheterocyclyl. Examples of bridged-heterocyclyl rings include, but are not limited to, 2,5-diazabicyclo[2.2.1]heptane, 2-oxa-5-azabicyclo[2.2.1]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. An "oxo-heterocyclyl" group is a heterocyclyl including at least one oxo substituent (e.g., 1, or 1 to 2 oxo substituents), whether or not additional substituents are permitted (i.e., an unsubstituted oxo-heterocyclyl includes an oxo and no other substitution). In some embodiments, an oxo-heterocyclyl includes a cyclic amide moiety.

"Heterocyclylalkyl" refers to a group "heterocyclyl-alkyl-."

"Oxime" refers to a group —CR$^y$(=NOH) wherein R$^y$ is hydrogen, alkyl, alkenyl, alkynyl, haloalkyl, cycloalkyl, heterocyclyl, aryl, heteroalkyl or heteroaryl; each of which may be optionally substituted, as defined herein.

"Sulfonyl" refers to a group —S(O)$_2$R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to a group —S(O)R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, —NR$^g$R$^h$, —NR$^g$C(=O) R$^h$, —NR$^g$C(=O)NR$^g$R$^h$, —NR$^g$C(=O)OR$^h$, —NR$^g$S (=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS (=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, or —SCF$_3$. In certain embodiments, "substituted" also means a group in which one or more (e.g., 1 to 5 or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or R$^g$ and R$^h$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to encompass compounds having chemically unfeasable or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Generally, an isotopically enriched analog includes compounds having any isotopic enrichment above the natural abundance of the isotope (e.g., at Earth's surface). Various isotopically labeled compounds are included in the present disclosure, for example those into which radioactive isotopes such as $^3$H, $^{18}$F, $^{11}$C, and $^{14}$C are incorporated. Compounds labeled with $^{18}$F, $^3$H, or $^{11}$C may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Isotopically labeled compounds of this disclosure and pharmaceutically acceptable salts, prodrugs, tautomers, stereoisomers, and mixtures of stereoisomers thereof can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compounds with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids. Suitable inorganic acids include, e.g., hydrochloric acid, hydrobromic acid, sulfuric acid, nitric acid, phosphoric acid and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN(substituted\ alkyl)_2$), tri(substituted alkyl) amines (i.e., $N(substituted\ alkyl)_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN(substituted\ alkenyl)_2$), tri(substituted alkenyl) amines (i.e., $N(substituted\ alkenyl)_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2$(aryl), $HN(aryl)_2$, $N(aryl)_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)- or (S)-, or as (D)- or (L)- for amino acids. Compounds described herein are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stereoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another. A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

In some embodiments, the term "neurodegenerative disease" refers to a disease or condition in which the function of a subject's nervous system becomes impaired. Examples of neurodegenerative diseases include those described herein.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The above-listed terms also include in vitro and ex vivo methods.

As used herein the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stereoisomers thereof, having pharmaceutical utility. For example an active agent may be an anti-neurodegenerative therapeutic.

The term "effective amount" means an amount, for example, of a compound described herein, sufficient to bring about a desired response in an individual or patient. In the context of use of an imaging agent, an effective amount may be an amount needed to produce an image having diagnostic or therapeutic utility. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, and disease or condition being treated, the weight and age of the subject, the severity of the disease or condition, and the manner of administering, which can readily be determined by one of ordinary skill in the art.

The term "huntingtin protein," or "HTT protein," as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein, refers to an aggregation of protein which may be, for example, an insoluble fibrous amyloid comprising mis-folded HTT protein molecules ("HTT protein aggregate") or mis-folded β-amyloid protein molecules ("β-amyloid aggregate"). A "protein susceptible to aggregation" is a protein that is capable of forming such aggregates, in its wild type or in a mutated form.

The term "imaging agent," as used herein, refers to a compound described herein labeled with one or more positron-emitting isotopes or radionuclides, or a composition comprising the labeled compound. A positron-emitter labeled compound need only be enriched with a detectable isotope to a degree that permits detection with a technique suitable for the particular application.

The term "PET imaging" (which may be referred to as positron emission tomography imaging), as used herein, refers to the use of a positron-emitter labeled compound to produce images of internal structures of the human or animal body.

The term "positron-emitting radionuclide," as used herein, refers to a radioactive isotope that exhibits particular type of radioactive decay referred to as β+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$.

The term "labeled," as used herein, refers to a compound which is associated with one or more positron-emitting radionuclides in greater than natural abundance. For example, a labeled compound described herein may contain one or more positron-emitting radionuclides, wherein an atom in the molecule (including any indicated substituent) is present as a positron-emitting isotope.

The term "tomography," as used herein, refers to a process of imaging by sections. The images may be looked at individually, as a series of two-dimensional slices or together, as a computer-generated three-dimensional representation.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including a) inhibiting the disease (e.g., decreasing one or more symptoms resulting from the disease or condition, and/or diminishing the extent of the disease or condition);

b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation or experiment. The methods described herein may be useful in both human therapy and veterinary applications. In some embodiments, the subject or patient is a mammal. In some embodiments the subject or patient is human.

The term "Curie" (Ci) is a unit of measurement of radioactivity and has its customary meaning to those of skill in the art.

The term "diagnostic imaging," as used herein, refers to the use of electromagnetic radiation to produce images of internal structures of the human or animal body for the purpose of diagnosis.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I' or Formula I or any other formula are specifically embraced herein just as if each and every combination was individually and explicitly recited, to the extent that such combinations result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| δ | Chemical shift |
| μ | Micro |
| Ac | Acetate |
| addn. | Addition |
| approx. | Approximately |
| aq | Aqueous |
| Ar | Aryl |
| atm | Atmosphere |
| BINAP | 2,2'-Bis(diphenylphosphino)-1,1'-binaphthyl |

| List of Abbreviations and Acronyms | |
|---|---|
| Bn | Benzyl |
| Boc | Tert-butyloxycarbonyl |
| br | Broad |
| BrettPhos | 2-(Dicyclohexylphosphino)3,6-dimethoxy-2',4',6'-triisopropyl-1,1'-biphenyl |
| Bz | Benzoyl |
| calcd | Calculated |
| CDI | Carbonyldiimidazole |
| CMBP | Cyanomethyltributylphosphorane |
| conc. | Concentrated |
| CyJohnPhos | (2-Biphenyl)dicyclohexylphosphine, 2-(Dicyclohexylphosphino)biphenyl |
| d | Deuterated |
| d | Doublet |
| dd | Doublet of doublets |
| dba | Dibenzylideneacetone |
| DCM | Dichloromethane |
| DIPEA | Diisopropylethylamine |
| dppf | Bisdiphenylphosphinyl ferrocene |
| DMA | Dimethylacetamide |
| DMAP | 4-Dimethylaminopyridine |
| DMF | N,N-dimethylformamide |
| DMSO | Dimethyl sulfoxide |
| EDC | 1-Ethyl-3-(3-dimethylaminopropyl)carbodiimide |
| ELS | Evaporative light scattering |
| eq | Equivalent |
| ES | Electrospray ionization |
| Et | Ethyl |
| EtOAc | Ethyl acetate |
| EtOH | Ethanol |
| FCC | Flash column chromatography |
| h | Hour(s) |
| HATU | N-[(Dimethylamino)-1H-1,2,3-triazolo-[4,5-b]pyridin-1-ylmethylene]-N-ethylmethanaminium hexafluorophosphate N-oxide |
| HPLC | High performance liquid chromatography |
| LCMS | Liquid chromatography-mass spectrometry |
| IPA | Isopropyl alcohol |
| J | Coupling constant |
| LiHMDS | Lithium hexamethyldisilazide |
| m | Multiplet |
| Me | Methyl |
| MeCN | Acetonitrile |
| MeOH | Methanol |
| min | Minute(s) |
| MS | Mass spectrometry |
| m/z | Mass to charge ratio |
| N | Normal |
| NMP | N-Methyl-2-pyrrolidone |
| NMR | Nuclear magnetic resonance |
| p | Para |
| Ph | Phenyl |
| ppm | Part(s) per million |
| prep | Preparative |
| q | Quartet |
| quant. | Quantitative |
| rt | Room temperature |
| RuPhos | 2-Dicyclohexylphosphino-2',6'-diisopropoxybiphenyl |
| RuPhos Pd G3 | 3rd Generation RuPhos Precatalyst, Chloro(2-dicyclohexylphosphino-2',6'-diisopropoxy-1,1'-biphenyl)[2-(2'-amino-1,1'-biphenyl)]palladium(II) |
| RVC | Reticulated vitreous carbon |
| s | Singlet |
| sat. | Saturated |
| SCX | Propylsulfonic acid (non-endcapped) functionalized silica |
| STAB | Sodium triacetoxyborohydride |
| T3P | Propanephosphonic acid anhydride |
| t | Triplet |
| TBAF | Tetrabutylammonium fluoride |
| TBME | tert-Butyl methyl ether |
| TFA | Trifluoroacetic acid |
| THF | Tetrahydrofuran |
| Tr | Retention time |
| Ts | p-Toluenesulfonyl |
| UV | Ultraviolet |

Compounds

The present disclosure relates to compounds useful for imaging a protein susceptible to aggregation, for example, Huntingtin protein.

Some embodiments provide for a compound of Formula I':

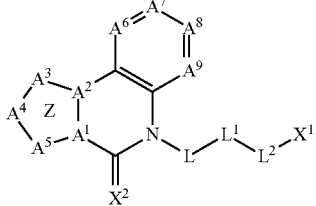

or an isotopically enriched analog, pharmaceutically acceptable salt, prodrug, tautomer, stereoisomer, or a mixture of stereoisomers thereof, wherein the compound is labeled with one or more radioactive isotopes;

$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$, $NR^3$, or N;

wherein ring Z formed by -$A^1$-$A^2$-$A^3$-$A^4$-$A^5$- is a 5-membered heteroaryl having up to three nitrogen atoms;

each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl; each $R^3$ is independently hydrogen, $C_{1-4}$alkyl, $C_{1-4}$haloalkyl, or $C_{3-6}$cycloalkyl;

$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;

each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or —Sn($C_{1-6}$alkyl)$_3$;

$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;

each $R^4$ is independently halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, Sn($C_{1-6}$alkyl)$_3$, or —I$^+$-(phenyl substituted with one to three methyl groups);

$X^2$ is O, S, or $NR^5$; $R^5$ is hydrogen, $C_{1-6}$alkyl, $C_{1-6}$haloalkyl, or $C_{1-6}$alkoxy;

L is —(C($R^6$)$_2$)$_m$—, wherein m is 1, 2, 3, or 4;

each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;

$L^1$ is C(O), C(O)$NR^a$, $NR^a$C(O), or O, or $L^1$ is absent;

$R^a$ is hydrogen, $C_{1-6}$alkyl, or $C_{1-6}$haloalkyl;

$L^2$ is $C_{1-2}$alkylene optionally substituted by 1 to 4 $R^7$, or $L^2$ is absent;

each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy.

Some embodiments provide for a compound of Formula I':

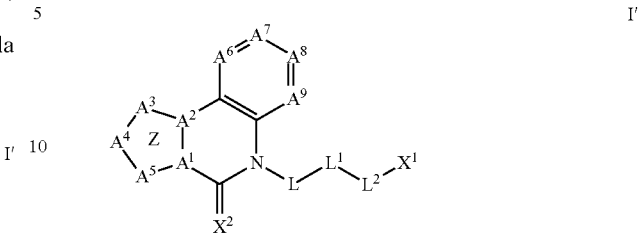

or an isotopically enriched analog, pharmaceutically acceptable salt, prodrug, tautomer, stereoisomer, or a mixture of stereoisomers thereof, wherein the compound is optionally labeled with one or more radioactive isotopes;

$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$, $NR^3$, or N;

wherein ring Z formed by -$A^1$-$A^2$-$A^3$-$A^4$-$A^5$- is a 5-membered heteroaryl having up to three nitrogen atoms;

each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl; each $R^3$ is independently hydrogen, $C_{1-4}$alkyl, $C_{1-4}$haloalkyl, or $C_{3-6}$cycloalkyl;

$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;

each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or —Sn($C_{1-6}$alkyl)$_3$;

$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;

each $R^4$ is independently halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, Sn($C_{1-6}$alkyl)$_3$, or —I$^+$-(phenyl substituted with one to three methyl groups);

$X^2$ is O, S, or $NR^5$; $R^5$ is hydrogen, $C_{1-6}$alkyl, $C_{1-6}$haloalkyl, or $C_{1-6}$alkoxy;

L is —(C($R^6$)$_2$)$_m$—, wherein m is 1, 2, 3, or 4;

each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;

$L^1$ is C(O), C(O)$NR^a$, $NR^a$C(O), or O, or $L^1$ is absent;

$R^a$ is hydrogen, $C_{1-6}$alkyl, or $C_{1-6}$haloalkyl;

$L^2$ is $C_{1-2}$alkylene optionally substituted by 1 to 4 $R^7$, or $L^2$ is absent;

each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy.

In some embodiments, a compound of Formula I' is labeled with a radioactive isotope.

In some embodiments, the compound is not 7-bromo-5-(4-oxo-4-(pyrrolidin-1-yl)butyl)pyrrolo[1,2-a]quinoxalin-4 (5H)-one, N-(2,4-dimethoxyphenyl)-3-(4-oxopyrrolo[1,2-a]quinoxalin-5(4H)-yl)propanamide, 7-fluoro-5-[4-

(morpholin-4-yl)-4-oxobutyl]-4H,5H-pyrrolo[1,2-a]quinoxalin-4-one, 5-[4-(3,5-dimethylpiperidin-1-yl)-4-oxobutyl]-4H,5H-pyrrolo[1,2-a]quinoxalin-4-one, N-(4-methylphenyl)-3-{4-oxo-4H,5H-pyrrolo[1,2-a]quinoxalin-5-yl}propanamide, 7-bromo-5-[4-oxo-4-(piperidin-1-yl)butyl]-4H,5H-pyrrolo[1,2-a]quinoxalin-4-one, or 7-fluoro-5-[2-oxo-2-(piperidin-1-yl)ethyl]-4H,5H-pyrrolo[1,2-a]quinoxalin-4-one.

Some embodiments provide for a compound of Formula I:

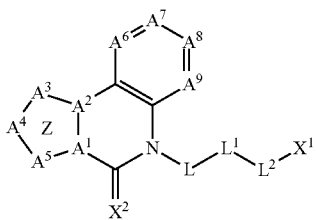

or an isotopically enriched analog, pharmaceutically acceptable salt, prodrug, tautomer, stereoisomer, or a mixture of stereoisomers thereof,
wherein the compound is optionally labeled with one or more radioactive isotopes;
$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$, $NR^3$, or N;
wherein ring Z formed by $-A^1-A^2-A^3-A^4-A^5-$ is a 5-membered heteroaryl having up to three nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;
each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^2$ is O, S, or $NR^5$; $R^5$ is hydrogen, $C_{1-6}$alkyl, $C_{1-6}$haloalkyl, or $C_{1-6}$alkoxy;
L is $-(C(R^6)_2)_m-$, wherein m is 1, 2, 3, or 4;
each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;
$L^1$ is C(O), C(O)$NR^a$, $NR^aC(O)$, or O, or $L^1$ is absent;
$R^a$ is hydrogen, $C_{1-6}$alkyl, or $C_{1-6}$haloalkyl;
$L^2$ is $C_{1-2}$alkylene optionally substituted by 1 to 4 $R^7$, or $L^2$ is absent;
each $R^7$ is independently halo, cyano, hydroxy, amino, alkylamino, dialkylamino, $C_{1-4}$ alkyl, $C_{1-4}$haloalkyl, $C_{1-4}$alkoxy, or $C_{1-4}$haloalkoxy.

In some embodiments, a compound of Formula I is labeled with a radioactive isotope.

In some embodiments, the compound is not 7-bromo-5-(4-oxo-4-(pyrrolidin-1-yl)butyl)pyrrolo[1,2-a]quinoxalin-4(5H)-one, N-(2,4-dimethoxyphenyl)-3-(4-oxopyrrolo[1,2-a]quinoxalin-5(4H)-yl)propanamide, 7-fluoro-5-[4-(morpholin-4-yl)-4-oxobutyl]-4H,5H-pyrrolo[1,2-a]quinoxalin-4-one, 5-[4-(3,5-dimethylpiperidin-1-yl)-4-oxobutyl]-4H,5H-pyrrolo[1,2-a]quinoxalin-4-one, N-(4-methylphenyl)-3-{4-oxo-4H,5H-pyrrolo[1,2-a]quinoxalin-5-yl}propanamide, 7-bromo-5-[4-oxo-4-(piperidin-1-yl)butyl]-4H,5H-pyrrolo[1,2-a]quinoxalin-4-one, or 7-fluoro-5-[2-oxo-2-(piperidin-1-yl)ethyl]-4H,5H-pyrrolo[1,2-a]quinoxalin-4-one.

In some embodiments, provided is a compound of Formula I, or an isotopically enriched analog, pharmaceutically acceptable salt, prodrug, tautomer, stereoisomer, or a mixture of stereoisomers thereof, wherein:
$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$;
wherein ring Z formed by $-A^1-A^2-A^3-A^4-A^5-$ is a 5-membered heteroaryl having up to 3 nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{13}$ or N, and $A^9$ is $CR^{14}$ or N, wherein no more than one of $A^6$, $A^7$, $A^8$, and $A^9$ is N;
each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^2$ is O, S, or $NR^5$; $R^5$ is hydrogen, $C_{1-6}$alkyl, $C_{1-6}$haloalkyl, or $C_{1-6}$alkoxy;
L is $-(C(R^6)_2)_m-$, wherein m is 2, 3, or 4;
each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$L^1$ is C(O), C(O)$NR^a$ or $NR^aC(O)$;
$R^a$ is hydrogen, $C_{1-6}$alkyl, or $C_{1-6}$haloalkyl;
$L^2$ is $C_{1-2}$alkylene optionally substituted by 1 to 4 $R^7$, or $L^2$ is absent;
each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
provided the compound is not 7-bromo-5-(4-oxo-4-(pyrrolidin-1-yl)butyl)pyrrolo[1,2-a]quinoxalin-4(5H)-one or N-(2,4-dimethoxyphenyl)-3-(4-oxopyrrolo[1,2-a]quinoxalin-5(4H)-yl)propanamide.

In some embodiments, provided is a compound of Formula I:

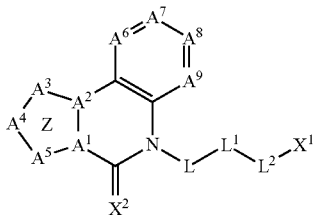

or an isotopically enriched analog, pharmaceutically acceptable salt, prodrug, tautomer, stereoisomer, or a mixture of stereoisomers thereof, wherein:
$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$;
wherein ring Z formed by $-A^1-A^2-A^3-A^4-A^5-$ is a 5-membered heteroaryl having up to 3 nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{11}$ or N, and $A^9$ is $CR^{14}$ or N, wherein no more than one of $A^6$, $A^7$, $A^8$, and $A^9$ is N;
each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^2$ is O, S, or $NR^5$; $R^5$ is hydrogen, $C_{1-6}$alkyl, $C_{1-6}$haloalkyl, or $C_{1-6}$alkoxy;
L is $-(C(R^6)_2)_m-$, wherein m is 2, 3, or 4;
each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$L^1$ is C(O), C(O)$NR^a$ or $NR^aC(O)$;
$R^a$ is hydrogen, $C_{1-6}$alkyl, or $C_{1-6}$haloalkyl;
$L^2$ is $C_{1-2}$alkylene optionally substituted by 1 to 4 $R^7$, or $L^2$ is absent;
each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
provided the compound is not 7-bromo-5-(4-oxo-4-(pyrrolidin-1-yl)butyl)pyrrolo[1,2-a]quinoxalin-4(5H)-one or N-(2,4-dimethoxyphenyl)-3-(4-oxopyrrolo[1,2-a]quinoxalin-5(4H)-yl)propanamide.

In some embodiments, provided is a compound of Formula I, or an isotopically enriched analog, pharmaceutically acceptable salt, prodrug, tautomer, stereoisomer, or a mixture of stereoisomers thereof, wherein:
$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$;
wherein ring Z formed by $-A^1-A^2-A^3-A^4-A^5-$ is a 5-membered heteroaryl having up to 3 nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{13}$ or N, and $A^9$ is $CR^{14}$ or N, wherein no more than one of $A^6$, $A^7$, $A^8$, and $A^9$ is N;
each of $R^{11}$, $R^{12}$, $R^{13}$ and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^2$ is O, S, or $NR^5$; $R^5$ is hydrogen, $C_{1-6}$alkyl, $C_{1-6}$haloalkyl, or $C_{1-6}$alkoxy;
L is $-(C(R^6)_2)_m-$, wherein m is 2, 3, or 4;
each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$L^1$ is C(O), C(O)$NR^a$ or $NR^aC(O)$;
$R^a$ is hydrogen, $C_{1-6}$alkyl, or $C_{1-6}$haloalkyl;
$L^2$ is $C_{1-2}$alkylene optionally substituted by 1 to 4 $R^7$, or $L^2$ is absent;
each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
provided the compound is not 7-bromo-5-(4-oxo-4-(pyrrolidin-1-yl)butyl)pyrrolo[1,2-a]quinoxalin-4(5H)-one or N-(2,4-dimethoxyphenyl)-3-(4-oxopyrrolo[1,2-a]quinoxalin-5(4H)-yl)propanamide; and provided the compound is not 7-fluoro-5-[4-(morpholin-4-yl)-4-oxobutyl]-4H,5H-pyrrolo[1,2-a]quinoxalin-4-one, 5-[4-(3,5-dimethylpiperidin-1-yl)-4-oxobutyl]-4H,5H-pyrrolo[1,2-a]quinoxalin-4-one, N-(4-methylphenyl)-3-{4-oxo-4H,5H-pyrrolo[1,2-a]quinoxalin-5-yl}propanamide, or 7-bromo-5-[4-oxo-4-(piperidin-1-yl)butyl]-4H,5H-pyrrolo[1,2-a]quinoxalin-4-one.

In some embodiments, the compound of Formula I is a compound of Formula Ia:

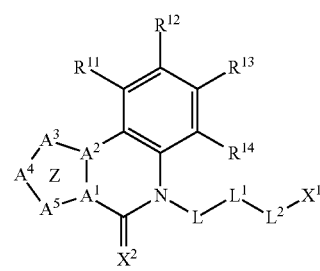

or an isotopically enriched analog, pharmaceutically acceptable salt, prodrug, tautomer, stereoisomer, or a mixture of stereoisomers thereof.

In some embodiments, the compound of Formula I is a compound of Formula IIa:

IIa

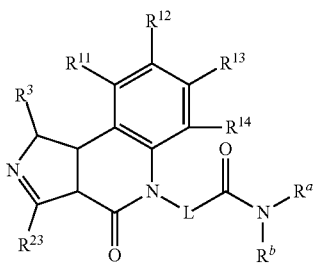

or an isotopically enriched analog, pharmaceutically acceptable salt, prodrug, tautomer, stereoisomer, or a mixture of stereoisomers thereof, $R^b$ is -$L^2$-$X^1$ and $R^a$ is as defined herein;

or $R^a$ and $R^b$, along with any intervening atoms, form a 3- to 10-membered heterocyclyl ring optionally substituted by 1 to 4 $R^4$.

In some embodiments, the compound of Formula I is a compound of Formula IIb:

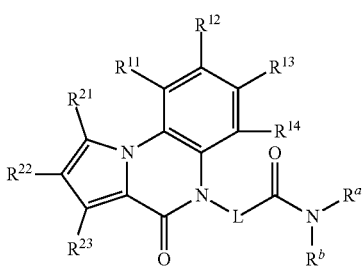

IIb or an isotopically enriched analog, pharmaceutically acceptable salt, prodrug, tautomer, stereoisomer, or a mixture of stereoisomers thereof, $R^b$ is -$L^2$-$X^1$ and $R^a$ is as defined herein;

or $R^a$ and $R^b$, along with any intervening atoms, form a 3- to 10-membered heterocyclyl ring optionally substituted by 1 to 4 $R^4$.

In some embodiments, the compound of Formula I is a compound of Formula IIc:

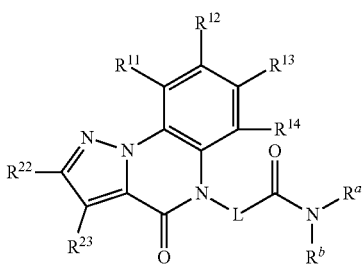

IIc or an isotopically enriched analog, pharmaceutically acceptable salt, prodrug, tautomer, stereoisomer, or a mixture of stereoisomers thereof, $R^b$ is -$L^2$-$X^1$ and $R^a$ is as defined herein;

or $R^a$ and $R^b$, along with any intervening atoms, form a 3- to 10-membered heterocyclyl ring optionally substituted by 1 to 4 $R^4$.

In some embodiments, the compound of Formula I is a compound of Formula IId:

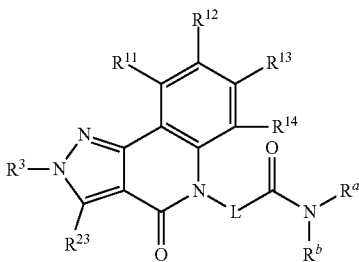

IId or an isotopically enriched analog, pharmaceutically acceptable salt, prodrug, tautomer, stereoisomer, or a mixture of stereoisomers thereof, $R^b$ is -$L^2$-$X^1$ and $R^a$ is as defined herein;

or $R^a$ and $R^b$, along with any intervening atoms, form a 3- to 10-membered heterocyclyl ring optionally substituted by 1 to 4 $R^4$.

In some embodiments, one of $R^{11}$, $R^{12}$, $R^{13}$, or $R^{14}$ is halo. In some embodiments, one of $R^{11}$, $R^{12}$, $R^{13}$, or $R^{14}$ is fluoro. In some embodiments, $R^{13}$ is halo. In some embodiments, $R^{13}$ is fluoro. In some embodiments, each of $R^1$, $R^{12}$, $R^{13}$, and $R^{14}$ is hydrogen.

In some embodiments, $R^{11}$, $R^{12}$, $R^{13}$, and $R^{14}$ may be other known functional groups for the introduction of a radioisotope, such as $^{18}F$. Such functional groups include, but are not limited to, boron derivatives, $NO_2$ derivatives, and the like.

In some embodiments, one of $R^{11}$, $R^{12}$, $R^{13}$, or $R^{14}$ is $C_{1-4}$alkoxy. In some embodiments, one of $R^{11}$, $R^{12}$, $R^{13}$, or $R^{14}$ is methoxy. In some embodiments, $R^{13}$ is methoxy.

In some embodiments, one of $R^{21}$, $R^{22}$, and $R^{23}$ is methyl. In some embodiments, one of $R^{21}$, $R^{22}$, and $R^{23}$ is halo. In some embodiments, one of $R^{21}$, $R^{22}$, and $R^{23}$ is fluoro. In some embodiments, each of $R^{21}$, $R^{22}$, and $R^{23}$ is hydrogen.

In some embodiments, $R^3$ is $C_{1-4}$alkyl. In some embodiment, $R^3$ is methyl. In some embodiments, $R^3$ is hydrogen.

In some embodiments, $X^1$ is $C_{3-10}$cycloalkyl, $C_{6-10}$aryl, heteroaryl, or heterocyclyl. In some embodiments, $X^1$ is $C_{3-10}$cycloalkyl or heterocyclyl. In some embodiments, $X^1$ is $C_{6-10}$aryl or heteroaryl.

In some embodiments, $X^1$ is $C_{6-10}$aryl. In some embodiments, $X^1$ is phenyl.

In some embodiments, $X^1$ is heteroaryl. In some embodiments, $X^1$ is pyridin-2-yl, pyridin-3-yl, or pyridin-4-yl.

In some embodiments, $X^1$ is heterocyclyl. In some embodiments, $X^1$ is 1-piperidinyl, 4-morpholinyl, piperazin-1-yl, piperazin-3-on-1-yl, pyrrolidin-1-yl, or pyridazin-3(2H)-on-6-yl. In some embodiments, $X^1$ is oxo-heterocyclyl.

In some embodiments, $R^4$ is halo, hydroxy, $C_{1-4}$alkyl, $C_{1-4}$haloalkyl, or $C_{1-4}$alkoxy. In some embodiments, $R^4$ is halo. In some embodiments, $R^4$ is fluoro. In some embodiments, $X^1$ is phenyl and $R^4$ is fluoro.

In some embodiments, $X^1$ is phenyl and $R^4$ is halo, hydroxy, $C_{1-4}$alkyl, $C_{1-4}$haloalkyl, or $C_{1-4}$alkoxy.

In some embodiments, $X^1$ is fluorophenyl. In some embodiments, $X^1$ is 2-fluorophenyl. In some embodiments, $X^1$ is difluorophenyl. In some embodiments, $X^1$ is 2,4-difluorophenyl. In some embodiments, $X^1$ is 2,5-difluorophenyl.

In some embodiments, $R^a$ and $R^b$, along with any intervening atoms, form a 3- to 10-membered heterocyclyl ring optionally substituted by 1 to 4 $R^4$. In some embodiments, $R^a$ and $R^b$, along with any intervening atoms, form a 1-piperidinyl, 4-morpholinyl, piperazin-1-yl, piperazin-3-on-1-yl, pyrrolidin-1-yl, or pyridazin-3(2H)-on-6-yl optionally substituted by 1 to 4 $R^4$.

In some embodiments, $X^2$ is O.

In some embodiments, m is 2. In some embodiments, m is 3.

In some embodiments, $L^2$ is absent.

In some embodiments, each $R^6$ is hydrogen.

In some embodiments, $A^6$ is $CR^{11}$, $A^7$ is $CR^{12}$, $A^8$ is $CR^{13}$, and $A^9$ is $CR^{14}$.

In some embodiments, one of $A^6$, $A^7$, $A^8$, and $A^9$ is N and the remainder are $CR^{11}$, $CR^{12}$, $CR^{13}$, or $CR^{14}$ as applicable. In some embodiments, $A^6$ is $CR^{11}$, $A^7$ is $CR^{12}$, $A^8$ is $CR^{13}$, and $A^9$ is N. In some embodiments, $A^6$ is $CR^{11}$, $A^7$ is $CR^{12}$, $A^8$ is N, and $A^9$ is $CR^{14}$. In some embodiments, $A^6$ is $CR^{11}$, $A^7$ is N, $A^8$ is $CR^{13}$, and $A^9$ is $CR^{14}$.

In some embodiments, provided is a compound selected from those in Table 1A, or an isotopically enriched analog, pharmaceutically acceptable salt, prodrug, tautomer, stereoisomer, or a mixture of stereoisomers thereof, optionally wherein the compound is labeled with one or more radioactive isotopes. In some embodiments, provided is a compound selected from those in Table 1B, or an isotopically enriched analog, pharmaceutically acceptable salt, prodrug, tautomer, stereoisomer, or a mixture of stereoisomers thereof, wherein the compound is labeled with one or more radioactive isotopes.

In some embodiments, the compound of Formula I is labeled with one or more radioactive isotopes.

In some embodiments, the compound of Formula I' contains one or more positron-emitting radioactive isotopes selected from $^{11}C$, $^{13}N$, $^{15}O$, and $^{18}F$. In some embodiments, the compound of Formula I contains one or more positron-emitting radioactive isotopes selected from $^{11}C$, $^{13}N$, $^{15}O$, and $^{18}F$.

In some embodiments, an imaging agent comprising the compound of Formula I', or an isotopically enriched analog, pharmaceutically acceptable salt, prodrug, tautomer, stereoisomer, or a mixture of stereoisomers thereof, is provided. In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are additional compounds as described herein. In some embodiments, provided is a compound selected from Table 1A, or an isotopically labeled analog, pharmaceutically acceptable salt, solvate, prodrug, stereoisomer, or mixture of stereoisomers thereof.

In some embodiments, provided is a pharmaceutical composition comprising the compound described herein, or an isotopically enriched analog, pharmaceutically acceptable salt, prodrug, tautomer, stereoisomer, or a mixture of stereoisomers thereof, and a pharmaceutically acceptable excipient.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

In some embodiments, provided is a compound selected from those in described in the Examples section provided herein.

Also is provided a compound, or an isotopically enriched analog, pharmaceutically acceptable salt, prodrug, tautomer, stereoisomer, or a mixture of stereoisomers thereof, selected from Table 1A:

TABLE 1A

| Ex. | Structure |
| --- | --- |
| 1-1 | 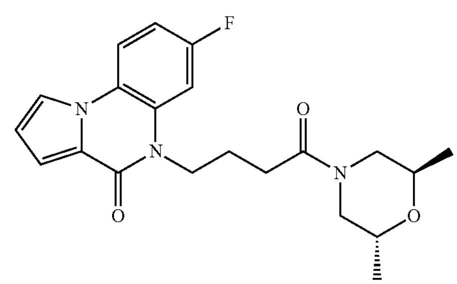 |
| 1-2 | 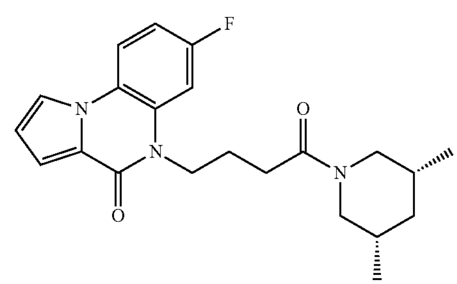 [SMILES: C[C@@H]1C[C@H](C)CN(C(=O)CCCn2c(=O)c3cccn3c3ccc(F)cc32)C1] |

TABLE 1A-continued

| Ex. | Structure |
|---|---|
| 1-3 | 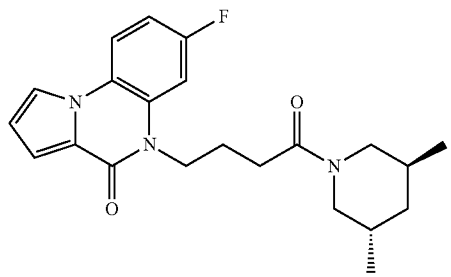 [SMILES: C[C@H]1C[C@H](C)CN(C(=O)CCCn2c(=O)c3cccn3c3ccc(F)cc32)C1] |
| 1-4 | 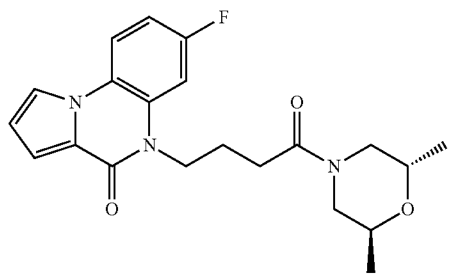 [SMILES: C[C@H]1CN(C(=O)CCCn2c(=O)c3cccn3c3ccc(F)cc32)C[C@H](C)O1] |
| 1-5 | 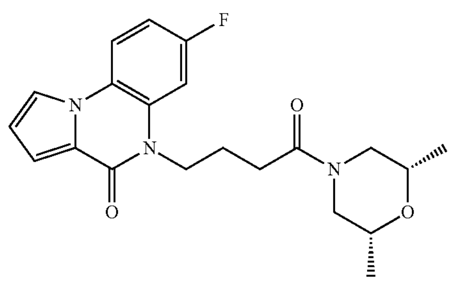 [SMILES: C[C@@H]1CN(C(=O)CCCn2c(=O)c3cccn3c3ccc(F)cc32)C[C@H](C)O1] |
| 1-6 | 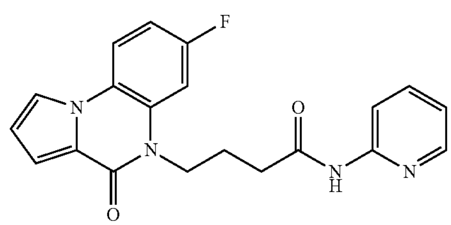 [SMILES: O=C(CCCn1c(=O)c2cccn2c2ccc(F)cc21)Nc1ccccn1] |
| 1-7 | 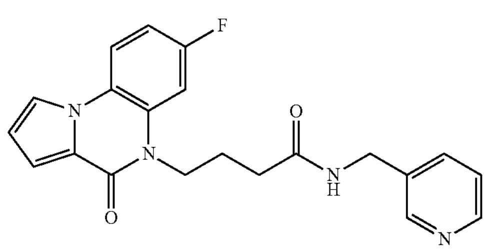 [SMILES: O=C(CCCn1c(=O)c2cccn2c2ccc(F)cc21)NCc1cccnc1] |
| 1-8 | 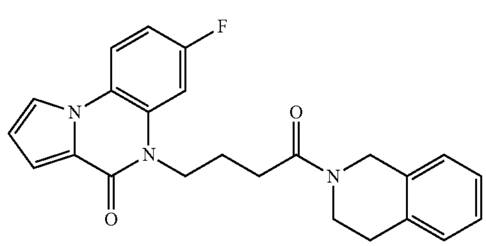 [SMILES: O=C(CCCn1c(=O)c2cccn2c2ccc(F)cc21)N1CCc2ccccc2C1] |

TABLE 1A-continued

| Ex. | Structure |
|---|---|
| 1-9 | 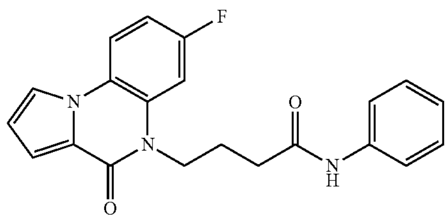 [SMILES: O=C(CCCn1c(=O)c2cccn2c2ccc(F)cc21)Nc1ccccc1] |
| 1-10 | 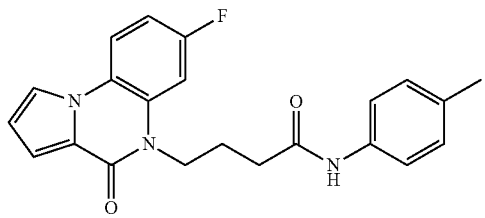 [SMILES: Cc1ccc(NC(=O)CCCn2c(=O)c3cccn3c3ccc(F)cc32)cc1] |
| 1-11 | 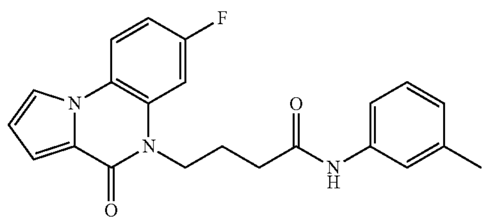 [SMILES: Cc1cccc(NC(=O)CCCn2c(=O)c3cccn3c3ccc(F)cc32)c1] |
| 1-12 | 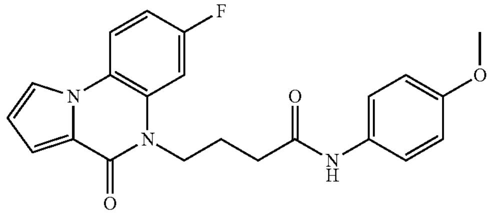 [SMILES: COc1ccc(NC(=O)CCCn2c(=O)c3cccn3c3ccc(F)cc32)cc1] |
| 1-13 | 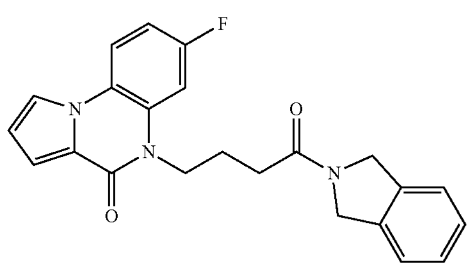 [SMILES: O=C(CCCn1c(=O)c2cccn2c2ccc(F)cc21)N1Cc2ccccc2C1] |
| 1-14 | 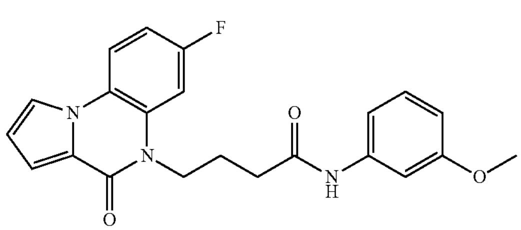 [SMILES: COc1cccc(NC(=O)CCCn2c(=O)c3cccn3c3ccc(F)cc32)c1] |

TABLE 1A-continued

| Ex. | Structure |
| --- | --- |
| 1-15 | 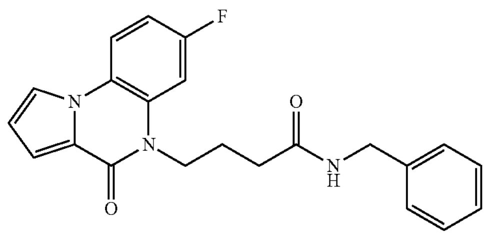 [SMILES: O=C(CCCn1c(=O)c2cccn2c2ccc(F)cc21)NCc1ccccc1] |
| 1-16 | 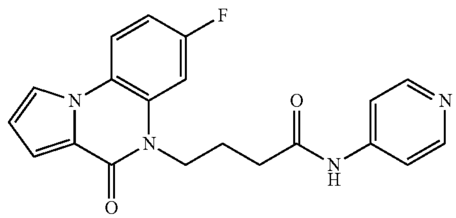 [SMILES: O=C(CCCn1c(=O)c2cccn2c2ccc(F)cc21)Nc1ccncc1] |
| 1-17 | 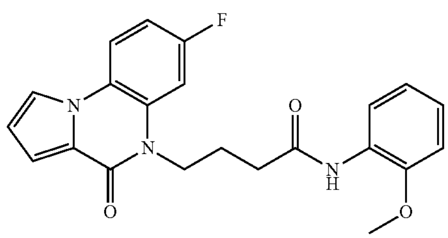 [SMILES: COc1ccccc1NC(=O)CCCn1c(=O)c2cccn2c2ccc(F)cc21] |
| 1-18 | 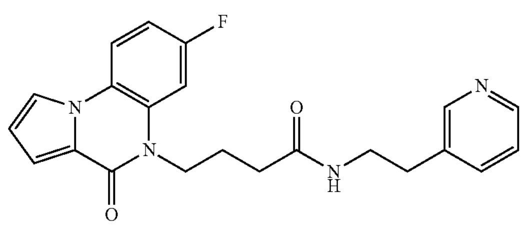 [SMILES: O=C(CCCn1c(=O)c2cccn2c2ccc(F)cc21)NCCc1cccnc1] |
| 1-19 | 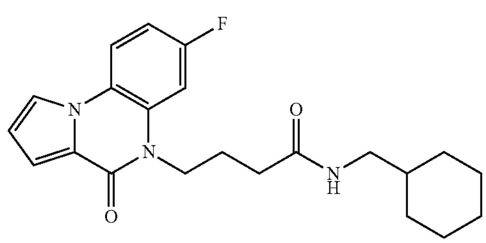 [SMILES: O=C(CCCn1c(=O)c2cccn2c2ccc(F)cc21)NCC1CCCCC1] |
| 1-20 | 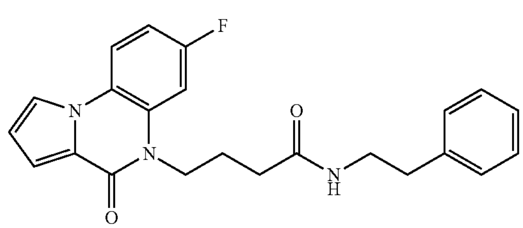 [SMILES: O=C(CCCn1c(=O)c2cccn2c2ccc(F)cc21)NCCc1ccccc1] |

TABLE 1A-continued

| Ex. | Structure |
|---|---|
| 1-21 | 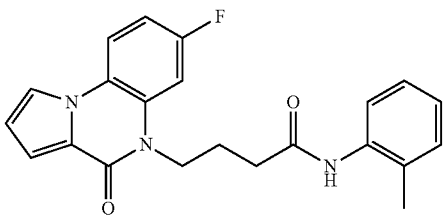 [SMILES: Cc1ccccc1NC(=O)CCCn1c(=O)c2cccn2c2ccc(F)cc21] |
| 1-22 | 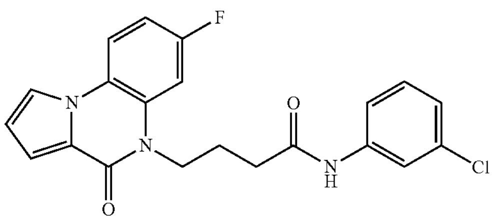 [SMILES: O=C(CCCn1c(=O)c2cccn2c2ccc(F)cc21)Nc1cccc(Cl)c1] |
| 1-23 | 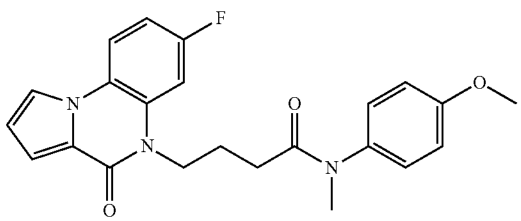 [SMILES: COc1ccc(N(C)C(=O)CCCn2c(=O)c3cccn3c3ccc(F)cc32)cc1] |
| 1-24 | 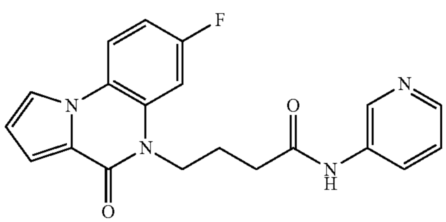 |
| 1-25 | 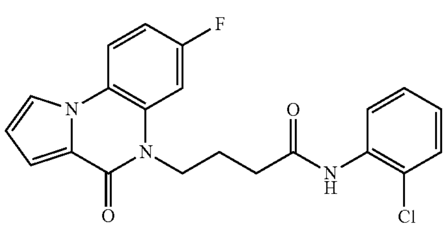 [SMILES: O=C(CCCn1c(=O)c2cccn2c2ccc(F)cc21)Nc1ccccc1Cl] |
| 1-26 | 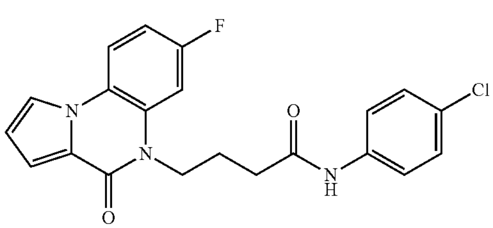 [SMILES: O=C(CCCn1c(=O)c2cccn2c2ccc(F)cc21)Nc1ccc(Cl)cc1] |
| 1-27 | 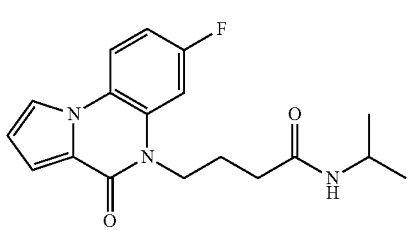 [SMILES: CC(C)NC(=O)CCCn1c(=O)c2cccn2c2ccc(F)cc21] |

TABLE 1A-continued

| Ex. | Structure |
|---|---|
| 1-28 | 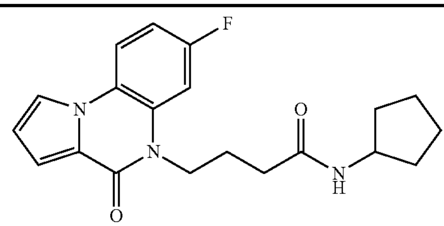 |
| 1-29 | 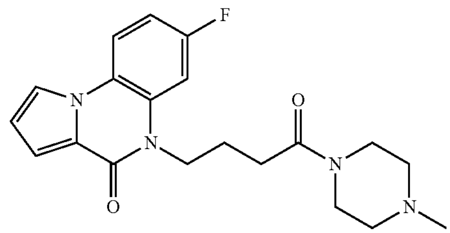 [SMILES: CN1CCN(C(=O)CCCn2c(=O)c3cccn3c3ccc(F)cc32)CC1] |
| 1-30 | 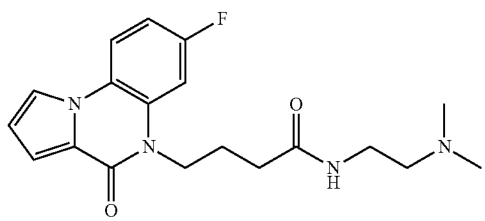 [SMILES: CN(C)CCNC(=O)CCCn1c(=O)c2cccn2c2ccc(F)cc21] |
| 1-31 | 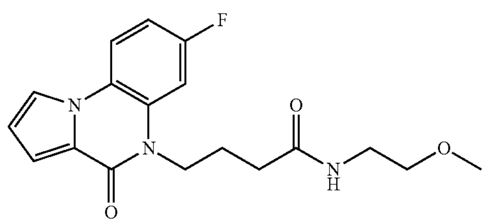 [SMILES: COCCNC(=O)CCCn1c(=O)c2cccn2c2ccc(F)cc21] |
| 1-32 | 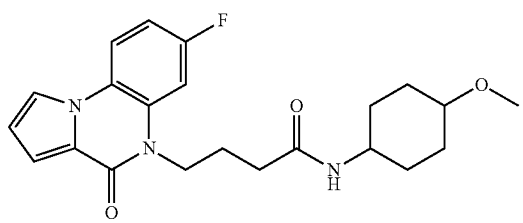 [SMILES: COC1CCC(NC(=O)CCCn2c(=O)c3cccn3c3ccc(F)cc32)CC1] |
| 1-33 | 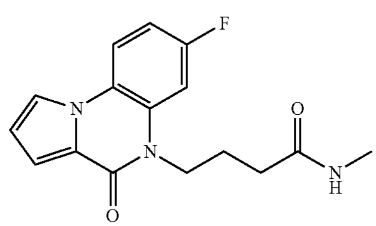 [SMILES: CNC(=O)CCCn1c(=O)c2cccn2c2ccc(F)cc21] |
| 1-34 | 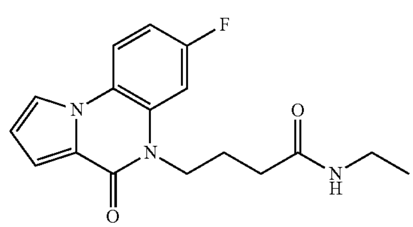 [SMILES: CCNC(=O)CCCn1c(=O)c2cccn2c2ccc(F)cc21] |

TABLE 1A-continued

| Ex. | Structure |
|---|---|
| 1-35 | 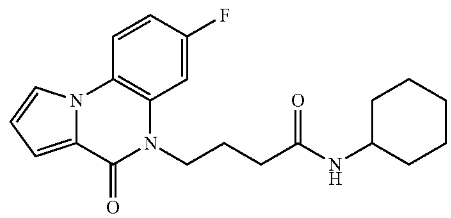 [SMILES: O=C(CCCn1c(=O)c2cccn2c2ccc(F)cc21)NC1CCCCC1] |
| 1-36 | 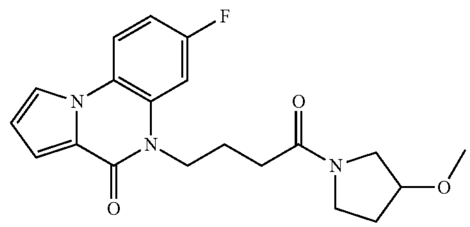 [SMILES: COC1CCN(C(=O)CCCn2c(=O)c3cccn3c3ccc(F)cc32)C1] |
| 1-37 | 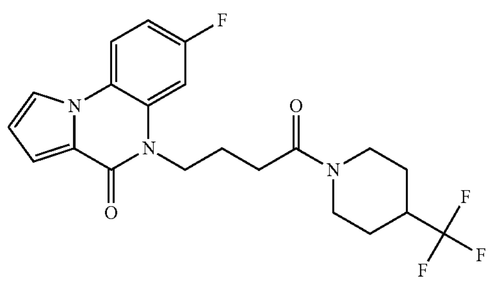 [SMILES: O=C(CCCn1c(=O)c2cccn2c2ccc(F)cc21)N1CCC(C(F)(F)F)CC1] |
| 1-38 | 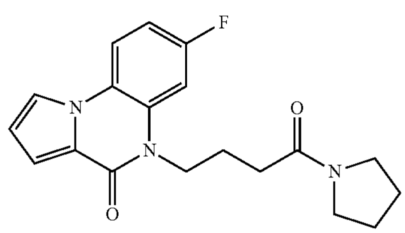 [SMILES: O=C(CCCn1c(=O)c2cccn2c2ccc(F)cc21)N1CCCC1] |
| 1-39 | 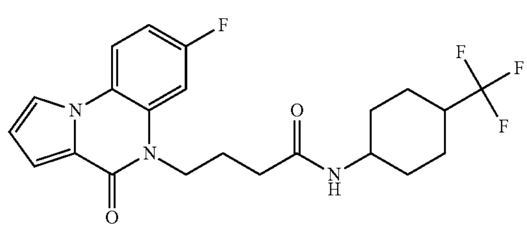 [SMILES: O=C(CCCn1c(=O)c2cccn2c2ccc(F)cc21)NC1CCC(C(F)(F)F)CC1] |
| 1-40 | 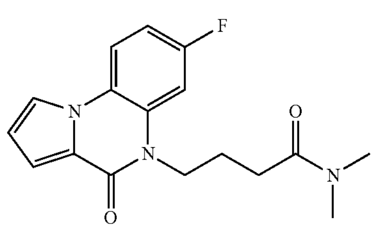 [SMILES: CN(C)C(=O)CCCn1c(=O)c2cccn2c2ccc(F)cc21] |

TABLE 1A-continued
| Ex. | Structure |
|---|---|
| 1-41 | 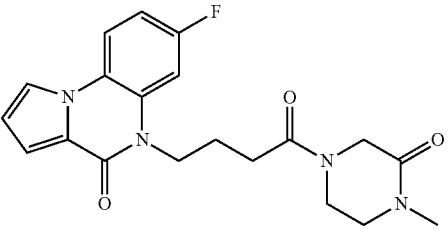 [SMILES: CN1CCN(C(=O)CCCn2c(=O)c3cccn3c3ccc(F)cc32)CC1=O] |
| 1-42 | 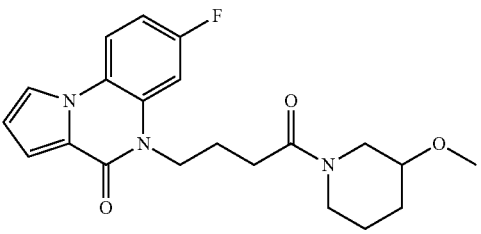 [SMILES: COC1CCCN(C(=O)CCCn2c(=O)c3cccn3c3ccc(F)cc32)C1] |
| 1-43 | 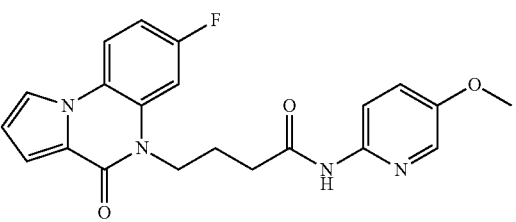 [SMILES: COc1ccc(NC(=O)CCCn2c(=O)c3cccn3c3ccc(F)cc32)nc1] |
| 1-44 | 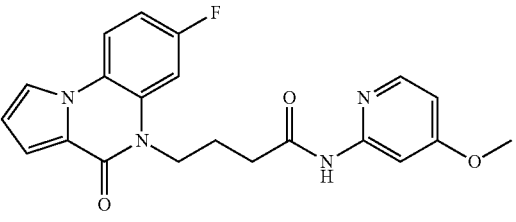 [SMILES: COc1ccnc(NC(=O)CCCn2c(=O)c3cccn3c3ccc(F)cc32)c1] |
| 1-45 | 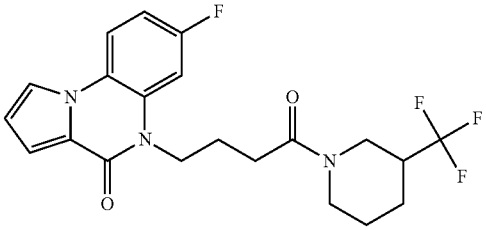 [SMILES: O=C(CCCn1c(=O)c2cccn2c2ccc(F)cc21)N1CCCC(C(F)(F)F)C1] |
| 1-46 | 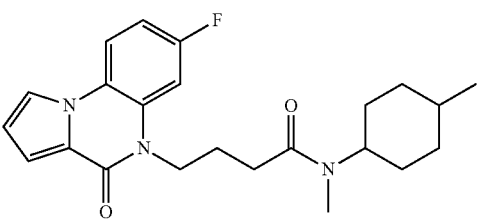 [SMILES: CC1CCC(N(C)C(=O)CCCn2c(=O)c3cccn3c3ccc(F)cc32)CC1] |

TABLE 1A-continued

| Ex. | Structure |
|---|---|
| 1-47 | 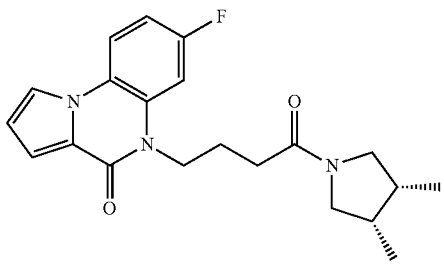 [SMILES: C[C@@H]1CN(C(=O)CCCn2c(=O)c3cccn3c3ccc(F)cc32)C[C@@H]1C] |
| 1-48 | 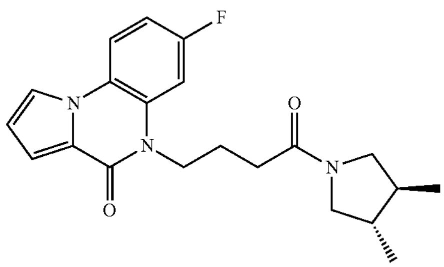 [SMILES: C[C@@H]1CN(C(=O)CCCn2c(=O)c3cccn3c3ccc(F)cc32)C[C@H]1C] |
| 1-49 | 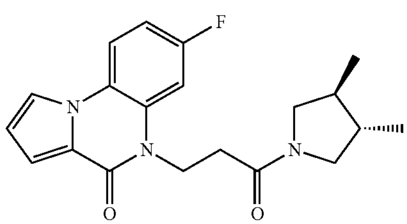 [SMILES: C[C@@H]1CN(C(=O)CCn2c(=O)c3cccn3c3ccc(F)cc32)C[C@H]1C] |
| 2-1 | 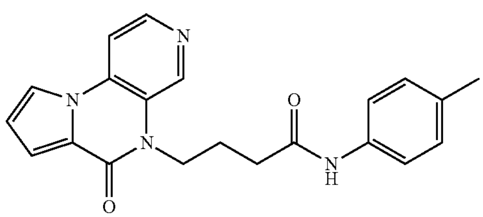 [SMILES: Cc1ccc(NC(=O)CCCn2c(=O)c3cccn3c3ccncc32)cc1] |
| 2-2 | 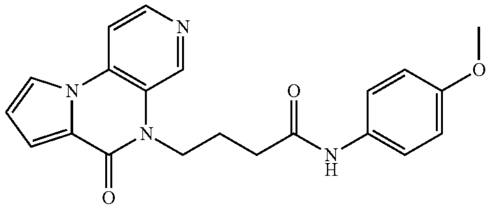 [SMILES: COc1ccc(NC(=O)CCCn2c(=O)c3cccn3c3ccncc32)cc1] |
| 2-3 | 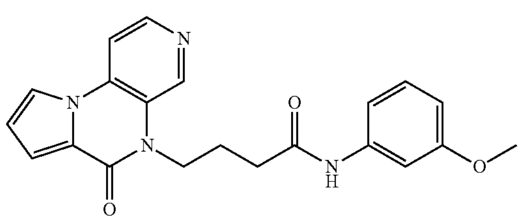 [SMILES: COc1cccc(NC(=O)CCCn2c(=O)c3cccn3c3ccncc32)c1] |

TABLE 1A-continued

| Ex. | Structure |
|---|---|
| 2-4 | 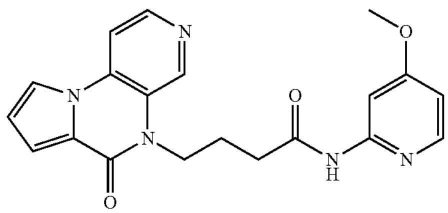 [SMILES: COc1ccnc(NC(=O)CCCn2c(=O)c3cccn3c3ccncc32)c1] |
| 2-5 | 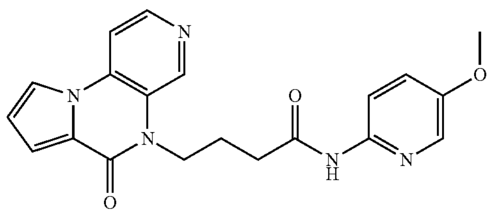 [SMILES: COc1ccc(NC(=O)CCCn2c(=O)c3cccn3c3ccncc32)nc1] |
| 3-1 | 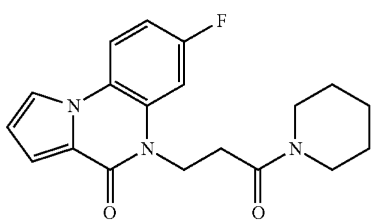 [SMILES: O=C(CCn1c(=O)c2cccn2c2ccc(F)cc21)N1CCCCC1] |
| 3-2 | 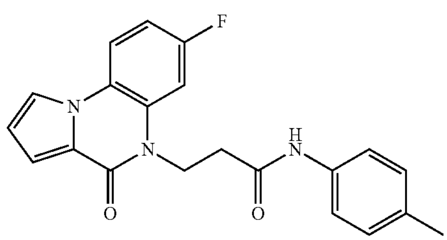 [SMILES: Cc1ccc(NC(=O)CCn2c(=O)c3cccn3c3ccc(F)cc32)cc1] |
| 3-3 | 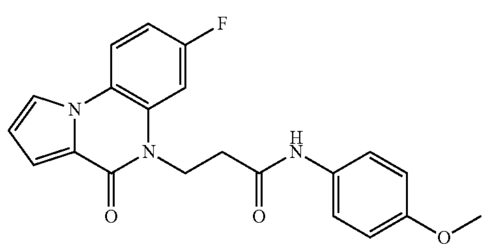 [SMILES: COc1ccc(NC(=O)CCn2c(=O)c3cccn3c3ccc(F)cc32)cc1] |
| 3-4 | 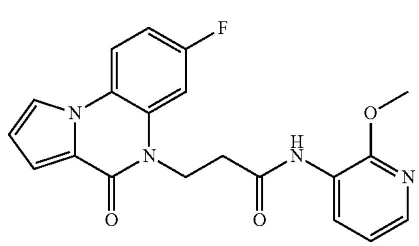 [SMILES: COc1ncccc1NC(=O)CCn1c(=O)c2cccn2c2ccc(F)cc21] |

TABLE 1A-continued

| Ex. | Structure |
|---|---|
| 3-5 | 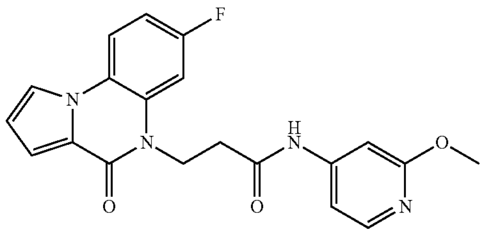 [SMILES: COc1cc(NC(=O)CCn2c(=O)c3cccn3c3ccc(F)cc32)ccn1] |
| 3-6 | 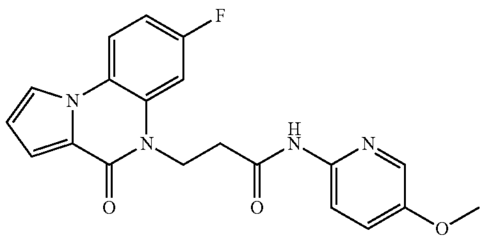 [SMILES: COc1ccc(NC(=O)CCn2c(=O)c3cccn3c3ccc(F)cc32)nc1] |
| 3-7 | 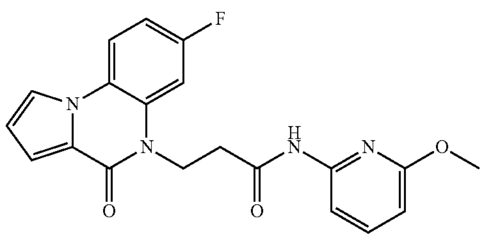 [SMILES: COc1cccc(NC(=O)CCn2c(=O)c3cccn3c3ccc(F)cc32)n1] |
| 3-8 | 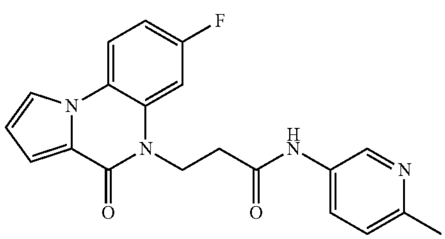 [SMILES: Cc1ccc(NC(=O)CCn2c(=O)c3cccn3c3ccc(F)cc32)cn1] |
| 3-9 | 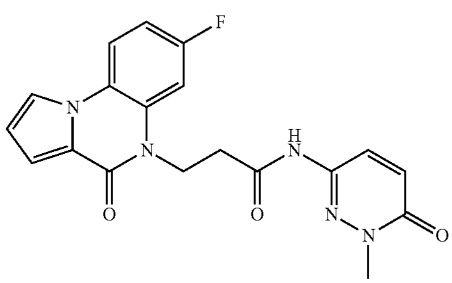 [SMILES: Cn1nc(NC(=O)CCn2c(=O)c3cccn3c3ccc(F)cc32)ccc1=O] |
| 3-10 | 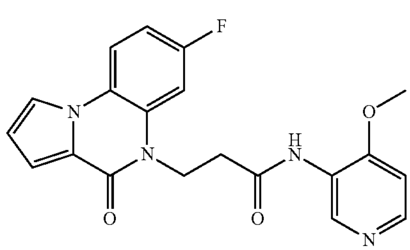 [SMILES: COc1ccncc1NC(=O)CCn1c(=O)c2cccn2c2ccc(F)cc21] |

TABLE 1A-continued

| Ex. | Structure |
|---|---|
| 3-11 | 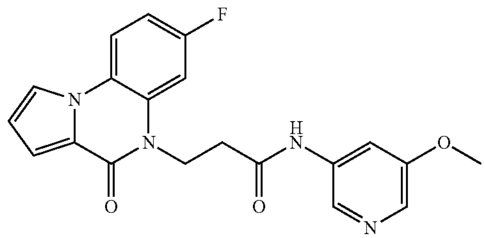 [SMILES: COc1cncc(NC(=O)CCn2c(=O)c3cccn3c3ccc(F)cc32)c1] |
| 3-12 | 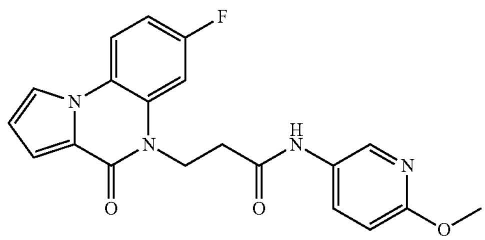 [SMILES: COc1ccc(NC(=O)CCn2c(=O)c3cccn3c3ccc(F)cc32)cn1] |
| 3-13 | 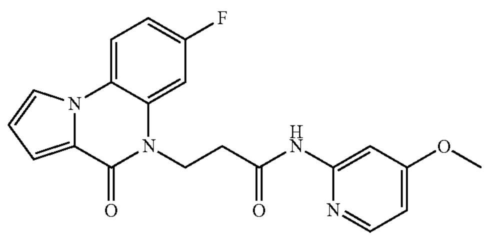 [SMILES: COc1ccnc(NC(=O)CCn2c(=O)c3cccn3c3ccc(F)cc32)c1] |
| 3-14 | 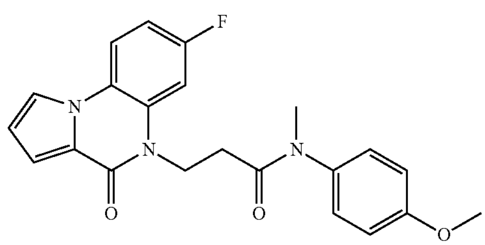 [SMILES: COc1ccc(N(C)C(=O)CCn2c(=O)c3cccn3c3ccc(F)cc32)cc1] |
| 3-15 | 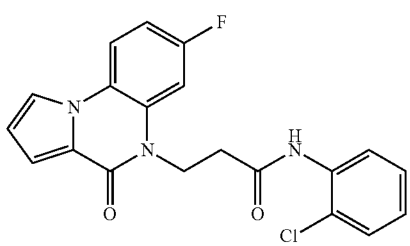 [SMILES: O=C(CCn1c(=O)c2cccn2c2ccc(F)cc21)Nc1ccccc1Cl] |
| 3-16 | 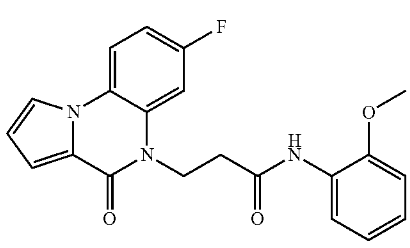 [SMILES: COc1ccccc1NC(=O)CCn1c(=O)c2cccn2c2ccc(F)cc21] |

TABLE 1A-continued
| Ex. | Structure |
|---|---|
| 3-17 | 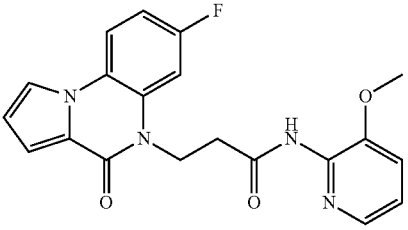 [SMILES: COc1cccnc1NC(=O)CCn1c(=O)c2cccn2c2ccc(F)cc21] |
| 3-18 | 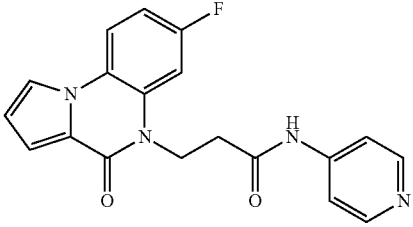 [SMILES: O=C(CCn1c(=O)c2cccn2c2ccc(F)cc21)Nc1ccncc1] |
| 3-19 | 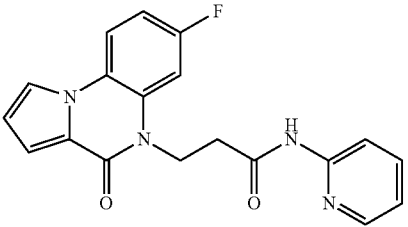 [SMILES: O=C(CCn1c(=O)c2cccn2c2ccc(F)cc21)Nc1ccccn1] |
| 3-20 | 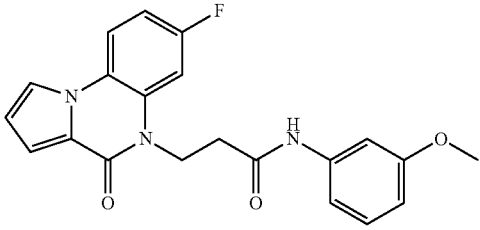 [SMILES: COc1cccc(NC(=O)CCn2c(=O)c3cccn3c3ccc(F)cc32)c1] |
| 3-21 | 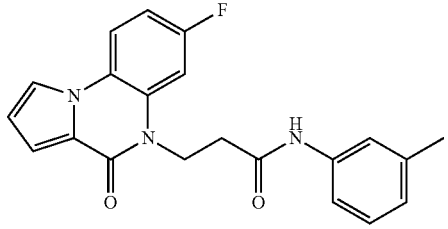 [SMILES: Cc1cccc(NC(=O)CCn2c(=O)c3cccn3c3ccc(F)cc32)c1] |
| 3-22 | 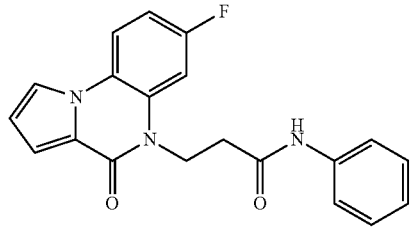 [SMILES: O=C(CCn1c(=O)c2cccn2c2ccc(F)cc21)Nc1ccccc1] |

TABLE 1A-continued

| Ex. | Structure |
|---|---|
| 3-23 | 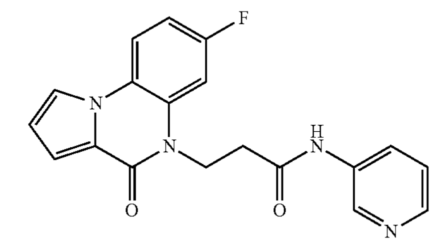 [SMILES: O=C(CCn1c(=O)c2cccn2c2ccc(F)cc21)Nc1cccnc1] |
| 3-24 | 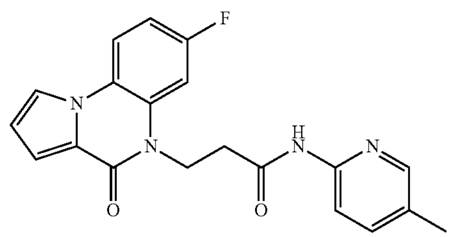 [SMILES: Cc1ccc(NC(=O)CCn2c(=O)c3cccn3c3ccc(F)cc32)nc1] |
| 3-25 | 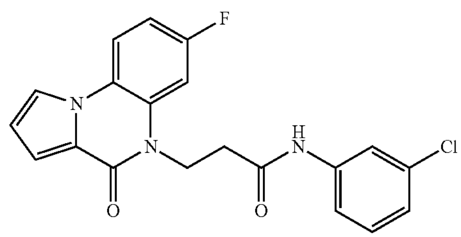 [SMILES: O=C(CCn1c(=O)c2cccn2c2ccc(F)cc21)Nc1cccc(Cl)c1] |
| 3-26 | 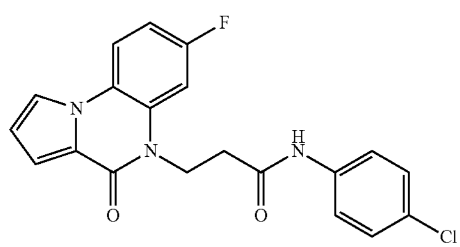 [SMILES: O=C(CCn1c(=O)c2cccn2c2ccc(F)cc21)Nc1ccc(Cl)cc1] |
| 3-27 | 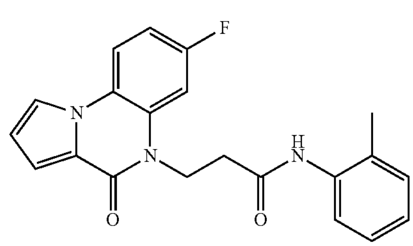 [SMILES: Cc1ccccc1NC(=O)CCn1c(=O)c2cccn2c2ccc(F)cc21] |
| 3-28 | 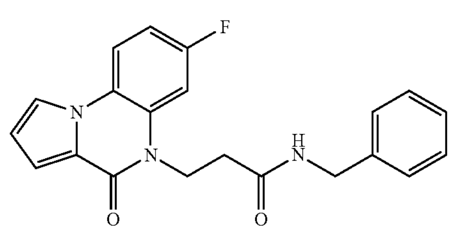 [SMILES: O=C(CCn1c(=O)c2cccn2c2ccc(F)cc21)NCc1ccccc1] |

TABLE 1A-continued
| Ex. | Structure |
|---|---|
| 3-29 | 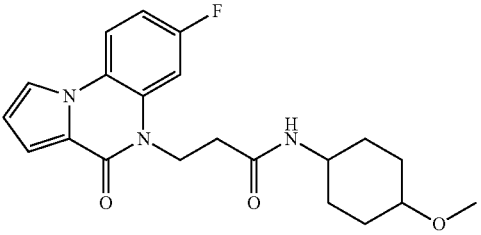 [SMILES: COC1CCC(NC(=O)CCn2c(=O)c3cccn3c3ccc(F)cc32)CC1] |
| 3-30 | 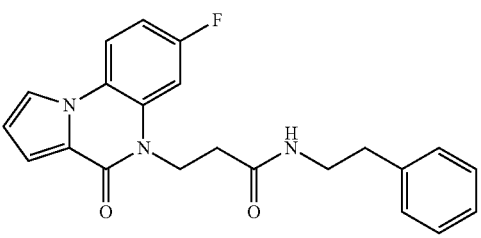 [SMILES: O=C(CCn1c(=O)c2cccn2c2ccc(F)cc21)NCCc1ccccc1] |
| 3-31 | 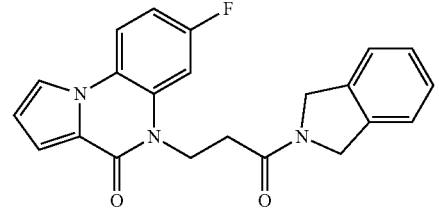 |
| 3-32 | 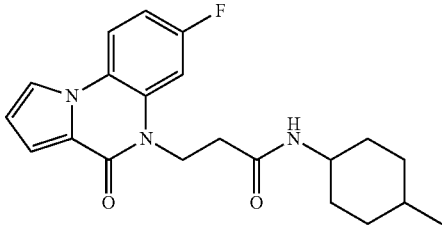 [SMILES: CC1CCC(NC(=O)CCn2c(=O)c3cccn3c3ccc(F)cc32)CC1] |
| 3-33 | 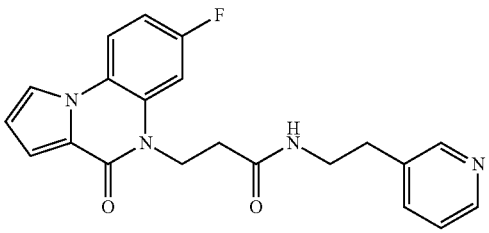 [SMILES: O=C(CCn1c(=O)c2cccn2c2ccc(F)cc21)NCCc1cccnc1] |
| 3-34 | 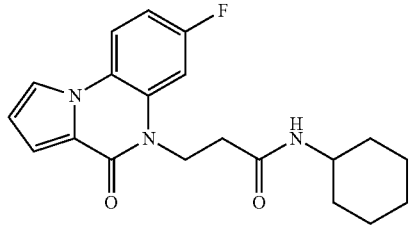 [SMILES: O=C(CCn1c(=O)c2cccn2c2ccc(F)cc21)NC1CCCCC1] |

TABLE 1A-continued

| Ex. | Structure |
|---|---|
| 3-35 | 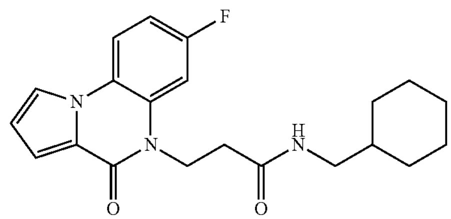 [SMILES: O=C(CCn1c(=O)c2cccn2c2ccc(F)cc21)NCC1CCCCC1] |
| 3-36 | 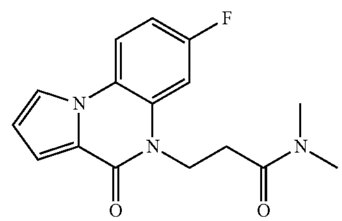 [SMILES: CN(C)C(=O)CCn1c(=O)c2cccn2c2ccc(F)cc21] |
| 3-37 | 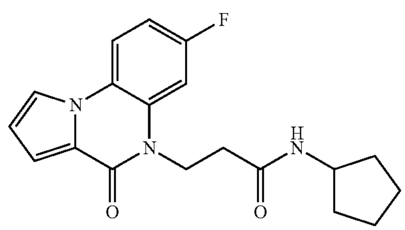 [SMILES: O=C(CCn1c(=O)c2cccn2c2ccc(F)cc21)NC1CCCC1] |
| 3-38 | 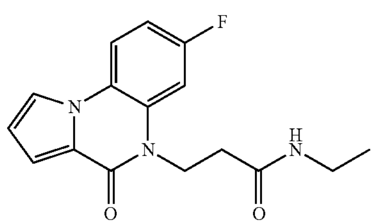 [SMILES: CCNC(=O)CCn1c(=O)c2cccn2c2ccc(F)cc21] |
| 3-39 | 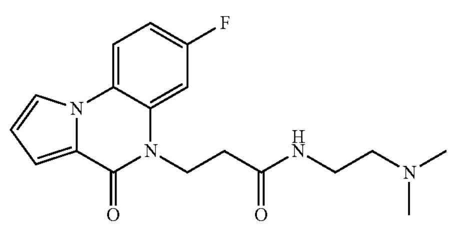 [SMILES: CN(C)CCNC(=O)CCn1c(=O)c2cccn2c2ccc(F)cc21] |
| 3-40 | 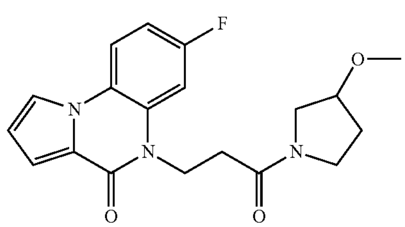 [SMILES: COC1CCN(C(=O)CCn2c(=O)c3cccn3c3ccc(F)cc32)C1] |
| 3-41 | 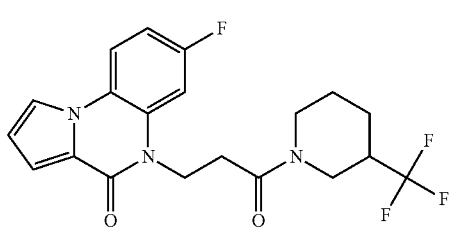 [SMILES: O=C(CCn1c(=O)c2cccn2c2ccc(F)cc21)N1CCCC(C(F)(F)F)C1] |

TABLE 1A-continued

| Ex. | Structure |
|---|---|
| 3-42 | 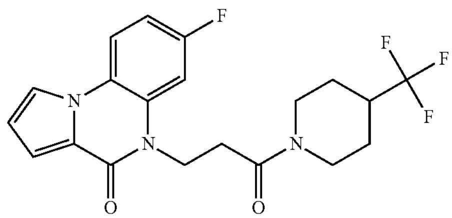 [SMILES: O=C(CCn1c(=O)c2cccn2c2ccc(F)cc21)N1CCC(C(F)(F)F)CC1] |
| 3-43 | 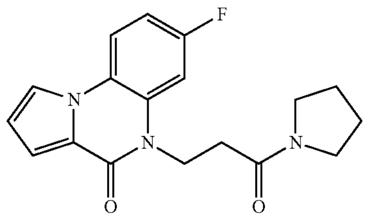 [SMILES: O=C(CCn1c(=O)c2cccn2c2ccc(F)cc21)N1CCCC1] |
| 3-44 | 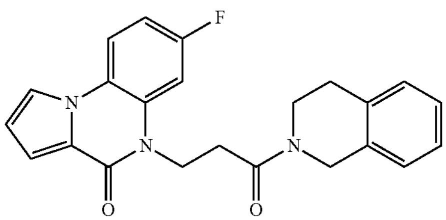 [SMILES: O=C(CCn1c(=O)c2cccn2c2ccc(F)cc21)N1CCc2ccccc2C1] |
| 3-45 | 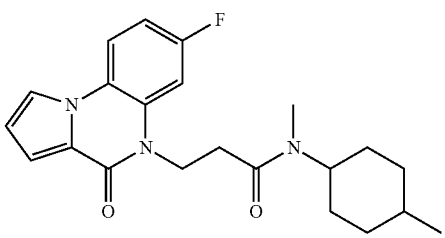 [SMILES: CC1CCC(N(C)C(=O)CCn2c(=O)c3cccn3c3ccc(F)cc32)CC1] |
| 3-46 | 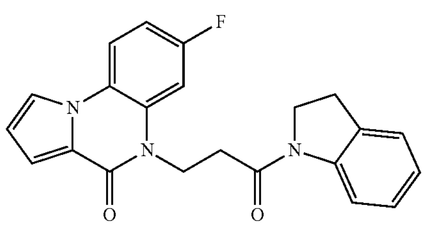 |
| 3-47 | 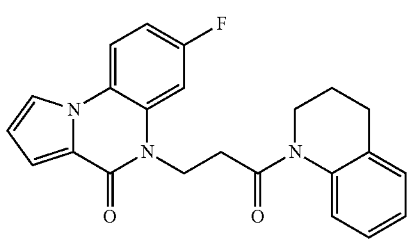 [SMILES: O=C(CCn1c(=O)c2cccn2c2ccc(F)cc21)N1CCCc2ccccc21] |
| 3-48 | 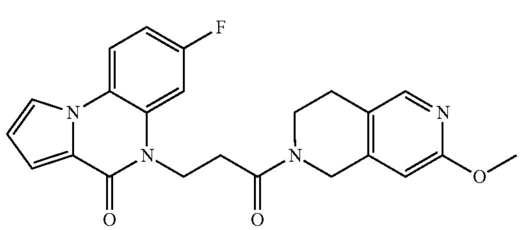 [SMILES: COc1cc2c(cn1)CCN(C(=O)CCn1c(=O)c3cccn3c3ccc(F)cc31)C2] |

TABLE 1A-continued

| Ex. | Structure |
|---|---|
| 3-49 | 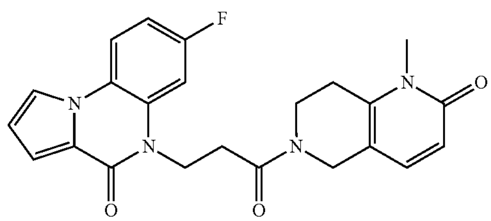 [SMILES: Cn1c2c(ccc1=O)CN(C(=O)CCn1c(=O)c3cccn3c3ccc(F)cc31)CC2] |
| 3-50 | 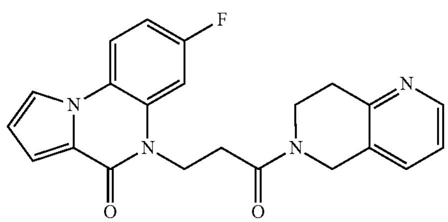 [SMILES: O=C(CCn1c(=O)c2cccn2c2ccc(F)cc21)N1CCc2ncccc2C1] |
| 3-51 | 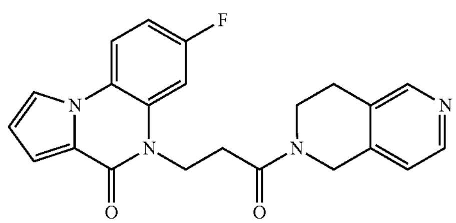 [SMILES: O=C(CCn1c(=O)c2cccn2c2ccc(F)cc21)N1CCc2cnccc2C1] |
| 3-52 | 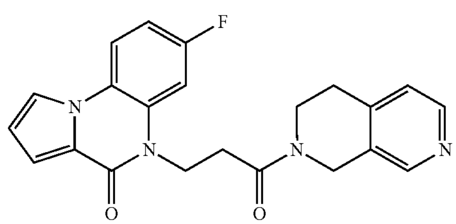 [SMILES: O=C(CCn1c(=O)c2cccn2c2ccc(F)cc21)N1CCc2ccncc2C1] |
| 3-53 | 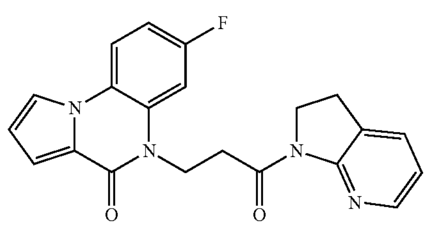 |
| 3-54 | 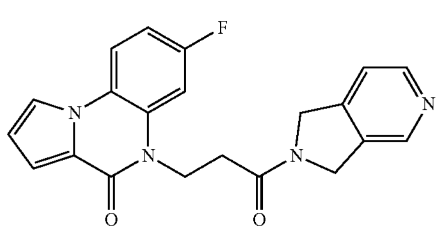 [SMILES: O=C(CCn1c(=O)c2cccn2c2ccc(F)cc21)N1Cc2ccncc2C1] |
| 3-55 | 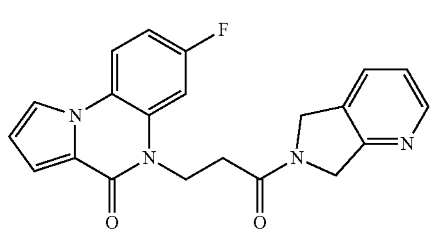 [SMILES: O=C(CCn1c(=O)c2cccn2c2ccc(F)cc21)N1Cc2cccnc2C1] |

TABLE 1A-continued
| Ex. | Structure |
|---|---|
| 3-56 | 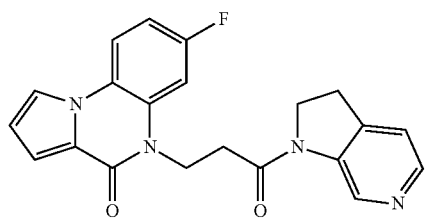 [SMILES: O=C(CCn1c(=O)c2cccn2c2ccc(F)cc21)N1CCc2ccncc21] |
| 3-57 | 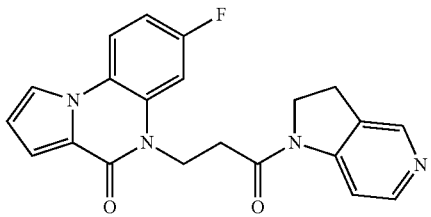 [SMILES: O=C(CCn1c(=O)c2cccn2c2ccc(F)cc21)N1CCc2cnccc21] |
| 3-58 | 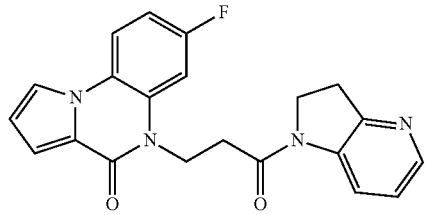 [SMILES: O=C(CCn1c(=O)c2cccn2c2ccc(F)cc21)N1CCc2ncccc21] |
| 3-59 | 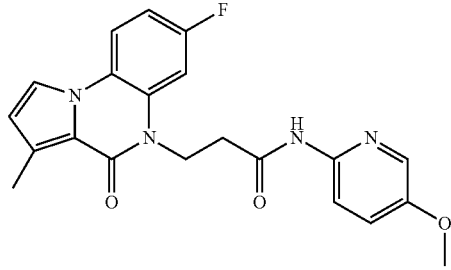 [SMILES: COc1ccc(NC(=O)CCn2c(=O)c3c(C)ccn3c3ccc(F)cc32)nc1] |
| 3-60 | 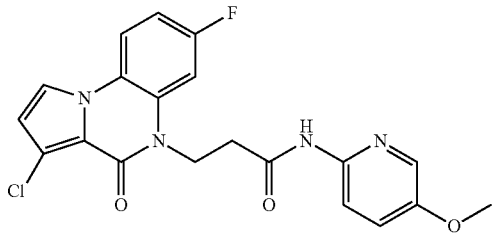 |
| 3-61 | 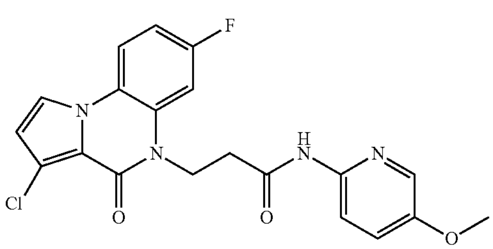 [SMILES: COc1ccc(NC(=O)CCn2c(=O)c3c(Cl)ccn3c3ccc(F)cc32)nc1] |

TABLE 1A-continued

| Ex. | Structure |
|---|---|
| 3-62 | 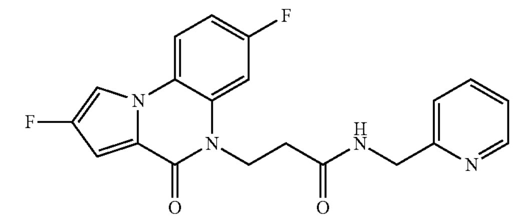 [SMILES: O=C(CCn1c(=O)c2cc(F)cn2c2ccc(F)cc21)NCc1ccccn1] |
| 3-63 | 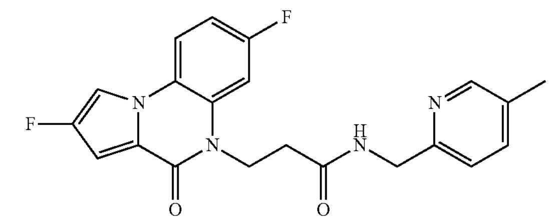 [SMILES: Cc1ccc(CNC(=O)CCn2c(=O)c3cc(F)cn3c3ccc(F)cc32)nc1] |
| 3-64 | 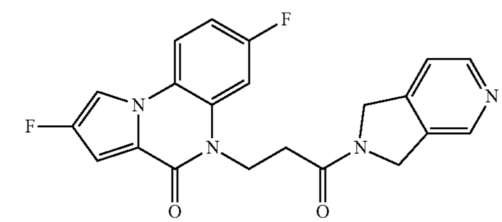 [SMILES: O=C(CCn1c(=O)c2cc(F)cn2c2ccc(F)cc21)N1Cc2ccncc2C1] |
| 3-65 | 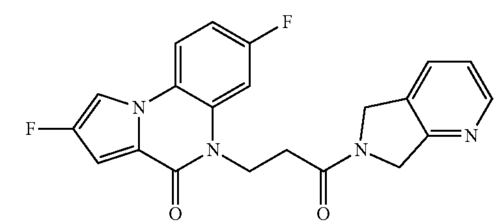 [SMILES: O=C(CCn1c(=O)c2cc(F)cn2c2ccc(F)cc21)N1Cc2cccnc2C1] |
| 3-66 | 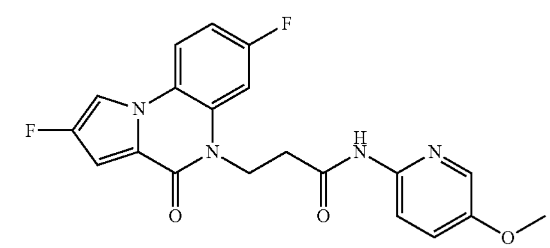 [SMILES: COc1ccc(NC(=O)CCn2c(=O)c3cc(F)cn3c3ccc(F)cc32)nc1] |
| 3-67 | 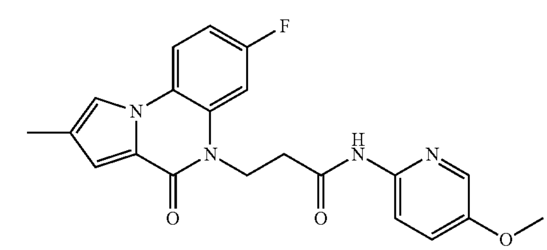 |

TABLE 1A-continued

| Ex. | Structure |
|---|---|
| 3-68 | 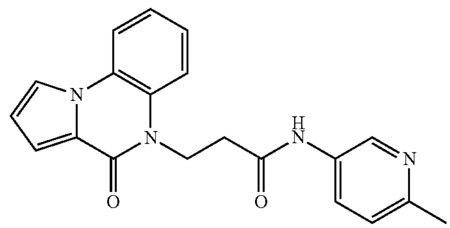 [SMILES: Cc1ccc(NC(=O)CCn2c(=O)c3cccn3c3ccccc32)cn1] |
| 3-69 | 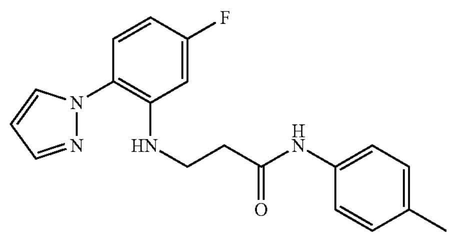 [SMILES: Cc1ccc(NC(=O)CCNc2cc(F)ccc2-n2cccn2)cc1] |
| 4-1 | 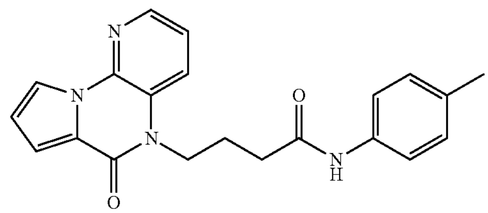 [SMILES: Cc1ccc(NC(=O)CCCn2c(=O)c3cccn3c3ncccc32)cc1] |
| 4-2 | 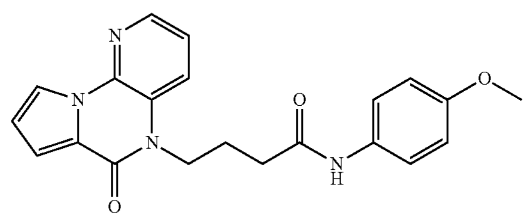 [SMILES: COc1ccc(NC(=O)CCCn2c(=O)c3cccn3c3ncccc32)cc1] |
| 4-3 | 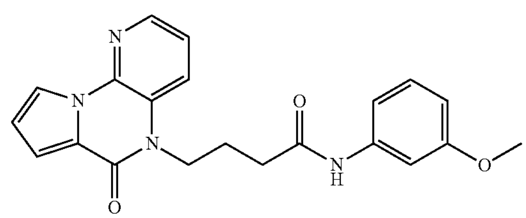 [SMILES: COc1cccc(NC(=O)CCCn2c(=O)c3cccn3c3ncccc32)c1] |
| 4-4 | 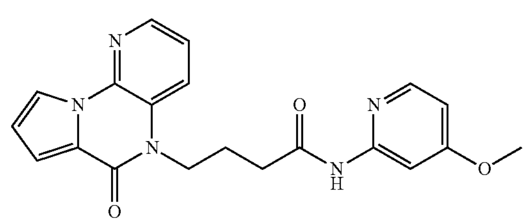 [SMILES: COc1ccnc(NC(=O)CCCn2c(=O)c3cccn3c3ncccc32)c1] |
| 4-5 | 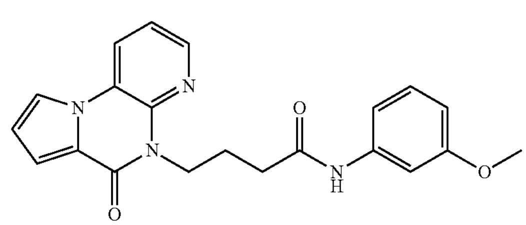 |

TABLE 1A-continued

| Ex. | Structure |
|---|---|
| 4-6 | 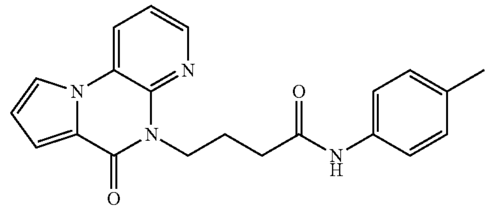 [SMILES: Cc1ccc(NC(=O)CCCn2c(=O)c3cccn3c3cccnc32)cc1] |
| 4-7 | 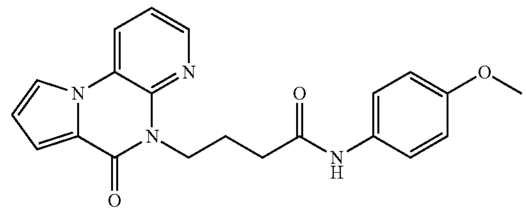 [SMILES: COc1ccc(NC(=O)CCCn2c(=O)c3cccn3c3cccnc32)cc1] |
| 4-8 | 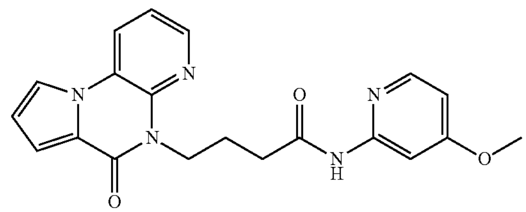 [SMILES: COc1ccnc(NC(=O)CCCn2c(=O)c3cccn3c3cccnc32)c1] |
| 4-9 | 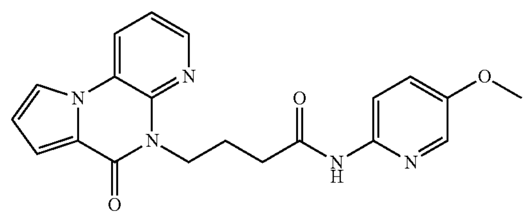 [SMILES: COc1ccc(NC(=O)CCCn2c(=O)c3cccn3c3cccnc32)nc1] |
| 4-10 | 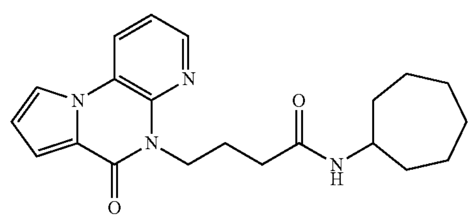 [SMILES: O=C(CCCn1c(=O)c2cccn2c2cccnc21)NC1CCCCCC1] |
| 5-1 | 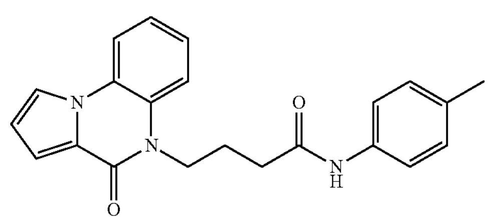 [SMILES: Cc1ccc(NC(=O)CCCn2c(=O)c3cccn3c3ccccc32)cc1] |
| 5-2 | 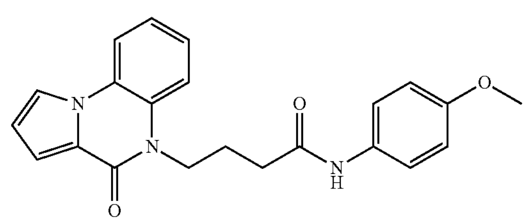 [SMILES: COc1ccc(NC(=O)CCCn2c(=O)c3cccn3c3ccccc32)cc1] |

TABLE 1A-continued
| Ex. | Structure |
|---|---|
| 5-3 | 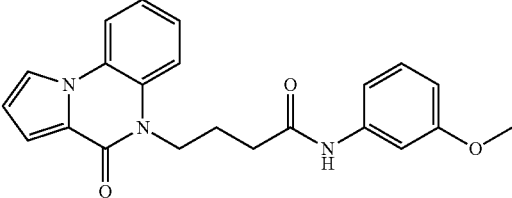 |
| 5-4 | 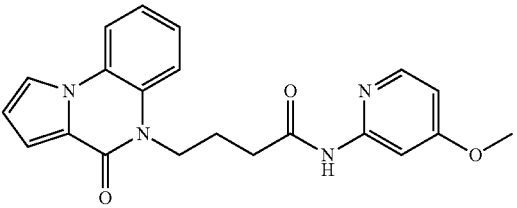 [SMILES: COc1cccc(NC(=O)CCCn2c(=O)c3cccn3c3ccccc32)c1] |
| 5-5 | 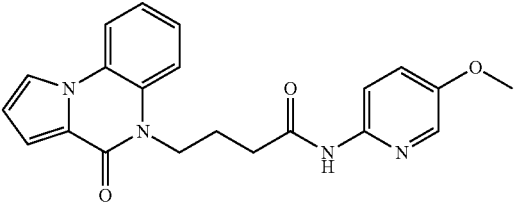 [SMILES: COc1ccc(NC(=O)CCCn2c(=O)c3cccn3c3ccccc32)nc1] |
| 5-6 | 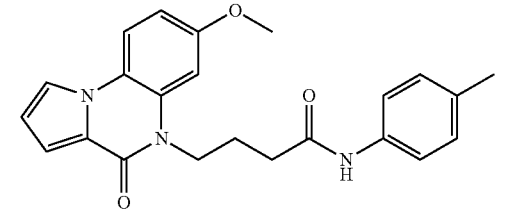 [SMILES: COc1ccc2c(c1)n(CCCC(=O)Nc1ccc(C)cc1)c(=O)c1cccn12] |
| 5-7 | 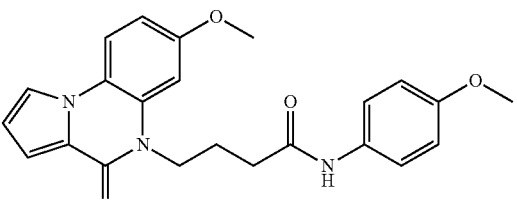 |
| 5-8 | 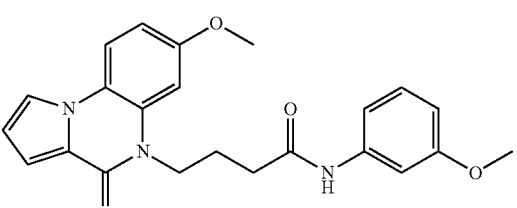 |
| 5-9 | 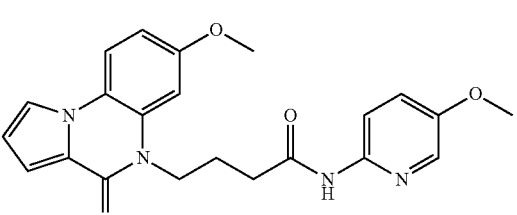 |

TABLE 1A-continued
| Ex. | Structure |
|---|---|
| 5-10 | 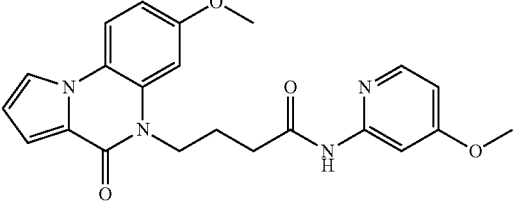 |
| 5-11 | 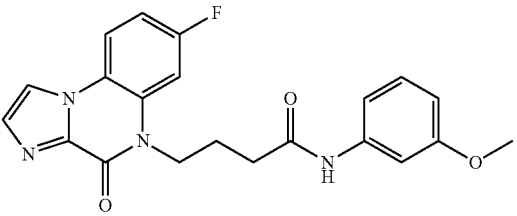 [SMILES: COc1cccc(NC(=O)CCCn2c(=O)c3nccn3c3ccc(F)cc32)c1] |
| 5-12 | 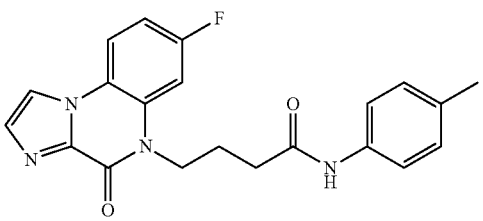 [SMILES: Cc1ccc(NC(=O)CCCn2c(=O)c3nccn3c3ccc(F)cc32)cc1] |
| 5-13 | 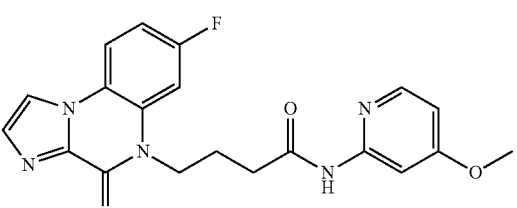 |
| 5-14 | 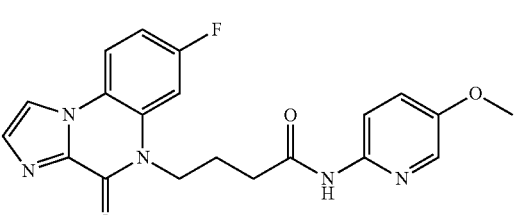 |
| 5-15 | 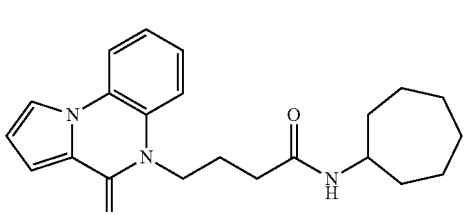 |
| 5-16 | 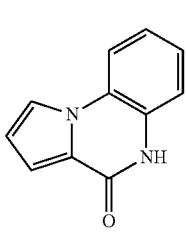 [SMILES: O=c1[nH]c2ccccc2n2cccc12] |

TABLE 1A-continued

| Ex. | Structure |
|---|---|
| 5-17 | 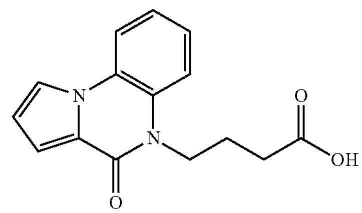 [SMILES: O=C(O)CCCn1c(=O)c2cccn2c2ccccc21] |
| 5-18 | 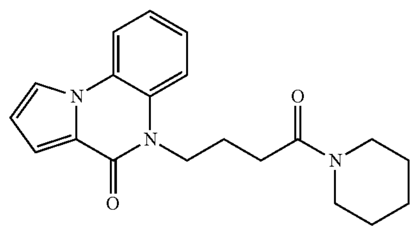 [SMILES: O=C(CCCn1c(=O)c2cccn2c2ccccc21)N1CCCCC1] |
| 6-1 | 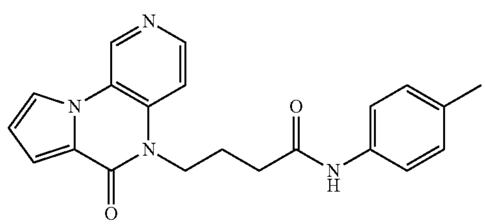 [SMILES: Cc1ccc(NC(=O)CCCn2c(=O)c3cccn3c3cnccc32)cc1] |
| 6-2 | 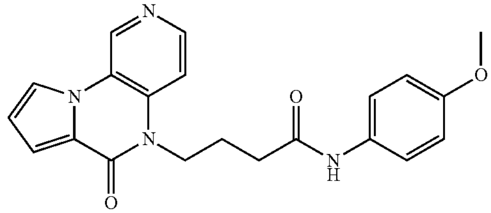 [SMILES: COc1ccc(NC(=O)CCCn2c(=O)c3cccn3c3cnccc32)cc1] |
| 6-3 | 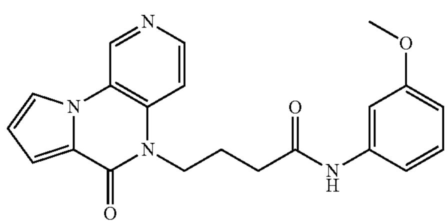 [SMILES: COc1cccc(NC(=O)CCCn2c(=O)c3cccn3c3cnccc32)c1] |
| 6-4 | 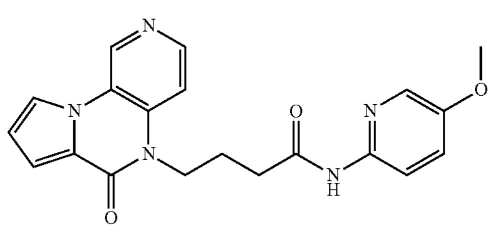 [SMILES: COc1ccc(NC(=O)CCCn2c(=O)c3cccn3c3cnccc32)nc1] |
| 6-5 | 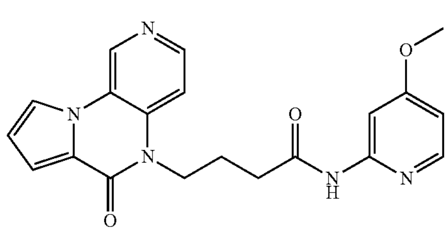 [SMILES: COc1ccnc(NC(=O)CCCn2c(=O)c3cccn3c3cnccc32)c1] |

TABLE 1A-continued

| Ex. | Structure |
|---|---|
| 7-1 | 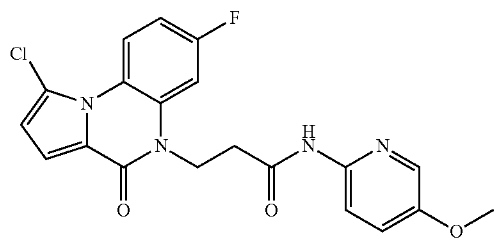 [SMILES: COc1ccc(NC(=O)CCn2c(=O)c3ccc(Cl)n3c3ccc(F)cc32)nc1] |
| 8-1 | 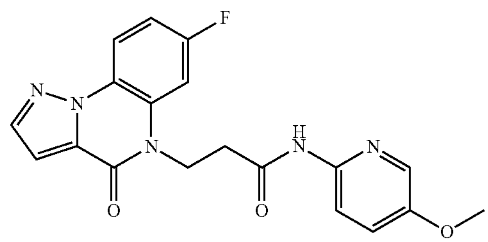 [SMILES: COc1ccc(NC(=O)CCn2c(=O)c3ccnn3c3ccc(F)cc32)nc1] |
| 8-2 | 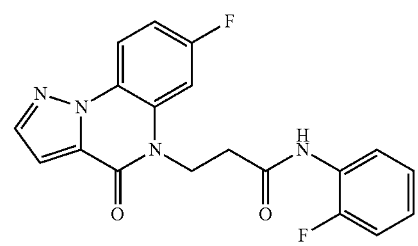 [SMILES: O=C(CCn1c(=O)c2ccnn2c2ccc(F)cc21)Nc1ccccc1F] |
| 8-3 | 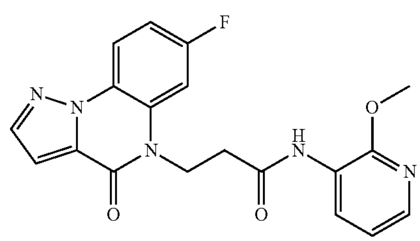 [SMILES: COc1ncccc1NC(=O)CCn1c(=O)c2ccnn2c2ccc(F)cc21] |
| 8-4 | 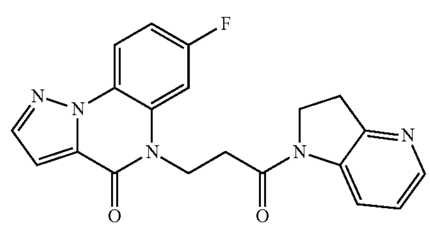 |
| 8-5 | 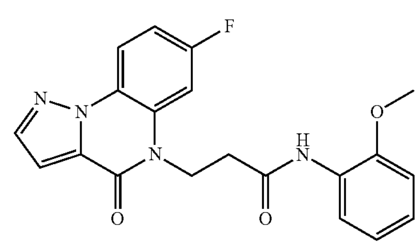 [SMILES: COc1ccccc1NC(=O)CCn1c(=O)c2ccnn2c2ccc(F)cc21] |

TABLE 1A-continued

| Ex. | Structure |
|---|---|
| 8-6 | 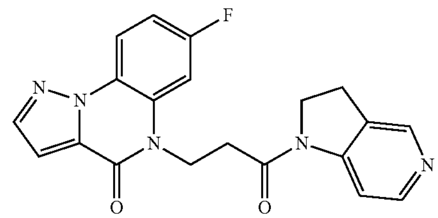 [SMILES: O=C(CCn1c(=O)c2ccnn2c2ccc(F)cc21)N1CCc2cnccc21] |
| 8-7 | 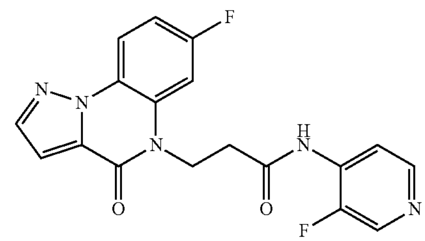 [SMILES: O=C(CCn1c(=O)c2ccnn2c2ccc(F)cc21)Nc1ccncc1F] |
| 8-8 | 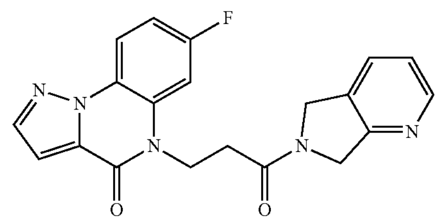 [SMILES: O=C(CCn1c(=O)c2ccnn2c2ccc(F)cc21)N1Cc2cccnc2C1] |
| 8-9 | 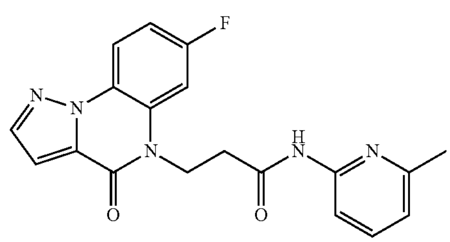 [SMILES: Cc1cccc(NC(=O)CCn2c(=O)c3ccnn3c3ccc(F)cc32)n1] |
| 8-10 | 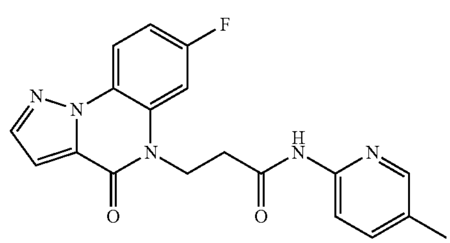 [SMILES: Cc1ccc(NC(=O)CCn2c(=O)c3ccnn3c3ccc(F)cc32)nc1] |
| 8-11 | 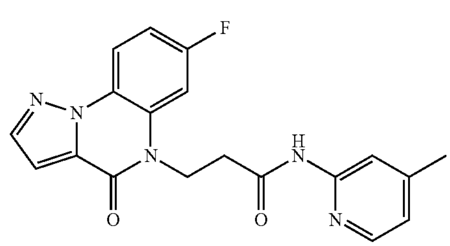 [SMILES: Cc1ccnc(NC(=O)CCn2c(=O)c3ccnn3c3ccc(F)cc32)c1] |

TABLE 1A-continued

| Ex. | Structure |
|---|---|
| 8-12 | 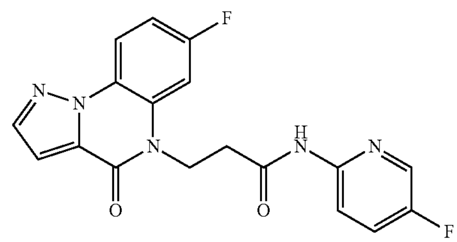 [SMILES: O=C(CCn1c(=O)c2ccnn2c2ccc(F)cc21)Nc1ccc(F)cn1] |
| 8-13 | 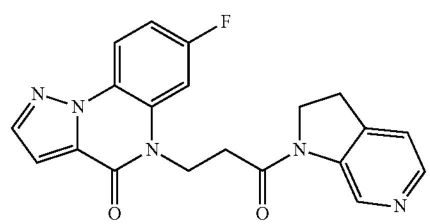 [SMILES: O=C(CCn1c(=O)c2ccnn2c2ccc(F)cc21)N1CCc2ccncc21] |
| 9-1 | 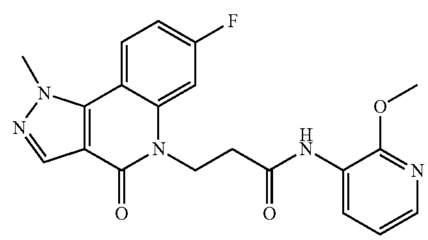 [SMILES: COc1ncccc1NC(=O)CCn1c(=O)c2cnn(C)c2c2ccc(F)cc21] |
| 9-2 | 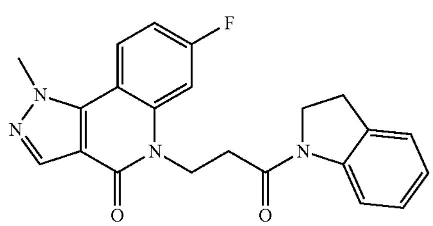 [SMILES: Cn1ncc2c(=O)n(CCC(=O)N3CCc4ccccc43)c3cc(F)ccc3c21] |
| 9-3 | 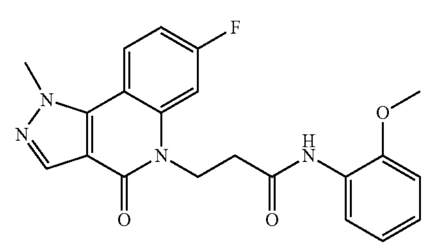 [SMILES: COc1ccccc1NC(=O)CCn1c(=O)c2cnn(C)c2c2ccc(F)cc21] |
| 9-4 | 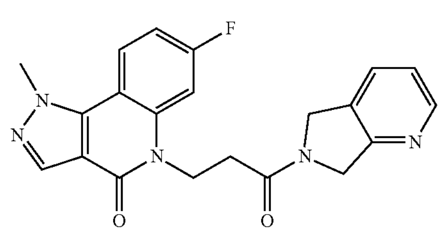 |

TABLE 1A-continued

| Ex. | Structure |
|---|---|
| 9-5 | 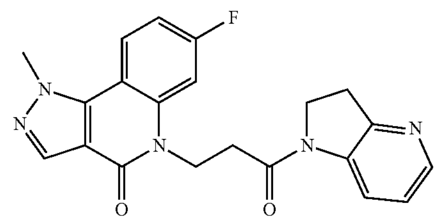 |
| 9-6 | 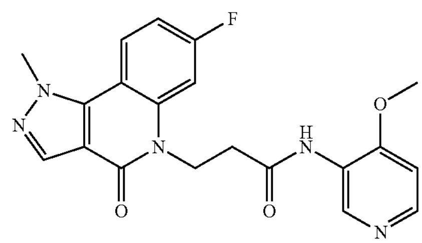 [SMILES: COc1ccncc1NC(=O)CCn1c(=O)c2cnn(C)c2c2ccc(F)cc21] |
| 9-7 | 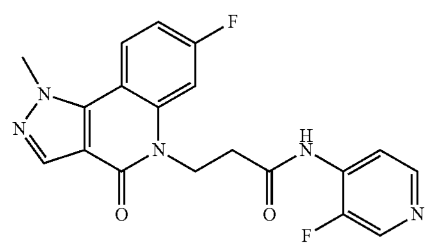 [SMILES: Cn1ncc2c(=O)n(CCC(=O)Nc3ccncc3F)c3cc(F)ccc3c21] |
| 9-8 | 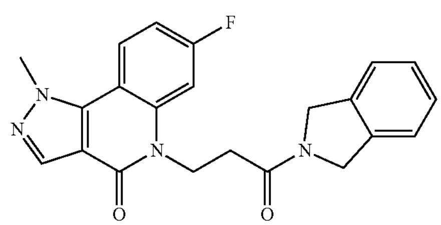 [SMILES: Cn1ncc2c(=O)n(CCC(=O)N3Cc4ccccc4C3)c3cc(F)ccc3c21] |
| 9-9 | 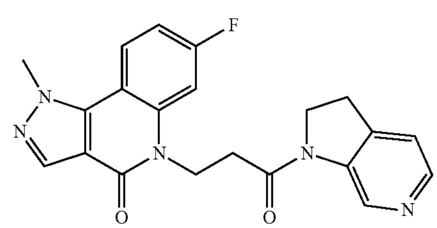 [SMILES: Cn1ncc2c(=O)n(CCC(=O)N3CCc4ccncc43)c3cc(F)ccc3c21] |
| 9-10 | 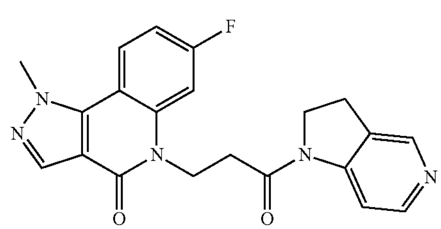 [SMILES: Cn1ncc2c(=O)n(CCC(=O)N3CCc4cnccc43)c3cc(F)ccc3c21] |

TABLE 1A-continued

| Ex. | Structure |
|---|---|
| 9-11 | 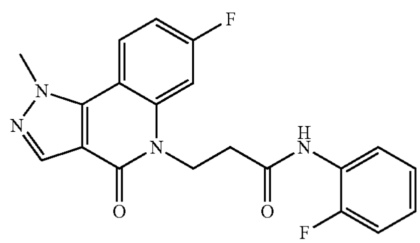 [SMILES: Cn1ncc2c(=O)n(CCC(=O)Nc3ccccc3F)c3cc(F)ccc3c21] |
| 9-12 | 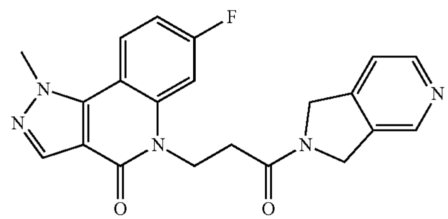 [SMILES: Cn1ncc2c(=O)n(CCC(=O)N3Cc4ccncc4C3)c3cc(F)ccc3c21] |
| 9-13 | 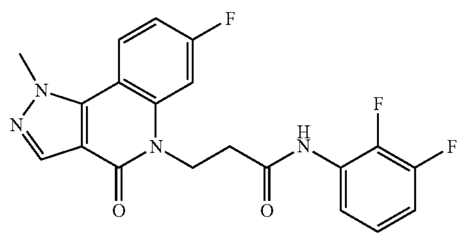 [SMILES: Cn1ncc2c(=O)n(CCC(=O)Nc3cccc(F)c3F)c3cc(F)ccc3c21] |
| 9-14 | 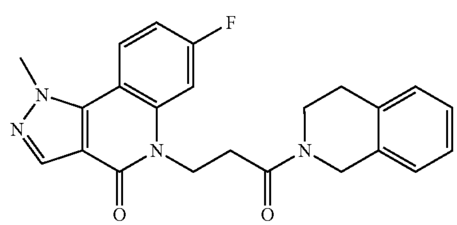 [SMILES: Cn1ncc2c(=O)n(CCC(=O)N3CCc4ccccc4C3)c3cc(F)ccc3c21] |
| 9-15 | 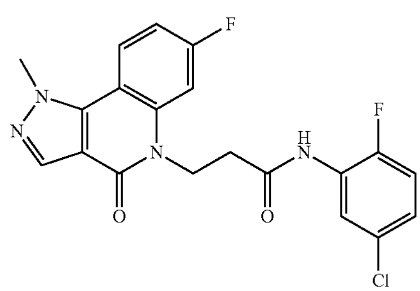 [SMILES: Cn1ncc2c(=O)n(CCC(=O)Nc3cc(Cl)ccc3F)c3cc(F)ccc3c21] |
| 9-16 | 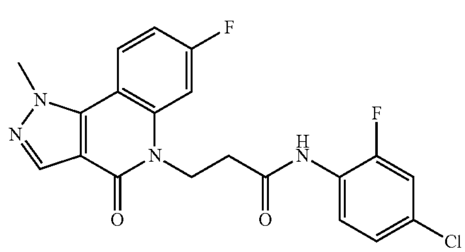 [SMILES: Cn1ncc2c(=O)n(CCC(=O)Nc3ccc(Cl)cc3F)c3cc(F)ccc3c21] |

TABLE 1A-continued

| Ex. | Structure |
|---|---|
| 9-17 | 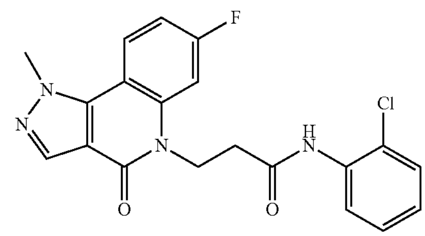 [SMILES: Cn1ncc2c(=O)n(CCC(=O)Nc3ccccc3Cl)c3cc(F)ccc3c21] |
| 9-18 | 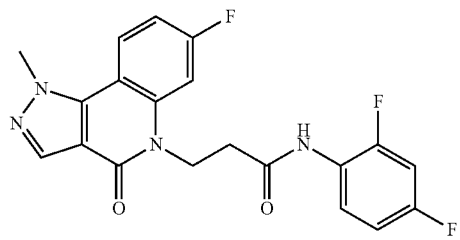 [SMILES: Cn1ncc2c(=O)n(CCC(=O)Nc3ccc(F)cc3F)c3cc(F)ccc3c21] |
| 9-19 | 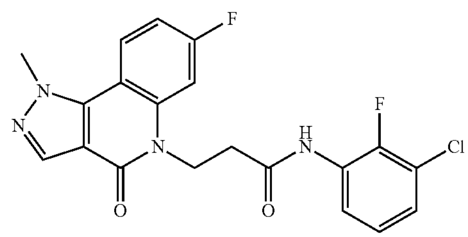 [SMILES: Cn1ncc2c(=O)n(CCC(=O)Nc3cccc(Cl)c3F)c3cc(F)ccc3c21] |
| 9-20 | 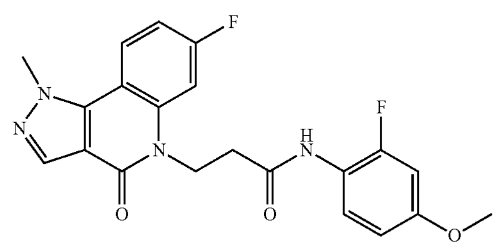 [SMILES: COc1ccc(NC(=O)CCn2c(=O)c3cnn(C)c3c3ccc(F)cc32)c(F)c1] |
| 9-21 | 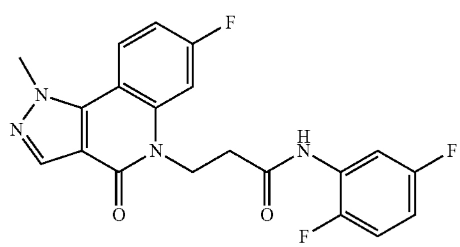 [SMILES: Cn1ncc2c(=O)n(CCC(=O)Nc3cc(F)ccc3F)c3cc(F)ccc3c21] |
| 9-22 | 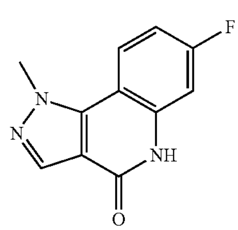 [SMILES: Cn1ncc2c(=O)[nH]c3cc(F)ccc3c21] |

TABLE 1A-continued

| Ex. | Structure |
|---|---|
| 9-23 | 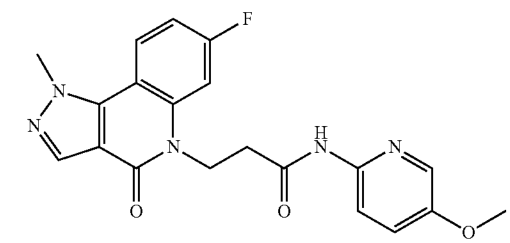 [SMILES: COc1ccc(NC(=O)CCn2c(=O)c3cnn(C)c3c3ccc(F)cc32)nc1] |
| 9-24 | 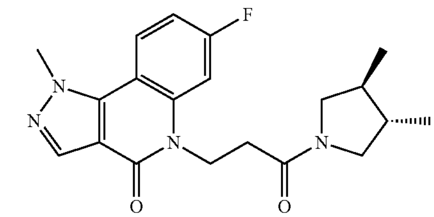 [SMILES: C[C@@H]1CN(C(=O)CCn2c(=O)c3cnn(C)c3c3ccc(F)cc32)C[C@H]1C] |
| 9-25 | 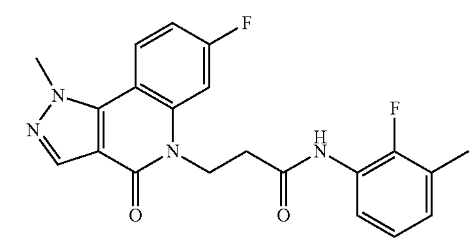 [SMILES: Cc1cccc(NC(=O)CCn2c(=O)c3cnn(C)c3c3ccc(F)cc32)c1F] |
| 9-26 | 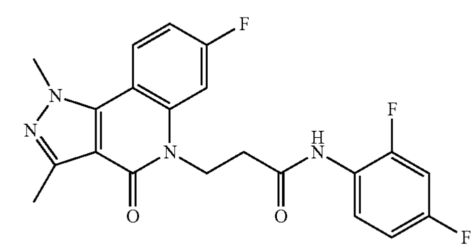 [SMILES: Cc1nn(C)c2c1c(=O)n(CCC(=O)Nc1ccc(F)cc1F)c1cc(F)ccc21] |
| 9-27 | 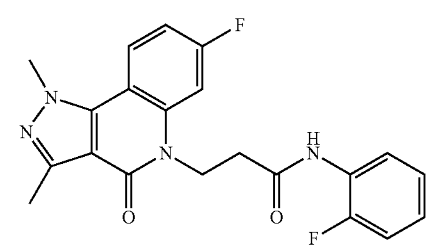 [SMILES: Cc1nn(C)c2c1c(=O)n(CCC(=O)Nc1ccccc1F)c1cc(F)ccc21] |
| 9-28 | 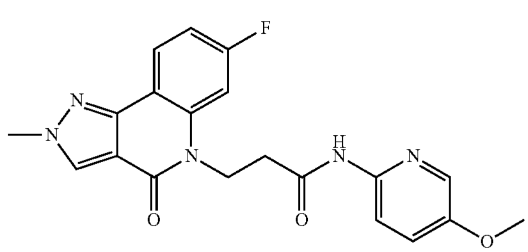 |

TABLE 1A-continued

| Ex. | Structure |
|---|---|
| 9-29 | 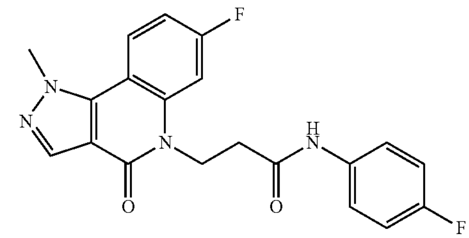 [SMILES: Cn1ncc2c(=O)n(CCC(=O)Nc3ccc(F)cc3)c3cc(F)ccc3c21] |
| 9-30 | 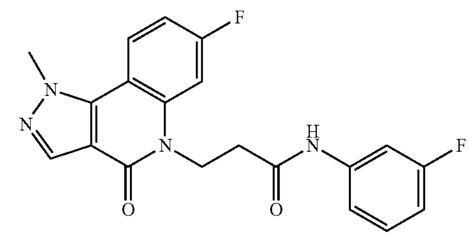 [SMILES: Cn1ncc2c(=O)n(CCC(=O)Nc3cccc(F)c3)c3cc(F)ccc3c21] |
| 9-31 | 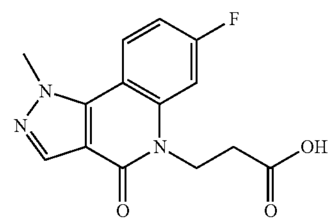 [SMILES: Cn1ncc2c(=O)n(CCC(=O)O)c3cc(F)ccc3c21] |
| 10-1 | 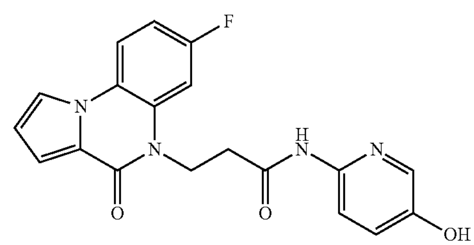 [SMILES: O=C(CCn1c(=O)c2cccn2c2ccc(F)cc21)Nc1ccc(O)cn1] |
| 11-1 | 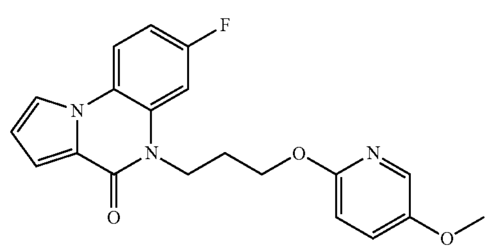 [SMILES: COc1ccc(OCCCn2c(=O)c3cccn3c3ccc(F)cc32)nc1] |
| 12-1 | 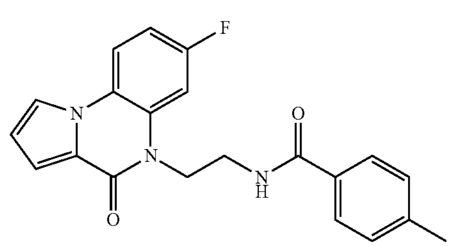 [SMILES: Cc1ccc(C(=O)NCCn2c(=O)c3cccn3c3ccc(F)cc32)cc1] |

TABLE 1A-continued
| Ex. | Structure |
|---|---|
| 12-2 | 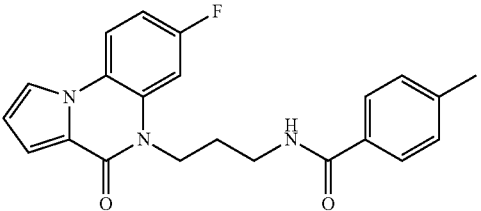 [SMILES: Cc1ccc(C(=O)NCCCn2c(=O)c3cccn3c3ccc(F)cc32)cc1] |
| 13-1 | 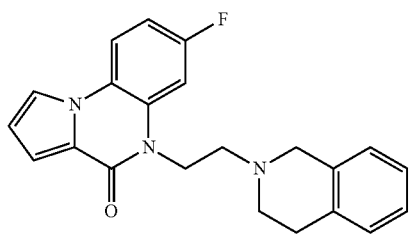 [SMILES: O=c1c2cccn2c2ccc(F)cc2n1CCN1CCc2ccccc2C1] |
| 13-2 | 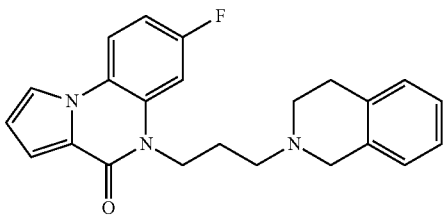 [SMILES: O=c1c2cccn2c2ccc(F)cc2n1CCCN1CCc2ccccc2C1] |
| 14-1 | 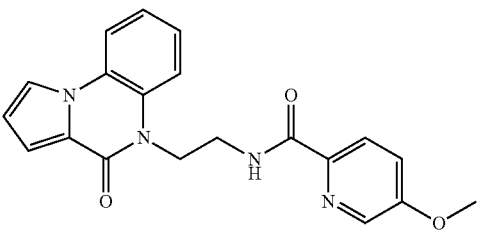 [SMILES: COc1ccc(C(=O)NCCn2c(=O)c3cccn3c3ccccc32)nc1] |
| 14-2 | 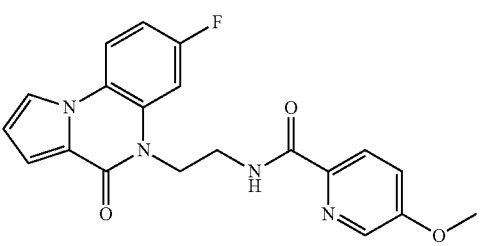 [SMILES: COc1ccc(C(=O)NCCn2c(=O)c3cccn3c3ccc(F)cc32)nc1] |
| 15-1 | 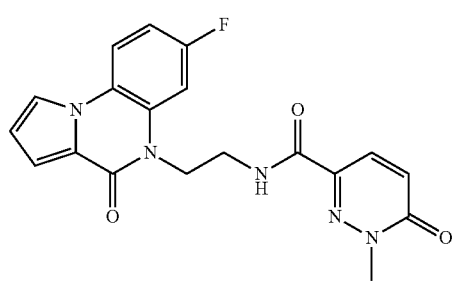 [SMILES: Cn1nc(C(=O)NCCn2c(=O)c3cccn3c3ccc(F)cc32)ccc1=O] |

TABLE 1A-continued

| Ex. | Structure |
|---|---|
| 16-1 | 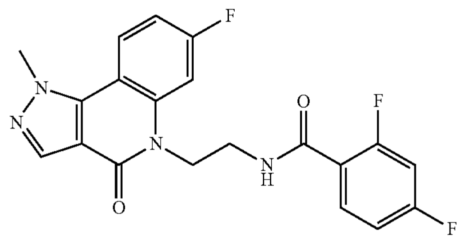 [SMILES: Cn1ncc2c(=O)n(CCNC(=O)c3ccc(F)cc3F)c3cc(F)ccc3c21] |
| 16-2 | 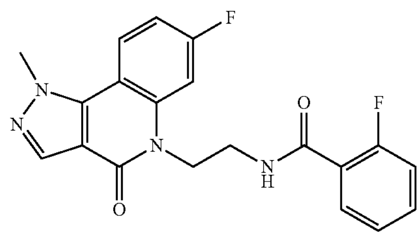 [SMILES: Cn1ncc2c(=O)n(CCNC(=O)c3ccccc3F)c3cc(F)ccc3c21] |
| 17-1 | 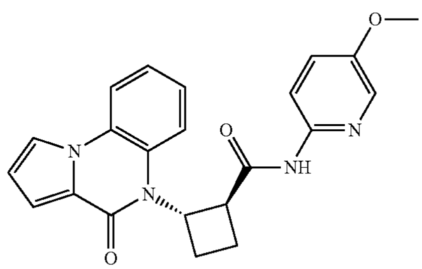 [SMILES: COc1ccc(NC(=O)[C@H]2CC[C@@H]2n2c(=O)c3cccn3c3ccccc32)nc1] |
| 18-1 | 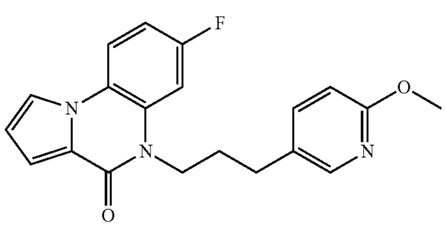 [SMILES: COc1ccc(CCCn2c(=O)c3cccn3c3ccc(F)cc32)cn1] |
| 19-1 | 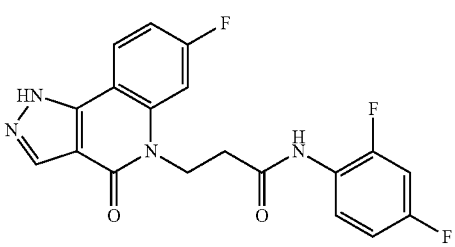 [SMILES: O=C(CCn1c(=O)c2cn[nH]c2c2ccc(F)cc21)Nc1ccc(F)cc1F] |
| 19-2 | 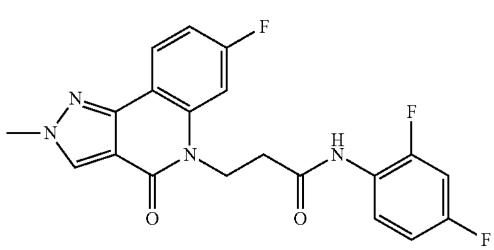 [SMILES: Cn1cc2c(=O)n(CCC(=O)Nc3ccc(F)cc3F)c3cc(F)ccc3c2n1] |

TABLE 1A-continued

| Ex. | Structure |
|---|---|
| 19-3 | 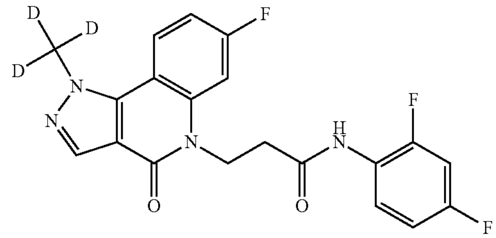 [SMILES: [2H]C([2H])([2H])n1ncc2c(=O)n(CCC(=O)Nc3ccc(F)cc3F)c3cc(F)ccc3c21] |
| 19-4 | 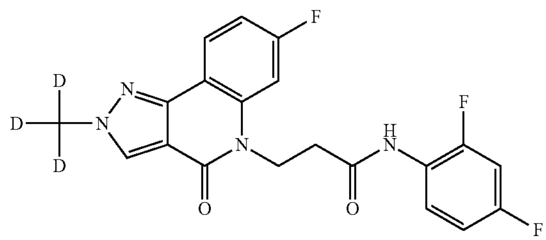 [SMILES: [2H]C([2H])([2H])n1cc2c(=O)n(CCC(=O)Nc3ccc(F)cc3F)c3cc(F)ccc3c2n1] |
| 20-1 | 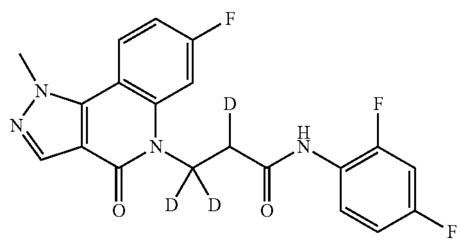 [SMILES: [2H]C(C(=O)Nc1ccc(F)cc1F)C([2H])([2H])n1c(=O)c2cnn(C)c2c2ccc(F)cc21] |
| 21-1 | 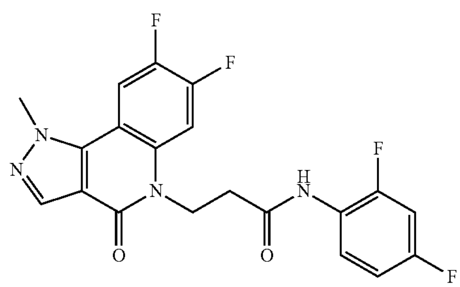 [SMILES: Cn1ncc2c(=O)n(CCC(=O)Nc3ccc(F)cc3F)c3cc(F)c(F)cc3c21] |
| 21-2 | 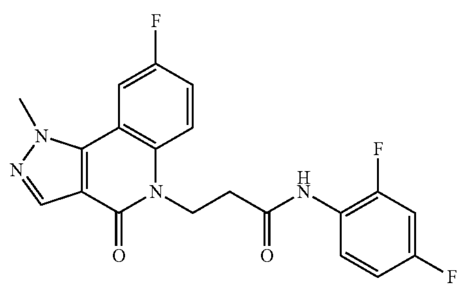 [SMILES: Cn1ncc2c(=O)n(CCC(=O)Nc3ccc(F)cc3F)c3ccc(F)cc3c21] |
| 21-3 | 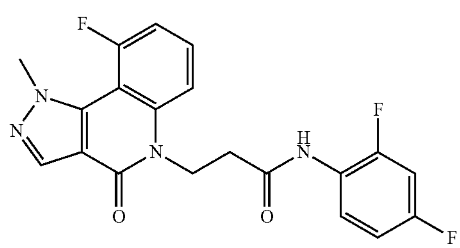 [SMILES: Cn1ncc2c(=O)n(CCC(=O)Nc3ccc(F)cc3F)c3cccc(F)c3c21] |

TABLE 1A-continued

| Ex. | Structure |
|---|---|
| 22-1 | 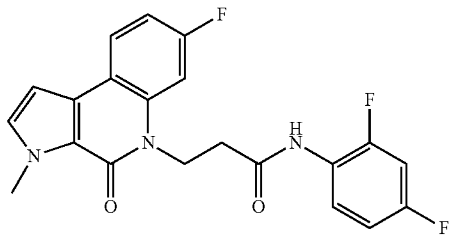 [SMILES: Cn1ccc2c3ccc(F)cc3n(CCC(=O)Nc3ccc(F)cc3F)c(=O)c21] |
| 23-1 | 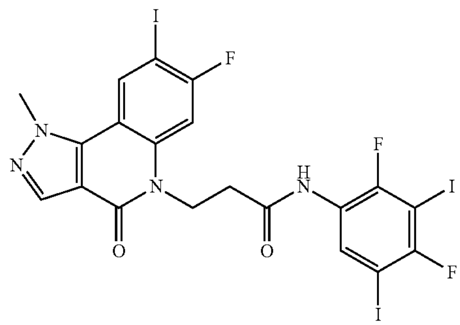 [SMILES: Cn1ncc2c(=O)n(CCC(=O)Nc3cc(I)c(F)c(I)c3F)c3cc(F)c(I)cc3c21] |
| 24-1 | 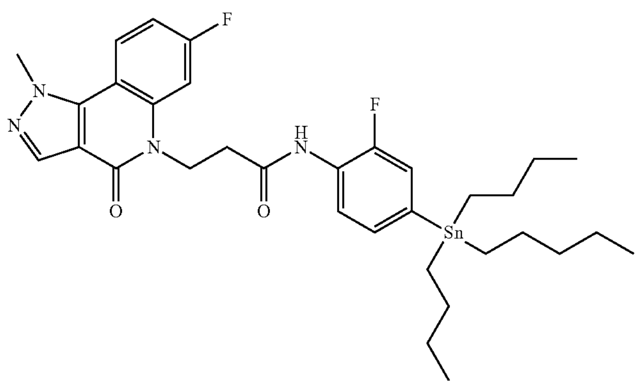 [SMILES: CCCC[CH2][Sn]([CH2]CCC)([CH2]CCC)[c]1ccc(NC(=O)CCn2c(=O)c3cnn(C)c3c3ccc(F)cc32)c(F)c1] |
| 25-1 | 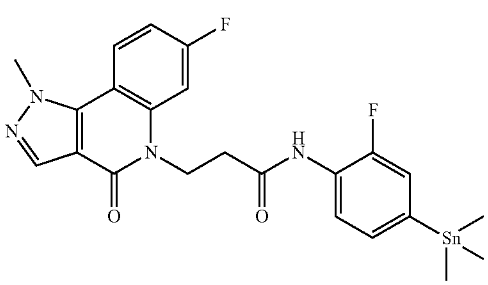 [SMILES: Cn1ncc2c(=O)n(CCC(=O)Nc3cc[c]([Sn]([CH3])([CH3])[CH3])cc3F)c3cc(F)ccc3c21] |
| 26-1 | 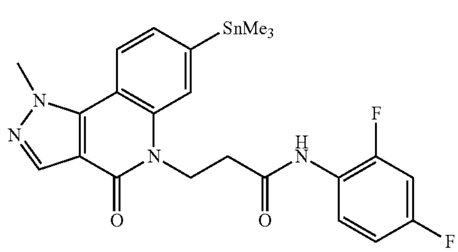 |

TABLE 1A-continued
| Ex. | Structure |
|---|---|
| 27-1 | 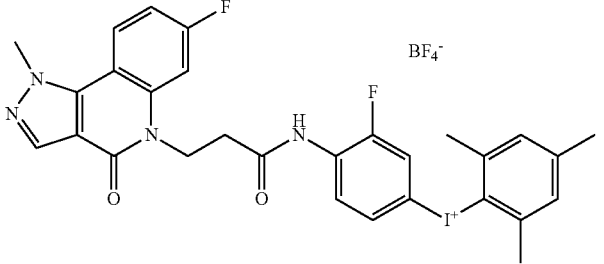 [SMILES: Cc1cc(C)c([I+]c2ccc(NC(=O)CCn3c(=O)c4cnn(C)c4c4ccc(F)cc43)c(F)c2)c(C)c1 ; "BF4-"] |
| 28-1 | 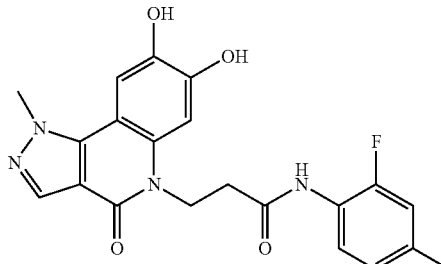 |
| 100-1 | 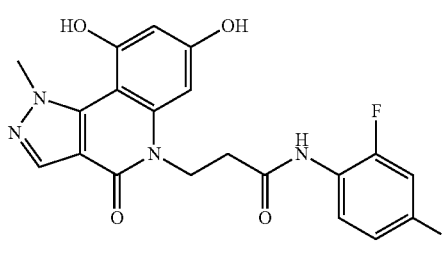 |
| 100-2 | 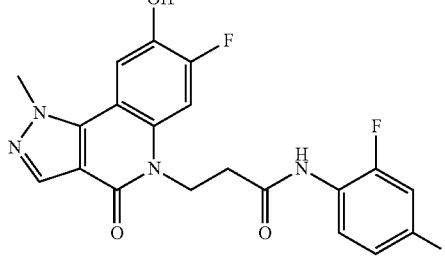 |
| 100-3 | 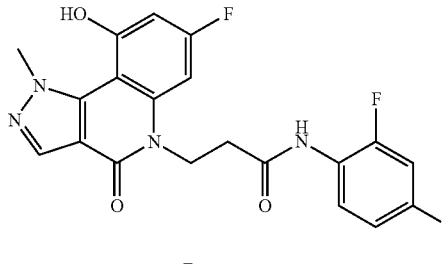 |
| 100-4 | 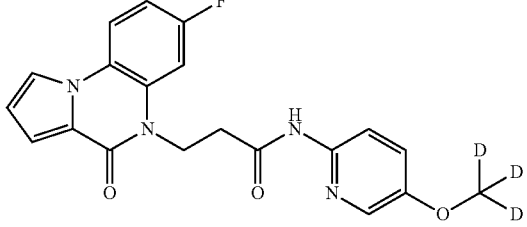 |

Compounds, or an isotopically enriched analog, pharmaceutically acceptable salt, prodrug, tautomer, stereoisomer, or a mixture of stereoisomers thereof, of Table 1B are as follows:

TABLE 1B

| Ex. | Structure |
|---|---|
| 29-1 | 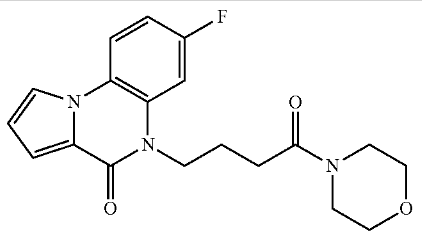 [SMILES: O=C(CCCn1c(=O)c2cccn2c2ccc(F)cc21)N1CCOCC1] |
| 29-2 | 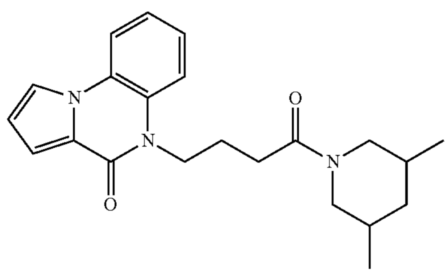 [SMILES: CC1CC(C)CN(C(=O)CCCn2c(=O)c3cccn3c3ccccc32)C1] |
| 29-3 | 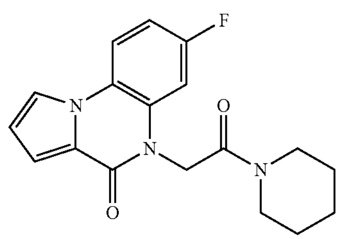 [SMILES: O=C(Cn1c(=O)c2cccn2c2ccc(F)cc21)N1CCCCC1] |
| 29-4 | 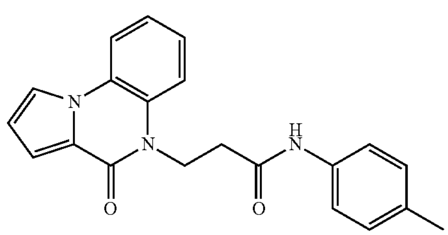 [SMILES: Cc1ccc(NC(=O)CCn2c(=O)c3cccn3c3ccccc32)cc1] |
| 29-5 | 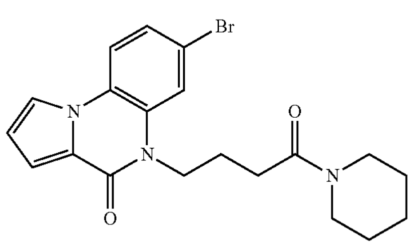 [SMILES: O=C(CCCn1c(=O)c2cccn2c2ccc(Br)cc21)N1CCCCC1] |

Diagnostic Methods and Uses

In some embodiments, a method of generating diagnostic images in an individual is provided, comprising administering an effective amount of a compound or an imaging agent described herein to an individual, and generating an image of a body part or body area of the individual. Generating an image of a body part or body area of the individual may comprise generating an image to detect the presence or absence of a protein susceptible to aggregation in the image. Thus, the compounds disclosed herein are useful for detecting a disease or condition mediated, at least in part, by a protein susceptible to protein aggregation. In some embodiments, the presence or absence of a protein aggregate corresponds to the presence or absence of a neurodegenerative disease. In some embodiments, the neurodegenerative disease is selected from Alzheimer's disease, amyotrophic lateral sclerosis, Huntington's disease, Parkinson's disease, Prion disease and spinocerebellar ataxias.

Some embodiments provide for a method generating diagnostic images in an individual comprising administering an effective amount of a compound of Formula I', or an isotopically enriched analog, pharmaceutically acceptable salt, prodrug, tautomer, stereoisomer, or a mixture of stereoisomers thereof.

In some embodiments, a method of generating diagnostic images in an individual is provided, comprising administering an effective amount of a compound of Formula I:

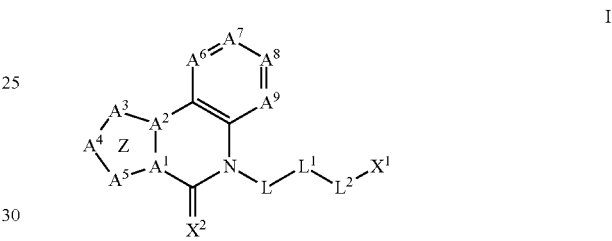

I or an isotopically enriched analog, pharmaceutically acceptable salt, prodrug, tautomer, stereoisomer, or a mixture of stereoisomers thereof, wherein the compound is optionally labeled with one or more radioactive isotopes;

$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$, $NR^3$, or N;
wherein ring Z formed by $-A^1-A^2-A^3-A^4-A^5-$ is a 5-membered heteroaryl having up to three nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;
each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^2$ is O, S, or $NR^5$; $R^5$ is hydrogen, $C_{1-6}$alkyl, $C_{1-6}$haloalkyl, or $C_{1-6}$alkoxy;
L is $-(C(R^6)_2)_m-$, wherein m is 1, 2, 3, or 4;
each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;

$L^1$ is C(O), C(O)NR$^a$, NR$^a$C(O), or O, or $L^1$ is absent;

$R^a$ is hydrogen, $C_{1-6}$alkyl, or $C_{1-6}$haloalkyl;

$L^2$ is $C_{1-2}$alkylene optionally substituted by 1 to 4 $R^7$, or $L^2$ is absent;

each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy.

Some embodiments provide for a method generating diagnostic images in an individual comprising administering an effective amount of a compound selected from Table 1A or Table 1B, or an isotopically enriched analog, pharmaceutically acceptable salt, prodrug, tautomer, stereoisomer, or a mixture of stereoisomers thereof.

Provided are methods of generating diagnostic images using positron emission tomography (PET). PET imaging may be conducted as known to those of skill in the art, or as follows. PET imaging may involve the administration of a positron-emitting radionuclide tracer, for example, a compound or imaging agent described herein, to an individual. The tracer is then given sufficient time to associate with the protein of interest, at which time the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons. The photons are detected by a scintillator in the scanning device. Photons that do not arrive in pairs are ignored.

Also provided are methods of generating diagnostic images comprising PET with concurrent computed tomography imaging (PET/CT), with concurrent magnetic resonance imaging (PET/MRI), or single-photon emission computed tomography (SPECT) imaging. In general, computed tomography uses X-rays or gamma rays to detect the structure of the brain, while magnetic resonance imaging uses magnetic fields and radio waves.

Thus, a compound or an imaging agent described herein may be administered by methods known in the art including those described herein. The compound or imaging agent may enter circulation and bind to the protein susceptible to aggregation, or to aggregates thereof. When the compound or imaging agent is labeled with a radioactive isotope, the emitted particles may be detected.

In some embodiments the compound or imaging agent is administered into the individual's vascular system. The compound or imaging agent may pass through the blood-brain barrier. Thus, generating an image may comprise generating an image of at least part of the individual's brain, for example, the part to which the compound has distributed.

Also provided are methods of generating diagnostic images in a biological sample comprising contacting the biological sample with an effective amount of a compound or an imaging agent described herein and generating an image associated with the biological sample. In some embodiments, the contacting and the generating may be conducted in vitro. In some embodiments the contacting is in vivo and the generating is in vitro.

Also provided are methods for detecting the presence or absence of a pathologic process associated with a protein susceptible to protein aggregation, for example huntingtin protein (HTT protein), in an individual comprising: administering an effective amount of a compound or an imaging agent described herein; generating an image to detect the presence or absence of huntingtin protein (HTT protein) in the image; and detecting the presence or absence of a pathologic process, e.g., a neurodegenerative disease. In some embodiments, the HTT protein is present as monomers, oligomers, or aggregates, or a combination thereof. In some embodiments, the protein susceptible to aggregation is huntingtin protein (HTT protein). The HTT protein may be mutant. In some embodiments, the HTT protein is found in the brain, for example, in basal ganglia.

In some embodiments, the body part or body area is selected from head, spinal cord, limb, thorax, and/or abdomen. In some embodiments, the body part or body area is brain. In some embodiments, the HTT protein is found in basal ganglia. In some embodiments, the protein susceptible to aggregation, e.g., HTT protein, is present in the brain, liver, heart, and/or muscle of the individual. In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, generating an image comprises PET imaging. In some embodiments, the protein susceptible to aggregation, e.g., HTT protein, is present in the basal ganglia, cortex, hippocampus, and/or brain stem of the brain of the individual. In some embodiments, the protein susceptible to aggregation, e.g., HTT protein, is present as monomers, oligomers, or aggregates, or a combination thereof.

In some embodiments, the individual has, or is discovered to have, Huntington's disease.

Also provided are methods for detecting the presence or absence of a pathologic process associated with β-amyloid protein in an individual comprising: administering an effective amount of a compound or an imaging agent described herein; generating an image of a body part or body area of the individual; and detecting the presence or absence of the pathologic process. In some embodiments, the individual has, or is discovered to have, Alzheimer's Disease (AD).

Also provided are diagnostic methods of using a compound or an imaging agent described herein to monitor disease progression in a patient by quantifying the change in levels of the protein susceptible to aggregation in the patient.

In some embodiments, provided is a compound having suitable protein aggregate, e.g., HTT protein aggregate or β-amyloid protein aggregate, binding kinetics to function as imaging agents. Thus, a compound described herein may be characterized by one or more of: 1) a high affinity for such protein aggregates; 2) a low affinity for nearby structures; and/or 3) slow dissociation kinetics from such protein aggregates. Dissociation kinetics may be expressed as the dissociation rate constant $k_{diss}$ as defined in the equation below (wherein A and B refer to the protein aggregate and the imaging agent, and $k_{assn}$ is the association rate constant):

$$d[AB]/dt = k_{assn}[A][B] - k_{diss}[AB]$$

In some embodiments, the effective amount of the compound or imaging agent described herein comprises from about 0.1 to about 20 mCi. In some embodiments, the effective amount of the compound or imaging agent described herein comprises about 0.1, about 0.3, about 0.5, about 0.7, about 1, about 3, about 5, about 7, about 10, about 15, or about 20 mCi, or a range of values therebetween. In some embodiments, the effective amount of the compound or imaging agent described herein comprises about 10 mCi.

Suitable radionuclides that may be incorporated in a compound described herein include, but are not limited to, $^3$H (also written as T), $^{11}$C, $^{18}$F, $^{35}$S, $^{123}$I, $^{125}$I, $^{75}$Br, $^{76}$Br, $^{77}$Br, $^{82}$Br, $^{131}$I, $^{15}$O, $^{13}$N, and $^{211}$At. The radionuclide that is incorporated in the compound will depend on the specific imaging application. In some embodiments including PET imaging, compounds that incorporate a radionuclide selected from $^{11}$C, $^{18}$F, $^{123}$I, $^{131}$I, $^{75}$Br, $^{76}$Br or $^{77}$Br may be used. In certain applications incorporation of a chelating radionuclide such as $^{99m}$Tc may also be useful. In some embodiments, $^{18}$F may be preferable over $^{11}$C because with the longer half-life of $^{18}$F, imaging can be carried out long enough to allow a stronger signal to develop. In some embodiments, a compound or imaging agent described herein can be labeled with a positron emitting radionuclide or a gamma emitting radionuclide. Some examples of positron-emitting radionuclides include $^{15}$O, $^{13}$N, $^{11}$C, $^{18}$F, $^{76}$Br, and $^{124}$I, which have half-lives of about 2, 10, 20, 110 minutes, 16 hours, and 4.2 days respectively.

In some embodiments, a compound or an imaging agent described herein may be labelled with a positron emitter selected from $^{11}$C and $^{18}$F. Methods for the introduction of $^{11}$C may include, but are not limited to, alkylation with [$^{11}$C]iodomethane or [$^{11}$C]methyl triflate. Carbon-11 has a half-life of approximately 20 minutes, thus $^{11}$C generally needs to be generated in an on-site cyclotron, and may be produced as [$^{11}$C]carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F include but are not limited to nucleophilic and electrophilic methods. Nucleophilic methods include displacement of a halide, tosylate, or other leaving group with labeled cesium fluoride, potassium fluoride, tetrabutylamonium fluoride tetramethylamonium fluoride, or potassium fluoride kryptofix-222. Electrophilic reagents that may be suitable for introducing [$^{18}$F] isotopes include labeled diethylaminosulfur trifluoride (DAST), bis(2-methoxyethyl)aminosulfur trifluoride (Deoxofluor), N-fluorobenzenesulfonimide (NFSI), N-fluoropyridinium salts, 1-chloromethyl-4-fluoro-1,4-diazoniabicyclo[2.2.2]octane bis(tetrafluoroborate) (Selectfluor), N-fluoropyridinium triflate, xenon fluoride, 2-pyridinesulfonyl fluoride (PyFluor), 3-pyridinesulfonyl fluoride, 4-pyridinesulfonyl fluoride, 4-chloro-2-pyridinesulfonyl fluoride, ethenesulfonyl fluoride, fluoro-benziodoxole, p-fluorophenylaminosulfur trifluoride, p-nitrophenylaminosulfur trifluoride, or pentafluorophenylaminosulfur trifluoride. General methods for the introduction of positron emitters are described in the literature (e.g., see Miller et al., *Angewandte Chemie International Edition*, 47 (2008), 8998-9033; Jacobson, O. et al., Bioconjugate Chem., 26 (2015), 1-18; Deng, X. et al., *Angewandte Chemie International Edition*, 58(9), (2019), 2580-2605).

Fluorine-18 has a half life of approximately 110 minutes, thus synthesis of [$^{18}$F] radiopharmaceuticals need not necessarily have to occur at the site of the cyclotron nor proximal to the PET imaging study center. Fluorine-18 is also thought to exhibit favorable nuclear and physical characteristics, including high positron decay ratio (97%), relatively short half life (109.7 min), and low positron energy (up to 0.635 MeV). The positron energy may correspond to a short diffusion range (<2.4 mm) in vivo that may provide superior resolution limits of a PET image.

As will be recognized, the steps of the methods described herein need not be performed any particular number of times or in any particular sequence. Additional objects, advantages and novel features of the disclosure will become apparent to those skilled in the art upon examination of the examples provided below, which are intended to be illustrative and are not limiting.

Indications and Treatment Methods

A compound or an imaging agent described herein may be useful for treating a disease or condition mediated, at least in part, by a protein susceptible to aggregation. In some embodiments, a compound or an imaging agent described herein is useful for treating a disease or condition mediated, at least in part, by HTT protein. In some embodiments, treatment of a disease or condition mediated, at least in part, by a protein susceptible to aggregation may comprise administration of a compound or an imaging agent described herein. Treatment may include coadministration of a compound or an imaging agent described herein and one or more other active agents and/or therapies. Thus, in some embodiments, provided is a method of treating or preventing a disease or condition mediated, at least in part, by a protein susceptible to aggregation in a patient in need thereof, comprising administering to the patient a therapeutically effective amount of a compound or an imaging agent described herein.

Some embodiments provide for a method for treating a disease or condition mediated, at least in part, by a protein susceptible to aggregation in a patient in need thereof, comprising administering to the patient a therapeutically effective amount of a compound of Formula I', or an isotopically enriched analog, pharmaceutically acceptable salt, prodrug, tautomer, stereoisomer, or a mixture of stereoisomers thereof.

In some embodiments, provided is a method for treating a disease or condition mediated, at least in part, by a protein susceptible to aggregation in a patient in need thereof, comprising administering to the patient a therapeutically effective amount of a compound of Formula I, or an isotopically enriched analog, pharmaceutically acceptable salt, prodrug, tautomer, stereoisomer, or a mixture of stereoisomers thereof, wherein the compound is optionally labeled with one or more radioactive isotopes;

$A^1$ is C;
$A^2$ is C or N;
$A^3$ is $CR^{21}$, $NR^3$, or N;
$A^4$ is $CR^{22}$, $NR^3$, or N;
$A^5$ is $CR^{23}$, $NR^3$, or N;
wherein ring Z formed by $-A^1-A^2-A^3-A^4-A^5-$ is a 5-membered heteroaryl having up to three nitrogen atoms;
each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;
each $R^3$ is independently hydrogen, $C_{1-4}$alkyl, $C_{1-4}$haloalkyl, or $C_{3-6}$cycloalkyl;
$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;
each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;
$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;
each $R^4$ is independently halo, cyano, hydroxy, amino, alkylamino, dialkylamino, $C_{1-4}$ alkyl, $C_{1-4}$haloalkyl, $C_{1-4}$alkoxy, or $C_{1-4}$haloalkoxy;

$X^2$ is O, S, or $NR^5$; $R^5$ is hydrogen, $C_{1-6}$alkyl, $C_{1-6}$haloalkyl, or $C_{1-6}$alkoxy;

L is —$(C(R^6)_2)_m$—, wherein m is 1, 2, 3, or 4;

each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;

$L^1$ is C(O), C(O)$NR^a$, $NR^a$C(O), or O, or $L^1$ is absent;

$R^a$ is hydrogen, $C_{1-6}$alkyl, or $C_{1-6}$haloalkyl;

$L^2$ is $C_{1-2}$alkylene optionally substituted by 1 to 4 $R^7$, or $L^2$ is absent;

each $R^7$ is independently halo, cyano, hydroxy, amino, alkylamino, dialkylamino, $C_{1-4}$ alkyl, $C_{1-4}$haloalkyl, $C_{1-4}$alkoxy, or $C_{1-4}$haloalkoxy.

Some embodiments provide for a method for treating a disease or condition mediated, at least in part, by a protein susceptible to aggregation in a patient in need thereof, comprising administering to the patient a therapeutically effective amount of a compound selected from Table 1A or Table 1B, or an isotopically enriched analog, pharmaceutically acceptable salt, prodrug, tautomer, stereoisomer, or a mixture of stereoisomers thereof.

Exemplary diseases and conditions are as follows.

Huntington's Disease (HD)

Huntington's disease (HD) is an inherited progressive neurodegenerative disorder, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DRPLA), spinal and bulbar muscular atrophy (SBMA) and the spinocerebellar ataxias (SCAs). In HD, the selective neurodegeneration of the γ-aminobutyric acid-releasing spiny-projection neurons of the striatum had been observed, although neuron loss in many other brain regions has also been reported. Symptoms of HD include loss of motor control, psychiatric symptoms, memory and/or cognitive impairment.

HD protein huntingtin (HTT protein) is a 348-kDa multidomain protein that contains a polymorphic glutamine/proline-rich domain at its amino-terminus. The number of CAG repeats in the $IT_{15}$ gene that encodes the varies from 6 to 35 in healthy individuals; repeats of 36 or more define an HD allele. The length of the CAG expansion has been inversely correlated with age of disease onset, with cases of juvenile onset characterized by expansions of more than 60 repeats. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

The administration of a compound described herein may result in a decrease, for example, at least a 10% decrease (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance or Tabes dorsalis.

In some embodiments, the disease or condition is selected from Huntington's disease (HD), dentatorubropalliduluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art. The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease and spinocerebellar ataxias. In some embodiments, the neurodegnerative disease is classified as a trinucleotide repeat disorder. In some embodiments, the trinucleotide repeat disorder is classified as belonging to Category I, Category II, or Category III.

In some embodiments, the pathologic process is associated with, or caused by, a disease or condition selected from Huntington's disease (HD), dentatorubropallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma. In some embodiments, the pathologic process is a neurodegenerative disease selected from Alzheimer's disease, amyotrophic lateral sclerosis, Huntington's disease, Parkinson's disease, Prion disease and spinocerebellar ataxias. In some embodiments, the neurodegnerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Imaging Agents and Pharmaceutical Compositions

An imaging agent will generally comprise a compound described herein labeled with a positron emitting radionuclide. Imaging agents labeled with positron emitting radionuclides are generally administered via intravenous injection shortly after (for example, within one hour of synthesis) due to the short half-life of the radionuclides. The amount of imaging agent required will normally be determined by the prescribing physician. The dose may vary according to various factors, including but not limited to the associative kinetics of the compound, the quantity of emission from the radionuclide used, the half life of the radionuclide, the body part, body area, and/or tissue to be imaged, and the characteristics of the individual. Those of ordinary skill in the art will appreciate that an effective amount will generally be the amount of labeled compound sufficient to produce emissions in the range of from about 0.1 to about 20 mCi, or about 1 to about 5 mCi. The mass of labeled compound in an effective amount of imaging agent may be about 0.1 to about 500 mg.

Generally, a compound or an imaging agent described herein may be administered to a patient in need thereof via any suitable route. Routes of administration may include, for example, parenteral administration, including subcutaneous, intramuscular, intravenous, by means of, for example a drip patch. Further suitable routes of administration include, but are not limited to, oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

With regard to PET imaging, administration of a compound or an imaging agent described herein to the individual may be intravenous. The pharmaceutical composition may be in the form of a sterile injectable aqueous or oleaginous suspension. This suspension may be formulated according to the known art using those suitable dispersing or wetting agents and suspending agents that have been mentioned herein. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound or imaging agent described herein may be administered parenterally in a sterile medium. Parenteral administration includes subcutaneous injections, intravenous, intramuscular, intrathecal injection or infusion techniques. The compound or imaging agent described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an α-cyclodextrin, a β-cyclodextrin, or a γ-cyclodextrin.

A compound or an imaging agent described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

In some embodiments, the compound or imaging agent described herein is administered as a pharmaceutical composition. Accordingly, provided are pharmaceutical compositions comprising at least one compound or imaging agent described herein, together with at least one pharmaceutically acceptable vehicle chosen from carriers, adjuvants, and excipients. A compound or imaging agent of the present disclosure can be formulated into a pharmaceutical composition using techniques known to those of skill in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or imaging agent may be sufficient to provide a practical quantity of material for administration per dose of the compound or imaging agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or imaging agent described herein.

Effective concentrations of at least one compound or imaging agent described herein are mixed with a suitable pharmaceutically acceptable vehicle. In instances in which the compound or imaging agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous buffer, for example, sodium bicarbonate.

Upon mixing or addition of a compound or imaging agent described herein, the resulting mixture may be a solution, suspension, emulsion or the like. The form of the resulting mixture depends upon a number of factors, including the intended mode of administration and the solubility of the compound or imaging agent in the chosen vehicle. The effective concentration sufficient for imaging or treatment may be empirically determined according to known methods in the art.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of the compound or imaging agent described herein. In some embodiments, oral pharmaceutical compositions contain at least 5% (weight %) of the compound or imaging agent. Some embodiments contain from 25% to 50% or from 5% to 75% of the compound or imaging agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound or imaging agent described herein can be incorporated into oral liquid preparations such as aqueous or oily suspensions, solutions, emulsions, syrups, or elixirs, for example. Furthermore, pharmaceutical compositions containing the compound or imaging agent described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions containing the compound or imaging agent in admixture with excipients suitable for the manufacture of aqueous suspensions are provided. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the compound or imaging agent in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of an oil-in-water emulsion. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

The pharmaceutical composition may also be coated by conventional methods, typically with pH or time-dependent coatings, such that the compound or imaging agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The compound or imaging agent described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound or imaging agent described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Topical pharmaceutical compositions comprising at least one compound, or an isotopically labeled analog, pharmaceutically acceptable salt, solvate, prodrug, stereoisomer, or mixture of stereoisomers thereof, described herein or imaging agent described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound or imaging agent described herein may also be formulated for transdermal administration as a transdermal patch.

The compound or imaging agent described herein may also be administered in a liposome delivery system. Liposomes may be classified as small unilamellar vesicles, large unilamellar vesicles, and multilamellar vesicles. Liposomes can be formed from a variety of amphiphathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound or imaging agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound or imaging agent described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound or imaging agent described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

The dose of the compound or imaging agent described herein depends upon a variety of factors including the particular pathologic process to be treated or detected, the physiology of the individual, the severity of the symptoms, the route of administration, the frequency of the dosage interval, the particular compound utilized, the efficacy, toxicology profile, pharmacokinetic profile of the compound, and the presence of any deleterious side-effects, among other considerations. The dose under a given set of circumstances generally will be determined by a practitioner on a case-by-case basis based on the above and other factors.

The compound or imaging agent described herein is typically administered at a dosage level and in a manner determined by a practitioner such as a physician. For example, the compound or imaging agent can be administered, in single or multiple doses, at a dosage level of generally 0.001-100 mg/kg, for example, 0.01-100 mg/kg, such as 0.1-70 mg/kg, for example, 0.5-10 mg/kg. The dose can be, for example, for administration once a day or twice a day. Unit dosage forms can contain generally 0.01-1000 mg of the compound or imaging agent described herein, for example, 0.1-50 mg. For intravenous administration, the compound or imaging agent can be administered, in single or multiple dosages, at a dosage level of, for example, 0.001-50 mg/kg, such as 0.001-10 mg/kg, for example, 0.01-1 mg/kg. Unit dosage forms can contain, for example, 0.1-10 mg of the compound or imaging agent.

Kits and Packaging

Also provided herein are kits that include a compound or imaging agent described herein and suitable packaging. In certain embodiments, a kit further includes instructions for use. In some embodiments, a kit includes a compound or an imaging agent described herein and a label and/or instructions for use of the compounds in the treatment of the indications, including the diseases or conditions, described herein.

Also provided herein are articles of manufacture that include a compound or an imaging agent described herein in a suitable container. The container may be a vial, jar, ampoule, preloaded syringe and intravenous bag.

Also provided are packaged pharmaceutical compositions. Such packaged compositions include a pharmaceutical composition comprising a compound or imaging agent described herein, and instructions for using the composition to treat a subject (typically a human patient). In some embodiments, the instructions are for using the pharmaceutical composition to detect a disease or condition described herein. The packaged pharmaceutical composition can include prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound or imaging agent can be administered alone, as mixtures, or in combination with other active agents.

Also provided is use of a compound or imaging agent described herein for the manufacture of a medicament for use in diagnosis, prevention, or treatment of a disease or condition described herein. For example, the disease or condition may be Huntington's disease.

Also provided is use of a compound described herein for the manufacture of an imaging agent for use in diagnosis, prevention, or treatment of a disease or condition described herein. For example, the disease or condition may be Huntington's disease.

Combination Therapy

The methods described herein include methods for detecting, treating or preventing a disease or condition described herein, comprising administering to a subject, simultaneously or sequentially, a compound or imaging agent described herein and one or more additional active agents. For example, the disease or condition may be Huntington's disease. In methods using simultaneous administration, the agents can be present in a combined composition or can be administered separately. When used in combination with one or more additional active agent or agents, a compound or imaging agent described herein may be administered prior to, concurrently with, or following administration of the additional active agent or agents. The administration can be by the same route or by different routes.

Also provided is a pharmaceutical composition comprising a compound or imaging agent described herein and one or more additional active agents used in the treatment of Huntington's disease, such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound or imaging agent described herein, and another composition comprising one or more additional active agents used in the treatment of Huntington's disease, such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound or imaging agent described herein and one or more additional agents. In some embodiments, the active agent is Reminyl® (galantamine), Cognex® (tacrine), Aricept® (donepezil), Exelon® (rivastigmine), Akatinol® (memantine), Neotropin™ (somatropin), Eldepryl® (selegiline), Estrogen, or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound or imaging agent described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound or imaging agent described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound or imaging agent described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Generally, the term inert, as used herein with respect to a solvent, refers to a material that does not undergo reaction to form the target compound of interest though carbon-carbon bond forming reactions.

Scheme 1 provides exemplary synthetic routes for the synthesis of compounds provided herein (e.g., compounds of Formula I' or Formula I). The compounds of Formula I' or Formula I, or other formulas or compounds disclosed herein, are typically prepared by first preparing the core from Formula Va and Vb and then attaching the desired substituents using suitable conditions (e.g., nucleophilic addition, amide bond formation, or cross coupling).

In some embodiments, synthesis of a compound described herein proceeds according to Scheme 1.

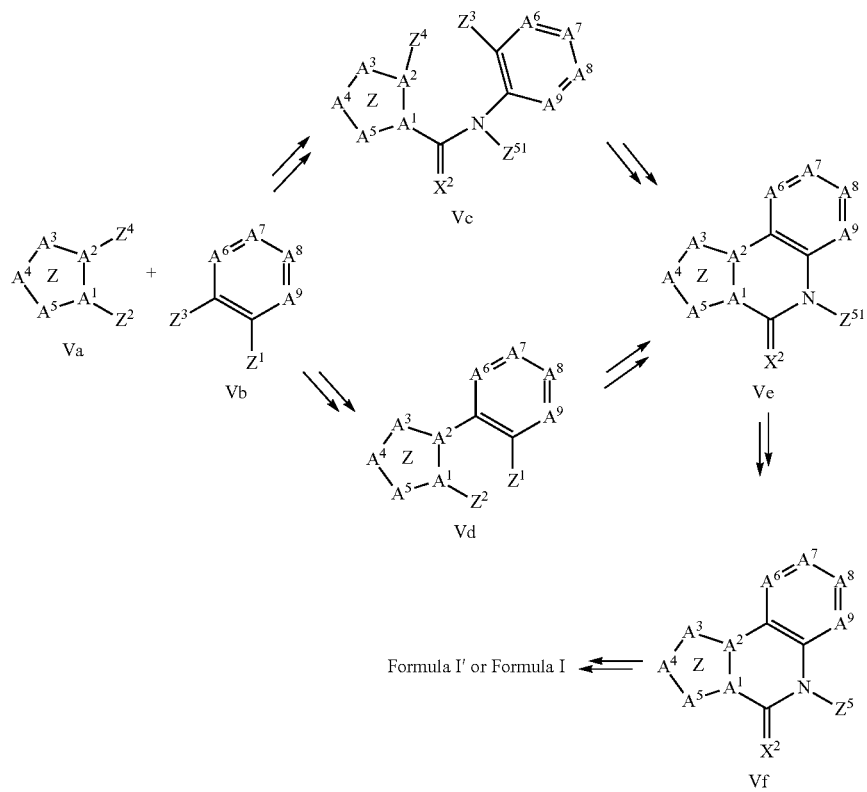

Scheme 1

Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the below schemes, the addition of any substituent may result in the production of a number of isomeric products (including, but not limited to, enantiomers or one or more diastereomers) any or all of which may be isolated and purified using conventional techniques.

Incorporation of a label into a compound or imaging agent described herein may be conducted by reacting an appropriate starting material(s) with a reagent including a radioactive isotope. Methods typically follow the same principles as standard organic chemical reactions, and may be carried out by any method known to those of skill in the art, including those provided in the present disclosure.

In Scheme 1, $A^1$, $A^2$, $A^3$, $A^4$, $A^5$, $A^6$, $A^7$, $A^8$, $A^9$, ring Z, and $X^2$ are as defined herein; $Z^1$, $Z^2$, $Z^3$, $Z^4$, $Z^5$, and $Z^{51}$ are as defined below.

In Scheme 1, a compound Vf is converted to the compound of Formula I' or Formula I by one or more steps.

Compound Vf may be synthesized from Compound Ve by one or more steps. In Compound Vf, $Z^5$ is -L-$L^1$-$L^2$-$X^1$ or a derivative, for example, a protected derivative or isotopically enriched analog thereof, or $Z^5$ is L-N(PG)$_2$, L-NH(PG), L-NH$_2$ or L-C(O)Z$^6$, where PG is a suitable amine protecting group (e.g., benzyl, tert-butoxycarbonyl or benzyloxycarbonyl, or two PG form a phthalimide). For example, in $Z^5$, a hydroxyl group on $X^1$ may be protected by a typical hydroxyl protecting group (e.g., benzyl). In Compound Ve, $Z^{51}$ is $Z^5$ or H. Where $Z^5$ is L-NH$_2$ or L-C(O)Z$^6$, $L^1$-$L^2$-$X^1$ may be appended by an amide bond formation reaction (e.g., a coupling agent such as HATU, CDI, or T3P, and a base such as triethylamine, diisopropylethylamine, or piperidine, or other conditions known in the art). Where $Z^5$ is L-N(PG)$_2$ or L-NH(PG), amine deprotection may be carried out under standard conditions. Where $Z^{51}$ is H, -L-L$^1$-L$^2$-X$^1$ may be appended by, e.g. a nucleophilic displacement reaction (e.g., with a base such as K$_2$CO$_3$, NaH or NaOH, and a suitable electrophile $Z^5$-$Z^6$ where $Z^6$ is an electrophile, e.g., an alkyl halide such as chloride or bromide, or a pseudohalide such as p-toluenesulfonate, or alternatively where $Z^5$—$Z^6$ comprises a conjugate addition substrate such as an α,β-unsaturated carbonyl, e.g., an alkyl prop-2-enoate such as ethyl prop-2-enoate). Where $Z^5$-$Z^6$ comprises an ester, hydrolysis may be carried out under conditions described herein or as known in the art (e.g., LiOH, NaOH, or KOH in a solvent comprising water such as methanol or THF).

Compound Ve may be synthesized from Compound Vc or Compound Vd by one or more steps as described herein or as known in the art. Compound Vc or Compound Vd, as appropriate, may be synthesized from Compound Va and Compound Vb.

$Z^3$ and $Z^4$ are suitable groups for formation of an aryl-aryl bond. For example, $Z^3$ may be a leaving group, e.g., fluoro or a pseudohalide such as a sulfonyl (e.g., mesyl), and synthesis proceeds by, e.g, a nucleophilic addition or an aryl coupling reaction between $Z^3$ and $Z^4$. For example, $Z^4$ may be a hydrogen atom and a nucleophilic aromatic substitution proceeds by addition of a nucleophilic center at $A^{21}$ to displace a suitable leaving group $Z^3$ (e.g., a fluoride or a nitro), where the reaction conditions include a suitable inert solvent (e.g., a polar aprotic solvent such as DMF or acetonitrile) and elevated temperature (e.g., 50 to 200° C.), optionally in the presence of a base (e.g., NaH or Cs$_2$CO$_3$).

$Z^1$ and $Z^2$ are suitable groups for formation of a cyclic amide.

For example, $Z^1$ may include an amine or an amide (e.g., —C(O)NH(PG), —C(O)N(PG)$_2$ or —C(O)NH—$Z^{51}$). In such embodiments, $Z^1$ may comprise a nitrogen-containing functional group such as a nitro, an amine, or a protected amine (where the protecting group is, e.g., benzyl, a carbamate such as benzyl tert-butoxycarbonyl or benzyloxycarbonyl, or a phthalimide), where when $Z^1$ is a nitro, reduction may be carried out (e.g., in situ) to form an amine. In embodiments where $Z^1$ is an amine, $Z^2$ may comprise a carbonyl (e.g., as an ester, such as a methyl or ethyl ester, or a carboxylic acid), and bond formation at $Z^1$ to $Z^2$ may be carried out by conditions for amide bond formation as described herein or as known in the art.

Alternatively, $Z^1$ may be a leaving group, e.g., a fluoro or a nitro, and a nucleophilic addition or an aryl coupling reaction may be conducted between $Z^1$ and $Z^2$. Thus, where $Z^2$ includes a nucleophilic center (e.g., where $Z^2$ is —C(O)NH(PG)) $Z^2$ may undergo nucleophilic displacement of $Z^1$, e.g., at an amide nitrogen atom of $Z^2$.

In some embodiments, $Z^1$ is nitro. Where $Z^1$ is a nitro, $Z^1$ may be reduced under suitable conditions, e.g., using sodium dithionite, iron metal and acid (e.g., acetic acid), or trichlorosilane. In some embodiments, nitro reduction at $Z^1$ and formation of a bond at $Z^1$ to $Z^2$ may be carried out in a one-pot reaction. Alternatively, when $Z^1$ is a nitro, $Z^1$ may act as a leaving group in a nucleophilic displacement. In some embodiments, $Z^1$ is a nitro group, synthesis proceeds though Compound Vd by exposing Compound Vd to reduction and cyclization conditions comprising a reducing agent (e.g., sodium dithionite, iron metal, or trichlorosilane) in a solvent (e.g., ethanol and water, acetic acid, or DCM), at a temperature of 0 to 150° C.).

In some embodiments, reaction at $Z^1$ to $Z^2$ and at $Z^3$ to $Z^4$ may occur in a single pot, in which case neither Compound Vc nor Compound Vd need be isolated.

A person of skill in the art will appreciate that any of Compound Va, Vb, Vc, Vd, Ve, or Vf may be available from a commercial supplier for a particular embodiment. Alternative synthesis of Compound Va, Vb, Vc, Vd, Ve, or Vf may be as described herein or as known to those of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

1. General Experimental Procedures

Commercially available reagents and solvents (HPLC grade) were used without further purification. 1H NMR spectra were recorded on a Bruker DRX 500 MHz spectrometer or Bruker DPX 250 MHz spectrometer or a Bruker AVANCE 300 or on a Bruker AVANCE 500 spectrometer in deuterated solvents. Chemical shifts (δ) are in parts per million. Flash column chromatography refers to automated purification on Biotage Isolera systems using an appropriately sized SNAP or KPNH pre-packed silica columns and the solvents recorded in the experimental section. Thin-layer chromatography (TLC) analysis was performed with Kieselgel 60 F254 (Merck) plates and visualized using UV light. SCX chromatography was performed with Biotage Isolute Flash SCX-2, loading the sample in methanol and eluting with methanol then 5% ammonia in methanol.

2. Analytical Methods

Acidic-Phase HPLC Methods

Analytical HPLC-MS (METCR1673) was performed on Shimadzu LCMS-2010EV systems using a reverse phase Supelco Ascentis Express column (2.7 μm, 2.1×30 mm), gradient 5-100% B (A=water/0.1% formic acid, B=acetonitrile/0.1% formic acid) at a column temp of 40° C. over 1.5 min then 100% B for 0.1 min, injection volume 3 μL, flow=1.0 mL/min. UV spectra were recorded at 215 nm using a SPD-M20A photo diode array (PDA) detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, HPLC-MS (METCR1410) was performed on Shimadzu LCMS-2010EV systems using a reverse phase Kinetix Core-Shell C18 column (5 μm, 2.1×50 mm) at a column temp of 40° C., gradient 5-100% B (A=water/0.1% formic acid, B=acetonitrile/0.1% formic acid) over 1.2 min, then 100% B over 0.1 min, injection volume 3 μL, flow=1.2 mL/min. All other aspects of the method were unchanged.

Alternatively, (METCR1416) analytical HPLC-MS was performed on Shimadzu LCMS-2010EV systems using reverse phase Waters Atlantis dC18 columns (3 μm, 2.1×100 mm), gradient 5-100% B (A=water/0.1% formic acid, B=acetonitrile/0.1% formic acid) at a column temp of 40° C. over 5.0 min then 100% B for 0.4 min, injection volume 3 μL, flow=0.6 mL/min. UV spectra were recorded at 215 nm using a SPD-M20A PDA detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 µm, 2.1 mm×100 mm at a column temp of 40° C., gradient 5-100% B (A=water/0.1% formic acid; B=acetonitrile/0.1% formic acid) over 5.3 min, then 100% B for 0.5 min, flow=0.6 ml/min. UV spectra were recorded at 215 nm using a Waters Acquity PDA detector. Mass spectra were obtained over the range m/z 150 to 850 at a sampling rate of 2 scans per second using a Waters ZQ. Data were integrated and reported using OpenLynx software.

Alternatively, (MET-AMRI001) mass spectra and LCMS analyses were obtained using a Waters Acquity SQD (ESI, UP-LCMS). HPLC analyses were obtained on an XBridge C18 column, 3.5 µm (4.6×150 mm), eluted according to solvent gradient Method 1. Detection was by UV at 254 and 215 nm.

| Method 1 Time (min) | Flow (mL/min) | % A | % B |
|---|---|---|---|
| 0.0 | 1.0 | 95 | 5 |
| 20.0 | 1.0 | 0 | 100 |
| 25.0 | 1.0 | 0 | 100 |

A = Water with 0.1% v/v Trifluoroacetic Acid
B = Acetonitrile with 0.1% v/v Trifluoroacetic Acid Alternatively, (METCR1704) analytical UHPLC-MS were performed in reverse phase system using a Waters UPLC™ BEH™ C18 column (2.1 mm×50 mm, 1.7 µm; temperature: 40° C.), with an injection volume of 1 µL at a flow rate of 0.9 mL/min and a gradient of 5-100% B (A=0.1% formic acid in water; B=0.1% formic acid in acetonitrile) over 1.1 min, then 100% B for 0.25 min. A second gradient of 100-5% B was then applied over 0.05 min and held for 0.1 min. UV spectra were recorded at 215 nm, spectrum range: 200-400 nm. Mass spectra were obtained using a Waters SQD or QDA detector; ionization mode: electrospray positive or negative. Data were integrated and reported using Waters MassLynx and OpenLynx software.

Alternatively, analytical (METCR1503) HPLC-MS were performed in reverse phase using a Phenomenex Kinetex Core shell C8 column (2.1 mm×50 mm, 2.6 µm; temperature: 40° C.), with an injection volume of 3 µL at a flow rate of 0.6 mL/min and a gradient of 5-100% B (A=0.1% formic acid in water; B=0.1% formic acid in acetonitrile) over 4.4 min, then 100% B for 1.0 min. A second gradient of 100-5% B was then applied over 0.2 min and held for 0.58 min. UV spectra were recorded at 215 nm, spectrum range: 210-400 nm. Mass spectra were obtained using a 2010EV detector; ionization mode: electrospray positive or negative. Data were integrated and reported using Shimadzu LCMS-Solutions and PsiPort software.

Alternatively, Analytical (MET-CR-AB106) UHPLC-MS were performed in reverse phase using a Waters UPLC™ CORTECS™ C8 column (2.1 mm×100 mm, 1.6 µm; temperature: 40° C.), with an injection volume of 1 µL at a flow rate of 0.6 mL/min and a gradient of 5-100% B (A=0.1% formic acid in water; B=0.1% formic acid in acetonitrile) over 5.3 min, then 100% B for 0.5 min. A second gradient of 100-5% B was then applied over 0.02 min and held for 1.18 min. UV spectra were recorded at 215 nm, spectrum range: 200-400 nm, ELS data was collected using a Waters ACQUITY™ ELS detector when reported. Mass spectra were obtained using a Waters SQD or Waters ACQUITY™ QDa; ionization mode: electrospray positive or negative. Data were integrated and reported using Waters MassLynx and OpenLynx software.

Alternatively, analytical (METCR1906) UHPLC-MS were performed in reverse phase using a Waters UPLC™ CORTECS™ C8 column (2.1 mm×50 mm, 1.6 µm; temperature: 40° C.), with an injection volume of 1 µL at a flow rate of 0.9 mL/min and a gradient of 5-100% B (A=0.1% formic acid in water; B=0.1% formic acid in acetonitrile) over 1.1 min, then 100% B for 0.3 min. A second gradient of 100-5% B was then applied over 0.02 min and held for 0.28 min. UV spectra were recorded at 215 nm, spectrum range: 200-400 nm, ELS data was collected using a Waters ACQUITY™ ELS detector when reported. Mass spectra were obtained using a Waters SQD or Waters ACQUITY™ QDa; ionization mode: electrospray positive or negative. Data were integrated and reported using Waters MassLynx and OpenLynx software.

Basic-Phase HPLC Methods

Analytical HPLC-MS (METCR0990), was performed on Hewlett Packard HPLC systems using reverse phase Phenomenex Gemini C18 columns (3 µm, 2.0×50 mm), at a column temp of 60° C.; gradient 1-100% B (A=2 mM ammonium bicarbonate in water buffered to pH10, B=acetonitrile) over 1.8 min then 100% B for 0.3 min, injection volume 3 µL, flow=1 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

Analytical HPLC-MS (METCR1600), was performed on Hewlett Packard HPLC systems using reverse phase Phenomenex Gemini C18 columns (3 µm, 2.0×100 mm), gradient 5-100% B (A=2 mM ammonium bicarbonate in water buffered to pH 10, B=acetonitrile) over 5.5 min then 100% B for 0.4 min, injection volume 3 µL, flow=0.5 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

The METCR1600 method was subsequently replaced with the METCR1603 method where the flow rate increased to 0.6 mL/min. All other parameters were unchanged.

Alternatively, (MET-uHPLC-AB-102) analytical HPLC-MS were performed on a Waters Acquity UPLC system with Waters PDA and ELS detectors using a Waters UPLC® CSH™ (1.7 µm, 2.1×100 mm) column, at a column temp of 40° C.; gradient 5-100% B (A=2 mM ammonium bicarbonate in water buffered to pH 10, B=acetonitrile) over 5.3 min then 100% B for 0.5 min, injection volume 1 µL, flow=0.6 mL/minute. UV spectra were recorded at 215 nm using a Waters Acquity PDA detector. Mass spectra were obtained over the range m/z 150 to 850 at a sampling rate of 2 scans per second using a Waters Quattro Premier XE. Data were integrated and reported using OpenLynx software.

All example compounds display an LC purity of >95% unless stated otherwise.

Scheme for Method 1

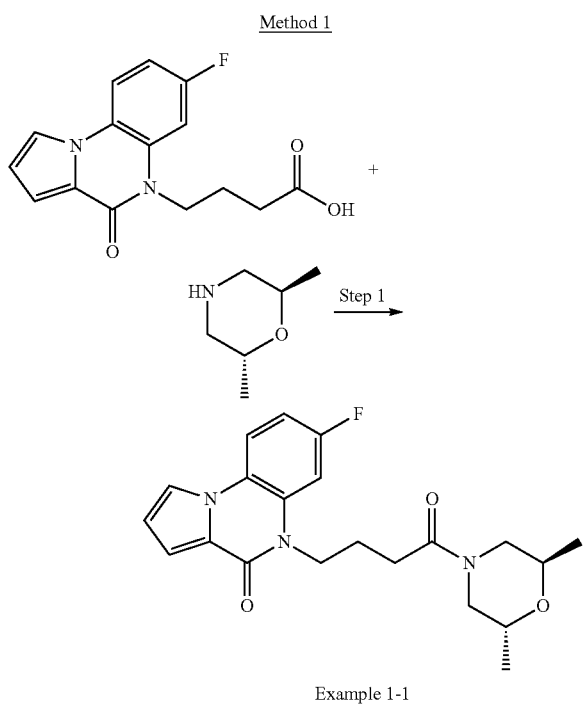

Example 1-1

Example 1-1

Step 1: 5-{4-[(2R,6R)-2,6-Dimethylmorpholin-4-yl]-4-oxobutyl}-7-fluoro-4H,5H-pyrrolo[1,2-a]quinoxalin-4-one 4-(7-Fluoro-4-oxo-pyrrolo[1,2-a]quinoxalin-5-yl)butanoic acid (50 mg, 0.17 mmol) was dissolved in DMF (5 mL). HATU (100 mg, 0.26 mmol) and DIPEA (0.1 mL, 0.52 mmol) were added followed by (2R,6R)-2,6-dimethylmorpholine (20 μL, 0.17 mmol). The reaction mixture was stirred at room temperature for 5 min. The reaction mixture was concentrated to dryness and the residue was partitioned between DCM (5 mL) and water (5 mL) and extracted with DCM (2×3 mL). The combined organics were dried (MgSO$_4$) and concentrated. Further purification by basic prep HPLC gave the title compound. $^1$H NMR (500 MHz, DMSO-d$_6$) δ 8.54-7.99 (m, 2H), 7.76 (d, J=11.3 Hz, 1H), 7.39-7.09 (m, 1H), 7.08-6.98 (m, 1H), 6.80-6.45 (m, 1H), 4.39-4.03 (m, 2H), 3.96-3.71 (m, 2H), 3.54 (m, 2H), 3.16 (m, 2H), 2.50-2.42 (m, 2H), 1.94-1.64 (m, 2H), 1.09 (m, 6.4 Hz, 6H). $^{19}$F NMR (235 MHz, DMSO-d$_6$) −115.02. Tr(METCR1603)=3.85 min, (ES$^+$) (M+H)$^+$ 386.3, 100%.

Also prepared by this route:

| Ex. | Structure | LCMS data | NMR data |
|---|---|---|---|
| 1-2 | 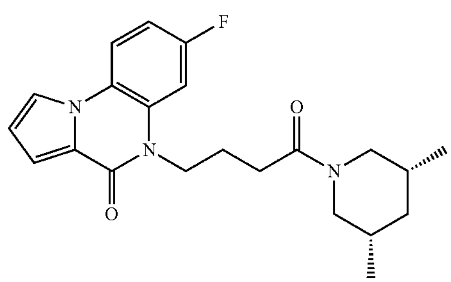 [SMILES: C[C@@H]1C[C@H](C)CN(C(=O)CCCn2c(=O)c3cccn3c3ccc(F)cc32)C1] | Tr(MET-uHPLC-AB-101) = 3.78 min, (ES$^+$) (M + H)$^+$ 384.3, 99% | 1H NMR (500 MHz, DMSO-d6) d 8.20-8.13 (m, 2H), 7.77 (dd, J = 11.4, 2.6 Hz, 1H), 7.21-7.13 (m, 1H), 7.04 (dd, J = 3.9, 1.4 Hz, 1H), 6.69 (dd, J = 3.8, 2.8 Hz, 1H), 4.41 (dd, J = 10.7, 1.8 Hz, 1H), 4.20-4.10 (m, 2H), 3.77 (d, J = 11.3 Hz, 1H), 2.49-2.41 (m, 3H), 1.97 (t, J = 12.1 Hz, 1H), 1.89-1.78 (m, 2H), 1.74 (d, J = 12.8 Hz, 1H), 1.59-1.47 (m, 1H), 1.47-1.35 (m, 1H), 0.85 (d, J = 6.6 Hz, 6H), 0.74 (q, J = 11.9 Hz, 1H). 19F NMR (235 MHz, DMSO-d6) d-115.03. |
| 1-3 | 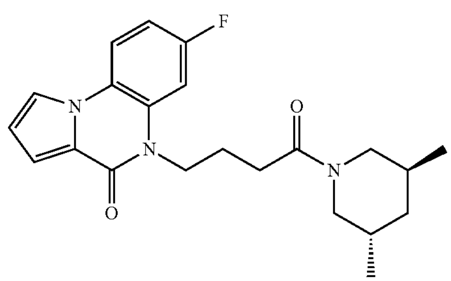 | Tr(MET-uHPLC-AB-101) = 3.69 min, (ES$^+$) (M + H)$^+$ 384.3, 99% | 1H NMR (500 MHz, DMSO-d6) 8.21-8.13 (m, 2H), 7.78 (dd, J = 11.4, 2.6 Hz, 1H), 7.17 (td, J = 8.9, 2.6 Hz, 1H), 7.05 (dd, J = 3.9, 1.4 Hz, 1H), 6.69 (dd, J = 3.8, 2.8 Hz, 1H), 4.21-4.05 (m, 2H), 3.59 (dd, J = 12.7, 3.7 Hz, 1H), 3.40 (dd, J = 13.3, 3.6 Hz, 1H), 3.11 (dd, J = 13.3, 6.4 Hz, 1H), 3.04 (dd, J = 12.7, 7.3 Hz, 1H), 2.58-2.40 (m, 2H), 1.92-1.73 (m, 4H), 1.44-1.35 (m, 2H), 0.87 (d, J = 6.8 Hz, 3H), 0.84 (d, J = 6.8 Hz, 3H). 19F NMR (235 MHz, DMSO-d6) −114.99. |

-continued

| Ex. | Structure | LCMS data | NMR data |
|---|---|---|---|
| 1-4 | 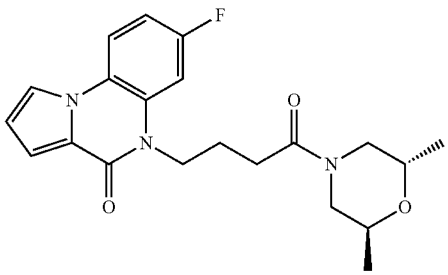 [SMILES: C[C@H]1CN(C(=O)CCCn2c(=O)c3cccn3c3ccc(F)cc32)C[C@H](C)O1] | Tr(METCR1603) = 3.86 min, (ES⁺) (M + H)⁺ 386.3, 100% | 1H NMR (500 MHz, DMSO-d6) 8.21-8.14 (m, 2H), 7.76 (dd, J = 11.4, 2.6 Hz, 1H), 7.21-7.13 (m, 1H), 7.05 (dd, J = 3.9, 1.4 Hz, 1H), 6.69 (dd, J = 3.8, 2.8 Hz, 1H), 4.19-4.11 (m, 2H), 3.95-3.83 (m, 2H), 3.60-3.48 (m, 2H), 3.20-3.12 (m, 2H), 2.52-2.40 (m, 2H), 1.85 (p, J = 6.8 Hz, 2H), 1.12-1.05 (m, 6H). 19F NMR (235 MHz, DMSO-d6) −115.02. |
| 1-5 | 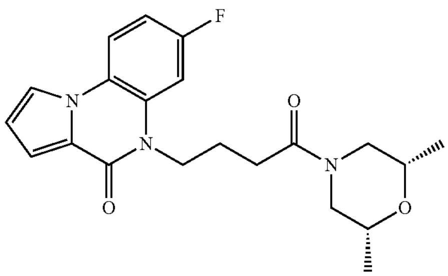 | Tr(MET-uHPLC-AB-101) = 2.99 min, (ES⁺) (M + H)⁺ 386.3, 100% | 1H NMR (500 MHz, DMSO-d6) 8.22-8.15 (m, 2H), 7.76 (dd, J = 11.4, 2.6 Hz, 1H), 7.21-7.13 (m, 1H), 7.05 (dd, J = 3.9, 1.5 Hz, 1H), 6.69 (dd, J = 3.8, 2.8 Hz, 1H), 4.33-4.26 (m, 1H), 4.18-4.11 (m, 2H), 3.81-3.72 (m, 1H), 3.54-3.37 (m, 2H), 2.71-2.63 (m, 1H), 2.57 (dd, J = 15.0, 8.3 Hz, 1H), 2.47-2.40 (m, 1H), 2.21 (dd, J = 12.9, 11.0 Hz, 1H), 1.88-1.80 (m, 2H), 1.09 (d, J = 6.2 Hz, 6H). 19F NMR (235 MHz, DMSO-d6) −115.05. |
| 1-6 | 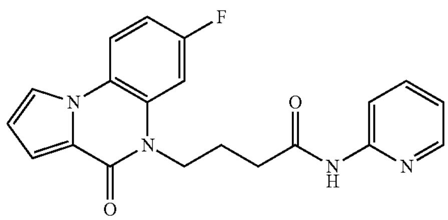 [SMILES: O=C(CCCn1c(=O)c2cccn2c2ccc(F)cc21)Nc1ccccn1] | Tr(METCR1603) = 4.01 min, (ES⁺) (M + H)⁺ 365.2, 100% | 1H NMR (500 MHz, DMSO-d6) 10.47 (s, 1H), 8.29 (dd, J = 4.9, 1.1 Hz, 1H), 8.22-8.16 (m, 2H), 8.07 (d, J = 8.4 Hz, 1H), 7.80-7.71 (m, 1H), 7.59 (dd, J = 11.3, 2.6 Hz, 1H), 7.18 (td, J = 8.5, 2.6 Hz, 1H), 7.10-7.03 (m, 2H), 6.69 (dd, J = 3.8, 2.8 Hz, 1H), 4.33-4.09 (m, 2H), 2.56 (t, J = 7.1 Hz, 2H), 1.93 (p, J = 7.3 Hz, 2H). 19F NMR (235 MHz, DMSO-d6) −115.10. |
| 1-7 | 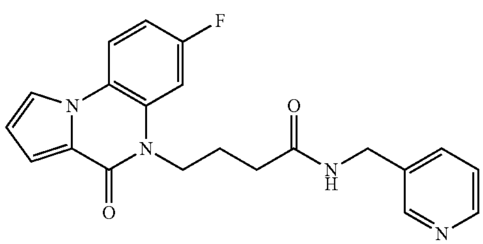 [SMILES: O=C(CCCn1c(=O)c2cccn2c2ccc(F)cc21)NCc1cccnc1] | Tr(METCR1603) = 3.45 min, (ES⁺) (M + H)⁺ 379.2, 96% | 1H NMR (500 MHz, DMSO-d6) 8.48 (d, J = 1.8 Hz, 1H), 8.46-8.40 (m, 2H), 8.22-8.14 (m, 2H), 7.68-7.62 (m, 1H), 7.58 (dd, J = 11.3, 2.6 Hz, 1H), 7.33 (dd, J = 7.8, 4.8 Hz, 1H), 7.20-7.13 (m, 1H), 7.05 (dd, J = 3.9, 1.5 Hz, 1H), 6.69 (dd, J = 3.8, 2.8 Hz, 1H), 4.30 (d, J = 5.9 Hz, 2H), 4.21-4.13 (m, 2H), 2.32 (t, J = 7.2 Hz, 2H), 1.87 (p, J = 7.2 Hz, 2H). 19F NMR (235 MHz, DMSO-d6) −115.02. |
| 1-8 | 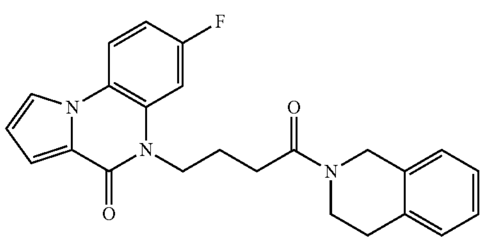 [SMILES: O=C(CCCn1c(=O)c2cccn2c2ccc(F)cc21)N1CCc2ccccc2C1] | Tr(MET-uHPLC-AB-101) = 3.55 min, (ES⁺) (M + H)⁺ 404.2, 100% | 1H NMR (500 MHz, CDCl3) 7.71-7.59 (m, 2H), 7.59 (dd, J = 2.7, 1.5 Hz, 1H), 7.24-7.07 (m, 5H), 6.94 (ddd, J = 9.8, 7.6, 2.5 Hz, 1H), 6.65 (dt, J = 4.0, 2.3 Hz, 1H), 4.76 (s, 1.2H, major rotamer), 4.62 (s, 0.8H, minor rotamer), 4.46-4.18 (m, 2H), 3.86 (t, J = 6.0 Hz, 0.8H, minor rotamer), 3.68 (t, J = 6.0 Hz, 1.2H, major rotamer), 2.91 (t, J = 5.9 Hz, 1.2H, major rotamer), 2.86 (t, J = 6.0 Hz, 0.8H, minor rotamer), 2.59 (q, J = 6.4 Hz, 2H), 2.27-2.07 (m, 2H). 19F NMR (235 MHz, CDCl3) −113.91 (d, J = 11.6 Hz). |
| 1-9 | 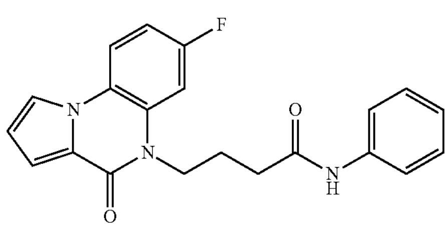 [SMILES: O=C(CCCn1c(=O)c2cccn2c2ccc(F)cc21)Nc1ccccc1] | Tr(MET-uHPLC-AB-101) = 3.26 min, (ES⁺) (M + H)⁺ 364.2, 100% | 1H NMR (500 MHz, CDCl3) 8.51 (s, 1H), 7.67 (dd, J = 9.0, 5.2 Hz, 1H), 7.63 (d, J = 8.2 Hz, 3H), 7.33 (t, J = 7.9 Hz, 2H), 7.26 (s, 2H), 7.10 (t, J = 7.4 Hz, 1H), 7.00 (ddd, J = 9.8, 7.5, 2.5 Hz, 1H), 6.69 (dd, J = 3.8, 2.8 Hz, 1H), 4.37 (t, J = 6.4 Hz, 2H), 2.47 (dd, J = 7.5, 5.4 Hz, 2H), 2.21 (p, J = 6.5 Hz, 2H). 19F NMR (235 MHz, CDCl3) −113.91. |

| Ex. | Structure | LCMS data | NMR data |
|---|---|---|---|
| 1-10 | 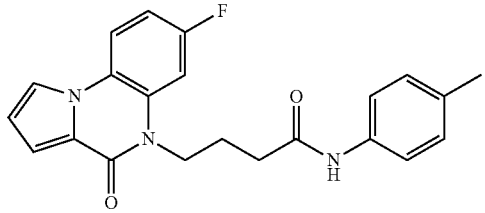 [SMILES: Cc1ccc(NC(=O)CCCn2c(=O)c3cccn3c3ccc(F)cc32)cc1] | Tr(METCR1603) = 4.48 min, (ES+) (M + H)+ 378.3, 100% | 1H NMR (500 MHz, DMSO-d6) 9.84 (s, 1H), 8.41-8.07 (m, 2H), 7.61 (dd, J = 11.3, 2.6 Hz, 1H), 7.54-7.38 (m, 2H), 7.18 (m, 1H), 7.12-6.90 (m, 3H), 6.69 (dd, J = 3.8, 2.8 Hz, 1H), 4.45-4.03 (m, 2H), 2.47-2.38 (m, 2H), 2.24 (s, 3H), 2.08-1.81 (m, 2H). 19F NMR (235 MHz, DMSO-d6) −115.01 |
| 1-11 | 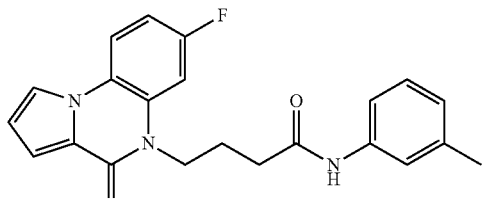 | Tr(MET-uHPLC-AB-101) = 3.47 min, (ES+) (M + H)+ 378.2, 100% | 1H NMR (500 MHz, DMSO-d6) 9.84 (s, 1H), 8.23-8.13 (m, 2H), 7.60 (dd, J = 11.3, 2.5 Hz, 1H), 7.40 (s, 1H), 7.35 (d, J = 8.3 Hz, 1H), 7.21-7.12 (m, 2H), 7.05 (dd, J = 3.8, 1.4 Hz, 1H), 6.84 (d, J = 7.5 Hz, 1H), 6.69 (dd, J = 3.8, 2.8 Hz, 1H), 4.28-4.19 (m, 2H), 2.46 (t, J = 7.2 Hz, 2H), 2.26 (s, 3H), 1.94 (p, J = 7.2 Hz, 2H). 19F NMR (235 MHz, DMSO-d6) −115.03. |
| 1-12 | 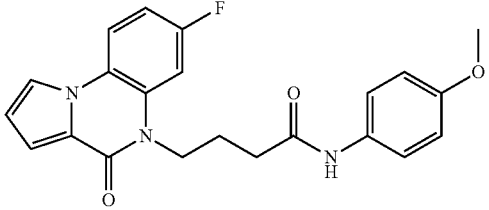 [SMILES: COc1ccc(NC(=O)CCCn2c(=O)c3cccn3c3ccc(F)cc32)cc1] | Tr(MET-uHPLC-AB-101) = 3.17 min, (ES+) (M + H)+ 394.2, 100% | 1H NMR (500 MHz, DMSO-d6) 9.79 (s, 1H), 8.24-8.13 (m, 2H), 7.61 (dd, J = 11.3, 2.5 Hz, 1H), 7.48 (d, J = 2.1 Hz, 1H), 7.47 (d, J = 2.1 Hz, 1H), 7.17 (td, J = 8.9, 2.6 Hz, 1H), 7.05 (dd, J = 3.8, 1.4 Hz, 1H), 6.87 (d, J = 2.1 Hz, 1H), 6.85 (d, J = 2.1 Hz, 1H), 6.69 (dd, J = 3.8, 2.8 Hz, 1H), 4.30-4.18 (m, 2H), 3.71 (s, 3H), 2.44 (t, J = 7.2 Hz, 2H), 1.93 (p, J = 7.2 Hz, 2H). 19F NMR (235 MHz, DMSO-d6) −115.02. |
| 1-13 | 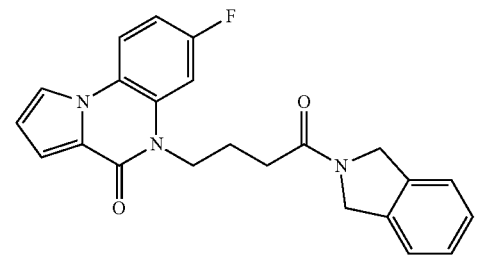 [SMILES: O=C(CCCn1c(=O)c2cccn2c2ccc(F)cc21)N1Cc2ccccc2C1] | Tr(MET-uHPLC-AB-101) = 3.35 min, (ES+) (M + H)+ 390.2, 97% | 1H NMR (500 MHz, CDCl3) 7.70-7.55 (m, 3H), 7.36-7.26 (m, 4H), 7.18 (dd, J = 3.9, 1.3 Hz, 1H), 7.01-6.91 (m, 1H), 6.64 (dd, J = 3.8, 2.9 Hz, 1H), 4.81 (s, 4H), 4.49-4.18 (m, 2H), 2.57 (t, J = 6.5 Hz, 2H), 2.17 (p, J = 6.7 Hz, 2H). 19F NMR (235 MHz, CDCl3) −113.86. |
| 1-14 | 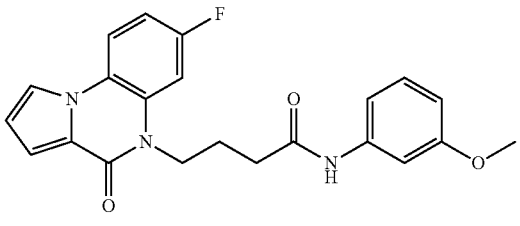 [SMILES: COc1cccc(NC(=O)CCCn2c(=O)c3cccn3c3ccc(F)cc32)c1] | Tr(METCR1603) = 4.33 min, (ES+) (M + H)+ 394.3, 100% | 1H NMR (500 MHz, DMSO-d6) 9.92 (s, 1H), 8.24-8.13 (m, 2H), 7.61 (dd, J = 11.3, 2.6 Hz, 1H), 7.36-7.24 (m, 1H), 7.23-7.14 (m, 2H), 7.11 (d, J = 8.7 Hz, 1H), 7.05 (dd, J = 3.9, 1.4 Hz, 1H), 6.69 (dd, J = 3.8, 2.8 Hz, 1H), 6.65-6.56 (m, 1H), 4.36-4.16 (m, 2H), 3.71 (s, 3H), 2.49-2.42 (m, 2H), 2.04-1.85 (m, 2H). 19F NMR (235 MHz, DMSO-d6) −115.05. |
| 1-15 | 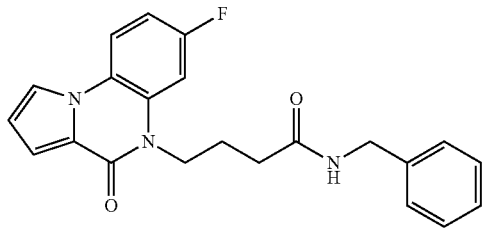 [SMILES: O=C(CCCn1c(=O)c2cccn2c2ccc(F)cc21)NCc1ccccc1] | Tr(METCR1603) = 3.64 min, (ES+) (M + H)+ 378.3, 100% | 1H NMR (500 MHz, DMSO-d6) 8.37 (t, J = 5.8 Hz, 1H), 8.22-8.14 (m, 2H), 7.59 (dd, J = 11.3, 2.6 Hz, 1H), 7.34-7.27 (m, 2H), 7.27-7.20 (m, 3H), 7.19-7.15 (m, 1H), 7.05 (dd, J = 3.9, 1.5 Hz, 1H), 6.69 (dd, J = 3.8, 2.8 Hz, 1H), 4.28 (d, J = 5.9 Hz, 2H), 4.21-4.14 (m, 2H), 2.32 (t, J = 7.2 Hz, 2H), 1.87 (p, J = 7.2 Hz, 2H). 19F NMR (235 MHz, DMSO-d6) −114.99. |

| Ex. | Structure | LCMS data | NMR data |
|---|---|---|---|
| 1-16 | 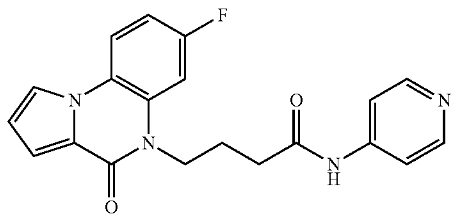 [SMILES: O=C(CCCn1c(=O)c2cccn2c2ccc(F)cc21)Nc1ccncc1] | Tr(METCR1603) = 3.6 min, (ES⁺) (M + H)⁺ 365.2, 96% | 1H NMR (500 MHz, DMSO-d6) 10.30 (s, 1H), 8.55-8.33 (m, 2H), 8.29-7.99 (m, 2H), 7.59 (dd, J = 11.3, 2.6 Hz, 1H), 7.55-7.40 (m, 2H), 7.37-7.09 (m, 1H), 7.04 (dd, J = 3.9, 1.4 Hz, 1H), 6.68 (dd, J = 3.8, 2.8 Hz, 1H), 4.44-4.16 (m, 2H), 2.54-2.51 (m, 2H), 1.95 (m, 2H). 19F NMR (235 MHz, DMSO-d6) −115.07. |
| 1-17 | 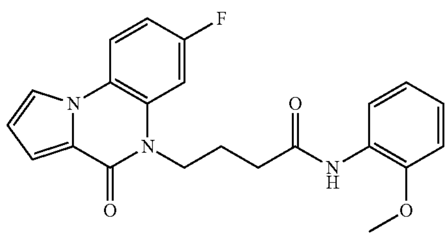 [SMILES: COc1ccccc1NC(=O)CCCn1c(=O)c2cccn2c2ccc(F)cc21] | Tr(MET-uHPLC-AB-101) = 3.36 min m/z (ES⁺) (M + H)⁺ 394.3, 100% | 1H NMR (500 MHz, DMSO-d6) 9.14 (s, 1H), 8.24-8.14 (m, 2H), 7.91 (d, J = 7.7 Hz, 1H), 7.60 (dd, J = 11.3, 2.6 Hz, 1H), 7.22-7.14 (m, 1H), 7.10-6.99 (m, 3H), 6.95-6.85 (m, 1H), 6.69 (dd, J = 3.8, 2.8 Hz, 1H), 4.28-4.15 (m, 2H), 3.81 (s, 3H), 2.55 (t, J = 7.0 Hz, 2H), 1.92 (p, J = 7.1 Hz, 2H). 19F NMR (235 MHz, DMSO-d6) −115.04. |
| 1-18 | 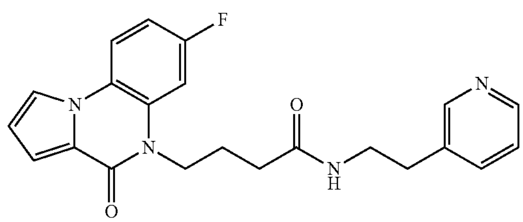 [SMILES: O=C(CCCn1c(=O)c2cccn2c2ccc(F)cc21)NCCc1cccnc1] | Tr(METCR1603) = 3.43 min m/z (ES⁺) (M + H)⁺ 393.3, 100% | 1H NMR (500 MHz, DMSO-d6) 8.41 (d, J = 1.7 Hz, 1H), 8.37 (dd, J = 4.7, 1.4 Hz, 1H), 8.21-8.15 (m, 2H), 7.97 (t, J = 5.5 Hz, 1H), 7.62 (dt, 1H), 7.54 (dd, 1H), 7.28 (dd, J = 7.7, 4.8 Hz, 1H), 7.17 (td, J = 8.8, 2.5 Hz, 1H), 7.05 (dd, J = 3.8, 1.4 Hz, 1H), 6.69 (dd, J = 3.7, 2.9 Hz, 1H), 4.10 (t, 2H), 3.30-3.25 (m, 2H), 2.72 (t, J = 7.1 Hz, 2H), 2.20 (t, J = 7.1 Hz, 2H), 1.80 (p, J = 7.2 Hz, 2H). 19F NMR (235 MHz, DMSO-d6) −114.99. |
| 1-19 | 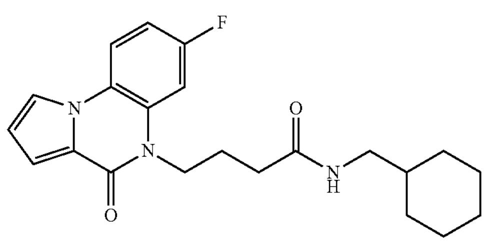 [SMILES: O=C(CCCn1c(=O)c2cccn2c2ccc(F)cc21)NCC1CCCCC1] | Tr(METCR1603) = 4.54 min m/z (ES⁺) (M + H)⁺ 384.4, 100% | 1H NMR (500 MHz, DMSO-d6) 8.21-8.15 (m, 2H), 7.81 (t, J = 5.7 Hz, 1H), 7.57 (dd, J = 11.3, 2.6 Hz, 1H), 7.17 (td, J = 8.9, 2.6 Hz, 1H), 7.04 (dd, J = 3.9, 1.5 Hz, 1H), 6.69 (dd, J = 3.8, 2.8 Hz, 1H), 4.19-4.11 (m, 2H), 2.93-2.85 (m, 2H), 2.23 (t, J = 7.2 Hz, 2H), 1.83 (p, J = 7.2 Hz, 2H), 1.70-1.54 (m, 5H), 1.42-1.31 (m, 1H), 1.21-1.06 (m, 3H), 0.91-0.79 (m, 2H). 19F NMR (235 MHz, DMSO-d6) −115.00. |
| 1-20 | 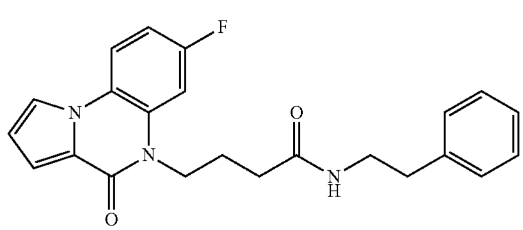 [SMILES: O=C(CCCn1c(=O)c2cccn2c2ccc(F)cc21)NCCc1ccccc1] | Tr(METCR1603) = 4.21 min m/z (ES⁺) (M + H)⁺ 392.3, 98% | 1H NMR (500 MHz, DMSO-d6) 8.21-8.15 (m, 2H), 7.95 (t, J = 5.5 Hz, 1H), 7.55 (dd, J = 11.3, 2.6 Hz, 1H), 7.29-7.23 (m, 2H), 7.22-7.12 (m, 4H), 7.05 (dd, J = 3.9, 1.4 Hz, 1H), 6.69 (dd, J = 3.8, 2.8 Hz, 1H), 4.11 (t, 2H), 3.31-3.23 (m, 2H), 2.70 (t, J = 7.4 Hz, 2H), 2.21 (t, J = 7.1 Hz, 2H), 1.82 (p, J = 7.2 Hz, 2H). 19F NMR (235 MHz, DMSO-d6) −115.02. |
| 1-21 | 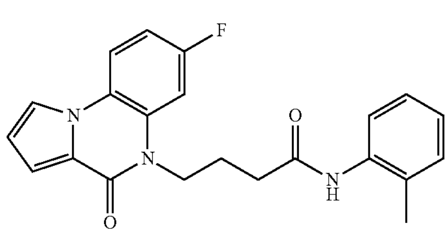 [SMILES: Cc1ccccc1NC(=O)CCCn1c(=O)c2cccn2c2ccc(F)cc21] | Tr(METCR1603) = 4.27 min m/z (ES⁺) (M + H)⁺ 378.3, 97% | 1H NMR (500 MHz, DMSO-d6) 9.32 (s, 1H), 8.49-7.95 (m, 2H), 7.60 (dd, J = 11.3, 2.6 Hz, 1H), 7.36 (d, J = 7.9 Hz, 1H), 7.26-6.91 (m, 5H), 6.70 (dd, J = 3.8, 2.8 Hz, 1H), 4.82-4.09 (m, 2H), 2.53-2.52 (m, 2H), 2.19 (s, 3H), 2.02-1.75 (m, 2H). 19F NMR (235 MHz, DMSO-d6) −115.03. |

| Ex. | Structure | LCMS data | NMR data |
|---|---|---|---|
| 1-22 | 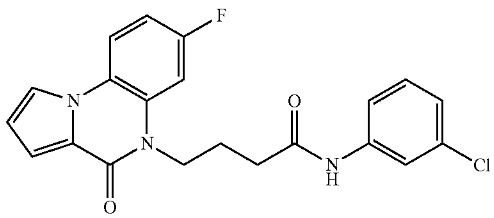 [SMILES: O=C(CCCn1c(=O)c2cccn2c2ccc(F)cc21)Nc1cccc(Cl)c1] | Tr(METCR1603) = 4.63 min m/z (ES+) (M + H)+ 398.2, 100% | 1H NMR (500 MHz, DMSO-d6) 10.12 (s, 1H), 8.48-7.99 (m, 2H), 7.94-7.72 (m, 1H), 7.60 (dd, J = 11.3, 2.6 Hz, 1H), 7.52-7.36 (m, 1H), 7.36-7.25 (m, 1H), 7.23-7.13 (m, 1H), 7.11-6.89 (m, 2H), 6.68 (dd, J = 3.8, 2.8 Hz, 1H), 4.54-4.07 (m, 2H), 2.49-2.45 (m, 2H), 2.07-1.77 (m, 2H). 19F NMR (235 MHz, DMSO-d6) −115.07. |
| 1-23 | 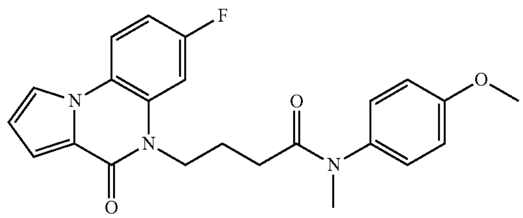 [SMILES: COc1ccc(N(C)C(=O)CCCn2c(=O)c3cccn3c3ccc(F)cc32)cc1] | Tr(METCR1603) = 4.20 min m/z (ES+) (M + H)+ 408.3, 97% | 1H NMR (500 MHz, DMSO-d6) 8.35-8.06 (m, 2H), 7.61 (dd, J = 11.2, 2.2 Hz, 1H), 7.30-7.10 (m, 3H), 7.03 (d, J = 2.5 Hz, 1H), 6.91 (d, J = 8.9 Hz, 2H), 6.69 (dd, J = 3.8, 2.8 Hz, 1H), 4.41-3.99 (m, 2H), 3.76 (s, 3H), 3.11 (s, 3H), 2.20-2.04 (m, 2H), 1.90-1.66 (m, 2H). 19F NMR (235 MHz, DMSO-d6) −115.09. |
| 1-24 | 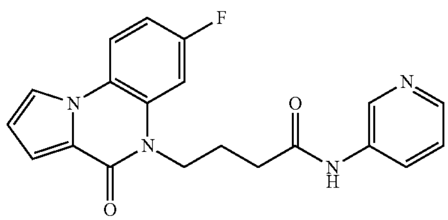 [SMILES: O=C(CCCn1c(=O)c2cccn2c2ccc(F)cc21)Nc1cccnc1] | Tr(METCR1603) = 3.55 min m/z (ES+) (M + H)+ 365.3, 100% | 1H NMR (500 MHz, DMSO-d6) 10.14 (s, 1H), 8.70 (s, 1H), 8.28-8.21 (m, 1H), 8.20-8.15 (m, 2H), 8.00 (d, J = 8.4 Hz, 1H), 7.60 (dd, J = 11.3, 2.6 Hz, 1H), 7.32 (dd, J = 8.3, 4.7 Hz, 1H), 7.22-7.13 (m, 1H), 7.04 (dd, J = 3.9, 1.5 Hz, 1H), 6.68 (dd, J = 3.8, 2.8 Hz, 1H), 4.29-4.22 (m, 2H), 2.54-2.52 (m, 2H), 1.96 (p, J = 7.1 Hz, 2H). 19F NMR (235 MHz, DMSO-d6) −115.07. |
| 1-25 | 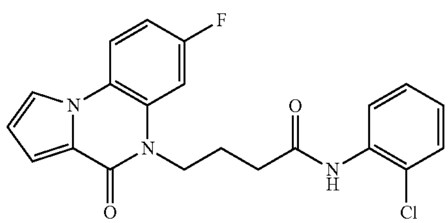 | Tr(MET-uHPLC-AB-101) = 3.47 min m/z (ES+) (M + H)+ 398.2, 100% | 1H NMR (500 MHz, DMSO-d6) 9.56 (s, 1H), 8.24-8.14 (m, 2H), 7.66 (d, J = 7.6 Hz, 1H), 7.59 (dd, J = 11.3, 2.6 Hz, 1H), 7.48 (dd, J = 8.0, 1.4 Hz, 1H), 7.31 (td, J = 7.8, 1.4 Hz, 1H), 7.22-7.14 (m, 2H), 7.06 (dd, J = 3.9, 1.4 Hz, 1H), 6.70 (dd, J = 3.8, 2.8 Hz, 1H), 4.30-4.17 (m, 2H), 2.55 (t, J = 6.9 Hz, 2H), 1.95 (p, J = 7.2 Hz, 2H). 19F NMR (376 MHz, DMSO-d6) −115.02 |
| 1-26 | 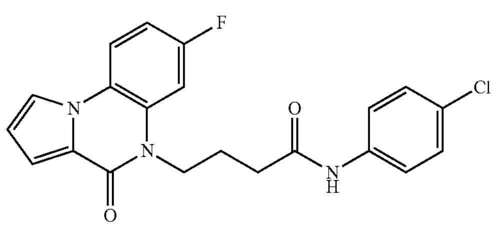 [SMILES: O=C(CCCn1c(=O)c2cccn2c2ccc(F)cc21)Nc1ccc(Cl)cc1] | Tr(METCR1603) = 4.59 min m/z (ES+) (M + H)+ 398.2, 100% | 1H NMR (500 MHz, DMSO-d6) 10.06 (s, 1H), 8.22-8.15 (m, 2H), 7.64-7.55 (m, 3H), 7.38-7.30 (m, 2H), 7.18 (td, J = 8.9, 2.6 Hz, 1H), 7.05 (dd, J = 3.9, 1.4 Hz, 1H), 6.69 (dd, J = 3.8, 2.8 Hz, 1H), 4.24 (t, 2H), 2.48-2.44 (m, 2H), 1.94 (p, J = 7.3 Hz, 2H). 19F NMR (376 MHz, DMSO-d6) −115.03. |
| 1-27 | 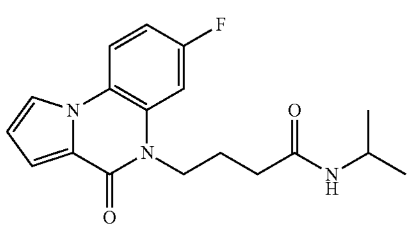 [SMILES: CC(C)NC(=O)CCCn1c(=O)c2cccn2c2ccc(F)cc21] | Tr(METCR1603) = 3.64 min m/z (ES+) (M + H)+ 330.2, 100% | 1H NMR (500 MHz, DMSO-d6) 8.43-8.07 (m, 2H), 7.72 (d, J = 7.7 Hz, 1H), 7.58 (dd, J = 11.3, 2.6 Hz, 1H), 7.26-7.10 (m, 1H), 7.04 (dd, J = 3.9, 1.5 Hz, 1H), 6.69 (dd, J = 3.8, 2.8 Hz, 1H), 4.43-4.05 (m, 2H), 3.96-3.71 (m, 1H), 2.19 (t, J = 7.1 Hz, 2H), 1.96-1.73 (m, 2H), 1.03 (d, J = 6.6 Hz, 6H). 19F NMR (376 MHz, DMSO-d6) −115.05. |
| 1-28 | 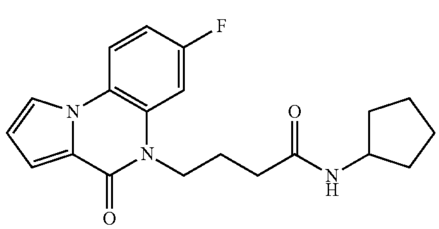 [SMILES: O=C(CCCn1c(=O)c2cccn2c2ccc(F)cc21)NC1CCCC1] | Tr(MET-uHPLC-AB-101) = 3.05 min m/z (ES+) (M + H)+ 356.2, 100% | 1H NMR (500 MHz, DMSO-d6) 8.22-8.14 (m, 2H), 7.80 (d, J = 7.2 Hz, 1H), 7.58 (dd, J = 11.3, 2.6 Hz, 1H), 7.17 (td, J = 8.9, 2.6 Hz, 1H), 7.04 (dd, J = 3.9, 1.4 Hz, 1H), 6.69 (dd, J = 3.8, 2.8 Hz, 1H), 4.21-4.10 (m, 2H), 3.99 (h, J = 6.9 Hz, 1H), 2.20 (t, J = 7.1 Hz, 2H), 1.86-1.74 (m, 4H), 1.67-1.55 (m, 2H), 1.53-1.42 (m, 2H), 1.37-1.30 (m, 2H). 19F NMR |

| Ex. | Structure | LCMS data | NMR data |
|---|---|---|---|
| | | | (376 MHz, DMSO-d6) −115.02. |
| 1-29 | 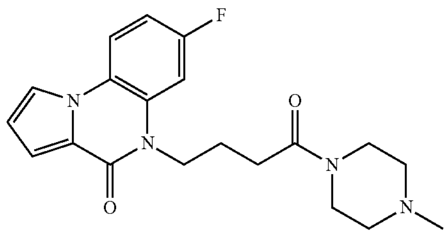 [SMILES: CN1CCN(C(=O)CCCn2c(=O)c3cccn3c3ccc(F)cc32)CC1] | Tr(METCR1603) = 3.36 min m/z (ES⁺) (M + H)⁺ 371.2, 100% | 1H NMR (500 MHz, DMSO-d6) 8.29-8.05 (m, 2H), 7.75 (dd, J = 11.4, 2.6 Hz, 1H), 7.26-7.11 (m, 1H), 7.04 (dd, J = 3.8, 1.5 Hz, 1H), 6.69 (dd, J = 3.8, 2.8 Hz, 1H), 4.30-4.01 (m, 2H), 3.53-3.43 (m, 2H), 3.45-3.37 (m, 2H), 2.50 (s, 2H), 2.35-2.26 (m, 2H), 2.27-2.21 (m, 2H), 2.18 (s, 3H), 1.87-1.81 (m, 2H). 19F NMR (376 MHz, DMSO-d6) −115.00. |
| 1-30 | 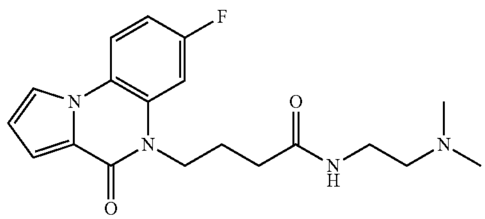 [SMILES: CN(C)CCNC(=O)CCCn1c(=O)c2cccn2c2ccc(F)cc21] | Tr(METCR1603) = 3.45 min m/z (ES⁺) (M + H)⁺ 359.2, 100% | 1H NMR (500 MHz, DMSO-d6) 8.33-8.07 (m, 2H), 7.78 (t, J = 5.5 Hz, 1H), 7.57 (dd, J = 11.3, 2.6 Hz, 1H), 7.30-7.12 (m, 1H), 7.04 (dd, J = 3.9, 1.5 Hz, 1H), 6.69 (dd, J = 3.8, 2.8 Hz, 1H), 4.27-4.05 (m, 2H), 3.14 (q, J = 6.6 Hz, 2H), 2.34-2.18 (m, 4H), 2.12 (s, 6H), 1.83 (p, J = 7.2 Hz, 2H). 19F NMR (376 MHz, DMSO-d6) −115.02. |
| 1-31 | 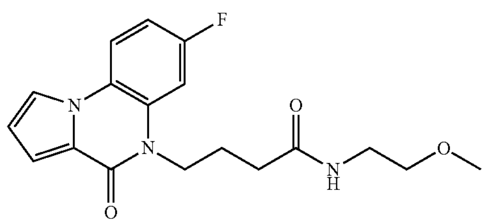 [SMILES: COCCNC(=O)CCCn1c(=O)c2cccn2c2ccc(F)cc21] | Tr(MET-uHPLC-AB-101) = 2.38 min m/z (ES⁺) (M + H)⁺ 346.2, 99% | 1H NMR (500 MHz, DMSO-d6) 8.21-8.14 (m, 2H), 7.94 (t, J = 5.4 Hz, 1H), 7.58 (dd, J = 11.3, 2.6 Hz, 1H), 7.21-7.13 (m, 1H), 7.04 (dd, J = 3.9, 1.5 Hz, 1H), 6.69 (dd, J = 3.8, 2.8 Hz, 1H), 4.20-4.10 (m, 2H), 3.32 (s, 2H), 3.23 (s, 3H), 3.22-3.19 (m, 2H), 2.24 (t, J = 7.1 Hz, 2H), 1.83 (p, J = 7.2 Hz, 2H). 19F NMR (376 MHz, DMSO-d6) −115.04. |
| 1-32 | 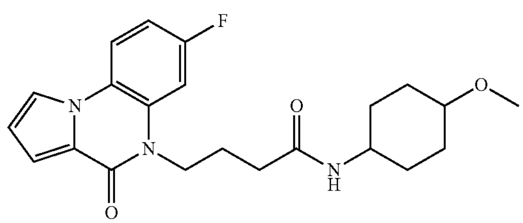 [SMILES: COC1CCC(NC(=O)CCCn2c(=O)c3cccn3c3ccc(F)cc32)CC1] | Tr(MET-uHPLC-AB-101) = 2.76 min m/z (ES⁺) (M + H)⁺ 400.2, 100% | 1H NMR (500 MHz, DMSO-d6) 8.22-8.14 (m, 2H), 7.73 (d, J = 7.6 Hz, 1H), 7.57 (dd, J = 11.3, 2.6 Hz, 1H), 7.21-7.14 (m, 1H), 7.04 (dd, J = 3.9, 1.5 Hz, 1H), 6.69 (dd, J = 3.8, 2.8 Hz, 1H), 4.19-4.09 (m, 2H), 3.57-3.45 (m, 1H), 3.21 (s, 3H), 3.11-3.02 (m, 1H), 2.20 (t, J = 7.1 Hz, 2H), 2.00-1.89 (m, 2H), 1.87-1.72 (m, 4H), 1.19-1.11 (m, 4H). 19F NMR (376 MHz, DMSO-d6) −115.03. |
| 1-33 | 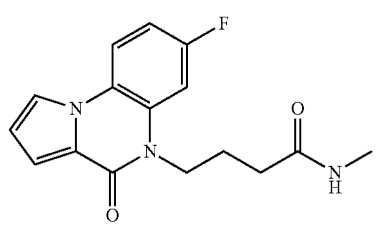 [SMILES: CNC(=O)CCCn1c(=O)c2cccn2c2ccc(F)cc21] | Tr(MET-uHPLC-AB-101) = 2.23 min m/z (ES⁺) (M + H)⁺ 302.2, 98% | 1H NMR (500 MHz, DMSO-d6) 8.20-8.16 (m, 2H), 7.82-7.74 (m, 1H), 7.61 (dd, J = 11.4, 2.6 Hz, 1H), 7.17 (td, J = 8.9, 8.5, 2.6 Hz, 1H), 7.05 (dd, J = 3.9, 1.5 Hz, 1H), 6.69 (dd, J = 3.8, 2.8 Hz, 1H), 4.18-4.12 (m, 2H), 2.57 (d, J = 4.6 Hz, 3H), 2.22 (t, J = 7.1 Hz, 2H), 1.83 (p, J = 7.1 Hz, 2H). 19F NMR (376 MHz, DMSO-d6) −115.03. |
| 1-34 | 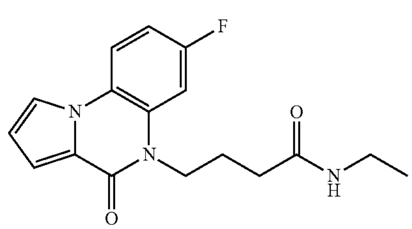 [SMILES: CCNC(=O)CCCn1c(=O)c2cccn2c2ccc(F)cc21] | Tr(METCR1603) = 3.41 min m/z (ES⁺) (M + H)⁺ 316.3, 95% | 1H NMR (500 MHz, DMSO-d6) 8.21-8.14 (m, 2H), 7.83 (t, J = 4.5 Hz, 1H), 7.59 (dd, J = 11.3, 2.6 Hz, 1H), 7.21-7.13 (m, 1H), 7.05 (dd, J = 3.9, 1.5 Hz, 1H), 6.69 (dd, J = 3.8, 2.8 Hz, 1H), 4.19-4.12 (m, 2H), 3.11-3.02 (m, 2H), 2.21 (t, J = 7.1 Hz, 2H), 1.83 (p, J = 7.3 Hz, 2H), 1.00 (t, J = 7.2 Hz, 3H). 19F NMR (376 MHz, DMSO-d6) −115.03. |

| Ex. | Structure | LCMS data | NMR data |
|---|---|---|---|
| 1-35 | 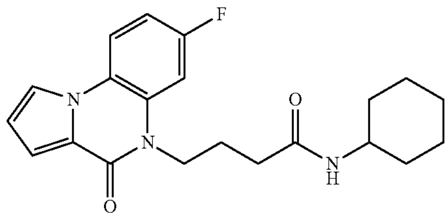 [SMILES: O=C(CCCn1c(=O)c2cccn2c2ccc(F)cc21)NC1CCCCC1] | Tr(METCR1603) = 4.19 min m/z (ES+) (M + H)+ 370.2, 100% | 1H NMR (500 MHz, DMSO-d6) 8.22-8.13 (m, 2H), 7.72 (d, J = 7.8 Hz, 1H), 7.57 (dd, J = 11.3, 2.6 Hz, 1H), 7.17 (td, J = 8.9, 2.6 Hz, 1H), 7.04 (dd, J = 3.8, 1.4 Hz, 1H), 6.69 (dd, J = 3.8, 2.8 Hz, 1H), 4.20-4.09 (m, 2H), 3.58-3.47 (m, 1H), 2.20 (t, J = 7.1 Hz, 2H), 1.82 (p, J = 7.1 Hz, 2H), 1.78-1.60 (m, 4H), 1.58-1.49 (m, 1H), 1.30-1.03 (m, 5H). 19F NMR (376 MHz, DMSO-d6) −115.03. |
| 1-36 | 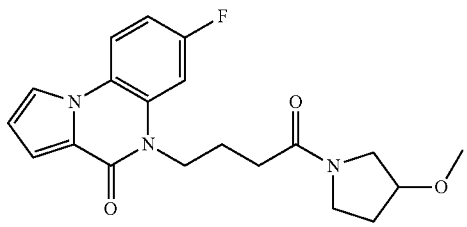 [SMILES: COC1CCN(C(=O)CCCn2c(=O)c3cccn3c3ccc(F)cc32)C1] | Tr(METCR1603) = 3.50 min m/z (ES+) (M + H)+ 372.2, 95% | 1H NMR (500 MHz, DMSO-d6) 8.23-8.09 (m, 2H), 7.73 (ddd, J = 21.6, 11.4, 2.3 Hz, 1H), 7.16 (td, J = 8.8, 2.4 Hz, 1H), 7.04 (dd, J = 3.9, 1.4 Hz, 1H), 6.68 (dd, J = 3.8, 2.8 Hz, 1H), 4.18-4.11 (m, 2H), 4.07 (s, 1H), 3.99 (s, 1H), 3.71-3.67 (m, 2H), 3.36 (t, J = 5.4 Hz, 1H), 3.30-3.26 (m, 1H), 2.86 (s, 3H), 2.57-2.53 (m, 3H), 1.91-1.76 (m, 2H). 19F NMR (376 MHz, DMSO-d6) −114.98 (app d, J = 9.4 Hz). |
| 1-37 | 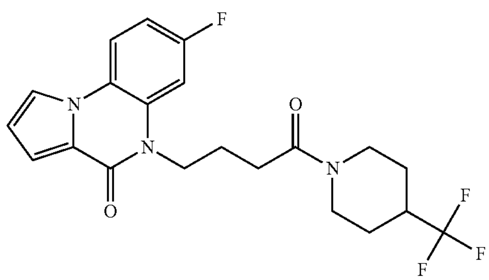 [SMILES: O=C(CCCn1c(=O)c2cccn2c2ccc(F)cc21)N1CCC(C(F)(F)F)CC1] | Tr(METCR1603) = 4.36 min m/z (ES+) (M + H)+ 424.1, 100% | 1H NMR (500 MHz, DMSO-d6) 8.30-8.06 (m, 2H), 7.75 (dd, J = 11.4, 2.6 Hz, 1H), 7.34-7.07 (m, 1H), 7.03 (dd, J = 3.9, 1.5 Hz, 1H), 6.69 (dd, J = 3.8, 2.8 Hz, 1H), 4.53 (d, J = 12.8 Hz, 1H), 4.28-4.06 (m, 2H), 3.95 (d, J = 13.0 Hz, 1H), 3.13-2.91 (m, 1H), 2.77-2.49 (m, 4H), 2.07-1.67 (m, 4H), 1.60-1.06 (m, 2H). 19F NMR (376 MHz, DMSO-d6) −72.43, −115.06. |
| 1-38 | 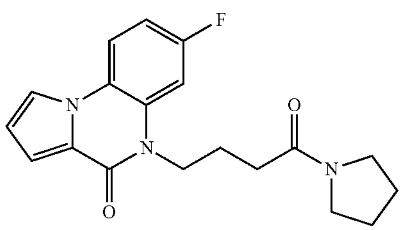 [SMILES: O=C(CCCn1c(=O)c2cccn2c2ccc(F)cc21)N1CCCC1] | Tr(MET-uHPLC-AB-101) = 2.77 min m/z (ES+) (M + H)+ 342.2, 98% | 1H NMR (500 MHz, DMSO-d6) 8.21-8.13 (m, 2H), 7.80 (dd, J = 11.4, 2.6 Hz, 1H), 7.16 (td, J = 8.9, 2.6 Hz, 1H), 7.04 (dd, J = 3.8, 1.4 Hz, 1H), 6.69 (dd, J = 3.8, 2.8 Hz, 1H), 4.20-4.11 (m, 2H), 3.38 (t, J = 6.8 Hz, 2H), 3.28 (t, J = 6.9 Hz, 2H), 2.42 (t, J = 6.5 Hz, 2H), 1.86 (dq, J = 11.3, 5.9, 5.0 Hz, 4H), 1.75 (p, J = 6.9 Hz, 2H). 19F NMR (376 MHz, DMSO-d6) −115.00. |
| 1-39 | 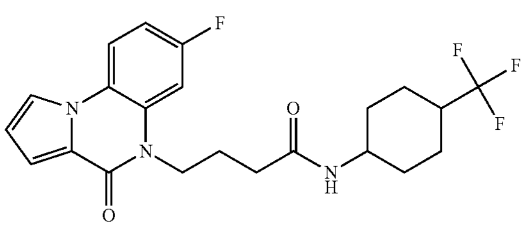 [SMILES: O=C(CCCn1c(=O)c2cccn2c2ccc(F)cc21)NC1CCC(C(F)(F)F)CC1] | Tr(METCR1603) = 4.41 min m/z (ES+) (M + H)+ 438.2, 100% | 1H NMR (500 MHz, DMSO-d6) 8.22-8.13 (m, 2H), 7.86 (d, J = 7.1 Hz, 1H), 7.56 (dd, J = 11.3, 2.6 Hz, 1H), 7.17 (td, J = 8.5, 2.6 Hz, 1H), 7.04 (dd, J = 3.8, 1.4 Hz, 1H), 6.69 (dd, J = 3.8, 2.8 Hz, 1H), 4.21-4.13 (m, 2H), 3.91-3.88 (m, 1H), 2.27 (t, J = 7.1 Hz, 3H), 1.84 (p, J = 7.1 Hz, 2H), 1.69 (d, J = 12.8 Hz, 2H), 1.66-1.45 (m, 6H). 19F NMR (376 MHz, DMSO-d6) −71.47 (major rotamer), −72.09 (minor rotamer), −115.07. |
| 1-40 | 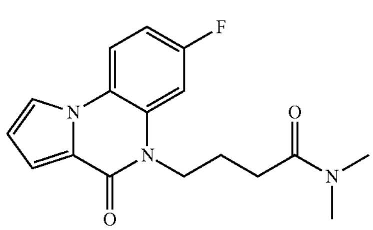 [SMILES: CN(C)C(=O)CCCn1c(=O)c2cccn2c2ccc(F)cc21] | Tr(METCR1603) = 3.47 min m/z (ES+) (M + H)+ 316.2, 100% | 1H NMR (500 MHz, DMSO-d6) 8.22-8.13 (m, 2H), 7.80 (dd, J = 11.4, 2.6 Hz, 1H), 7.22-7.12 (m, 1H), 7.05 (dd, J = 3.9, 1.5 Hz, 1H), 6.69 (dd, J = 3.8, 2.8 Hz, 1H), 4.18-4.10 (m, 2H), 2.96 (s, 3H), 2.84 (s, 3H), 2.52-2.44 (m, 2H), 1.88-1.78 (m, 2H). 19F NMR (376 MHz, DMSO-d6) −114.99. |

| Ex. | Structure | LCMS data | NMR data |
|---|---|---|---|
| 1-41 | 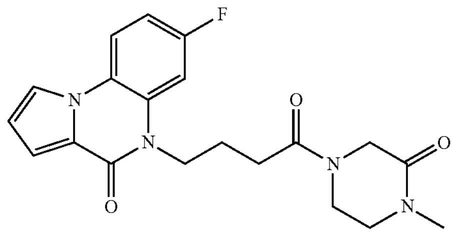 [SMILES: CN1CCN(C(=O)CCCn2c(=O)c3cccn3c3ccc(F)cc32)CC1=O] | Tr(METCR1603) = 3.16 min m/z (ES⁺) (M + H)⁺ 385.3, 100% | 1H NMR (500 MHz, 338 K, DMSO-d6) 8.27-7.95 (m, 2H), 7.65 (d, J = 10.3 Hz, 1H), 7.13 (ddd, J = 8.9, 8.1, 2.6 Hz, 1H), 7.04 (dd, J = 3.9, 1.5 Hz, 1H), 6.68 (dd, J = 3.8, 2.8 Hz, 1H), 4.30-4.10 (m, 2H), 4.10-3.86 (m, 2H), 3.82-3.61 (m, 2H), 3.52-3.29 (m, 2H), 2.88 (s, 3H), 2.50 (d, J = 3.7 Hz, 2H), 2.03-1.76 (m, 2H). 19F NMR (376 MHz, DMSO-d6) −115.08 (app d, J = 3.2 Hz). |
| 1-42 | 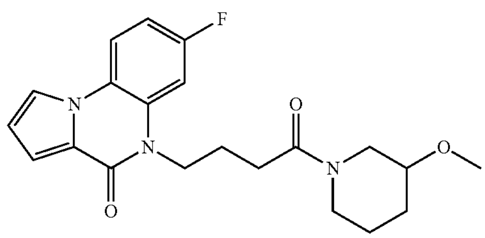 [SMILES: COC1CCCN(C(=O)CCCn2c(=O)c3cccn3c3ccc(F)cc32)C1] | Tr(METCR1603) = 3.77 min m/z (ES⁺) (M + H)⁺ 386.2, 100% | 1H NMR (500 MHz, DMSO-d6) 8.25-8.12 (m, 2H), 7.76 (ddd, J = 10.9, 8.0, 2.5 Hz, 1H), 7.17 (td, J = 8.8, 2.6 Hz, 1H), 7.05 (dd, J = 3.8, 1.4 Hz, 1H), 6.69 (dd, J = 3.8, 2.8 Hz, 1H), 4.21-4.09 (m, 2H), 3.93-3.52 (m, 1H), 3.52-3.41 (m, 1H), 3.29-3.08 (m, 6H), 2.48-2.40 (m, 2H), 1.89-1.81 (m, 3H), 1.77-1.23 (m, 3H). 19F NMR (376 MHz, DMSO-d6) −115.02. |
| 1-43 | 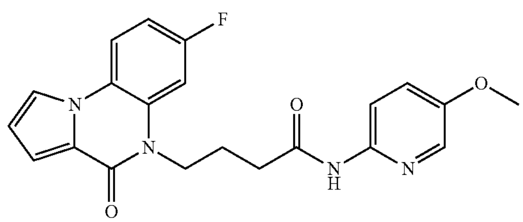 | Tr(METCR1603) = 3.93 min m/z (ES⁺) (M + H)⁺ 395.2, 100% | 1H NMR (500 MHz, DMSO-d6) 10.34 (s, 1H), 8.35-8.12 (m, 2H), 8.05-7.84 (m, 2H), 7.58 (dd, J = 11.3, 2.6 Hz, 1H), 7.41 (dd, J = 9.1, 3.1 Hz, 1H), 7.26-7.09 (m, 1H), 7.04 (dd, J = 3.9, 1.5 Hz, 1H), 6.68 (dd, J = 3.8, 2.8 Hz, 1H), 4.34-4.08 (m, 2H), 3.79 (s, 3H), 2.57-2.48 (m, 2H), 2.00-1.59 (m, 2H). 19F NMR (376 MHz, DMSO-d6) −115.08. |
| 1-44 | 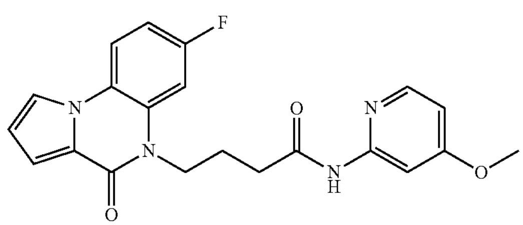 [SMILES: COc1ccnc(NC(=O)CCCn2c(=O)c3cccn3c3ccc(F)cc32)c1] | Tr(METCR1603) = 3.93 min m/z (ES⁺) (M + H)⁺ 395.2, 100% | 1H NMR (500 MHz, DMSO-d6) 10.43 (s, 1H), 8.31-8.14 (m, 2H), 8.10 (d, J = 5.8 Hz, 1H), 7.89-7.65 (m, 1H), 7.58 (dd, J = 11.3, 2.6 Hz, 1H), 7.28-7.09 (m, 1H), 7.04 (dd, J = 3.9, 1.5 Hz, 1H), 6.81-6.42 (m, 2H), 4.34-4.08 (m, 2H), 3.80 (s, 3H), 2.61-2.48 (m, 2H), 1.98-1.62 (m, 2H). 19F NMR (376 MHz, DMSO-d6) −115.15 |
| 1-45 | 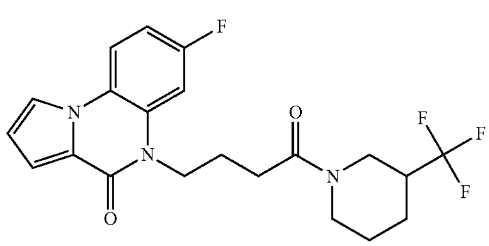 [SMILES: O=C(CCCn1c(=O)c2cccn2c2ccc(F)cc21)N1CCCC(C(F)(F)F)C1] | Tr(METCR1603) = 4.47 min m/z (ES⁺) (M + H)⁺ 424.2, 96% | 1H NMR (500 MHz, DMSO-d6) 8.47-8.03 (m, 2H), 7.96-7.47 (m, 1H), 7.28-7.09 (m, 1H), 7.11-6.93 (m, 1H), 6.85-6.56 (m, 1H), 4.52-4.26 (m, 1H), 4.26-4.06 (m, 2H), 3.94-3.80 (m, 1H), 3.21-2.87 (m, 1H), 2.82-2.59 (m, 1H), 2.54-2.52 (m, 2H), 2.44-2.18 (m, 1H), 1.96-1.92 (br. m, 1H), 1.87-1.84 (br m, 2H), 1.76-1.64 (m, 1H), 1.63-1.24 (m, 2H). 19F NMR (376 MHz, DMSO-d6) −70.86 (app d, J = 132.5 Hz), −115.08. |
| 1-46 | 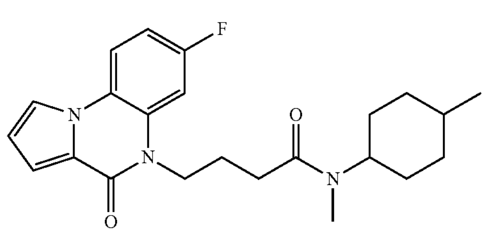 [SMILES: CC1CCC(N(C)C(=O)CCCn2c(=O)c3cccn3c3ccc(F)cc32)CC1] | Tr(METCR1603) = 4.88 min m/z (ES⁺) (M + H)⁺ 398.2, 100% | 1H NMR (500 MHz, DMSO-d6) 8.22-8.14 (m, 2H), 7.81-7.74 (m, 1H), 7.17 (td, J = 8.9, 2.6 Hz, 1H), 7.08-7.00 (m, 1H), 6.72-6.65 (m, 1H), 4.32-4.23 (m, 0.5H, Isomer A), 4.20-4.11 (m, 2H), 3.59-3.49 (m, 0.5H, Isomer B), 2.85-2.68 (m, 3H), 2.49-2.42 (m, 2H), 1.88-1.78 (m, 2H), 1.73-1.41 (m, 6H), 1.36-1.21 (m, 1H), 1.08-0.83 (m, 5H). |

-continued

| Ex. | Structure | LCMS data | NMR data |
|---|---|---|---|
| 1-47 | 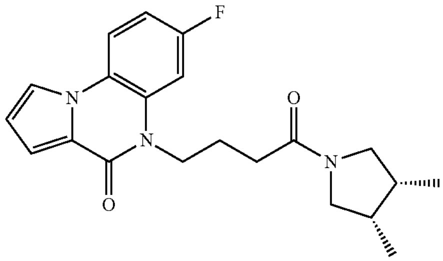 [SMILES: C[C@@H]1CN(C(=O)CCCn2c(=O)c3cccn3c3ccc(F)cc32)C[C@@H]1C] | Tr(MET-uHPLC-AB-101) = 3.29 min m/z (ES⁺) (M + H)⁺ 370.2, 100% | 1H NMR (500 MHz, DMSO-d6) 8.20-8.13 (m, 2H), 7.79 (dd, J = 11.4, 2.5 Hz, 1H), 7.20-7.13 (m, 1H), 7.04 (dd, J = 3.8, 1.3 Hz, 1H), 6.71-6.66 (m, 1H), 4.21-4.09 (m, 2H), 3.51 (dd, J = 9.9, 7.0 Hz, 1H), 3.38 (dd, J = 11.5, 6.9 Hz, 1H), 3.12-3.01 (m, 2H), 2.43-2.34 (m, 2H), 2.32-2.23 (m, 1H), 2.20-2.11 (m, 1H), 1.89-1.78 (m, 2H), 0.89 (d, J = 7.0 Hz, 3H), 0.87 (d, J = 7.0 Hz, 3H). 19F NMR (376 MHz, DMSO-d6) −115.00. |
| 1-48 | 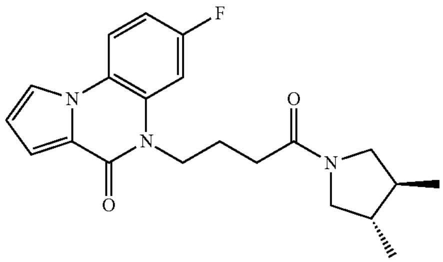 [SMILES: C[C@@H]1CN(C(=O)CCCn2c(=O)c3cccn3c3ccc(F)cc32)C[C@H]1C] | Tr(MET-uHPLC-AB-101) = 3.33 min m/z (ES⁺) (M + H)⁺ 370.2, 100% | 1H NMR (500 MHz, DMSO-d6) 8.21-8.13 (m, 2H), 7.78 (dd, J = 11.4, 2.6 Hz, 1H), 7.20-7.12 (m, 1H), 7.04 (dd, J = 3.8, 1.4 Hz, 1H), 6.69 (dd, J = 3.7, 2.9 Hz, 1H), 4.20-4.11 (m, 2H), 3.68-3.57 (m, 2H), 2.98-2.90 (m, 1H), 2.78-2.69 (m, 1H), 2.46-2.30 (m, 2H), 1.89-1.79 (m, 2H), 1.79-1.68 (m, 1H), 1.68-1.55 (m, 1H), 1.01-0.95 (m, 6H). 19F NMR (376 MHz, DMSO-d6) −115.03. |
| 1-49 | 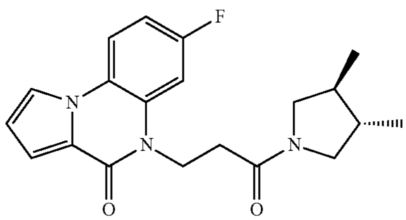 [SMILES: C[C@@H]1CN(C(=O)CCn2c(=O)c3cccn3c3ccc(F)cc32)C[C@H]1C] | Tr(METCR1416) = 4.12 min m/z (ES⁺) (M + H)⁺ 356.3, 100% | 1H NMR (500 MHz, DMSO-d6) 8.34-8.05 (m, 2H), 7.47 (dd, J = 11.3, 2.6 Hz, 1H), 7.25-7.12 (m, 1H), 7.05 (dd, J = 3.9, 1.5 Hz, 1H), 6.69 (dd, J = 3.8, 2.8 Hz, 1H), 4.54-4.28 (m, 2H), 3.75-3.55 (m, 2H), 2.99-2.83 (m, 1H), 2.81-2.71 (m, 1H), 2.69-2.54 (m, 2H), 1.77-1.64 (m, 1H), 1.65-1.47 (m, 1H), 0.96 (d, J = 6.4 Hz, 3H), 0.92 (d, J = 6.5 Hz, 3H). 19F NMR (376 MHz, DMSO-d6) −115.09. |

Scheme for Method 2

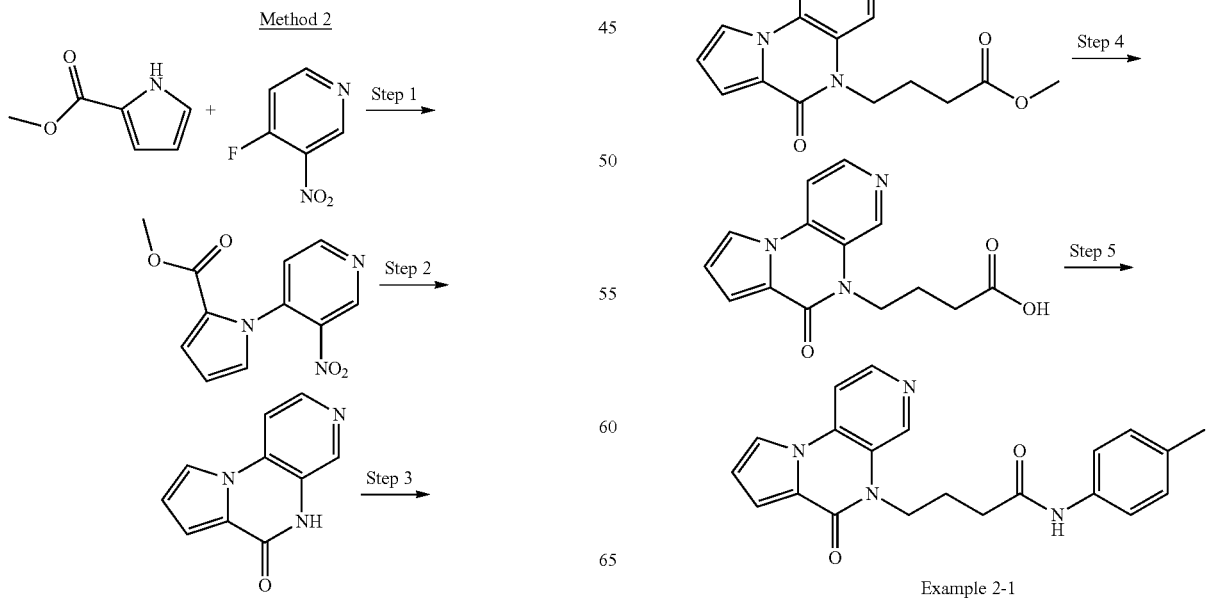

Example 2-1

Example 2-1

Step 1: Methyl 1-(3-nitro-4-pyridyl)pyrrole-2-carboxylate

NaH (60%, 1.24 g, 31.0 mmol) and methyl 1H-pyrrole-2-carboxylate (3.17 g, 25.3 mmol) were dissolved in DMF (10 mL) and 4-fluoro-3-nitro-pyridine (4.00 g, 28.2 mmol) was added. The reaction mixture was stirred at rt for 2 h. The reaction mixture was concentrated. The residue was triturated with water (50 mL) to give the title compound. $^1$H NMR (500 MHz DMSO-$d_6$) δ 9.34 (s, 1H), 9.02 (d, J=5.2 Hz, 1H), 7.76 (d, J=5.2 Hz, 1H), 7.41 (dd, J=2.8, 1.7 Hz, 1H), 7.14 (dd, J=3.9, 1.7 Hz, 1H), 6.48 (dd, J=3.9, 2.8 Hz, 1H), 3.62 (s, 3H). Tr(METCR1410)=1.05 min, (ES$^+$) (M+H)$^+$ 247.9, 95%.

Step 2: 2,8,11-Triazatricyclo[7.4.0.0$^{2,6}$]trideca-1(9),3,5,10,12-pentaen-7-one Ethanol (30 mL) and water (30 mL) were added to a mixture of methyl 1-(3-nitro-4-pyridyl)pyrrole-2-carboxylate (700 mg, 2.83 mmol) and sodium dithionite (1.97 g, 11.3 mmol). The mixture was heated at 75° C. for 8 h. Further sodium dithionite (1.97 g, 11.3 mmol) was added and the reaction was stirred at rt overnight. The mixture was concentrated in vacuo to approximately 30 mL, diluted with water (10 mL) and filtered. The solids were dried under vacuum overnight to give the title compound. $^1$H NMR (500 MHz, DMSO-$d_6$) δ 11.45 (s, 1H), 8.54 (s, 1H), 8.35 (d, J=5.5 Hz, 1H), 8.31-8.22 (m, 1H), 8.04 (d, J=5.5 Hz, 1H), 7.18-6.99 (m, 1H), 6.78 (dd, J=3.8, 2.9 Hz, 1H).

Step 3: Methyl 4-(7-oxo-2,8,11-triazatricyclo[7.4.0.0$^{2,6}$]trideca-1(9),3,5,10,12-pentaen-8-yl)butanoate NaH (60%, 131 mg, 3.27 mmol) was added portionwise over 5 min to a cold (0° C.) solution of 2,8,11-triazatricyclo[7.4.0.0$^{2,6}$]trideca-1(9),3,5,10,12-pentaen-7-one (550 mg, 2.97 mmol) in anhydrous DMF (5 mL). The reaction mixture was stirred at 0° C. for 10 min and methyl 4-bromobutanoate (97%, 1.11 g, 5.94 mmol) was added dropwise over 5 minutes. After completion of the addition, the reaction mixture was allowed to warm to rt and stirred for 7 h. The reaction mixture was concentrated to dryness and triturated with water (50 mL). Purification by column chromatography (silica, 10-60% EtOAc in heptane) gave the title compound. $^1$H NMR (500 MHz DMSO-$d_6$) δ 8.89 (s, 1H), 8.44 (d, J=5.4 Hz, 1H), 8.29 (dd, J=2.9, 1.4 Hz, 1H), 8.11 (d, J=5.4 Hz, 1H), 7.14 (dd, J=3.8, 1.4 Hz, 1H), 6.79 (dd, J=3.7, 2.9 Hz, 1H), 4.61-4.12 (m, 2H), 3.56 (s, 3H), 2.49 (m, 2H), 1.93 (p, J=7.2 Hz, 2H). Tr(METCR1410)=0.80 min, (ES$^+$) (M+H)$^+$ 286, 100%.

Step 4: 4-(7-Oxo-2,8,11-triazatricyclo[7.4.0.0$^{2,6}$]trideca-1(9),3,5,10,12-pentaen-8-yl)butanoic acid Methyl 4-(7-oxo-2,8,11-triazatricyclo[7.4.0.0$^{2,6}$]trideca-1(9),3,5,10,12-pentaen-8-yl)butanoate (210 mg, 0.736 mmol) was dissolved in 2 M sodium hydroxide (3.7 mL, 7.36 mmol) and stirred at rt for 2 h. The reaction mixture was acidified with 2 M aqueous HCl to pH 1 and the resultant precipitate filtered. Trituration with methanol (2 mL) gave the title compound. $^1$H NMR (500 MHz DMSO-$d_6$) δ 9.06 (s, 1H), 8.67 (d, J=6.1 Hz, 1H), 8.53-8.00 (m, 2H), 7.26 (dd, J=3.8, 1.3 Hz, 1H), 6.91 (dd, J=3.7, 3.1 Hz, 1H), 4.49-4.08 (m, 2H), 2.42 (t, J=7.1 Hz, 2H), 1.88 (p, J=7.2 Hz, 2H). Tr(METCR1410)=0.74 min, (ES$^+$) (M+H)$^+$ 272, 92%.

Step 5: 4-(7-Oxo-2,8,11-triazatricyclo[7.4.0.0$^{2,6}$]trideca-1(9),3,5,10,12-pentaen-8-yl)-N-(p-tolyl)butanamide p-Methyl aniline (1.7 mg, 0.111 mmol) was treated with a solution of HATU (63 mg, 0.166 mmol), 4-(7-oxo-2,8,11-triazatricyclo[7.4.0.0$^{2,6}$]trideca-1(9),3,5,10,12-pentaen-8-yl)butanoic acid (30 mg, 0.111 mmol) and DIPEA (0.058 mL, 0.332 mmol) in DMF (1 mL). The reaction mixture stood at rt for 1 h. Purification by basic preparative HPLC gave the title compound. $^1$H NMR (500 MHz, DMSO-$d_6$) δ 9.83 (s, 1H), 8.94 (s, 1H), 8.45 (d, J=5.4 Hz, 1H), 8.29 (dd, J=2.9, 1.4 Hz, 1H), 8.11 (d, J=5.5 Hz, 1H), 7.44 (d, J=8.4 Hz, 2H), 7.13 (dd, J=3.8, 1.4 Hz, 1H), 7.08 (d, J=8.3 Hz, 2H), 6.78 (dd, J=3.7, 2.9 Hz, 1H), 4.80-4.10 (m, 2H), 2.46 (t, J=7.3 Hz, 2H), 2.23 (s, 3H), 2.03-1.75 (m, 2H). Tr(METCR1603)=3.59 min m/z (ES$^+$) (M+H)$^+$ 361.2, 100%.

Also prepared by this route:

| Ex. | Structure | LCMS data | NMR data |
|---|---|---|---|
| 2-2 | 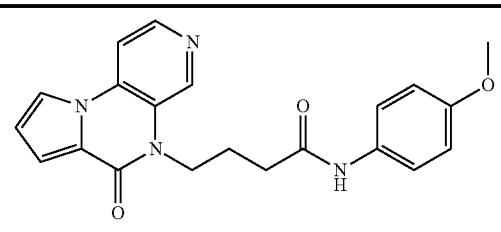 | Tr(METCR1603) = 3.31 min m/z (ES$^+$) (M + H)$^+$ 377.2, 100% | 1H NMR (500 MHz, DMSO-d6) 9.78 (s, 1H), 8.94 (s, 1H), 8.45 (d, J = 5.4 Hz, 1H), 8.29 (dd, J = 2.9, 1.4 Hz, 1H), 8.11 (d, J = 5.5 Hz, 1H), 7.57-7.35 (m, 2H), 7.14 (dd, J = 3.8, 1.4 Hz, 1H), 6.94-6.82 (m, 2H), 6.78 (dd, J = 3.8, 2.9 Hz, 1H), 4.72-4.10 (m, 2H), 3.71 (s, 3H), 2.45 (t, J = 7.2 Hz, 2H), 2.02-1.89 (m, 2H). |
| 2-3 | 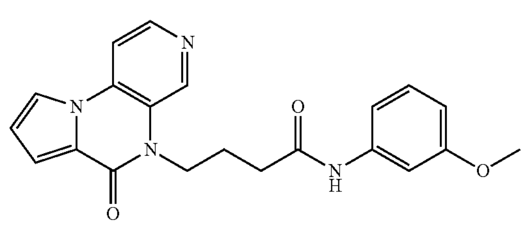 [SMILES: COc1cccc(NC(=O)CCCn2c(=O)c3cccn3c3ccncc32)c1] | Tr(METCR1603) = 3.43 min m/z (ES$^+$) (M + H)$^+$ 377.1, 100% | 1H NMR (500 MHz, DMSO-d6) 9.91 (s, 1H), 8.93 (s, 1H), 8.45 (d, J = 5.4 Hz, 1H), 8.29 (dd, J = 2.9, 1.5 Hz, 1H), 8.11 (d, J = 5.4 Hz, 1H), 7.36-7.21 (m, 1H), 7.23-6.93 (m, 3H), 6.78 (dd, J = 3.8, 2.9 Hz, 1H), 6.66-6.40 (m, 1H), 4.44-4.18 (m, 2H), 3.71 (s, 3H), 2.48-2.41 (m, 2H), 2.03-1.58 (m, 2H). |

| Ex. | Structure | LCMS data | NMR data |
|---|---|---|---|
| 2-4 | 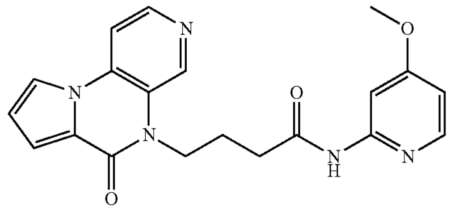 [SMILES: COc1ccnc(NC(=O)CCCn2c(=O)c3cccn3c3ccncc32)c1] | Tr(METCR1603) = 3.12 min m/z (ES+) (M + H)+ 378.2, 100% | 1H NMR (400 MHz, DMSO-d6) 10.42 (s, 1H), 8.91 (s, 1H), 8.45 (d, J = 5.4 Hz, 1H), 8.29 (dd, J = 2.9, 1.4 Hz, 1H), 8.20-7.95 (m, 2H), 7.69 (d, J = 2.2 Hz, 1H), 7.12 (dd, J = 3.8, 1.4 Hz, 1H), 6.94-6.74 (m, 1H), 6.68 (dd, J = 5.8, 2.4 Hz, 1H), 4.46-4.16 (m, 2H), 3.80 (s, 3H), 2.56-2.54 (m, 2H), 2.02-1.83 (m, 2H). |
| 2-5 | 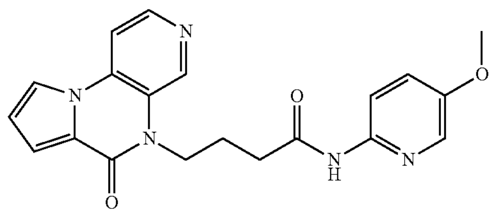 [SMILES: COc1ccc(NC(=O)CCCn2c(=O)c3cccn3c3ccncc32)nc1] | Tr(METCR1603) = 3.11 min m/z (ES+) (M + H)+ 378.1, 100% | 1H NMR (500 MHz, DMSO-d6) 10.34 (s, 1H), 8.92 (s, 1H), 8.45 (d, J = 5.4 Hz, 1H), 8.29 (dd, J = 2.9, 1.4 Hz, 1H), 8.11 (d, J = 5.5 Hz, 1H), 8.05-7.92 (m, 2H), 7.40 (dd, J = 9.1, 3.1 Hz, 1H), 7.13 (dd, J = 3.8, 1.4 Hz, 1H), 6.78 (dd, J = 3.7, 2.9 Hz, 1H), 4.47-4.20 (m, 2H), 3.79 (s, 3H), 2.60-2.52 (m, 2H), 2.01-1.84 (m, 2H). |

Scheme for Method 3

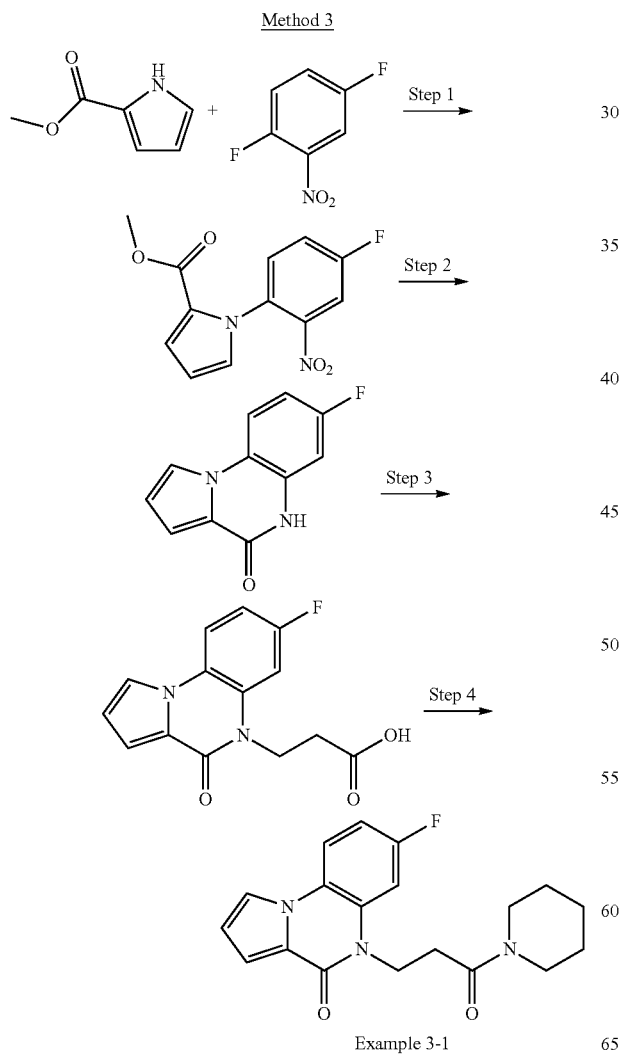

Example 3-1

Example 3-1

Step 1: Methyl 1-(4-fluoro-2-nitro-phenyl)pyrrole-2-carboxylate

Methyl 1H-pyrrole-2-carboxylate (5.00 g, 40.0 mmol) and $Cs_2CO_3$ (14.47 g, 44.4 mmol) were dissolved in DMF (10 mL) and 1,4-difluoro-2-nitro-benzene (7.06 g, 44.4 mmol) was added. The reaction mixture was heated to 60° C. overnight. $Cs_2CO_3$ (2.05 g, 6.29 mmol) was added and the reaction mixture was heated to 60° C. for 2 h. The reaction mixture was concentrated. The residue was partitioned between water (100 mL) and EtOAc (100 mL) and extracted with EtOAc (2×50 mL). The combined organics were dried ($MgSO_4$) and concentrated in vacuo. Trituration with MeCN (20 mL) gave the title compound. $^1H$ NMR (500 MHz, DMSO-$d_6$) δ 8.16 (dd, J=8.3, 2.9 Hz, 1H), 7.86-7.60 (m, 2H), 7.29 (dd, J=2.7, 1.8 Hz, 1H), 7.06 (dd, J=3.9, 1.8 Hz, 1H), 6.39 (dd, J=3.9, 2.7 Hz, 1H), 3.60 (s, 3H). Tr(METCR1410)=1.16 min, (ES+) (M+H)+ 265.0, 100%.

Step 2: 7-Fluoro-5H-pyrrolo[1,2-a]quinoxalin-4-one

Methyl 1-(4-fluoro-2-nitro-phenyl)pyrrole-2-carboxylate (1.00 g, 3.78 mmol) was dissolved in acetic acid (10 mL) before the addition of iron (845 mg, 15.1 mmol). The mixture was heated to 100° C. for 30 min. The mixture was concentrated in vacuo and the residue then stirred in methanol (100 ml) at 80° C. for 30 min. The slurry was filtered through Celite, washing with a further portion of hot methanol (100 mL). The combined filtrates were concentrated in vacuo to give the title compound. $^1H$ NMR (500 MHz, DMSO-$d_6$) δ 12.69-10.56 (m, 1H), 8.90-7.71 (m, 2H), 7.62-6.85 (m, 3H), 6.82-6.45 (m, 1H).

Step 3: 3-(7-Fluoro-4-oxo-pyrrolo[1,2-a]quinoxalin-5-yl)propanoic acid

7-Fluoro-5H-pyrrolo[1,2-a]quinoxalin-4-one (700 mg, 3.46 mmol) was suspended in THF (40 mL) before the addition of ethyl prop-2-enoate (1.8 mL, 17.3 mmol) and sodium hydroxide (692 mg, 17.3 mmol). The mixture was stirred at rt for 4 days. The mixture was acidified by slow addition of 2 N HCl (25 ml), then the cloudy white mixture was extracted with DCM (3×100 mL). The combined organic layers were dried (MgSO$_4$) and concentrated in vacuo. The crude material was triturated with methanol (5 mL) and dried on filter to give the title compound. $^1$H NMR (500 MHz, DMSO-d$_6$) δ 12.39 (s, 1H), 8.32-8.06 (m, 2H), 7.52 (dd, J=11.2, 2.5 Hz, 1H), 7.17 (td, J=8.8, 2.5 Hz, 1H), 7.05 (dd, J=3.8, 1.3 Hz, 1H), 6.82-6.60 (m, 1H), 4.57-4.29 (m, 2H), 2.74-2.54 (m, 2H).

Step 4: 7-Fluoro-5-[3-oxo-3-(piperidin-1-yl)propyl]-4H,5H-pyrrolo[1,2-a]quinoxalin-4-one 3-(7-Fluoro-4-oxo-pyrrolo[1,2-a]quinoxalin-5-yl)propanoic acid (80 mg, 0.3 mmol) was dissolved in DMF (2 mL) before the addition of piperidine (89 µL, 0.9 mmol) then HATU (172 mg, 0.45 mmol). The mixture was stirred at rt for 15 min. The reaction mixture was purified by basic preparative HPLC to give the title compound. $^1$H NMR (500 MHz, Chloroform-d) δ 7.64 (dd, J=9.0, 5.2 Hz, 1H), 7.59 (dd, J=2.7, 1.5 Hz, 1H), 7.23 (dd, J=10.6, 2.6 Hz, 1H), 7.21 (dd, J=3.9, 1.5 Hz, 1H), 6.95 (ddd, J=9.0, 7.5, 2.6 Hz, 1H), 6.66 (dd, J=3.9, 2.8 Hz, 1H), 4.60-4.36 (m, 2H), 3.64-3.51 (i, 2H), 3.45-3.35 (m, 2H), 2.96-2.53 (m, 2H), 1.69-1.59 (m, 2H), 1.59-1.50 (m, 4H). $^{19}$F NMR (235 MHz, Chloroform-d) δ −114.07. Tr(MET-uHPLC-AB-101)=2.97 min, (ES$^+$) (M+H)$^+$ 342.3, 99%.

Also prepared by this route:

| Ex. | Structure | LCMS data | NMR data |
|---|---|---|---|
| 3-2 | 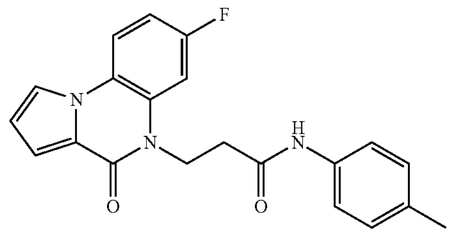 [SMILES: Cc1ccc(NC(=O)CCn2c(=O)c3cccn3c3ccc(F)cc32)cc1] | Tr(METCR1603) = 4.23 min m/z (ES$^+$) (M + H)$^+$ 364.2, 96% | 1H NMR (500 MHz, DMSO-d6) 9.94 (s, 1H), 8.35-8.01 (m, 2H), 7.56 (dd, J = 11.3, 2.6 Hz, 1H), 7.44 (d, J = 8.4 Hz, 2H), 7.27-7.13 (m, 1H), 7.13-6.95 (m, 3H), 6.71 (dd, J = 3.8, 2.8 Hz, 1H), 4.60-4.38 (m, 2H), 2.78-2.65 (m, 2H), 2.25 (s, 3H). 19F NMR (376 MHz, DMSO-d6) −115.14. |
| 3-3 | 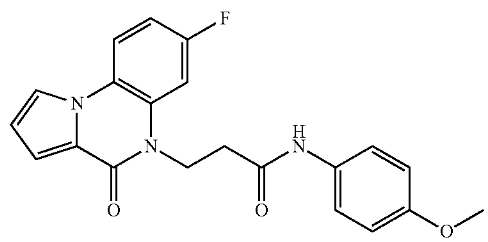 [SMILES: COc1ccc(NC(=O)CCn2c(=O)c3cccn3c3ccc(F)cc32)cc1] | Tr(METCR1603) = 3.96 min m/z (ES$^+$) (M + H)$^+$ 380.1, 100% | 1H NMR (500 MHz, DMSO-d6) 9.89 (s, 1H), 8.33-8.03 (m, 2H), 7.55 (dd, J = 11.2, 2.4 Hz, 1H), 7.45 (d, J = 9.0 Hz, 2H), 7.28-7.10 (m, 1H), 7.07 (d, J = 2.5 Hz, 1H), 6.86 (d, J = 9.0 Hz, 2H), 6.79-6.42 (m, 1H), 4.48 (t, J = 7.4 Hz, 2H), 3.71 (s, 3H), 2.68 (t, J = 7.4 Hz, 2H). 19F NMR (376 MHz, DMSO-d6) −115.14. |
| 3-4 | 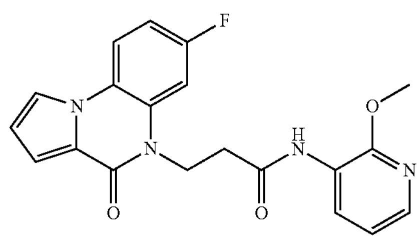 [SMILES: COc1ncccc1NC(=O)CCn1c(=O)c2cccn2c2ccc(F)cc21] | Tr(METCR1603) = 3.88 min m/z (ES$^+$) (M + H)$^+$ 381.2, 97% | 1H NMR (500 MHz, DMSO-d6) 9.52 (s, 1H), 8.25 (d, J = 6.5 Hz, 1H), 8.22-8.04 (m, 2H), 7.87 (dd, J = 4.9, 1.7 Hz, 1H), 7.53 (dd, J = 11.3, 2.5 Hz, 1H), 7.32-7.12 (m, 1H), 7.06 (dd, J = 3.8, 1.4 Hz, 1H), 6.96 (dd, J = 7.7, 5.0 Hz, 1H), 6.70 (dd, J = 3.8, 2.8 Hz, 1H), 4.48 (t, J = 7.3 Hz, 2H), 3.87 (s, 3H), 2.82 (t, J = 7.2 Hz, 2H). 19F NMR (376 MHz, DMSO-d6) −115.21. |
| 3-5 | 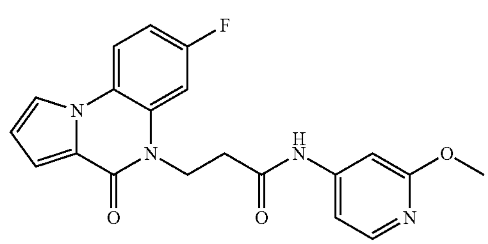 [SMILES: COc1cc(NC(=O)CCn2c(=O)c3cccn3c3ccc(F)cc32)ccn1] | Tr(METCR1603) = 3.83 min m/z (ES$^+$) (M + H)$^+$ 381.2, 100% | 1H NMR (500 MHz, DMSO-d6) 10.36 (s, 1H), 8.41-8.09 (m, 2H), 8.01 (d, J = 5.7 Hz, 1H), 7.57 (dd, J = 11.3, 2.6 Hz, 1H), 7.27-7.11 (m, 1H), 7.12-6.86 (m, 3H), 6.70 (dd, J = 3.8, 2.8 Hz, 1H), 4.78-4.31 (m, 2H), 3.81 (s, 3H), 2.98-2.68 (m, 2H). 19F NMR (376 MHz, DMSO-d6) −115.18. |
| 3-6 | 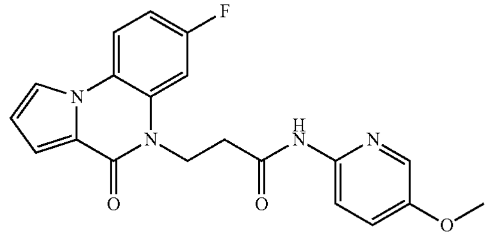 [SMILES: COc1ccc(NC(=O)CCn2c(=O)c3cccn3c3ccc(F)cc32)nc1] | Tr(MET-uHPLC-AB-101) = 2.76 min m/z (ES$^+$) (M + H)$^+$ 381.2, 98% | 1H NMR (500 MHz, DMSO-d6) 10.49 (s, 1H), 8.23-8.12 (m, 2H), 8.06-7.94 (m, 2H), 7.57 (dd, J = 11.3, 2.6 Hz, 1H), 7.42 (dd, J = 9.1, 3.0 Hz, 1H), 7.21-7.13 (m, 1H), 7.06 (dd, J = 3.9, 1.5 Hz, 1H), 6.70 (dd, J = 3.8, 2.8 Hz, 1H), 4.54-4.41 (m, 2H), 3.80 (s, 3H), 2.75 (t, J = 7.4 Hz, 2H). 19F NMR (376 MHz, DMSO-d6) −115.14. |

| Ex. | Structure | LCMS data | NMR data |
|---|---|---|---|
| 3-7 | 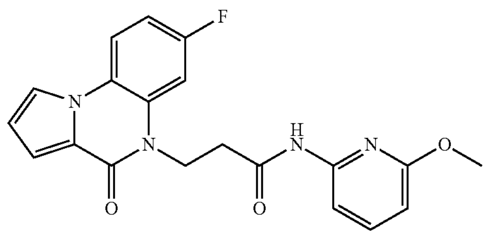 [SMILES: COc1cccc(NC(=O)CCn2c(=O)c3cccn3c3ccc(F)cc32)n1] | Tr(METCR1603) = 4.20 min m/z (ES+) (M + H)+ 381.2, 100% | 1H NMR (500 MHz, DMSO-d6) 10.38 (s, 1H), 8.36-8.01 (m, 2H), 7.76-7.61 (m, 2H), 7.57 (dd, J = 11.3, 2.6 Hz, 1H), 7.24-7.12 (m, 1H), 7.06 (dd, J = 3.9, 1.5 Hz, 1H), 6.70 (dd, J = 3.8, 2.8 Hz, 1H), 6.56-6.46 (m, 1H), 4.58-4.36 (m, 2H), 3.81 (s, 3H), 2.80 (t, J = 7.3 Hz, 2H). 19F NMR (376 MHz, DMSO-d6) −115.14. |
| 3-8 | 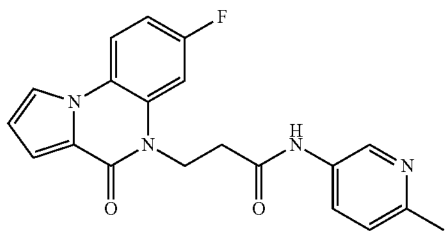 [SMILES: Cc1ccc(NC(=O)CCn2c(=O)c3cccn3c3ccc(F)cc32)cn1] | Tr(METCR1603) = 3.51 min m/z (ES+) (M + H)+ 365.2, 100% | 1H NMR (500 MHz, DMSO-d6) 10.14 (s, 1H), 8.54 (d, J = 2.5 Hz, 1H), 8.30-8.06 (m, 2H), 7.86 (dd, J = 8.4, 2.6 Hz, 1H), 7.55 (dd, J = 11.3, 2.6 Hz, 1H), 7.30-7.11 (m, 2H), 7.06 (dd, J = 3.9, 1.4 Hz, 1H), 6.70 (dd, J = 3.8, 2.8 Hz, 1H), 4.65-4.26 (m, 2H), 2.93-2.61 (m, 2H), 2.40 (s, 3H). 19F NMR (376 MHz, DMSO-d6) −115.18. |
| 3-9 | 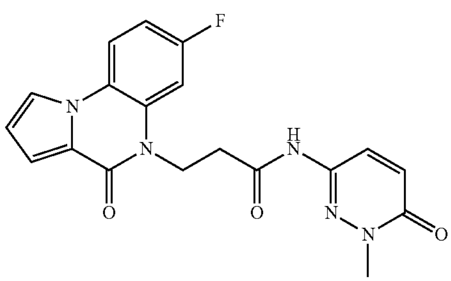 [SMILES: Cn1nc(NC(=O)CCn2c(=O)c3cccn3c3ccc(F)cc32)ccc1=O] | Tr(METCR1603) = 3.19 min m/z (ES+) (M + H)+ 382.2, 100% | 1H NMR (500 MHz, DMSO-d6) 10.67 (s, 1H), 8.25-8.14 (m, 2H), 7.94 (d, J = 9.9 Hz, 1H), 7.55 (dd, J = 11.3, 2.6 Hz, 1H), 7.26-7.12 (m, 1H), 7.06 (dd, J = 3.9, 1.5 Hz, 1H), 6.97 (d, J = 9.9 Hz, 1H), 6.70 (dd, J = 3.8, 2.8 Hz, 1H), 4.51-4.43 (m, 2H), 3.55 (s, 3H), 2.72 (t, J = 7.4 Hz, 2H). 19F NMR (376 MHz, DMSO-d6) −115.19. |
| 3-10 | 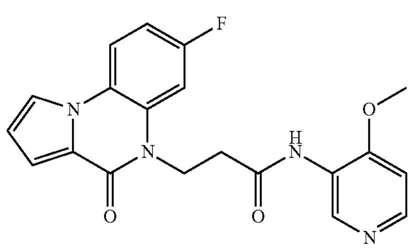 [SMILES: COc1ccncc1NC(=O)CCn1c(=O)c2cccn2c2ccc(F)cc21] | Tr(METCR1603) = 3.31 min m/z (ES+) (M + H)+ 381.2, 98% | 1H NMR (500 MHz, DMSO-d6) 9.51 (s, 1H), 8.81 (s, 1H), 8.25-8.15 (m, 3H), 7.53 (dd, J = 11.2, 2.4 Hz, 1H), 7.17 (td, J = 8.9, 2.6 Hz, 1H), 7.11-7.03 (m, 2H), 6.70 (dd, J = 3.8, 2.8 Hz, 1H), 4.48 (t, J = 7.2 Hz, 2H), 3.83 (s, 3H), 2.80 (t, J = 7.2 Hz, 2H). 19F NMR (376 MHz, DMSO-d6) −115.20. |
| 3-11 | 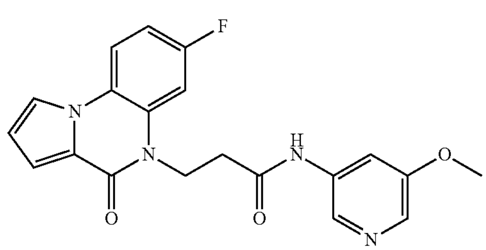 [SMILES: COc1cncc(NC(=O)CCn2c(=O)c3cccn3c3ccc(F)cc32)c1] | Tr(MET-uHPLC-AB-101) = 2.20 min m/z (ES+) (M + H)+ 381.2, 100% | 1H NMR (500 MHz, DMSO-d6) 10.26 (s, 1H), 8.26 (d, J = 2.0 Hz, 1H), 8.22-8.13 (m, 2H), 8.00 (d, J = 2.7 Hz, 1H), 7.69 (t, J = 2.3 Hz, 1H), 7.56 (dd, J = 11.3, 2.5 Hz, 1H), 7.21-7.13 (m, 1H), 7.07 (dd, J = 3.9, 1.4 Hz, 1H), 6.70 (dd, J = 3.8, 2.8 Hz, 1H), 4.55-4.45 (m, 2H), 3.80 (s, 3H), 2.78-2.70 (m, 2H). 19F NMR (376 MHz, DMSO-d6) −115.19. |
| 3-12 | 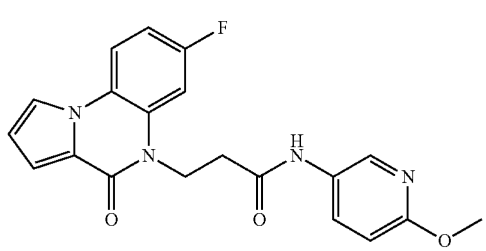 [SMILES: COc1ccc(NC(=O)CCn2c(=O)c3cccn3c3ccc(F)cc32)cn1] | Tr(MET-uHPLC-AB-101) = 2.76 min m/z (ES+) (M + H)+ 381.2, 99% | 1H NMR (500 MHz, DMSO-d6) 10.05 (s, 1H), 8.28 (d, J = 2.5 Hz, 1H), 8.24-8.14 (m, 2H), 7.84 (dd, J = 8.9, 2.7 Hz, 1H), 7.55 (dd, J = 11.3, 2.6 Hz, 1H), 7.17 (td, J = 8.9, 2.6 Hz, 1H), 7.07 (dd, J = 3.9, 1.5 Hz, 1H), 6.78 (d, J = 8.8 Hz, 1H), 6.70 (dd, J = 3.8, 2.8 Hz, 1H), 4.53-4.46 (m, 2H), 3.81 (s, 3H), 2.73-2.67 (m, 2H). 19F NMR (376 MHz, DMSO-d6) −115.19. |

| Ex. | Structure | LCMS data | NMR data |
|---|---|---|---|
| 3-13 | 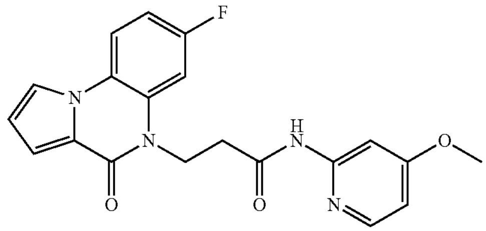 [SMILES: COc1ccnc(NC(=O)CCn2c(=O)c3cccn3c3ccc(F)cc32)c1] | Tr(METCR1603) = 3.82 min m/z (ES⁺) (M + H)⁺ 381.2, 100% | 1H NMR (500 MHz, DMSO-d6) 10.59 (s, 1H), 8.23-8.15 (m, 2H), 8.11 (d, J = 5.8 Hz, 1H), 7.71 (s, 1H), 7.57 (dd, J = 11.3, 2.6 Hz, 1H), 7.21-7.13 (m, 1H), 7.06 (dd, J = 3.9, 1.5 Hz, 1H), 6.74-6.66 (m, 2H), 4.52-4.44 (m, 2H), 3.81 (s, 3H), 2.82-2.72 (m, 2H). 19F NMR (376 MHz, DMSO-d6) −115.17 |
| 3-14 | 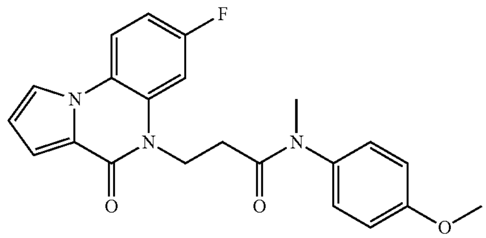 [SMILES: COc1ccc(N(C)C(=O)CCn2c(=O)c3cccn3c3ccc(F)cc32)cc1] | Tr(METCR1603) = 4.06 min m/z (ES⁺) (M + H)⁺ 394.2, 98% | 1H NMR (500 MHz, DMSO-d6) 8.16-8.10 (m, 2H), 7.26-7.20 (m, 3H), 7.13 (td, J = 8.8, 2.5 Hz, 1H), 7.00 (dd, J = 3.8, 1.3 Hz, 1H), 6.88 (d, J = 8.9 Hz, 2H), 6.68-6.63 (m, 1H), 4.34-4.28 (m, 2H), 3.71 (s, 3H), 3.12 (s, 3H), 2.40-2.33 (m, 2H). 19F NMR (376 MHz, DMSO-d6) −115.09. |
| 3-15 | 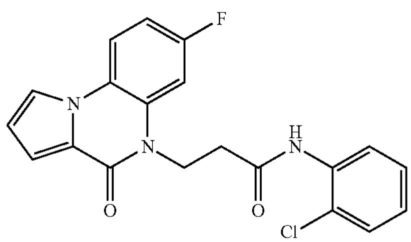 [SMILES: O=C(CCn1c(=O)c2cccn2c2ccc(F)cc21)Nc1ccccc1Cl] | Tr(METCR1603) = 4.27 min m/z (ES⁺) (M + H)⁺ 384.1, 97% | 1H NMR (500 MHz, DMSO-d6) 9.66 (s, 1H), 8.39-8.06 (m, 2H), 7.66 (d, J = 7.8 Hz, 1H), 7.54 (d, J = 9.1 Hz, 1H), 7.47 (dd, J = 8.0, 1.4 Hz, 1H), 7.37-7.25 (m, 1H), 7.25-7.12 (m, 2H), 7.07 (dd, J = 3.8, 1.4 Hz, 1H), 6.70 (dd, J = 3.8, 2.8 Hz, 1H), 4.50 (t, J = 7.2 Hz, 2H), 2.80 (t, J = 6.9 Hz, 2H). 19F NMR (376 MHz, DMSO-d6) −115.18. |
| 3-16 | 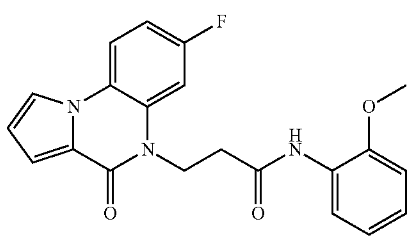 | Tr(METCR1603) = 4.14 min m/z (ES⁺) (M + H)⁺ 380.2, 100% | 1H NMR (500 MHz, DMSO-d6) 9.29 (s, 1H), 8.39-8.05 (m, 2H), 7.89 (d, J = 7.4 Hz, 1H), 7.54 (dd, J = 11.3, 2.3 Hz, 1H), 7.27-7.11 (m, 1H), 7.12-6.96 (m, 3H), 6.94-6.79 (m, 1H), 6.70 (dd, J = 3.8, 2.8 Hz, 1H), 4.47 (t, J = 7.3 Hz, 2H), 3.77 (s, 3H), 2.80 (t, J = 7.3 Hz, 2H). 19F NMR (376 MHz, DMSO-d6) −115.16. |
| 3-17 | 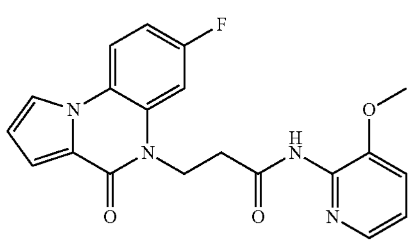 [SMILES: COc1cccnc1NC(=O)CCn1c(=O)c2cccn2c2ccc(F)cc21] | Tr(METCR 1603) = 3.44 min m/z (ES⁺) (M + H)⁺ 381.2, 100% | 1H NMR (500 MHz, DMSO-d6) 9.73 (s, 1H), 8.37-8.11 (m, 2H), 7.91 (dd, J = 4.8, 1.3 Hz, 1H), 7.55 (dd, J = 11.3, 2.6 Hz, 1H), 7.44 (dd, J = 8.2, 1.3 Hz, 1H), 7.30-7.11 (m, 2H), 7.07 (dd, J = 3.9, 1.4 Hz, 1H), 6.70 (dd, J = 3.8, 2.8 Hz, 1H), 4.75-4.23 (m, 2H), 3.76 (s, 3H), 2.88-2.75 (m, 2H). 19F NMR (376 MHz, DMSO-d6) −115.09. |
| 3-18 | 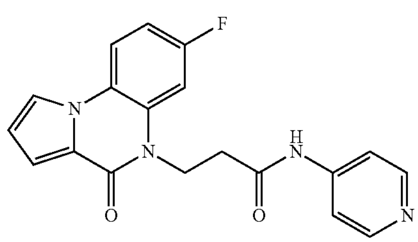 [SMILES: O=C(CCn1c(=O)c2cccn2c2ccc(F)cc21)Nc1ccncc1] | Tr(METCR1603) = 3.42 min m/z (ES⁺) (M + H)⁺ 351.2, 100% | 1H NMR (500 MHz, DMSO-d6) 10.40 (s, 1H), 8.41 (d, J = 6.3 Hz, 2H), 8.27-8.07 (m, 2H), 7.57 (dd, J = 11.3, 2.6 Hz, 1H), 7.55-7.49 (m, 2H), 7.28-7.10 (m, 1H), 7.06 (dd, J = 3.9, 1.5 Hz, 1H), 6.70 (dd, J = 3.8, 2.8 Hz, 1H), 4.75-4.20 (m, 2H), 2.98-2.60 (m, 2H). 19F NMR (376 MHz, DMSO-d6) −115.18. |

| Ex. | Structure | LCMS data | NMR data |
|---|---|---|---|
| 3-19 | 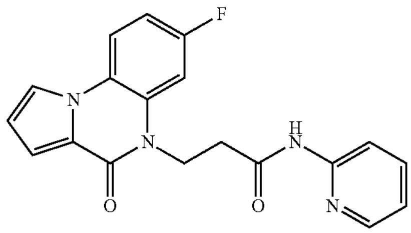 [SMILES: O=C(CCn1c(=O)c2cccn2c2ccc(F)cc21)Nc1ccccn1] | Tr(METCR1603) = 3.75 min m/z (ES⁺) (M + H)⁺ 351.2, 96% | 1H NMR (500 MHz, DMSO-d6) 10.61 (s, 1H), 8.29 (ddd, J = 4.9, 1.9, 0.8 Hz, 1H), 8.22-8.15 (m, 2H), 8.07 (d, J = 8.5 Hz, 1H), 7.87-7.71 (m, 1H), 7.58 (dd, J = 11.3, 2.6 Hz, 1H), 7.23-7.13 (m, 1H), 7.09 (ddd, J = 7.3, 4.9, 1.0 Hz, 1H), 7.06 (dd, J = 3.9, 1.5 Hz, 1H), 6.70 (dd, J = 3.8, 2.8 Hz, 1H), 4.62-4.16 (m, 2H), 2.86-2.68 (m, 2H). 19F NMR (376 MHz, DMSO-d6) −115.17. |
| 3-20 | 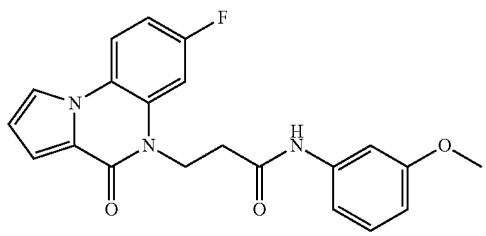 [SMILES: COc1cccc(NC(=O)CCn2c(=O)c3cccn3c3ccc(F)cc32)c1] | Tr(MET-uHPLC-AB-101) = 3.14 min m/z (ES⁺) (M + H)⁺ 380.2, 100% | 1H NMR (500 MHz, DMSO-d6) 10.01 (s, 1H), 8.25-8.09 (m, 2H), 7.56 (dd, J = 11.3, 2.5 Hz, 1H), 7.26 (t, J = 2.1 Hz, 1H), 7.20-7.15 (m, 2H), 7.11-7.04 (m, 2H), 6.70 (dd, J = 3.8, 2.8 Hz, 1H), 6.62 (dd, J = 8.2, 2.0 Hz, 1H), 4.52-4.30 (m, 2H), 3.72 (s, 3H), 2.87-2.62 (m, 2H). 19F NMR (376 MHz, DMSO-d6) −115.14. |
| 3-21 | 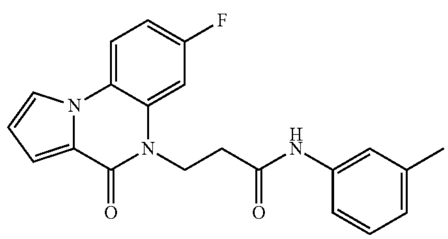 [SMILES: Cc1cccc(NC(=O)CCn2c(=O)c3cccn3c3ccc(F)cc32)c1] | Tr(MET-uHPLC-AB-101) = 3.31 min m/z (ES⁺) (M + H)⁺ 364.2, 99% | 1H NMR (500 MHz, DMSO-d6) 9.94 (s, 1H), 8.23-8.14 (m, 2H), 7.55 (dd, J = 11.3, 2.6 Hz, 1H), 7.38 (s, 1H), 7.33 (d, J = 8.5 Hz, 1H), 7.21-7.13 (m, 2H), 7.07 (dd, J = 3.9, 1.5 Hz, 1H), 6.86 (d, J = 7.5 Hz, 1H), 6.70 (dd, J = 3.8, 2.8 Hz, 1H), 4.53-4.44 (m, 2H), 2.75-2.68 (m, 2H), 2.26 (s, 3H). 19F NMR (376 MHz, DMSO-d6) −115.14. |
| 3-22 | 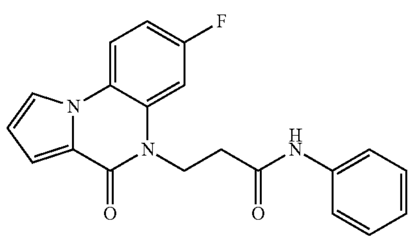 [SMILES: O=C(CCn1c(=O)c2cccn2c2ccc(F)cc21)Nc1ccccc1] | Tr(METCR1603) = 4.10 min m/z (ES⁺) (M + H)⁺ 350.2, 100% | 1H NMR (500 MHz, DMSO-d6) 10.02 (s, 1H), 8.24-8.14 (m, 2H), 7.62-7.50 (m, 3H), 7.33-7.25 (m, 2H), 7.21-7.13 (m, 1H), 7.09-7.00 (m, 2H), 6.70 (dd, J = 3.8, 2.8 Hz, 1H), 4.54-4.44 (m, 2H), 2.76-2.69 (m, 2H). 19F NMR (376 MHz, DMSO-d6) −115.14. |
| 3-23 | 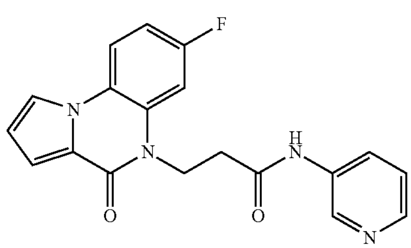 [SMILES: O=C(CCn1c(=O)c2cccn2c2ccc(F)cc21)Nc1cccnc1] | Tr(MET-uHPLC-AB-101) = 1.79 min m/z (ES⁺) (M + H)⁺ 351.1, 100% | 1H NMR (500 MHz, DMSO-d6) 10.24 (s, 1H), 8.67 (d, J = 2.3 Hz, 1H), 8.25 (dd, J = 4.7, 1.5 Hz, 1H), 8.20 (dd, J = 2.8, 1.6 Hz, 1H), 8.19-8.15 (m, 1H), 7.99 (ddd, J = 8.3, 2.5, 1.5 Hz, 1H), 7.56 (dd, J = 11.3, 2.6 Hz, 1H), 7.39-7.29 (m, 1H), 7.22-7.12 (m, 1H), 7.06 (dd, J = 3.9, 1.5 Hz, 1H), 6.70 (dd, J = 3.8, 2.8 Hz, 1H), 4.57-4.45 (m, 2H), 2.82-2.71 (m, 2H). 19F NMR (376 MHz, DMSO-d6) −115.18. |
| 3-24 | 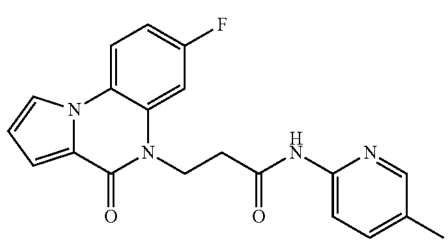 [SMILES: Cc1ccc(NC(=O)CCn2c(=O)c3cccn3c3ccc(F)cc32)nc1] | Tr(MET-uHPLC-AB-101) = 2.47 min m/z (ES⁺) (M + H)⁺ 365.2, 99% | 1H NMR (500 MHz, DMSO-d6) 10.53 (s, 1H), 8.20 (dd, J = 2.8, 1.5 Hz, 1H), 8.18 (dd, J = 9.1, 5.5 Hz, 1H), 8.12 (d, J = 2.2 Hz, 1H), 7.98 (d, J = 8.3 Hz, 1H), 7.63-7.55 (m, 2H), 7.20-7.12 (m, 1H), 7.06 (dd, J = 3.9, 1.5 Hz, 1H), 6.70 (dd, J = 3.8, 2.8 Hz, 1H), 4.52-4.44 (m, 2H), 2.77 (t, J = 7.4 Hz, 2H), 2.24 (s, 3H). 19F NMR (376 MHz, DMSO-d6) −115.17. |

| Ex. | Structure | LCMS data | NMR data |
|---|---|---|---|
| 3-25 | 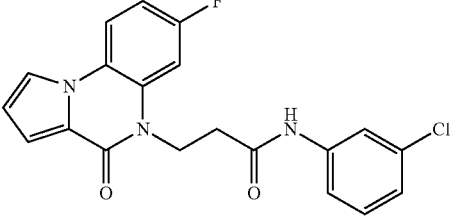 | Tr(MET-uHPLC-AB-101) = 3.49 min m/z (ES⁺) (M + H)⁺ 384.1, 386.1, 100% | 1H NMR (500 MHz, DMSO-d6) 10.22 (s, 1H), 8.23-8.14 (m, 2H), 7.77 (t, J = 2.0 Hz, 1H), 7.55 (dd, J = 11.3, 2.6 Hz, 1H), 7.41-7.35 (m, 1H), 7.32 (t, J = 8.0 Hz, 1H), 7.17 (td, J = 8.9, 2.6 Hz, 1H), 7.10 (ddd, J = 7.9, 2.1, 1.0 Hz, 1H), 7.06 (dd, J = 3.9, 1.5 Hz, 1H), 6.70 (dd, J = 3.8, 2.8 Hz, 1H), 4.54-4.45 (m, 2H), 2.76-2.69 (m, 2H). 19F NMR (376 MHz, DMSO-d6) −115.18. |
| 3-26 | 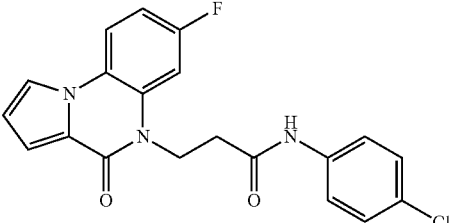 | Tr(MET-uHPLC-AB-101) = 3.46 min m/z (ES⁺) (M + H)⁺ 384.2, 386.1, 100% | 1H NMR (500 MHz, DMSO-d6) 10.17 (s, 1H), 8.25-8.14 (m, 2H), 7.64-7.52 (m, 3H), 7.40-7.29 (m, 2H), 7.19-7.13 (m, 1H), 7.06 (dd, J = 3.9, 1.4 Hz, 1H), 6.70 (dd, J = 3.8, 2.8 Hz, 1H), 4.54-4.44 (m, 2H), 2.80-2.67 (m, 2H). 19F NMR (376 MHz, DMSO-d6) −115.16. |
| 3-27 | 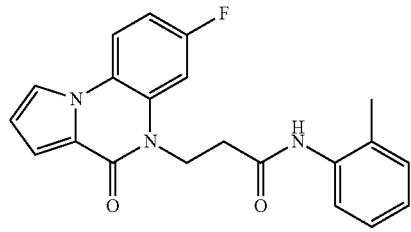 [SMILES: Cc1ccccc1NC(=O)CCn1c(=O)c2cccn2c2ccc(F)cc21] | Tr(MET-uHPLC-AB-101) = 3.11 min m/z (ES⁺) (M + H)⁺ 364.2, 100% | 1H NMR (500 MHz, DMSO-d6) 9.40 (s, 1H), 8.24-8.16 (m, 2H), 7.55 (dd, J = 11.2, 2.5 Hz, 1H), 7.33 (d, J = 7.7 Hz, 1H), 7.22-7.10 (m, 3H), 7.08-7.05 (m, 2H), 6.73-6.66 (m, 1H), 4.50 (t, J = 7.1 Hz, 2H), 2.75 (t, J = 7.2 Hz, 2H), 2.12 (s, 3H). 19F NMR (376 MHz, DMSO-d6) −115.15. |
| 3-28 | 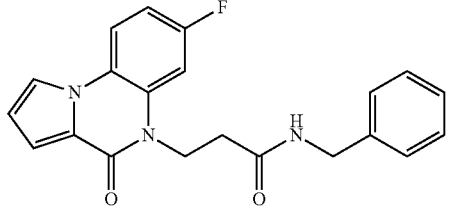 [SMILES: O=C(CCn1c(=O)c2cccn2c2ccc(F)cc21)NCc1ccccc1] | Tr(METCR1603) = 3.93 min m/z (ES⁺) (M + H)⁺ 364.3, 98% | 1H NMR (500 MHz, DMSO-d6) 8.73-8.39 (m, 1H), 8.39-8.01 (m, 2H), 7.51 (d, J = 11.4 Hz, 1H), 7.37-7.13 (m, 6H), 7.06 (d, J = 3.6 Hz, 1H), 6.83-6.56 (m, 1H), 4.43 (t, J = 7.0 Hz, 2H), 4.25 (d, J = 5.7 Hz, 2H), 2.62-2.52 (m, 2H). 19F NMR (376 MHz, DMSO-d6) −115.13. |
| 3-29 | 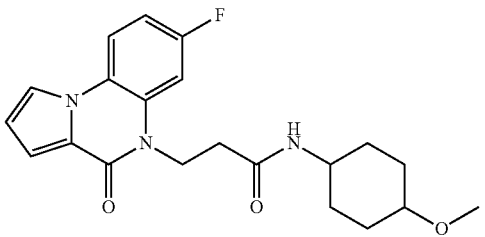 [SMILES: COC1CCC(NC(=O)CCn2c(=O)c3cccn3c3ccc(F)cc32)CC1] | Tr(METCR1603) = 3.53 min m/z (ES⁺) (M + H)⁺ 386.3, 100% | 1H NMR (500 MHz, DMSO-d6) 8.36-8.02 (m, 2H), 7.87 (d, J = 7.6 Hz, 1H), 7.45 (dd, J = 11.3, 2.6 Hz, 1H), 7.30-7.10 (m, 1H), 7.05 (dd, J = 3.9, 1.5 Hz, 1H), 6.69 (dd, J = 3.8, 2.8 Hz, 1H), 4.36 (t, J = 7.2 Hz, 2H), 3.67-3.39 (m, 1H), 3.20 (s, 3H), 3.12-2.83 (m, 1H), 2.44 (t, J = 7.2 Hz, 2H), 2.09-1.84 (m, 2H), 1.79-1.57 (m, 2H), 1.28-0.91 (m, 4H). 19F NMR (376 MHz, DMSO-d6) −115.24. |
| 3-30 | 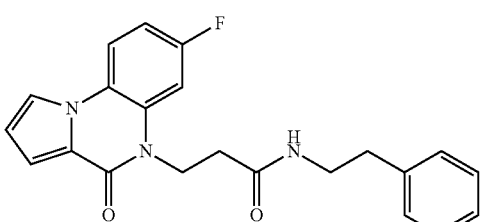 | Tr(METCR1603) = 4.07 min m/z (ES⁺) (M + H)⁺ 378.3, 100% | 1H NMR (500 MHz, DMSO-d6) 8.27-8.14 (m, 2H), 8.10 (t, J = 5.5 Hz, 1H), 7.47 (dd, J = 11.3, 2.6 Hz, 1H), 7.34-7.20 (m, 2H), 7.21-7.10 (m, 4H), 7.09-7.02 (m, 1H), 6.70 (dd, J = 3.8, 2.8 Hz, 1H), 4.36 (t, J = 7.3 Hz, 2H), 3.28-3.11 (m, 2H), 2.78-2.58 (m, 2H), 2.48-2.37 (m, 2H). 19F NMR (376 MHz, DMSO-d6) −115.21 |

| Ex. | Structure | LCMS data | NMR data |
|---|---|---|---|
| 3-31 | 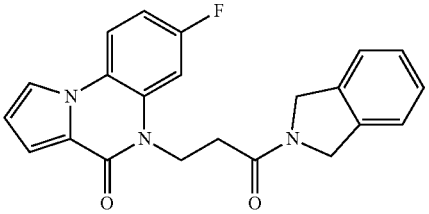 [SMILES: O=C(CCn1c(=O)c2cccn2c2ccc(F)cc21)N1Cc2ccccc2C1] | Tr(METCR 1603) = 4.13 min m/z (ES+) (M + H)+ 376.3, 100% | 1H NMR (500 MHz, DMSO-d6) 8.35-8.09 (m, 2H), 7.55 (dd, J = 11.2, 2.6 Hz, 1H), 7.37 (d, J = 4.7 Hz, 1H), 7.33-7.25 (m, 3H), 7.24-7.13 (m, 1H), 7.07 (dd, J = 3.9, 1.5 Hz, 1H), 6.70 (dd, J = 3.8, 2.8 Hz, 1H), 4.82 (s, 2H), 4.67 (s, 2H), 4.55-4.37 (m, 2H), 2.93-2.71 (m, 2H). 19F NMR (376 MHz, DMSO-d6) ? −115.05. |
| 3-32 | 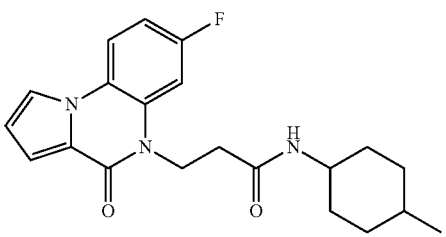 [SMILES: CC1CCC(NC(=O)CCn2c(=O)c3cccn3c3ccc(F)cc32)CC1] | Tr(MET-uHPLC-AB-101) = 3.37 min m/z (ES+) (M + H)+ 370.3, 98% | 1H NMR (500 MHz, DMSO-d6) 8.28-8.09 (m, 2H), 7.85 (d, J = 7.7 Hz, 0.7H, major), 7.81 (d, J = 7.5 Hz, 0.3H, minor), 7.45 (dd, J = 11.3, 2.6 Hz, 1H), 7.23-7.12 (m, 1H), 7.06 (dt, J = 3.8, 1.8 Hz, 1H), 6.70 (dd, J = 3.8, 2.8 Hz, 1H), 4.37 (q, J = 7.7 Hz, 2H), 3.42 (ddd, J = 15.5, 7.7, 3.9 Hz, 1H), 2.44 (t, J = 7.2 Hz, 2H), 1.68 (d, J = 9.8 Hz, 1.3H), 1.62 (d, J = 12.1 Hz, 1.3H), 1.50-1.32 (m, 2.4H), 1.31-1.20 (m, 0.7H), 1.20-1.10 (m, 0.7H), 1.11-1.00 (m, 1.3H), 1.00-0.87 (m, 1.3H), 0.85 (d, J = 6.5 Hz, 2H, major), 0.83 (d, J = 6.7 Hz, 1H, minor). 19F NMR (376 MHz, DMSO-d6) d −115.23 (d, J = 5.4 Hz). |
| 3-33 | 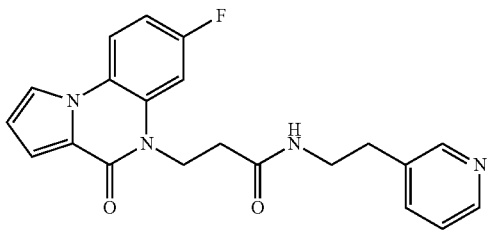 [SMILES: O=C(CCn1c(=O)c2cccn2c2ccc(F)cc21)NCCc1cccnc1] | Tr(MET-uHPLC-AB-101) = 1.44 min m/z (ES+) (M + H)+ 379.2, 99% | 1H NMR (500 MHz, DMSO-d6) 8.41-8.35 (m, 2H), 8.22-8.15 (m, 2H), 8.13 (t, J = 5.5 Hz, 1H), 7.55 (dt, J = 7.8, 1.9 Hz, 1H), 7.45 (dd, J = 11.3, 2.6 Hz, 1H), 7.25 (dd, J = 7.4, 5.1 Hz, 1H), 7.22-7.13 (m, 1H), 7.06 (dd, J = 3.9, 1.5 Hz, 1H), 6.70 (dd, J = 3.8, 2.8 Hz, 1H), 4.39-4.30 (m, 2H), 3.28-3.25 (m, 2H), 2.67 (t, J = 7.1 Hz, 2H), 2.47-2.43 (m, 2H). 19F NMR (376 MHz, DMSO-d6) −115.18. |
| 3-34 | 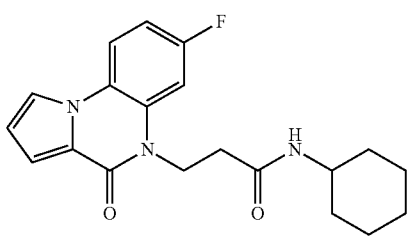 [SMILES: O=C(CCn1c(=O)c2cccn2c2ccc(F)cc21)NC1CCCCC1] | Tr(MET-uHPLC-AB-101) = 3.09 min m/z (ES+) (M + H)+ 356.2, 100% | 1H NMR (500 MHz, DMSO-d6) 8.21-8.13 (m, 2H), 7.85 (d, J = 8.1 Hz, 1H), 7.45 (dd, J = 11.3, 2.6 Hz, 1H), 7.20-7.13 (m, 1H), 7.05 (dd, J = 3.9, 1.5 Hz, 1H), 6.69 (dd, J = 3.8, 2.8 Hz, 1H), 4.36 (t, J = 7.2 Hz, 2H), 3.53-3.44 (m, 1H), 2.47-2.42 (m, 2H), 1.69-1.58 (m, 4H), 1.57-1.47 (m, 1H), 1.28-1.16 (m, 2H), 1.13-0.98 (m, 3H). 19F NMR (376 MHz, DMSO-d6) −115.23. |
| 3-35 | 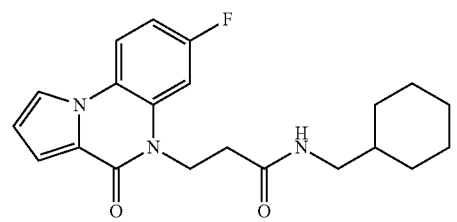 [SMILES: O=C(CCn1c(=O)c2cccn2c2ccc(F)cc21)NCC1CCCCC1] | Tr(METCR1603) = 4.31 min m/z (ES+) (M + H)+ 370.3, 100% | 1H NMR (500 MHz, DMSO-d6) 8.21-8.13 (m, 2H), 7.94 (t, J = 5.7 Hz, 1H), 7.46 (dd, J = 11.4, 2.6 Hz, 1H), 7.20-7.12 (m, 1H), 7.05 (dd, J = 3.9, 1.5 Hz, 1H), 6.69 (dd, J = 3.9, 2.8 Hz, 1H), 4.37 (t, J = 7.1 Hz, 2H), 2.86-2.82 (m, 2H), 2.49-2.44 (m, 2H), 1.62-1.50 (m, 5H), 1.31-1.21 (m, 1H), 1.14-1.02 (m, 3H), 0.81-0.70 (m, 2H). 19F NMR (376 MHz, DMSO-d6) −115.18. |

| Ex. | Structure | LCMS data | NMR data |
|---|---|---|---|
| 3-36 | 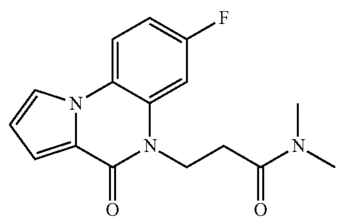 [SMILES: CN(C)C(=O)CCn1c(=O)c2cccn2c2ccc(F)cc21] | Tr(METCR 1603) = 3.35 min m/z (ES+) (M + H)+ 302.3, 100% | 1H NMR (500 MHz, DMSO-d6) 8.22-8.14 (m, 2H), 7.45 (dd, J = 11.2, 2.6 Hz, 1H), 7.21-7.13 (m, 1H), 7.05 (dd, J = 3.9, 1.5 Hz, 1H), 6.69 (dd, J = 3.8, 2.8 Hz, 1H), 4.41-4.33 (m, 2H), 2.92 (s, 3H), 2.84 (s, 3H), 2.72-2.65 (m, 2H). 19F NMR (376 MHz, DMSO-d6) −115.05. |
| 3-37 | 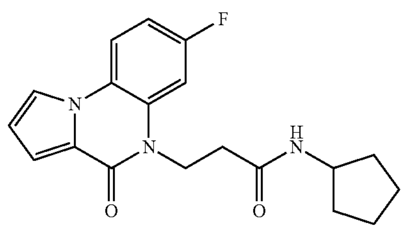 [SMILES: O=C(CCn1c(=O)c2cccn2c2ccc(F)cc21)NC1CCCC1] | Tr(METCR 1603) = 3.81 min m/z (ES+) (M + H)+ 342.3, 100% | 1H NMR (500 MHz, DMSO-d6) 8.22-8.13 (m, 2H), 7.93 (d, J = 7.2 Hz, 1H), 7.45 (dd, J = 11.3, 2.6 Hz, 1H), 7.20-7.11 (m, 1H), 7.05 (dd, J = 3.9, 1.5 Hz, 1H), 6.69 (dd, J = 3.8, 2.8 Hz, 1H), 4.36 (t, J = 7.2 Hz, 2H), 3.95 (h, J = 6.8 Hz, 1H), 2.44 (t, J = 7.2 Hz, 2H), 1.77-1.66 (m, 2H), 1.61-1.39 (m, 4H), 1.33-1.19 (m, 2H). 19F NMR (376 MHz, DMSO-d6) −115.19. |
| 3-38 | 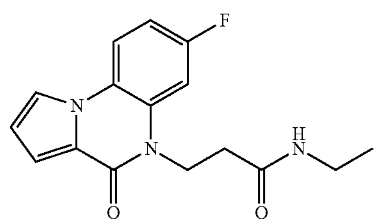 [SMILES: CCNC(=O)CCn1c(=O)c2cccn2c2ccc(F)cc21] | Tr(METCR1603) = 3.30 min m/z (ES+) (M + H)+ 302.3, 100% | 1H NMR (500 MHz, DMSO-d6) 8.22-8.13 (m, 2H), 7.98 (t, J = 5.1 Hz 1H), 7.46 (dd, J = 11.3, 2.6 Hz, 1H), 7.21-7.13 (m, 1H), 7.05 (dd, J = 3.9, 1.5 Hz, 1H), 6.69 (dd, J = 3.8, 2.8 Hz, 1H), 4.45-4.34 (m, 2H), 3.09-3.00 (m, 2H), 2.46-2.42 (m, 2H), 0.95 (t, J = 7.2 Hz, 3H). 19F NMR (376 MHz, DMSO-d6) −115.21. |
| 3-39 | 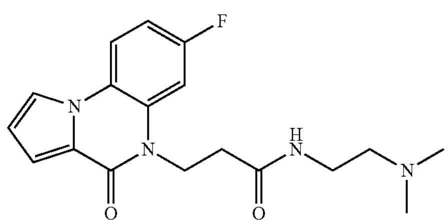 [SMILES: CN(C)CCNC(=O)CCn1c(=O)c2cccn2c2ccc(F)cc21] | Tr(METCR1603) = 3.20 min m/z (ES+) (M + H)+ 345.3, 100% | 1H NMR (500 MHz, DMSO-d6) 8.21-8.10 (m, 2H), 7.95 (t, J = 5.4 Hz, 1H), 7.46 (dd, J = 11.3, 2.6 Hz, 1H), 7.23-7.13 (m, 1H), 7.06 (dd, J = 3.9, 1.4 Hz, 1H), 6.70 (dd, J = 3.8, 2.8 Hz, 1H), 4.42-4.29 (m, 2H), 3.10 (q, J = 6.7 Hz, 2H), 2.49-2.41 (m, 2H), 2.18 (t, J = 6.8 Hz, 2H), 2.08 (s, 6H). 19F NMR (376 MHz, DMSO-d6) −115.18 |
| 3-40 | 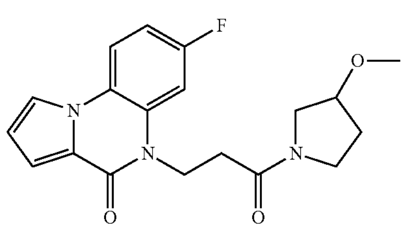 [SMILES: COC1CCN(C(=O)CCn2c(=O)c3cccn3c3ccc(F)cc32)C1] | Tr(METCR 1603) = 3.40 min m/z (ES+) (M + H)+ 358.3, 100% | 1H NMR (500 MHz, DMSO-d6) 8.23-8.13 (m, 2H), 7.48 (ddd, J = 11.2, 5.2, 2.6 Hz, 1H), 7.21-7.13 (m, 1H), 7.05 (dt, J = 3.8, 1.5 Hz, 1H), 6.73-6.65 (m, 1H), 4.43-4.34 (m, 2H), 3.99-3.87 (m, 1H), 3.54-3.40 (m, 2H), 3.27-3.15 (m, 5H), 2.72-2.60 (m, 2H), 1.90 (s, 2H). 19F NMR (376 MHz, DMSO-d6) −115.04 (d, J = 1.8 Hz). |
| 3-41 | 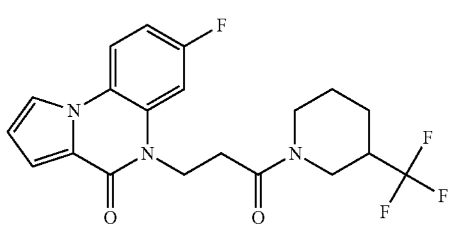 [SMILES: O=C(CCn1c(=O)c2cccn2c2ccc(F)cc21)N1CCCC(C(F)(F)F)C1] | Tr(MET-uHPLC-AB-101) = 3.33 min m/z (ES+) (M + H)+ 410.2, 97% | 1H NMR (500 MHz, DMSO-d6) 8.23-8.14 (m, 2H), 7.46-7.41 (m, 1H), 7.23-7.14 (m, 1H), 7.05 (dd, J = 3.9, 1.4 Hz, 1H), 6.70 (dd, J = 3.7, 2.9 Hz, 1H), 4.58-4.24 (m, 3H), 3.92-3.73 (m,1H), 3.10-2.96 (m, 1H), 2.85-2.60 (m, 3H), 2.42-2.31 (m, 1H), 1.97-1.87 (m, 1H), 1.76-1.63 (m, 1H), 1.57-1.31 (m, 2H). 19F NMR (376 MHz, DMSO-d6) −70.69 (minor rotamer), −71.05 (major rotamer), −115.09. |

-continued

| Ex. | Structure | LCMS data | NMR data |
|---|---|---|---|
| 3-42 | 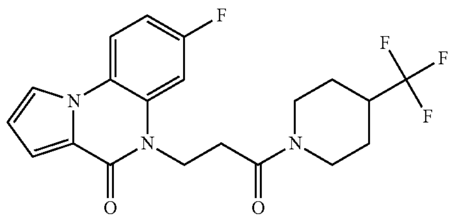 [SMILES: O=C(CCn1c(=O)c2cccn2c2ccc(F)cc21)N1CCC(C(F)(F)F)CC1] | Tr(MET-uHPLC-AB-101) = 3.23 min m/z (ES⁺) (M + H)⁺ 410.3, 95% | 1H NMR (500 MHz, DMSO-d6) 8.22-8.13 (m, 2H), 7.46 (dd, J = 11.2, 2.6 Hz, 1H), 7.22-7.13 (m, 1H), 7.05 (dd, J = 3.9, 1.5 Hz, 1H), 6.69 (dd, J = 3.8, 2.8 Hz, 1H), 4.51 (d, J = 13.0 Hz, 1H), 4.38 (t, J = 7.7 Hz, 2H), 3.89 (d, J = 13.8 Hz, 1H), 3.00 (td, J = 13.7, 2.4 Hz, 1H), 2.78 (dt, J = 15.7, 7.7 Hz, 1H), 2.68 (dt, J = 15.7, 7.5 Hz, 1H), 2.59-2.52 (m, 2H), 1.81 (d, J = 12.3 Hz, 1H), 1.73 (d, J = 12.2 Hz, 1H), 1.34 (qd, J = 12.5, 4.2 Hz, 1H), 1.22 (qd, J= 12.6, 4.4 Hz, 1H). 19F NMR (376 MHz, DMSO-d6) −72.47, −115.06. |
| 3-43 | 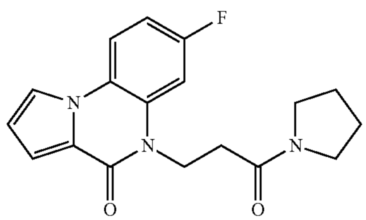 [SMILES: O=C(CCn1c(=O)c2cccn2c2ccc(F)cc21)N1CCCC1] | Tr(METCR1603) = 3.55 min m/z (ES⁺) (M + H)⁺ 328.3, 100% | 1H NMR (500 MHz, DMSO-d6) 8.23-8.11 (m, 2H), 7.48 (dd, J = 11.2, 2.6 Hz, 1H), 7.20-7.11 (m, 1H), 7.05 (dd, J = 3.9, 1.5 Hz, 1H), 6.69 (dd, J = 3.8, 2.8 Hz, IH), 4.54-4.31 (m, 2H), 3.49-3.21 (m, 4H), 2.69-2.55 (m, 2H), 1.83 (p, J = 6.6 Hz, 2H), 1.75 (p, J = 6.4 Hz, 2H). 19F NMR (376 MHz, DMSO-d6) −115.06. |
| 3-44 | 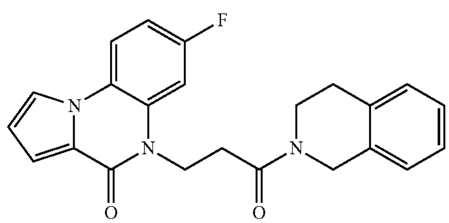 [SMILES: O=C(CCn1c(=O)c2cccn2c2ccc(F)cc21)N1CCc2ccccc2C1] | Tr(MET-uHPLC-AB-101) = 3.26 min m/z (ES⁺) (M + H)⁺ 390.2, 99% | 1H NMR (500 MHz, DMSO-d6) 8.23-8.09 (m, 2H), 7.48 (ddd, J = 21.9, 11.2, 2.6 Hz, 1H), 7.25-6.98 (m, 6H), 6.70-6.68 (m, 1H), 4.66-4.55 (m, 2H), 4.47-4.37 (m, 2H), 3.72-3.59 (m, 2H), 2.86-2.69 (m, 4H). 19F NMR (376 MHz, DMSO-d6) −115.07 (appt. d, J = 20.7 Hz). |
| 3-45 | 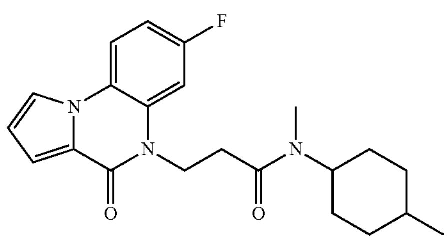 [SMILES: CC1CCC(N(C)C(=O)CCn2c(=O)c3cccn3c3ccc(F)cc32)CC1] | Tr(METCR1603) = 4.68 min m/z (ES⁺) (M + H)⁺ 384.3, 100% | 1H NMR (500 MHz, DMSO-d6) 8.22-8.14 (m, 2H), 7.49-7.40 (m, 1H), 7.21-7.12 (m, 1H), 7.09-7.02 (m, 1H), 6.73-6.67 (m, 1H), 4.43-4.34 (m, 2H), 4.29-4.18 (m, 0.5H, isomer A), 3.53-3.44 (m, 0.5H, isomer B), 2.80-2.63 (m, 5H), 1.74-1.20 (m, 7H), 1.07-0.76 (m, 5H). |
| 3-46 | 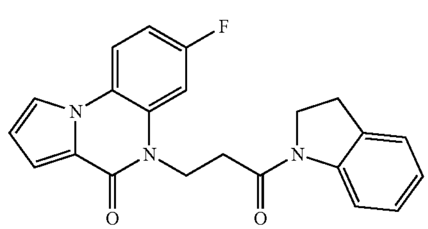 [SMILES: O=C(CCn1c(=O)c2cccn2c2ccc(F)cc21)N1CCc2ccccc21] | Tr(METCR1416) = 4.44 min m/z (ES⁺) (M + H)⁺ 376.2, 100% | 1H NMR (500 MHz, DMSO-d6) 8.32-8.15 (m, 2H), 8.11 (d, J = 8.0 Hz, 1H), 7.57 (dd, J = 11.1, 2.1 Hz, 1H), 7.23 (d, J = 7.4 Hz, 1H), 7.19-7.11 (m, 2H), 7.06 (d, J = 3.7 Hz, 1H), 7.02-6.86 (m, 1H), 6.84-6.62 (m, 1H), 4.76-4.23 (m, 2H), 4.05 (t, J = 8.5 Hz, 2H), 3.11 (t, J = 8.4 Hz, 2H), 2.96-2.72 (m, 2H). 19F NMR (376 MHz, DMSO-d6) −115.02. |
| 3-47 | 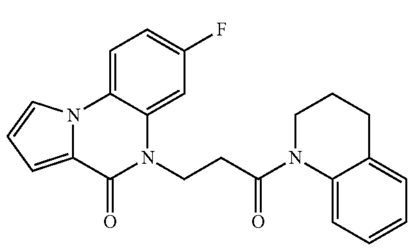 [SMILES: O=C(CCn1c(=O)c2cccn2c2ccc(F)cc21)N1CCCc2ccccc21] | Tr(METCR1603) = 4.42 min m/z (ES⁺) (M + H)⁺ 390.2, 100% | 1H NMR (500 MHz, DMSO-d6) 8.50-7.97 (m, 2H), 7.43 (m, 2H), 7.25-6.89 (m, 5H), 6.69 (dd, J = 3.8, 2.8 Hz, 1H), 4.59-4.26 (m, 2H), 3.67 (t, J = 6.4 Hz, 2H), 2.89 (t, J = 7.4 Hz, 2H), 2.77-2.59 (m, 2H), 2.02-1.57 (m, 2H). 19F NMR (376 MHz, DMSO-d6) −115.08. |

-continued

| Ex. | Structure | LCMS data | NMR data |
|---|---|---|---|
| 3-48 | 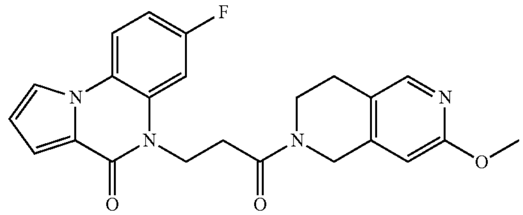 [SMILES: COc1cc2c(cn1)CCN(C(=O)CCn1c(=O)c3cccn3c3ccc(F)cc31)C2] | Tr(METCR1603) = 3.61 min m/z (ES+) (M + H)+ 421.2, 100% | 1H NMR (400 MHz, 355 K, DMSO-d6) 8.20-8.01 (m, 2H), 8.00-7.77 (m, 1H), 7.42 (d, J = 9.7 Hz, 1H), 7.24-6.91 (m, 2H), 6.83-6.31 (m, 2H), 4.60 (s, 2H), 4.52-4.20 (m, 2H), 3.82 (s, 3H), 3.67 (t, J = 5.9 Hz, 2H), 2.92-2.75 (m, 2H), 2.78-2.70 (m, 2H). 19F NMR (376 MHz, DMSO-d6) −109.94−−123.54 (m). |
| 3-49 | 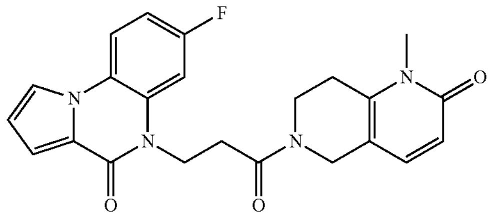 [SMILES: Cn1c2c(ccc1=O)CN(C(=O)CCn1c(=O)c3cccn3c3ccc(F)cc31)CC2] | Tr(METCR1603) = 2.75 min m/z (ES+) (M + H)+ 421.2, 100% | 1H NMR (400 MHz, 355 K, DMSO-d6) 8.35-7.78 (m, 2H), 7.40 (d, J = 10.6 Hz, 1H), 7.32-6.87 (m, 3H), 6.72-6.50 (m, 1H), 6.39-5.57 (m, 1H), 4.78-4.38 (m, 2H), 4.32 (s, 2H), 3.69 (t, J = 6.0 Hz, 2H), 3.32 (s, 3H), 2.95-2.78 (m, 4H). 19F NMR (376 MHz, DMSO-d6) −115.03 (d, J = 22.8 Hz). |
| 3-50 | 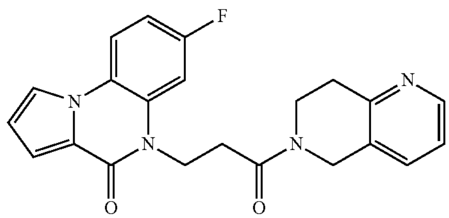 | Tr(METCR1603) = 3.26 min m/z (ES+) (M + H)+ 391.1, 100% | 1H NMR (400 MHz, 355 K, DMSO-d6) 8.55-8.23 (m, 1H), 8.20-7.79 (m, 2H), 7.83-7.30 (m, 2H), 7.27-6.94 (m, 3H), 6.84-6.46 (m, 1H), 4.65 (s, 2H), 4.53-4.12 (m, 2H), 3.78 (t, J = 6.0 Hz, 2H), 2.99-2.72 (m, 4H). 19F NMR (376 MHz, DMSO-d6) −115.06 (m). |
| 3-51 | 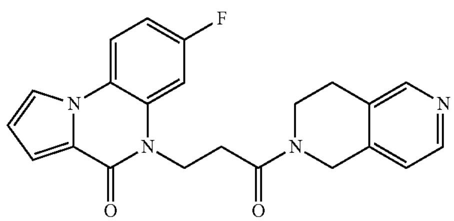 | Tr(METCR1603) = 3.25 min m/z (ES+) (M + H)+ 391.1, 100% | 1H NMR (400 MHz, 355 K, DMSO-d6) 8.43-7.74 (m, 4H), 7.42 (d, J = 10.7 Hz, 1H), 7.28-6.88 (m, 3H), 6.78-6.39 (m, 1H), 4.63 (s, 2H), 4.56-4.13 (m, 2H), 3.71 (t, J = 5.9 Hz, 2H), 2.96-2.69 (m, 4H). 19F NMR (376 MHz, DMSO-d6) −106.38−−128.49 (m). |
| 3-52 | 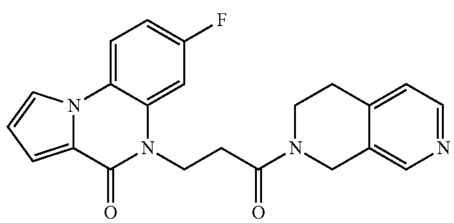 [SMILES: O=C(CCn1c(=O)c2cccn2c2ccc(F)cc21)N1CCc2ccncc2C1] | Tr(MET-uHPLC-AB-101) = 1.40 min m/z (ES+) (M + H)+ 391.2, 99% | 1H NMR (400 MHz, 355 K, DMSO-d6) 8.62-7.85 (m, 4H), 7.43 (d, J = 11.2 Hz, 1H), 7.24-6.93 (m, 3H), 6.82-6.43 (m, 1H), 4.66 (s, 2H), 4.58-4.18 (m, 2H), 3.70 (t, J = 5.9 Hz, 2H), 2.95-2.75 (m, 4H). 19F NMR (376 MHz, DMSO-d6) −115.05. |
| 3-53 | 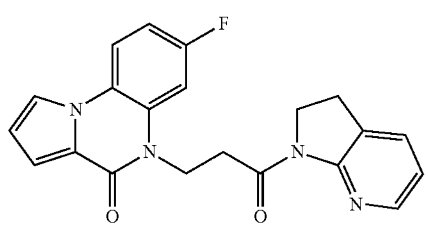 [SMILES: O=C(CCn1c(=O)c2cccn2c2ccc(F)cc21)N1CCc2cccnc21] | Tr(MET-uHPLC-AB-101) = 2.92 min m/z (ES+) (M + H)+ 377.2, 100% | 1H NMR (500 MHz, DMSO-d6) 8.25-8.08 (m, 2H), 7.97 (d, J = 3.8 Hz, 1H), 7.70 (dd, J = 11.4, 2.6 Hz, 1H), 7.61 (d, J = 6.2 Hz, 1H), 7.43-7.14 (m, 1H), 7.05 (dd, J = 3.9, 1.4 Hz, 1H), 6.94 (dd, J = 7.3, 5.1 Hz, 1H), 6.69 (dd, J = 3.8, 2.8 Hz, 1H), 4.60-4.28 (m, 2H), 3.97 (t, J = 8.5 Hz, 2H), 3.48-3.37 (m, 2H), 3.02 (t, J = 8.5 Hz, 2H). 19F NMR (471 MHz, DMSO-d6) −115.04 (ddd, J = 11.5, 7.8, 5.6 Hz). |
| 3-54 | 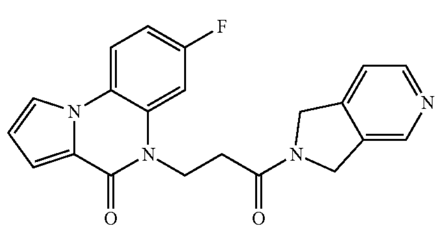 [SMILES: O=C(CCn1c(=O)c2cccn2c2ccc(F)cc21)N1Cc2ccncc2C1] | Tr(MET-uHPLC-AB-101) = 1.59 min m/z (ES+) (M + H)+ 377.2, 99% | 1H NMR (500 MHz, DMSO-d6) 8.73-8.51 (m, 1H), 8.51-8.35 (m, 1H), 8.27-7.92 (m, 2H), 7.54 (dd, J = 11.2, 2.1 Hz, 1H), 7.46-7.27 (m, 1H), 7.27-7.12 (m, 1H), 7.07 (dd, J = 3.8, 1.3 Hz, 1H), 6.70 (dd, J = 3.7, 2.9 Hz, 1H), 5.12-4.80 (m, 2H), 4.79-4.54 (m, 2H), 4.58-4.34 (m, 2H), 2.89-2.70 (m, 2H). 19F NMR (471 MHz, |

| Ex. | Structure | LCMS data | NMR data |
|---|---|---|---|
| | | | DMSO-d6) −115.03. |
| 3-55 | 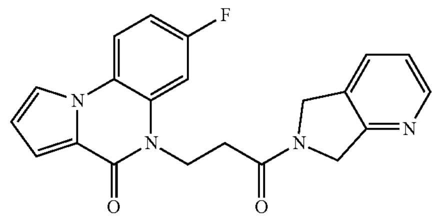 | Tr(MET-uHPLC-AB-101) = 2.35 min m/z (ES⁺) (M + H)⁺ 377.2, 100% | 1H NMR (400 MHz, DMSO-d6) 8.80-8.33 (m, 1H), 8.29-8.08 (m, 2H), 7.93-7.65 (m, 1H), 7.63-7.39 (m, 1H), 7.33-7.29 (m, 1H), 7.25-7.12 (m, 1H), 7.07 (dd, J = 3.9, 1.4 Hz, 1H), 6.70 (dd, J = 3.8, 2.8 Hz, 1H), 5.00-4.77 (m, 2H), 4.73-4.54 (m, 2H), 4.52-4.20 (m, 2H), 2.93-2.74 (m, 2H). 19F NMR (376 MHz, DMSO-d6) −115.04. |
| 3-56 | 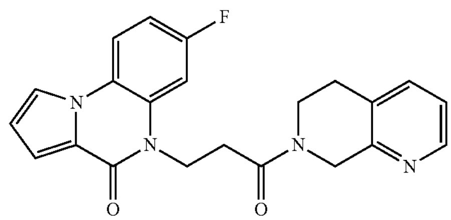 [SMILES: O=C(CCn1c(=O)c2cccn2c2ccc(F)cc21)N1CCc2cccnc2C1] | Tr(MET-uHPLC-AB-101) = 1.94 min m/z (ES⁺) (M + H)⁺ 391.2, 100% | 1H NMR (400 MHz, 355 K, DMSO-d6) 8.66-7.88 (m, 3H), 7.78-7.32 (m, 2H), 7.26-6.88 (m, 3H), 6.75-6.45 (m, 1H), 4.64 (s, 2H), 4.52-4.24 (m, 2H), 3.72 (t, J = 5.9 Hz, 2H), 2.95-2.65 (m, 4H). 19F NMR (376 MHz, DMSO-d6) −115.11 (app d, J = 48.5 Hz). |
| 3-57 | 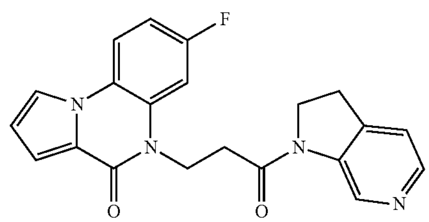 | Tr(MET-uHPLC-AB-101) = 1.63 min m/z (ES⁺) (M + H)⁺ 377.2, 100% | 1H NMR (400 MHz, DMSO-d6) 9.21 (s, 1H), 8.41-8.05 (m, 3H), 7.56 (dd, J = 11.2, 2.5 Hz, 1H), 7.32 (d, J = 4.7 Hz, 1H), 7.24-7.11 (m, 1H), 7.06 (dd, J = 3.8, 1.3 Hz, 1H), 6.70 (dd, J = 3.7, 2.9 Hz, 1H), 4.66-4.26 (m, 2H), 4.07 (t, J = 8.6 Hz, 2H), 3.17 (t, J = 8.5 Hz, 2H), 3.01-2.78 (m, 2H). 19F NMR (376 MHz, DMSO-d6) −114.99. |
| 3-58 | 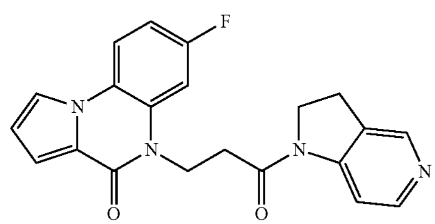 [SMILES: O=C(CCn1c(=O)c2cccn2c2ccc(F)cc21)N1CCc2cnccc21] | Tr(MET-uHPLC-AB-101) = 1.64 min m/z (ES⁺) (M + H)⁺ 377.2, 100% | 1H NMR (500 MHz, DMSO-d6) 8.48-8.28 (m, 2H), 8.27-8.12 (m, 2H), 7.92 (d, J = 5.3 Hz, 1H), 7.58 (dd, J = 11.2, 2.3 Hz, 1H), 7.23-7.11 (m, 1H), 7.06 (dd, J = 3.9, 1.4 Hz, 1H), 6.70 (dd, J = 3.8, 2.8 Hz, 1H), 4.71-4.41 (m, 2H), 4.10 (t, J = 8.6 Hz, 2H), 3.15 (t, J = 8.5 Hz, 2H), 3.01-2.78 (m, 2H). 19F NMR (471 MHz, DMSO-d6) −115.04. |
| 3-59 | 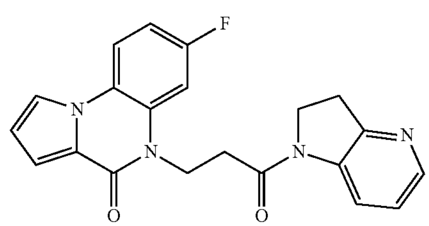 | Tr(MET-uHPLC-AB-101) = 2.33 min m/z (ES⁺) (M + H)⁺ 377.2, 100% | 1H NMR (400 MHz, DMSO-d6) 8.62-7.94 (m, 4H), 7.57 (dd, J = 11.2, 2.5 Hz, 1H), 7.32-7.11 (m, 2H), 7.06 (dd, J = 3.9, 1.4 Hz, 1H), 6.70 (dd, J = 3.9, 2.8 Hz, 1H), 4.83-4.24 (m, 2H), 4.10 (t, J = 8.6 Hz, 2H), 3.19 (t, J = 8.6 Hz, 2H), 2.97-2.77 (m, 2H). 19F NMR (376 MHz, DMSO-d6) −115.05. |
| 3-60 | 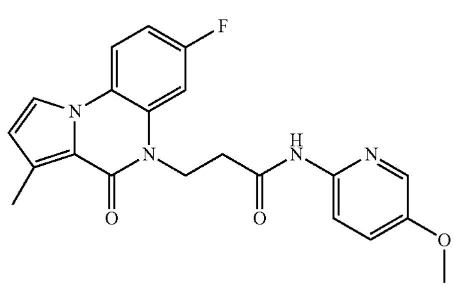 [SMILES: COc1ccc(NC(=O)CCn2c(=O)c3c(C)ccn3c3ccc(F)cc32)nc1] | Tr(MET-uHPLC-AB-101) = 3.13 min m/z (ES⁺) (M + H)⁺ 395.2, 100% | 1H NMR (400 MHz, DMSO-d6) 10.48 (s, 1H), 8.41-7.84 (m, 4H), 7.48 (dd, J = 11.3, 2.6 Hz, 1H), 7.42 (dd, J = 9.1, 3.0 Hz, 1H), 7.19-6.94 (m, 1H), 6.52 (d, J = 2.7 Hz, 1H), 4.73-4.20 (m, 2H), 3.80 (s, 3H), 2.73 (t, J = 7.4 Hz, 2H), 2.47 (s, 3H). 19F NMR (376 MHz, DMSO-d6) −115.88. |

-continued

| Ex. | Structure | LCMS data | NMR data |
|---|---|---|---|
| 3-61 | 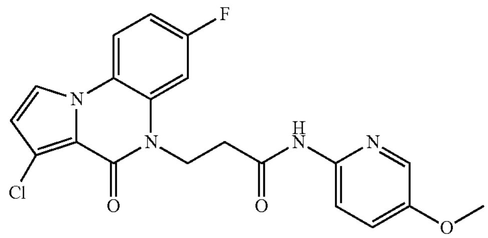 | Tr(MET-uHPLC-AB-101) = 3.01 min m/z (ES+) (M + H)+ 415.2/417.2, 100% | 1H NMR (400 MHz, DMSO-d6) 10.49 (s, 1H), 8.22 (d, J = 3.2 Hz, 1H), 8.16 (dd, J = 9.1, 5.4 Hz, 1H), 8.01 (d, J = 3.3 Hz, 2H), 7.55 (dd, J= 11.3, 2.5 Hz, 1H), 7.42 (dd, J = 9.1, 3.0 Hz, 1H), 7.24-7.00 (m, 1H), 6.78 (d, J = 3.1 Hz, 1H), 4.70-4.18 (m, 2H), 3.80 (s, 3H), 2.87-2.70 (m, 2H). 19F NMR (376 MHz, DMSO-d6) −114.58. |
| 3-62 | 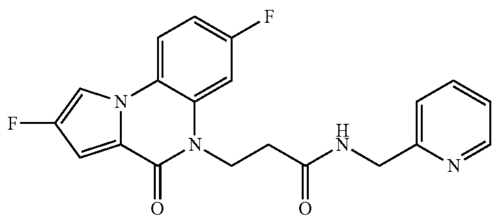 [SMILES: O=C(CCn1c(=O)c2cc(F)cn2c2ccc(F)cc21)NCc1ccccn1] | Tr(MET-uHPLC-AB-101) = 1.78 min m/z (ES+) (M + H)+ 383.2, 100% | 1H NMR (400 MHz, DMSO-d6) 8.61 (t, J = 5.8 Hz, 1H), 8.46 (ddd, J = 4.8, 1.6, 0.9 Hz, 1H), 8.27 (dd, J = 2.9, 2.0 Hz, 1H), 8.07 (dd, J = 9.1, 5.5 Hz, 1H), 7.81-7.62 (m, 1H), 7.53 (dd, J = 11.3, 2.6 Hz, 1H), 7.39-7.09 (m, 3H), 6.92 (d, J = 1.9 Hz, 1H), 4.65-4.38 (m, 2H), 4.34 (d, J = 5.9 Hz, 2H), 2.79-2.55 (m, 2H). 19F NMR (376 MHz, DMSO-d6) −113.68, −158.26. |
| 3-63 | 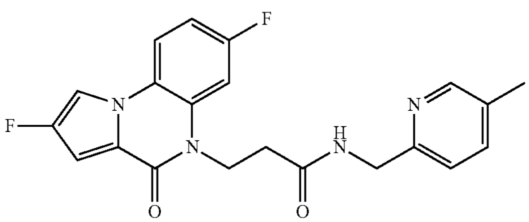 [SMILES: Cc1ccc(CNC(=O)CCn2c(=O)c3cc(F)cn3c3ccc(F)cc32)nc1] | Tr(MET-uHPLC-AB-101) = 1.80 min m/z (ES+) (M + H)+ 397.2, 100% | 1H NMR (400 MHz, DMSO-d6) 8.57 (t, J = 5.9 Hz, 1H), 8.26 (s, 1H), 8.23 (d, J = 2.3 Hz, 1H), 8.05 (dd, J = 9.1, 5.4 Hz, 1H), 7.64-7.37 (m, 2H), 7.31-7.12 (m, 1H), 7.08 (d, J = 7.9 Hz, 1H), 6.91 (d, J = 1.8 Hz, 1H), 4.47-4.32 (m, 2H), 4.27 (d, J = 5.9 Hz, 2H), 2.58 (t, J = 7.3 Hz, 2H), 2.25 (s, 3H). 19F NMR (376 MHz, DMSO-d6) −114.61, −159.16. |
| 3-64 | 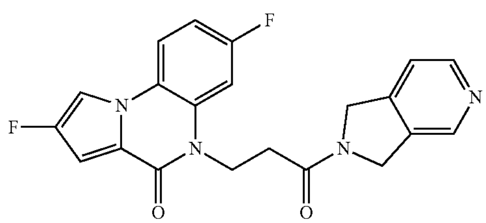 [SMILES: O=C(CCn1c(=O)c2cc(F)cn2c2ccc(F)cc21)N1Cc2ccncc2C1] | Tr(MET-uHPLC-AB-101) = 1.75 min m/z (ES+) (M + H)+ 395.2, 97% | 1H NMR (400 MHz, DMSO-d6) 8.71-8.50 (m, 1H), 8.50-8.38 (m, 1H), 8.32-8.17 (m, 1H), 8.06 (dd, J = 9.1, 5.4 Hz, 1H), 7.56 (dd, J = 11.2, 2.1 Hz, 1H), 7.51-7.28 (m, 1H), 7.25-7.04 (m, 1H), 6.92 (d, J = 1.8 Hz, 1H), 4.93-4.78 (m, 2H), 4.78-4.61 (m, 2H), 4.58-4.38 (m, 2H), 2.77 (m, 2H). 19F NMR (376 MHz, DMSO-d6) −114.52, −159.13. |
| 3-65 | 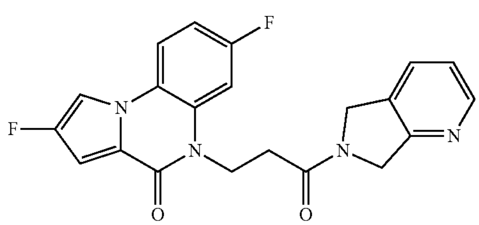 [SMILES: O=C(CCn1c(=O)c2cc(F)cn2c2ccc(F)cc21)N1Cc2cccnc2C1] | Tr(MET-uHPLC-AB-101) = 2.53 min m/z (ES+) (M + H)+ 395.2, 97% | 1H NMR (400 MHz, DMSO-d6) 8.57-8.41 (m, 1H), 8.28 (dd, J = 3.0, 2.0 Hz, 1H), 8.09 (dd, J = 9.1, 5.4 Hz, 1H), 7.89-7.68 (m, 1H), 7.68-7.49 (m, 1H), 7.43-7.27 (m, 1H), 7.27-7.09 (m, 1H), 6.93 (d, J = 1.9 Hz, 1H), 5.16-4.78 (m, 2H), 4.77-4.58 (m, 2H), 4.57-4.28 (m, 2H), 2.86-2.67 (m, 2H). 19F NMR (376 MHz, DMSO-d6) −114.63 (appd, J = 1.3 Hz), −159.28. |
| 3-66 | 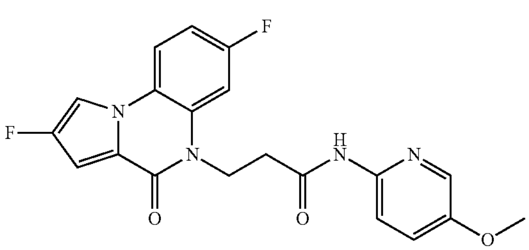 [SMILES: COc1ccc(NC(=O)CCn2c(=O)c3cc(F)cn3c3ccc(F)cc32)nc1] | Tr(MET-uHPLC-AB-101) = 2.92 min m/z (ES+) (M + H)+ 399.2, 100% | 1H NMR (400 MHz, DMSO-d6) 10.49 (s, 1H), 8.27 (dd, J = 2.9, 2.0 Hz, 1H), 8.07 (dd, J = 9.1, 5.5 Hz, 1H), 8.00 (d, J = 3.4 Hz, 2H), 7.60 (dd, J = 11.3, 2.6 Hz, 1H), 7.42 (dd, J = 9.1, 3.0 Hz, 1H), 7.19 (ddd, J = 9.0, 8.0, 2.6 Hz, 1H), 6.92 (d, J = 1.9 Hz, 1H), 4.78-4.34 (m, 2H), 3.80 (s, 3H), 2.75 (t, J = 7.4 Hz, 2H). 19F NMR (376 MHz, DMSO-d6) −114.76, −159.28. |

| Ex. | Structure | LCMS data | NMR data |
|---|---|---|---|
| 3-67 | 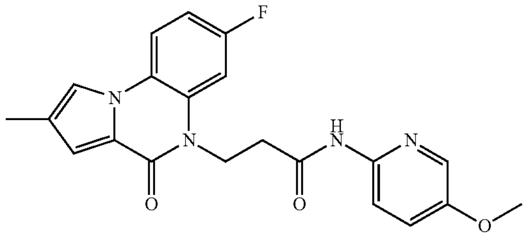 | Tr(MET-uHPLC-AB-101) = 3.01 min m/z (ES⁺) (M + H)⁺ 395.2, 100% | 1H NMR (400 MHz, DMSO-d6) 10.49 (s, 1H), 8.31-7.89 (m, 4H), 7.54 (dd, J = 11.3, 2.6 Hz, 1H), 7.42 (dd, J = 9.1, 3.0 Hz, 1H), 7.28-7.03 (m, 1H), 6.88 (d, J = 1.0 Hz, 1H), 4.57-4.33 (m, 2H), 3.80 (s, 3H), 2.74 (t, J = 7.4 Hz, 2H), 2.21 (s, 3H). 19F NMR (376 MHz, DMSO-d6) −115.70. |
| 3-68 | 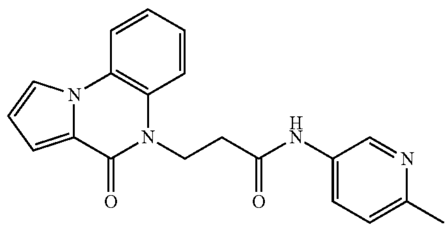 [SMILES: Cc1ccc(NC(=O)CCn2c(=O)c3cccn3c3ccccc32)cn1] | Tr(MET-uHPLC-AB-101) = 1.54 min m/z (ES⁺) (M + H)⁺ 347.2, 97% | 1H NMR (500 MHz, DMSO-d6) 10.15 (s, 1H), 8.55 (d, J = 2.5 Hz, 1H), 8.22 (dd, J = 2.8, 1.5 Hz, 1H), 8.14 (dd, J = 8.2, 1.3 Hz, 1H), 7.87 (dd, J = 8.4, 2.6 Hz, 1H), 7.64 (d, J = 7.8 Hz, 1H), 7.51-7.37 (m, 1H), 7.35-7.26 (m, 1H), 7.18 (d, J = 8.4 Hz, 1H), 7.06 (dd, J = 3.8, 1.5 Hz, 1H), 6.71 (dd, J = 3.8, 2.8 Hz, 1H), 4.64-4.42 (m, 2H), 2.94-2.69 (m, 2H), 2.40 (s, 3H). |
| 3-69 | 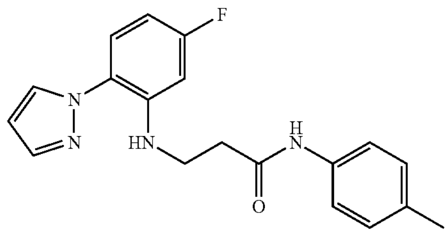 [SMILES: Cc1ccc(NC(=O)CCNc2cc(F)ccc2-n2cccn2)cc1] | Tr(MET-uHPLC-AB-101) = 3.35 min m/z (ES+) (M + H)+ 339.2, 100% | 1H NMR (500 MHz, DMSO-d6) 9.86 (s, 1H), 8.02 (d, J = 2.4 Hz, 1H), 7.68 (d, J = 1.8 Hz, 1H), 7.43 (d, J = 8.4 Hz, 2H), 7.25 (dd, J = 8.6, 6.1 Hz, 1H), 7.09 (d, J = 8.3 Hz, 2H), 6.71 (dd, J = 12.0, 2.7 Hz, 1H), 6.53-6.43 (m, 2H), 6.30 (t, J = 5.1 Hz, 1H), 3.41 (q, J = 6.4 Hz, 2H), 2.57 (t, J = 6.6 Hz, 2H), 2.24 (s, 3H). 19F NMR (376 MHz, DMSO-d6) −112.73. |

Scheme for Method 4

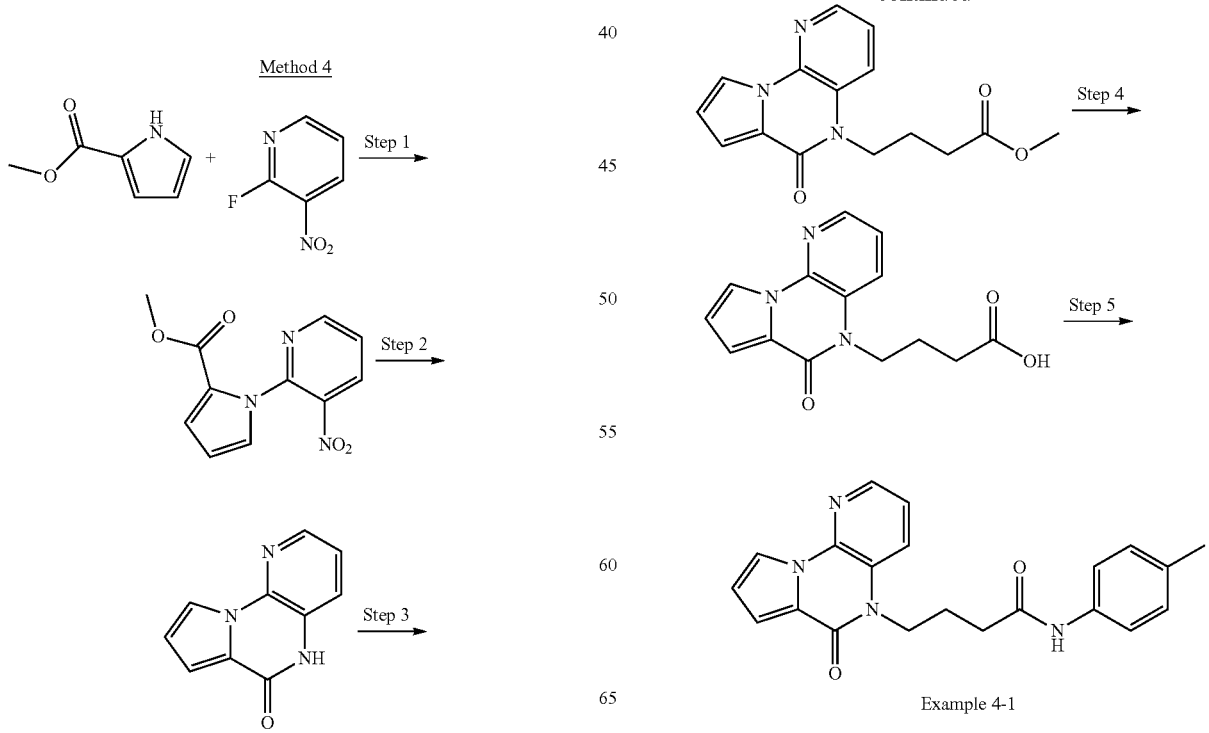

Example 4-1

Example 4-1

Step 1: Performed as for Method 3, Step 1

Step 2: 2,8,13-triazatricyclo[7.4.0.0$^{2,6}$]trideca-1(9),3,5,10,12-pentaen-7-one Methyl 1-(3-nitro-2-pyridyl)pyrrole-2-carboxylate (0.50 g, 2.02 mmol) was dissolved in DCM (10 mL) and cooled to 0° C. Trichlorosilane (0.71 mL, 7.08 mmol) was added followed by DIPEA (1.8 mL, 10.1 mmol) dropwise over 5 min. The reaction mixture was stirred at rt for 24 h. The reaction was diluted with DCM (40 mL) and added slowly to sat. aq. NaHCO$_3$ (50 ml) [Note: significant gas evolution occurred, reaction became very foamy]. The mixture was stirred at rt for 30 min then separated and extracted with DCM (2×25 mL). The combined organics were dried (MgSO$_4$) and concentrated to dryness to give methyl 1-(3-amino-2-pyridyl)pyrrole-2-carboxylate which was carried forward without further purification.

Methyl 1-(3-amino-2-pyridyl)pyrrole-2-carboxylate (439 mg, 2.02 mmol) was dissolved in acetic acid (10 mL) and heated to 100° C. for 30 min. The reaction mixture was concentrated to dryness and triturated with water (2 mL) to give the title compound. $^1$H NMR (400 MHz, DMSO-d$_6$) δ 11.42 (s, 1H), 8.27 (dd, J=4.7, 1.4 Hz, 1H), 8.18 (dd, J=2.7, 1.6 Hz, 1H), 7.72 (dd, J=8.0, 1.5 Hz, 1H), 7.44 (dd, J=8.0, 4.7 Hz, 1H), 7.16 (dd, J=3.8, 1.5 Hz, 1H), 6.86-6.65 (m, 1H). Tr(METCR1410)=0.86 min, (ES$^+$) (M+H)$^+$ 186.0, 90%.

Steps 3-5: Performed as for Method 2, Steps 3-5

Also prepared by this route:

| Ex. | Structure | LCMS data | NMR data |
|---|---|---|---|
| 4-1 | 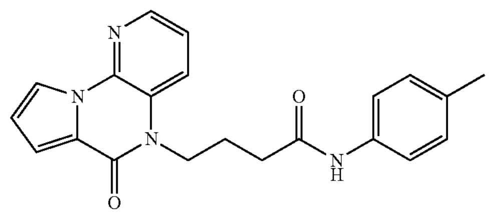 [SMILES: Cc1ccc(NC(=O)CCCn2c(=O)c3cccn3c3ncccc32)cc1] | Tr(METCR1603) = 4.14 min m/z (ES$^+$) (M + H)$^+$ 361.2, 100% | 1H NMR (500 MHz, DMSO-d6) 9.82 (s, 1H), 8.28 (dd, J = 4.7, 1.2 Hz, 1H), 8.14 (dd, J = 2.8, 1.6 Hz, 1H), 8.09 (dd, J = 8.4, 1.1 Hz, 1H), 7.50 (dd, J = 8.3, 4.7 Hz, 1H), 7.44 (d, J = 8.4 Hz, 2H), 7.12 (dd, J = 3.7, 1.6 Hz, 1H), 7.08 (d, J = 8.3 Hz, 2H), 6.73 (dd, J = 3.7, 2.9 Hz, 1H), 4.44-4.06 (m, 2H), 2.45 (t, J = 7.2 Hz, 2H), 2.23 (s, 3H), 2.00-1.71 (m, 2H). |
| 4-2 | 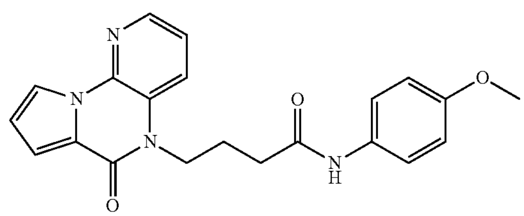 [SMILES: COc1ccc(NC(=O)CCCn2c(=O)c3cccn3c3ncccc32)cc1] | Tr(METCR1603) = 3.81 min m/z (ES$^+$) (M + H)$^+$ 377.2, 100% | 1H NMR (500 MHz, DMSO-d6) 9.76 (s, 1H), 8.28 (dd, J = 4.7, 1.2 Hz, 1H), 8.14 (dd, J = 2.8, 1.6 Hz, 1H), 8.09 (dd, J = 8.4, 1.2 Hz, 1H), 7.50 (dd, J = 8.3, 4.7 Hz, 1H), 7.46 (d, J = 9.1 Hz, 2H), 7.12 (dd, J = 3.8, 1.6 Hz, 1H), 6.95-6.82 (m, 2H), 6.74 (dd, J = 3.7, 2.8 Hz, 1H), 4.32-4.17 (m, 2H), 3.71 (s, 3H), 2.43 (t, J = 7.2 Hz, 2H), 2.03-1.81 (m, 2H). |
| 4-3 | 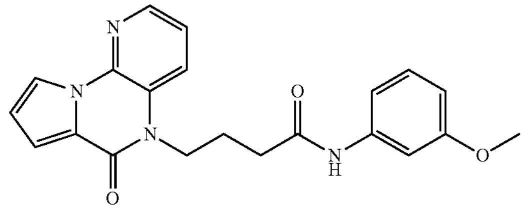 [SMILES: COc1cccc(NC(=O)CCCn2c(=O)c3cccn3c3ncccc32)c1] | Tr(METCR1603) = 3.94 min m/z (ES$^+$) (M + H)$^+$ 377.2, 100% | 1H NMR (500 MHz, DMSO-d6) 9.89 (s, 1H), 8.28 (dd, J = 4.7, 1.2 Hz, 1H), 8.14 (dd, J = 2.8, 1.6 Hz, 1H), 8.09 (dd, J = 8.3, 1.1 Hz, 1H), 7.50 (dd, J = 8.3, 4.7 Hz, 1H), 7.32-7.22 (m, 1H), 7.21-7.14 (m, 1H), 7.12 (dd, J = 3.7, 1.6 Hz, 1H), 7.09 (d, J = 8.7 Hz, 1H), 6.73 (dd, J = 3.7, 2.9 Hz, 1H), 6.60 (dd, J = 8.1, 1.9 Hz, 1H), 4.39-4.18 (m, 2H), 3.71 (s, 3H), 2.45 (t, J = 7.3 Hz, 2H), 2.01-1.88 (m, 2H). |
| 4-4 | 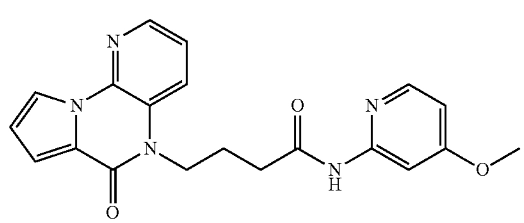 [SMILES: COc1ccnc(NC(=O)CCCn2c(=O)c3cccn3c3ncccc32)c1] | Tr(METCR1603) = 3.58 min m/z (ES$^+$) (M + H)$^+$ 378.2, 100% | 1H NMR (500 MHz, DMSO-d6) 10.40 (s, 1H), 8.27 (dd, J = 4.7, 1.2 Hz, 1H), 8.14 (dd, J = 2.8, 1.6 Hz, 1H), 8.09 (d, J = 5.8 Hz, 1H), 8.06 (dd, J = 8.4, 1.2 Hz, 1H), 7.67 (d, J = 2.1 Hz, 1H), 7.50 (dd, J = 8.3, 4.7 Hz, 1H), 7.11 (dd, J = 3.7, 1.6 Hz, 1H), 6.73 (dd, J = 3.7, 2.8 Hz, 1H), 6.68 (dd, J = 5.8, 2.4 Hz, 1H), 4.40-3.94 (m, 2H), 3.80 (s, 3H), 2.54-2.51 (m, 2H), 2.00-1.88 (m, 2H). |

| Ex. | Structure | LCMS data | NMR data |
| --- | --- | --- | --- |
| 4-5 | 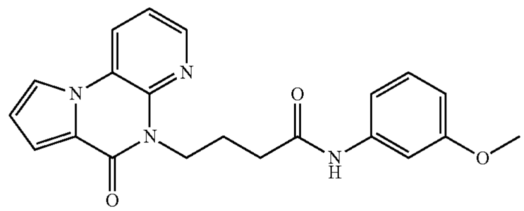 | Tr(MET-uHPLC-AB-101) = 2.86 min m/z (ES+) (M + H)+ 377.1, 100% | 1H NMR (500 MHz, DMSO-d6) 9.82 (s, 1H), 8.52 (dd, J = 8.1, 1.5 Hz, 1H), 8.38 (dd, J = 4.8, 1.5 Hz, 1H), 8.24 (dd, J = 2.8, 1.5 Hz, 1H), 7.34 (dd, J = 8.0, 4.8 Hz, 1H), 7.24 (t, J = 2.1 Hz, 1H), 7.15 (t, J = 8.1 Hz, 1H), 7.09 (dd, J = 3.8, 1.4 Hz, 1H), 7.05 (d, J = 8.9 Hz, 1H), 6.74 (dd, J = 3.8, 2.8 Hz, 1H), 6.62-6.53 (m, 1H), 4.42 (t, J = 7.0 Hz, 2H), 3.70 (s, 3H), 2.40-2.32 (m, 2H), 2.01 (p, J = 7.3 Hz, 2H). |
| 4-6 | 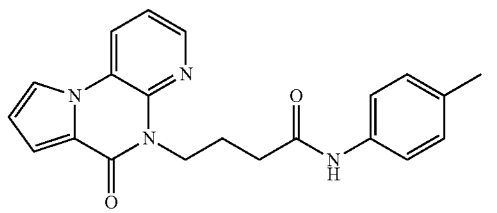 [SMILES: Cc1ccc(NC(=O)CCCn2c(=O)c3cccn3c3cccnc32)cc1] | Tr(METCR1603) = 4.03 min m/z (ES+) (M + H)+ 361.2, 100% | 1H NMR (500 MHz, DMSO-d6) 9.74 (s, 1H), 8.53 (dd, J = 8.1, 1.5 Hz, 1H), 8.39 (dd, J = 4.8, 1.5 Hz, 1H), 8.25 (dd, J = 2.8, 1.5 Hz, 1H), 7.41 (d, J = 8.4 Hz, 2H), 7.35 (dd, J = 8.0, 4.8 Hz, 1H), 7.10 (dd, J = 3.8, 1.4 Hz, 1H), 7.06 (d, J = 8.3 Hz, 2H), 6.75 (dd, J = 3.8, 2.8 Hz, 1H), 4.43 (t, J = 7.0 Hz, 2H), 2.40-2.33 (m, 2H), 2.23 (s, 3H), 2.02 (p, J = 7.5 Hz, 2H). |
| 4-7 | 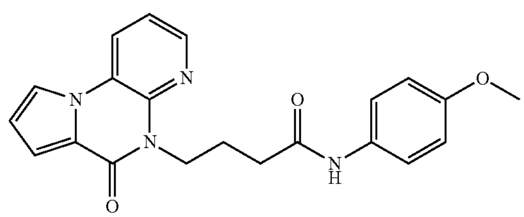 [SMILES: COc1ccc(NC(=O)CCCn2c(=O)c3cccn3c3cccnc32)cc1] | Tr(MET-uHPLC-AB-101) = 2.74 min m/z (ES+) (M + H)+ 377.1, 98% | 1H NMR (500 MHz, DMSO-d6) 9.68 (s, 1H), 8.52 (dd, J = 8.1, 1.4 Hz, 1H), 8.38 (dd, J = 4.7, 1.4 Hz, 1H), 8.24 (dd, J = 2.8, 1.5 Hz, 1H), 7.47-7.39 (m, 2H), 7.34 (dd, J = 8.0, 4.8 Hz, 1H), 7.09 (dd, J = 3.8, 1.4 Hz, 1H), 6.87-6.80 (m, 2H), 6.74 (dd, J = 3.8, 2.8 Hz, 1H), 4.42 (t, J = 7.0 Hz, 2H), 3.70 (s, 3H), 2.38-2.28 (m, 2H), 2.01 (p, J = 7.4 Hz, 2H). |
| 4-8 | 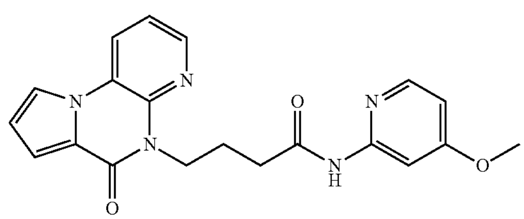 [SMILES: COc1ccnc(NC(=O)CCCn2c(=O)c3cccn3c3cccnc32)c1] | Tr(MET-uHPLC-AB-101) = 1.56 min m/z (ES+) (M + H)+ 378.1, 98% | 1H NMR (500 MHz, DMSO-d6) 10.32 (s, 1H), 8.51 (dd, J = 8.1, 1.5 Hz, 1H), 8.37 (dd, J = 4.7, 1.4 Hz, 1H), 8.24 (dd, J = 2.8, 1.5 Hz, 1H), 8.07 (d, J = 5.8 Hz, 1H), 7.65 (d, J = 2.2 Hz, 1H), 7.33 (dd, J = 8.0, 4.8 Hz, 1H), 7.08 (dd, J = 3.8, 1.4 Hz, 1H), 6.73 (dd, J = 3.8, 2.8 Hz, 1H), 6.66 (dd, J = 5.8, 2.4 Hz, 1H), 4.41 (t, J = 7.0 Hz, 2H), 3.78 (s, 3H), 2.44 (t, J = 7.5 Hz, 2H), 2.00 (p, J = 7.3 Hz, 2H). |
| 4-9 | 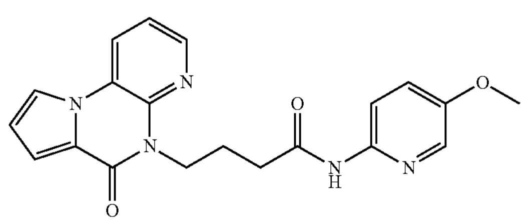 | Tr(MET-uHPLC-AB-101) = 2.33 min m/z (ES+) (M + H)+ 378.1, 95% | 1H NMR (500 MHz, DMSO-d6) 10.24 (s, 1H), 8.52 (dd, J = 8.1, 1.5 Hz, 1H), 8.38 (dd, J = 4.8, 1.5 Hz, 1H), 8.25 (dd, J = 2.8, 1.5 Hz, 1H), 7.99 (d, J = 3.0 Hz, 1H), 7.96 (d, J = 9.0 Hz, 1H), 7.38 (dd, J = 9.1, 3.1 Hz, 1H), 7.34 (dd, J = 8.0, 4.8 Hz, 1H), 7.09 (dd, J = 3.8, 1.4 Hz, 1H), 6.74 (dd, J = 3.8, 2.8 Hz, 1H), 4.41 (t, J = 7.0 Hz, 2H), 3.79 (s, 3H), 2.42 (t, J = 7.6 Hz, 2H), 2.01 (p, J = 7.4 Hz, 2H). |

| Ex. | Structure | LCMS data | NMR data |
|---|---|---|---|
| 4-10 | 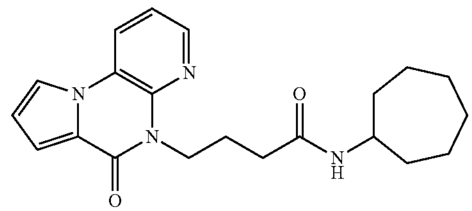 [SMILES: O=C(CCCn1c(=O)c2cccn2c2cccnc21)NC1CCCCCC1] | Tr(MET-uHPLC-AB-101) = 4.27 min, (ES⁺) (M + H)⁺ 367, 100% | 1H NMR (500 MHz, DMSO-d6) 8.54 (dd, J = 1.46, 8.09 Hz, 1H), 8.40 (dd, J = 1.45, 4.75 Hz, 1H), 8.26 (dd, J = 1.47, 2.78 Hz, 1H), 7.71 (d, J = 7.80 Hz, 1H), 7.36 (dd, J = 4.75, 8.04 Hz, 1H), 7.09 (dd, J = 1.42, 3.83 Hz, 1H), 6.75 (dd, J = 2.83, 3.79 Hz, 1H), 4.35 (t, J = 7.16 Hz, 2H), 3.67-3.65 (m, 1H), 2.14-2.05 (m, 2H), 1.88 (p, J = 7.54 Hz, 2H), 1.73-1.68 (m, 2H), 1.63-1.41 (m, 6H), 1.34 (p, J = 9.89 Hz, 4H). |

Scheme for Method 5

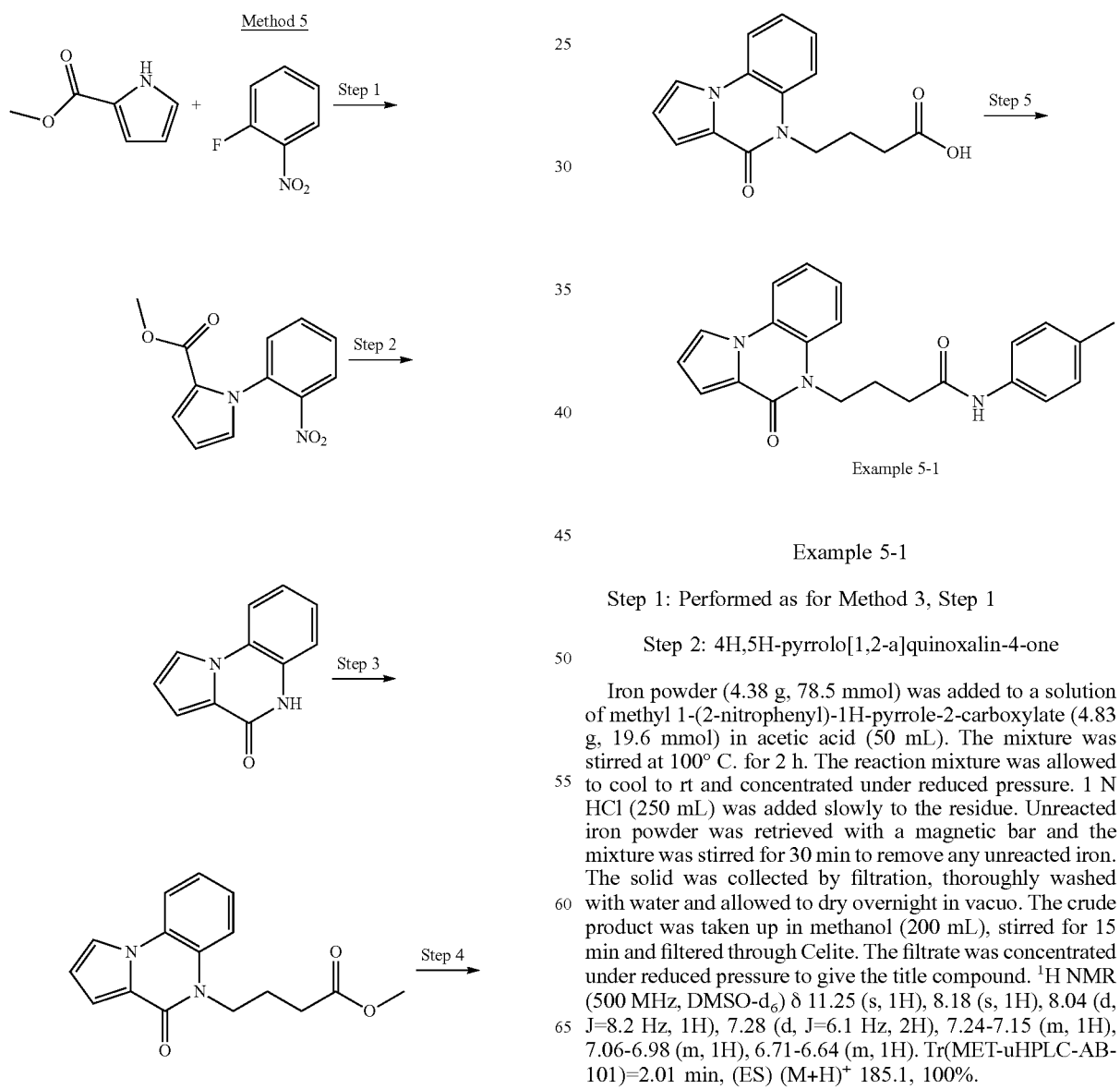

Example 5-1

Step 1: Performed as for Method 3, Step 1

Step 2: 4H,5H-pyrrolo[1,2-a]quinoxalin-4-one

Iron powder (4.38 g, 78.5 mmol) was added to a solution of methyl 1-(2-nitrophenyl)-1H-pyrrole-2-carboxylate (4.83 g, 19.6 mmol) in acetic acid (50 mL). The mixture was stirred at 100° C. for 2 h. The reaction mixture was allowed to cool to rt and concentrated under reduced pressure. 1 N HCl (250 mL) was added slowly to the residue. Unreacted iron powder was retrieved with a magnetic bar and the mixture was stirred for 30 min to remove any unreacted iron. The solid was collected by filtration, thoroughly washed with water and allowed to dry overnight in vacuo. The crude product was taken up in methanol (200 mL), stirred for 15 min and filtered through Celite. The filtrate was concentrated under reduced pressure to give the title compound. ¹H NMR (500 MHz, DMSO-d₆) δ 11.25 (s, 1H), 8.18 (s, 1H), 8.04 (d, J=8.2 Hz, 1H), 7.28 (d, J=6.1 Hz, 2H), 7.24-7.15 (m, 1H), 7.06-6.98 (m, 1H), 6.71-6.64 (m, 1H). Tr(MET-uHPLC-AB-101)=2.01 min, (ES) (M+H)⁺ 185.1, 100%.

Steps 3-5: Performed as for Method 2, Steps 3-5

Also prepared by this route:

| Ex. | Structure | LCMS data | NMR data |
| --- | --- | --- | --- |
| 5-1 | 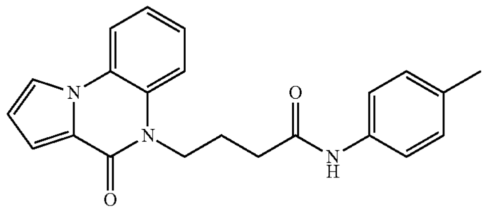 | Tr(METCR1603) = 4.31 min m/z (ES⁺) (M + H)⁺ 360.3, 100% | 1H NMR (500 MHz, DMSO-d6) 9.84 (s, 1H), 8.21 (dd, J = 2.8, 1.5 Hz, 1H), 8.14 (dd, J = 8.2, 1.3 Hz, 1H), 7.67 (d, J = 7.7 Hz, 1H), 7.54-7.37 (m, 3H), 7.36-7.23 (m, 1H), 7.16-6.96 (m, 3H), 6.70 (dd, J = 3.8, 2.8 Hz, 1H), 4.74-4.08 (m, 2H), 2.45 (t, J = 7.3 Hz, 2H), 2.24 (s, 3H), 2.06-1.89 (m, 2H). |
| 5-2 | 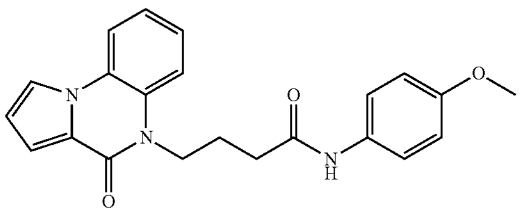 | Tr(METCR1603) = 4.00 min m/z (ES⁺) (M + H)⁺ 376.2, 100% | 1H NMR (500 MHz, DMSO-d6) 9.78 (s, 1H), 8.21 (dd, J = 2.8, 1.5 Hz, 1H), 8.14 (dd, J = 8.2, 1.2 Hz, 1H), 7.67 (d, J = 7.8 Hz, 1H), 7.48 (d, J = 9.1 Hz, 2H), 7.45-7.35 (m, 1H), 7.36-7.19 (m, 1H), 7.05 (dd, J = 3.8, 1.4 Hz, 1H), 6.86 (d, J = 9.1 Hz, 2H), 6.70 (dd, J = 3.8, 2.8 Hz, 1H), 4.46-4.12 (m, 2H), 3.71 (s, 3H), 2.43 (t, J = 7.3 Hz, 2H), 2.12-1.82 (m, 2H). |
| 5-3 | 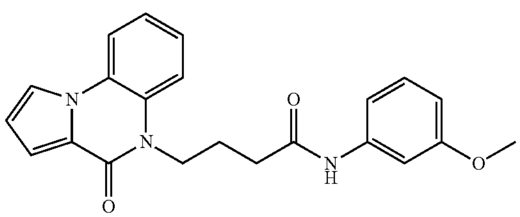 | Tr(METCR1603) = 4.12 min m/z (ES⁺) (M + H)⁺ 376.2, 100% | 1H NMR (500 MHz, DMSO-d6) 9.91 (s, 1H), 8.21 (dd, J = 2.8, 1.5 Hz, 1H), 8.14 (dd, J = 8.2, 1.3 Hz, 1H), 7.66 (d, J = 7.6 Hz, 1H), 7.47-7.38 (m, 1H), 7.36-7.24 (m, 2H), 7.24-7.14 (m, 1H), 7.11 (app. d, J = 8.7 Hz, 1H), 7.05 (dd, J = 3.8, 1.5 Hz, 1H), 6.70 (dd, J = 3.8, 2.8 Hz, 1H), 6.60 (dd, J = 8.1, 1.7 Hz, 1H), 4.42-4.06 (m, 2H), 3.71 (s, 3H), 2.45 (t, J = 7.3 Hz, 2H), 2.00-1.80 (m, 2H). |
| 5-4 | 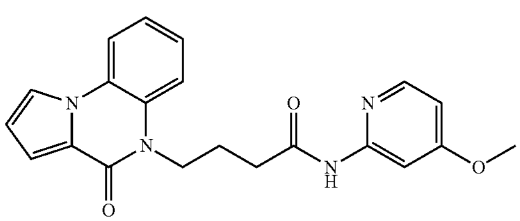 [SMILES: COc1ccnc(NC(=O)CCCn2c(=O)c3cccn3c3ccccc32)c1] | Tr(METCR1603) = 3.80 min m/z (ES⁺) (M + H)⁺ 377.2, 100% | 1H NMR (500 MHz, DMSO-d6) 10.43 (s, 1H), 8.21 (dd, J = 2.8, 1.5 Hz, 1H), 8.14 (dd, J = 8.2, 1.3 Hz, 1H), 8.10 (d, J = 5.8 Hz, 1H), 7.71 (d, J = 2.0 Hz, 1H), 7.64 (d, J = 7.7 Hz, 1H), 7.51-7.37 (m, 1H), 7.36-7.16 (m, 1H), 7.04 (dd, J = 3.8, 1.5 Hz, 1H), 6.76-6.59 (m, 2H), 4.35-4.14 (m, 2H), 3.81 (s, 3H), 2.57-2.52 (m, 2H), 1.98-1.78 (m, 2H). |
| 5-5 | 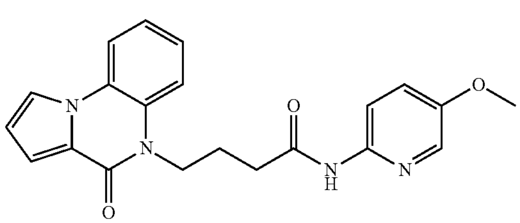 [SMILES: COc1ccc(NC(=O)CCCn2c(=O)c3cccn3c3ccccc32)nc1] | Tr(METCR1603) = 3.80 min m/z (ES⁺) (M + H)⁺ 377.2, 100% | 1H NMR (500 MHz, DMSO-d6) 10.34 (s, 1H), 8.21 (dd, J = 2.8, 1.5 Hz, 1H), 8.14 (dd, J = 8.2, 1.3 Hz, 1H), 8.05-7.88 (m, 2H), 7.65 (d, J = 7.7 Hz, 1H), 7.49-7.35 (m, 2H), 7.35-7.19 (m, 1H), 7.04 (dd, J = 3.8, 1.5 Hz, 1H), 6.69 (dd, J = 3.8, 2.8 Hz, 1H), 4.44-4.13 (m, 2H), 3.79 (s, 3H), 2.60-2.48 (m, 2H), 2.04-1.81 (m, 2H). |

-continued

| Ex. | Structure | LCMS data | NMR data |
|---|---|---|---|
| 5-6 | 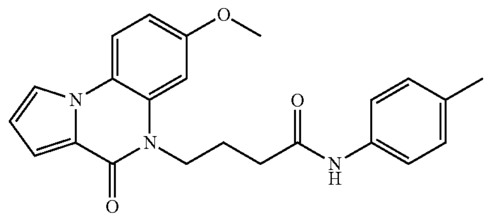 [SMILES: COc1ccc2c(c1)n(CCCC(=O)Nc1ccc(C)cc1)c(=O)c1cccn12] | Tr(METCR1603) = 4.50 min m/z (ES+) (M + H)+ 390.2, 100% | 1H NMR (500 MHz, DMSO-d6) 9.86 (s, 1H), 8.13 (dd, J = 2.7, 1.5 Hz, 1H), 8.06 (d, J = 9.0 Hz, 1H), 7.46 (d, J = 8.4 Hz, 2H), 7.22 (d, J = 2.5 Hz, 1H), 7.09 (d, J = 8.3 Hz, 2H), 7.00 (dd, J = 3.9, 1.5 Hz, 1H), 6.90 (dd, J = 9.0, 2.5 Hz, 1H), 6.65 (dd, J = 3.8, 2.7 Hz, 1H), 4.31-4.14 (m, 2H), 3.89 (s, 3H), 2.48-2.43 (m, 2H), 2.24 (s, 3H), 1.95 (p, J = 7.2 Hz, 2H). |
| 5-7 | 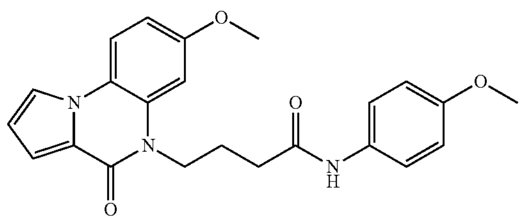 [SMILES: COc1ccc(NC(=O)CCCn2c(=O)c3cccn3c3ccc(OC)cc32)cc1] | Tr(METCR1603) = 4.15 min m/z (ES+) (M + H)+ 406.2, 100% | 1H NMR (500 MHz, DMSO-d6) 9.81 (s, 1H), 8.13 (dd, J = 2.7, 1.5 Hz, 1H), 8.06 (d, J = 9.0 Hz, 1H), 7.52-7.46 (m, 2H), 7.22 (d, J = 2.5 Hz, 1H), 7.00 (dd, J = 3.9, 1.5 Hz, 1H), 6.90 (dd, J = 8.9, 2.5 Hz, 1H), 6.88-6.84 (m, 2H), 6.65 (dd, J = 3.9, 2.7 Hz, 1H), 4.31-4.17 (m, 2H), 3.89 (s, 3H), 3.71 (s, 3H), 2.45 (t, J = 7.0 Hz, 2H), 1.95 (p, J = 7.1 Hz, 2H). |
| 5-8 | 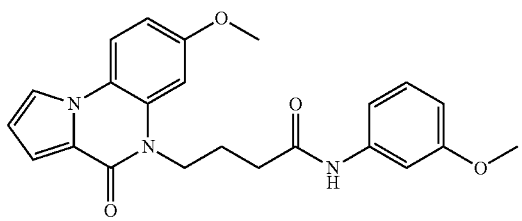 [SMILES: COc1cccc(NC(=O)CCCn2c(=O)c3cccn3c3ccc(OC)cc32)c1] | Tr(METCR1603) = 4.29 min m/z (ES+) (M + H)+ 406.2, | 1H NMR (500 MHz, DMSO-d6) 9.95 (s, 1H), 8.13 (dd, J = 2.7, 1.5 Hz, 1H), 8.06 (d, J = 9.0 Hz, 1H), 7.32 (t, J = 2.1 Hz, 1H), 7.23 (d, J = 2.5 Hz, 1H), 7.18 (t, J = 8.1 Hz, 1H), 7.10 (d, J = 8.8 Hz, 1H), 7.00 (dd, J = 3.9, 1.5 Hz, 1H), 6.90 (dd, J = 8.9, 2.5 Hz, 1H), 6.65 (dd, J = 3.8, 2.8 Hz, 1H), 6.61 (dd, J = 8.1, 1.9 Hz, 1H), 4.28-4.21 (m, 2H), 3.90 (s, 3H), 3.72 (s, 3H), 2.48-2.46 (part. obsc. m, 2H), 1.95 (p, J = 7.0 Hz, 2H). |
| 5-9 | 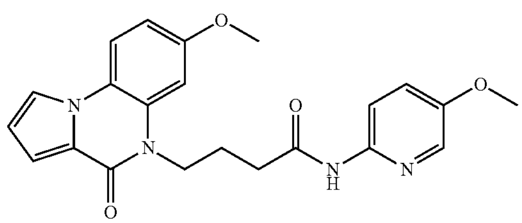 | Tr(MET-uHPLC-AB-101) = 2.91 min m/z (ES+) (M + H)+ 407.2, 96% | 1H NMR (400 MHz, DMSO-d6) 10.38 (s, 1H), 8.12 (dd, J = 2.8, 1.5 Hz, 1H), 8.09-7.98 (m, 3H), 7.42 (dd, J = 9.1, 3.1 Hz, 1H), 7.20 (d, J = 2.5 Hz, 1H), 7.00 (dd, J = 3.9, 1.5 Hz, 1H), 6.90 (dd, J = 9.0, 2.5 Hz, 1H), 6.64 (dd, J = 3.9, 2.7 Hz, 1H), 4.30-4.13 (m, 2H), 3.89 (s, 3H), 3.80 (s, 3H), 2.57-2.53 (m, 2H), 1.93 (p, J = 7.1 Hz, 2H). |
| 5-10 | 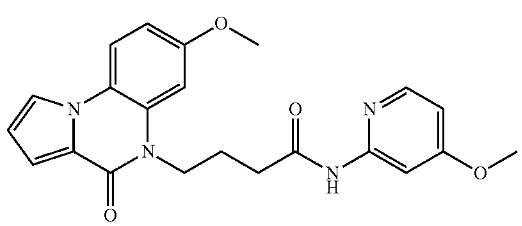 [SMILES: COc1ccnc(NC(=O)CCCn2c(=O)c3cccn3c3ccc(OC)cc32)c1] | Tr(METCR1603) = 3.99 min m/z (ES+) (M + H)+ 407.3, 100% | 1H NMR (400 MHz, DMSO-d6) 10.49 (s, 1H), 8.13 (dd, J = 2.8, 1.5 Hz, 1H), 8.11 (d, J = 5.8 Hz, 1H), 8.07 (d, J = 9.0 Hz, 1H), 7.74 (d, J = 2.1 Hz, 1H), 7.23 (d, J = 2.5 Hz, 1H), 7.00 (dd, J = 3.9, 1.5 Hz, 1H), 6.91 (dd, J = 9.0, 2.5 Hz, 1H), 6.70 (dd, J = 5.8, 2.4 Hz, 1H), 6.65 (dd, J = 3.9, 2.7 Hz, 1H), 4.28-4.18 (m, 2H), 3.91 (s, 3H), 3.82 (s, 3H), 2.57 (t, J = 6.8 Hz, 2H), 2.00-1.90 (m, 2H). |

| Ex. | Structure | LCMS data | NMR data |
|---|---|---|---|
| 5-11 | 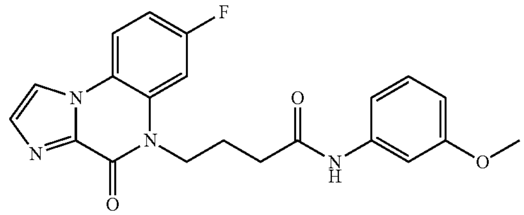 [SMILES: COc1cccc(NC(=O)CCCn2c(=O)c3nccn3c3ccc(F)cc32)c1] | Tr(METCR1603) = 3.56 min m/z (ES⁺) (M + H)⁺ 395.2, 100% | 1H NMR (400 MHz, DMSO-d6) 9.92 (s, 1H), 8.55 (s, 1H), 8.25 (dd, J = 9.0, 5.5 Hz, 1H), 7.73 (dd, J = 11.3, 2.5 Hz, 1H), 7.60 (s, 1H), 7.37-7.24 (m, 2H), 7.18 (t, J = 8.1 Hz, 1H), 7.10 (d, J = 8.1 Hz, 1H), 6.79-6.52 (m, 1H), 4.46-4.13 (m, 2H), 3.71 (s, 3H), 2.63-2.44 (m, 2H), 2.07-1.92 (m, 2H). 19F NMR (376 MHz, DMSO-d6) −113.22. |
| 5-12 | 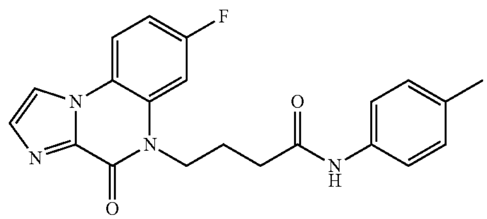 [SMILES: Cc1ccc(NC(=O)CCCn2c(=O)c3nccn3c3ccc(F)cc32)cc1] | Tr(METCR1603) = 3.74 min m/z (ES⁺) (M + H)⁺ 379.2, 98% | 1H NMR (400 MHz, DMSO-d6) 9.84 (s, 1H), 8.55 (s, 1H), 8.25 (dd, J = 9.0, 5.4 Hz, 1H), 7.73 (d, J = 11.2 Hz, 1H), 7.60 (s, 1H), 7.44 (d, J = 8.2 Hz, 2H), 7.28 (t, J = 7.3 Hz, 1H), 7.08 (d, J = 8.2 Hz, 2H), 4.43-4.18 (m, 2H), 2.50 (s, 2H), 2.24 (s, 3H), 2.04-1.90 (m, 2H). 19F NMR (376 MHz, DMSO-d6) −113.18. |
| 5-13 | 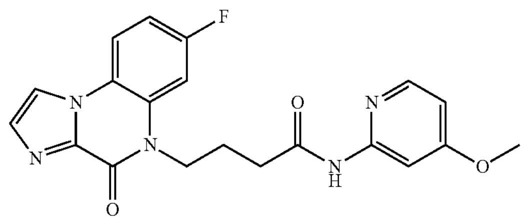 | Tr(METCR1603) = 3.28 min m/z (ES⁺) (M + H)⁺ 396.2, 95% | 1H NMR (400 MHz, DMSO-d6) 10.42 (s, 1H), 8.55 (d, J = 1.1 Hz, 1H), 8.25 (dd, J = 9.1, 5.5 Hz, 1H), 8.10 (d, J = 5.8 Hz, 1H), 7.76-7.65 (m, 2H), 7.60 (d, J = 1.1 Hz, 1H), 7.28 (td, J = 8.9, 2.5 Hz, 1H), 6.69 (dd, J = 5.8, 2.4 Hz, 1H), 4.41-4.19 (m, 2H), 3.80 (s, 3H), 2.64-2.53 (m, 2H), 2.04-1.87 (m, 2H). 19F NMR (376 MHz, DMSO-d6) −113.30. |
| 5-14 | 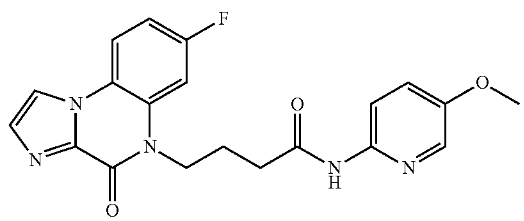 | Tr(METCR1603) = 3.26 min m/z (ES⁺) (M + H)⁺ 396.2, 100% | 1H NMR (400 MHz, DMSO-d6) 10.35 (s, 1H), 8.56 (d, J = 1.1 Hz, 1H), 8.26 (dd, J = 9.0, 5.5 Hz, 1H), 8.10-7.94 (m, 2H), 7.72 (dd, J = 11.3, 2.5 Hz, 1H), 7.61 (d, J = 1.0 Hz, 1H), 7.42 (dd, J = 9.1, 3.1 Hz, 1H), 7.29 (td, J = 8.9, 2.5 Hz, 1H), 4.41-4.15 (m, 2H), 3.80 (s, 3H), 2.59-2.52 (m, 2H), 1.96 (p, J = 7.3 Hz, 2H). 19F NMR (376 MHz, DMSO-d6) −113.24. |
| 5-15 | 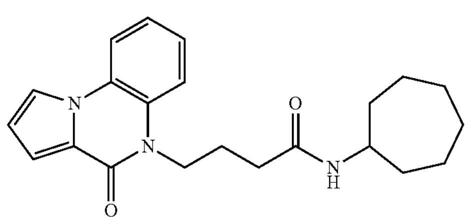 | Tr(MET-uHPLC-AB-101) = 3.42 min, (ES⁺) (M + H)⁺ 366, 99% | 1H NMR (500 MHz, DMSO-d6) 8.21 (dd, J = 2.7, 1.5 Hz, 1H), 8.13 (dd, J = 8.2, 1.2 Hz, 1H), 7.76 (d, J = 7.8 Hz, 1H), 7.63 (d, J = 8.0 Hz, 1H), 7.44-7.36 (m, 1H), 7.34-7.25 (m, 1H), 7.04 (dd, J = 3.8, 1.4 Hz, 1H), 6.69 (dd, J = 3.7, 2.9 Hz, 1H), 4.25-4.12 (m, 2H), 3.74-3.71 (m, 1H), 2.18 (t, J = 7.3 Hz, 2H), 1.84 (p, J = 7.3 Hz, 2H), 1.77-1.71 (m, 2H), 1.62-1.32 (m, 10H). |
| 5-16 | 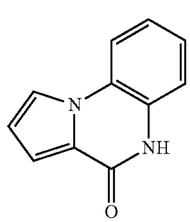 [SMILES: O=c1[nH]c2ccccc2n2cccc12] | Tr(MET-uHPLC-AB-101) = 2.01 min, (ES⁺) (M + H)⁺ 185, 100% | 1H NMR (500 MHz, DMSO-d6) 11.25 (s, 1H), 8.18 (s, 1H), 8.04 (d, J = 8.2 Hz, 1H), 7.33-7.24 (m, 2H), 7.24-7.15 (m, 1H), 7.06-6.98 (m, 1H), 6.71-6.64 (m, 1H). |

-continued

| Ex. | Structure | LCMS data | NMR data |
|---|---|---|---|
| 5-17 | 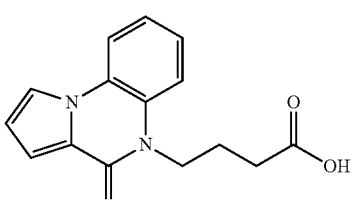 | Tr(MET-uHPLC-AB-101) = 2.31 min, (ES+) (M + H)+ 271, 99% | 1H NMR (500 MHz, DMSO-d6) 12.15 (s, 1H), 8.20 (dd, J = 2.5, 1.5 Hz, 1H), 8.13 (d, J = 8.1 Hz, 1H), 7.64 (d, J = 8.3 Hz, 1H), 7.43-7.36 (m, 1H), 7.30 (t, J = 7.7 Hz, 1H), 7.05 (dd, J = 3.8, 1.3 Hz, 1H), 6.73-6.65 (m, 1H), 4.32-4.14 (m, 2H), 2.38 (t, J = 7.2 Hz, 2H), 1.86 (p, J = 7.3 Hz, 2H). |
| 5-18 | 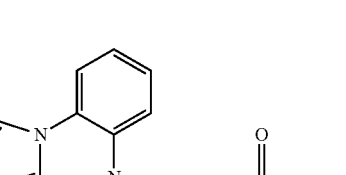 | Tr(MET-uHPLC-AB-101) = 2.99 min, (ES+) (M + H)+ 338, 100% | 1H NMR (500 MHz, DMSO-d6) 8.21 (dd, J = 2.6, 1.5 Hz, 1H), 8.18-8.08 (m, 1H), 7.80 (d, J = 8.3 Hz, 1H), 7.47-7.36 (m, 1H), 7.30 (t, J = 7.7 Hz, 1H), 7.05 (dd, J = 3.8, 1.4 Hz, 1H), 6.76-6.65 (m, 1H), 4.29-4.11 (m, 2H), 3.41 (dt, J = 31.4, 5.3 Hz, 4H), 2.47 (t, J = 6.8 Hz, 2H), 1.86 (p, J = 6.9 Hz, 2H), 1.69-1.33 (m, 6H). |

Scheme for Method 6

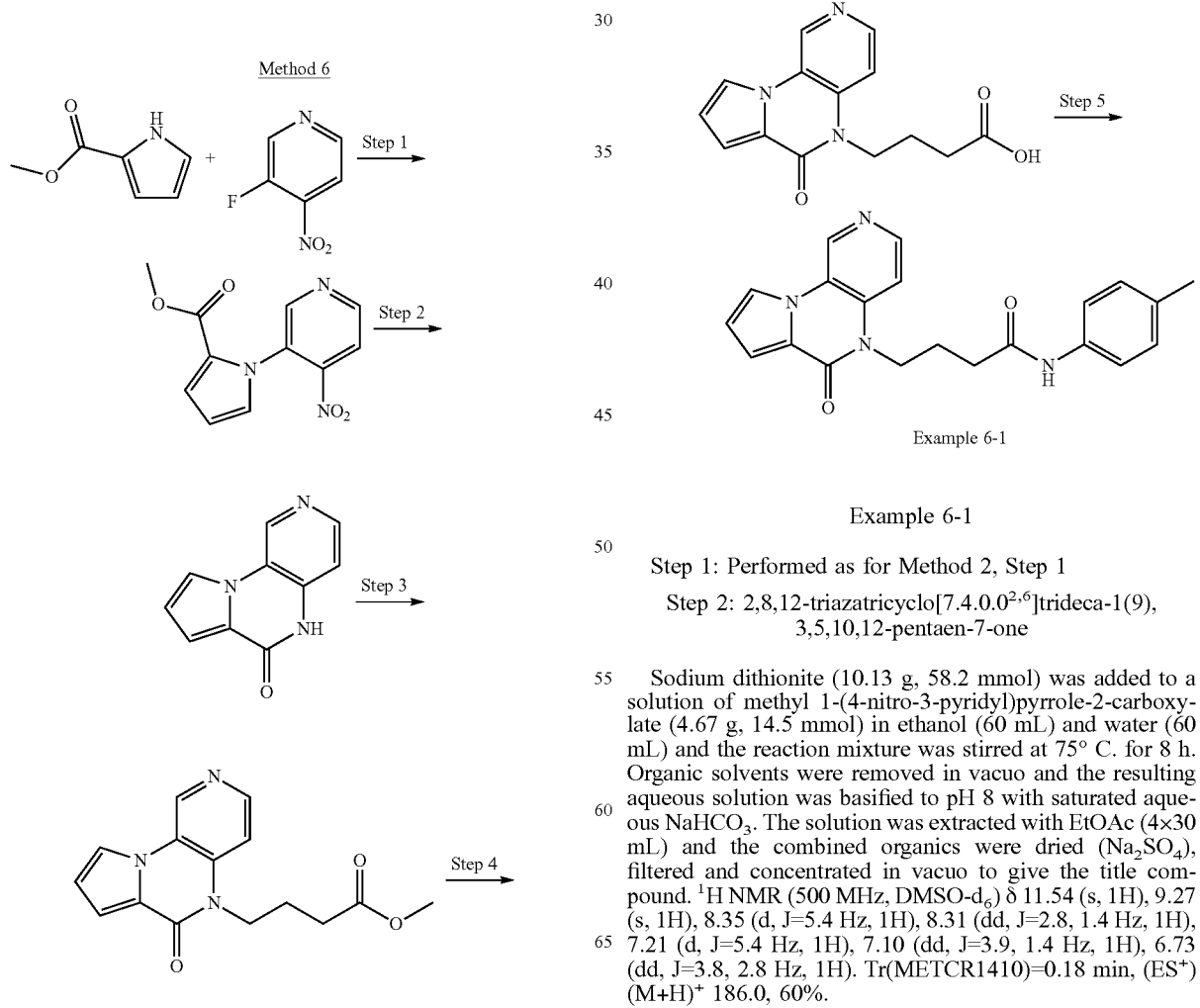

Example 6-1

Example 6-1

Step 1: Performed as for Method 2, Step 1

Step 2: 2,8,12-triazatricyclo[7.4.0.0$^{2,6}$]trideca-1(9),3,5,10,12-pentaen-7-one Sodium dithionite (10.13 g, 58.2 mmol) was added to a solution of methyl 1-(4-nitro-3-pyridyl)pyrrole-2-carboxylate (4.67 g, 14.5 mmol) in ethanol (60 mL) and water (60 mL) and the reaction mixture was stirred at 75° C. for 8 h. Organic solvents were removed in vacuo and the resulting aqueous solution was basified to pH 8 with saturated aqueous NaHCO$_3$. The solution was extracted with EtOAc (4×30 mL) and the combined organics were dried (Na$_2$SO$_4$), filtered and concentrated in vacuo to give the title compound. $^1$H NMR (500 MHz, DMSO-d$_6$) δ 11.54 (s, 1H), 9.27 (s, 1H), 8.35 (d, J=5.4 Hz, 1H), 8.31 (dd, J=2.8, 1.4 Hz, 1H), 7.21 (d, J=5.4 Hz, 1H), 7.10 (dd, J=3.9, 1.4 Hz, 1H), 6.73 (dd, J=3.8, 2.8 Hz, 1H). Tr(METCR1410)=0.18 min, (ES+) (M+H)+ 186.0, 60%.

Steps 3-5: Performed as for Method 2, Steps 3-5
Also prepared by this route:

| Ex. | Structure | LCMS data | NMR data |
| --- | --- | --- | --- |
| 6-1 | 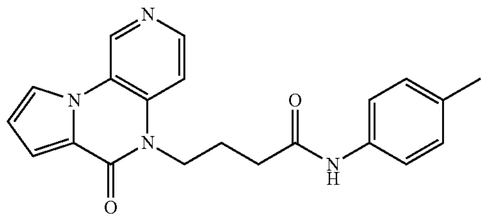 [SMILES: Cc1ccc(NC(=O)CCCn2c(=O)c3cccn3c3cnccc32)cc1] | Tr(METCR1603) = 3.64 min m/z (ES⁺) (M + H)⁺ 361.1, 100% | 1H NMR (500 MHz, DMSO-d6) 9.82 (s, 1H), 9.36 (s, 1H), 8.48 (d, J = 5.7 Hz, 1H), 8.35 (dd, J = 2.8, 1.4 Hz, 1H), 7.63 (d, J = 5.8 Hz, 1H), 7.44 (d, J = 8.4 Hz, 2H), 7.13 (dd, J = 3.9, 1.4 Hz, 1H), 7.08 (d, J = 8.3 Hz, 2H), 6.75 (dd, J = 3.8, 2.8 Hz, 1H), 4.28-4.19 (m, 2H), 2.45-2.40 (m, 2H), 2.24 (s, 3H), 1.94 (p, J = 7.4 Hz, 2H). |
| 6-2 | 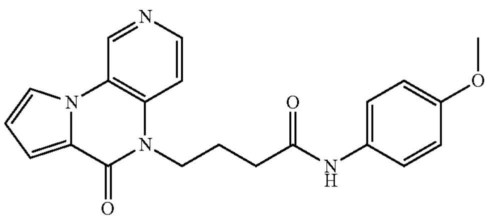 [SMILES: COc1ccc(NC(=O)CCCn2c(=O)c3cccn3c3cnccc32)cc1] | Tr(METCR1603) = 3.35 min m/z (ES⁺) (M + H)⁺ 377.2, 100% | 1H NMR (500 MHz, DMSO-d6) 9.76 (s, 1H), 9.36 (s, 1H), 8.48 (d, J = 5.7 Hz, 1H), 8.34 (dd, J = 2.8, 1.4 Hz, 1H), 7.63 (d, J = 5.8 Hz, 1H), 7.50-7.42 (m, 2H), 7.13 (dd, J = 3.9, 1.4 Hz, 1H), 6.89-6.82 (m, 2H), 6.75 (dd, J = 3.8, 2.8 Hz, 1H), 4.28-4.20 (m, 2H), 3.71 (s, 3H), 2.43 (t, J = 7.2 Hz, 2H), 1.94 (p, J = 7.3 Hz, 2H). |
| 6-3 | 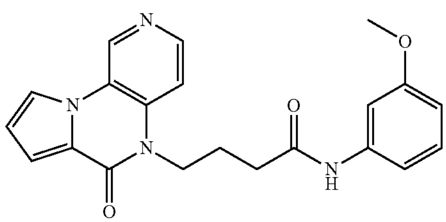 [SMILES: COc1cccc(NC(=O)CCCn2c(=O)c3cccn3c3cnccc32)c1] | Tr(METCR1603) = 3.44 min m/z (ES⁺) (M + H)⁺ 377.2, 100% | 1H NMR (500 MHz, DMSO-d6) 9.89 (s, 1H), 9.36 (s, 1H), 8.48 (d, J = 5.7 Hz, 1H), 8.34 (dd, J = 2.8, 1.4 Hz, 1H), 7.62 (d, J = 5.8 Hz, 1H), 7.25 (m, 1H), 7.17 (m, 1H), 7.13 (dd, J = 3.9, 1.4 Hz, 1H), 7.11-7.08 (m, 1H), 6.74 (dd, J = 3.8, 2.8 Hz, 1H), 6.60 (dd, J = 7.8, 2.1 Hz, 1H), 4.29-4.19 (m, 2H), 3.71 (s, 3H), 2.46-2.41 (m, 2H), 1.95 (p, J = 7.3 Hz, 2H). |
| 6-4 | 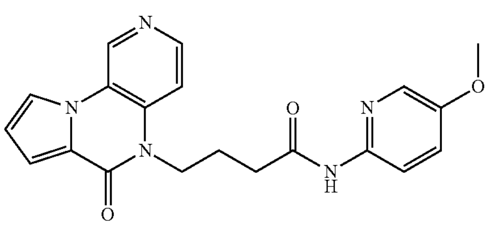 [SMILES: COc1ccc(NC(=O)CCCn2c(=O)c3cccn3c3cnccc32)nc1] | Tr(METCR1603) = 3.15 min m/z (ES⁺) (M + H)⁺ 378.2, 100% | 1H NMR (500 MHz, DMSO-d6) 10.32 (s, 1H), 9.35 (s, 1H), 8.48 (d, J = 5.7 Hz, 1H), 8.34 (dd, J = 2.8, 1.4 Hz, 1H), 8.03-7.95 (m, 2H), 7.61 (d, J = 5.8 Hz, 1H), 7.40 (dd, J = 9.1, 3.1 Hz, 1H), 7.12 (dd, J = 3.9, 1.4 Hz, 1H), 6.74 (dd, J = 3.8, 2.8 Hz, 1H), 4.28-4.17 (m, 2H), 3.79 (s, 3H), 2.54-2.52 (m, 2H), 1.93 (p, J = 7.1 Hz, 2H). |
| 6-5 | 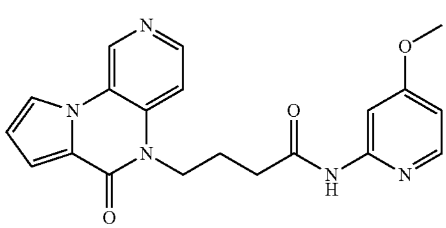 [SMILES: COc1ccnc(NC(=O)CCCn2c(=O)c3cccn3c3cnccc32)c1] | Tr(METCR1603) = 3.15 min m/z (ES⁺) (M + H)⁺ 378.2, 100% | 1H NMR (500 MHz, DMSO-d6) 10.41 (s, 1H), 9.36 (s, 1H), 8.49 (d, J = 5.7 Hz, 1H), 8.35 (dd, J = 2.8, 1.4 Hz, 1H), 8.10 (d, J = 5.8 Hz, 1H), 7.69 (s, 1H), 7.61 (d, J = 5.8 Hz, 1H), 7.12 (dd, J = 3.9, 1.4 Hz, 1H), 6.75 (dd, J = 3.8, 2.8 Hz, 1H), 6.69 (dd, J = 5.8, 2.4 Hz, 1H), 4.26-4.18 (m, 2H), 3.81 (s, 3H), 2.57-2.53 (m, 2H), 1.95 (p, J = 7.4 Hz, 2H). |

Scheme for Method 7

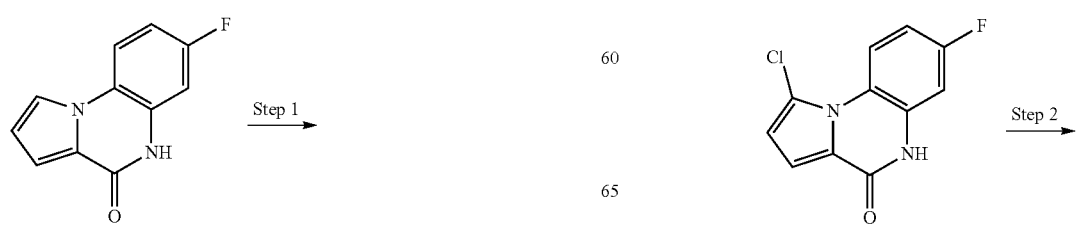

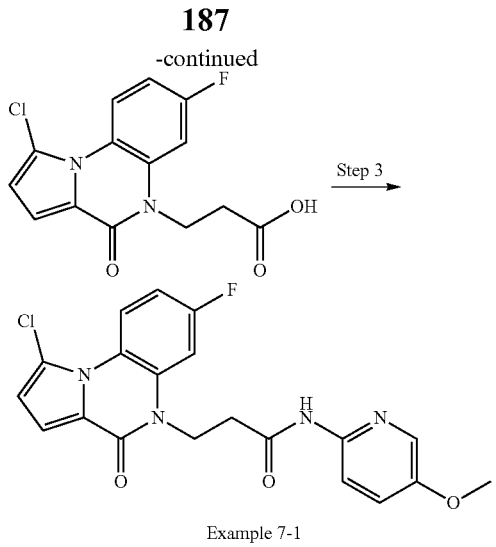

Example 7-1

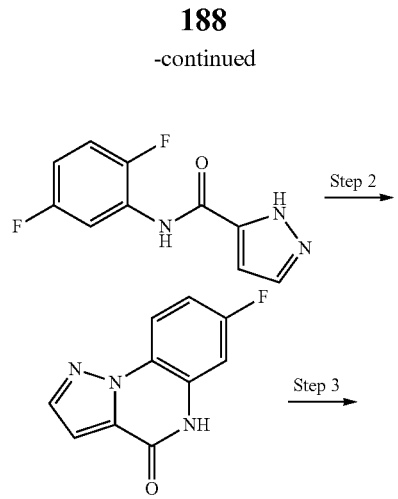

Example 8-1

Example 7-1

Step 1: 1-Chloro-7-fluoro-5H-pyrrolo[1,2-a]quinoxalin-4-one

7-Fluoro-5H-pyrrolo[1,2-a]quinoxalin-4-one (500 mg, 2.47 mmol) was suspended in THF (50 mL) and 1-chloropyrrolidine-2,5-dione (330 mg, 2.47 mmol) was added. The reaction mixture was heated to 60° C. overnight. The mixture was concentrated to dryness and partitioned between water and DCM. The organic layer was concentrated and purified by recrystallization from DMSO (50 mL) to give the title compound. $^1$H NMR (400 MHz, DMSO-d$_6$) δ 11.52 (s, 1H), 8.77 (dd, J=9.2, 5.1 Hz, 1H), 7.34-6.94 (m, 3H), 6.76 (d, J=4.2 Hz, 1H). Tr(METCR1410)=1.08 min, (ES$^+$) (M+H)$^+$ 236.9, 89%.

Steps 2-3: Performed as for Method 3, Steps 3-4

Also prepared by this route:

| Ex. | Structure | LCMS data | NMR data |
|---|---|---|---|
| 7-1 | ![structure] | Tr(MET-uHPLC-AB-101) = 3.23 min m/z (ES$^+$) (M + H)$^+$ 415.2, 94% | 1H NMR (400 MHz, DMSO-d6) 10.49 (s, 1H), 8.86 (dd, J = 9.4, 5.5 Hz, 1H), 8.39-7.92 (m, 2H), 7.62 (dd, J = 11.2, 2.7 Hz, 1H), 7.42 (dd, J = 9.1, 3.0 Hz, 1H), 7.29-6.93 (m, 2H), 6.79 (d, J = 4.2 Hz, 1H), 4.95-4.29 (m, 2H), 3.80 (s, 3H), 2.86-2.69 (m, 2H). 19F NMR (376 MHz, DMSO-d6) −113.82. |

Scheme for Method 8

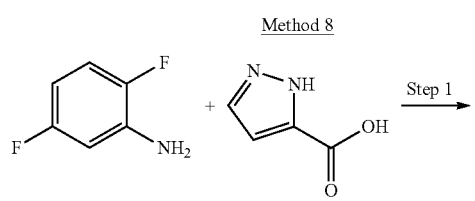

Method 8

Example 8-1

Step 1: N-(2,5-Difluorophenyl)-1H-pyrazole-5-carboxamide 2,5-Difluoroaniline (864 mg, 6.69 mmol), 1H-pyrazole-5-carboxylic acid (500 mg, 4.46 mmol) and EDC hydrochloride (1710 mg, 8.92 mmol) were suspended in pyridine (40 mL) and the reaction mixture stirred at rt for 16 h. The reaction mixture was filtered through filter paper, and the filtrate diluted with water and extracted with DCM (3×), dried (MgSO$_4$) and concentrated to dryness. The resultant was dried under vacuum at 40° C. to give the title compound, used with no further purification. ¹H NMR (400 MHz, DMSO-d₆) δ 13.54 (s, 1H), 9.63 (s, 1H), 7.93 (s, 1H), 7.83 (s, 1H), 7.37 (ddd, J=10.3, 9.2, 5.1 Hz, 1H), 7.05 (ddd, J=12.1, 8.3, 3.4 Hz, 1H), 6.83 (s, 1H).

Step 2: 7-Fluoro-4H,5H-pyrazolo[1,5-a]quinoxalin-4-one

N-(2,5-Difluorophenyl)-1H-pyrazole-5-carboxamide (294 mg, 1.32 mmol) was dissolved in anhydrous DMF (8.82 mL) and sodium hydride (60%, 63 mg, 2.63 mmol) was added. The reaction was heated to 150° C. for 48 h. A further portion of sodium hydride (1 eq.) was added and heating continued for a further 24 h at 150° C. The reaction was poured into an ammonium chloride solution, and the resultant precipitate isolated by filtration, washed with water and dried under vacuum to give the title compound. ¹H NMR (500 MHz, Chloroform-d) δ 10.41 (s, 1H), 8.28 (dd, J=9.0, 5.2 Hz, 1H), 7.99 (d, J=2.0 Hz, 1H), 7.26 (d, J=2.0 Hz, 1H), 7.16-7.06 (m, 2H).

Step 3: 3-{7-Fluoro-4-oxo-4H,5H-pyrazolo[1,5-a]quinoxalin-5-yl}propanoic acid 7-Fluoro-4H,5H-pyrazolo[1,5-a]quinoxalin-4-one (126 mg, 0.620 mmol) was dissolved in THF (6 mL) in a sealed tube and sodium hydroxide (149 mg, 3.72 mmol) was added followed by ethyl prop-2-enoate (0.33 mL, 3.10 mmol). The mixture was stirred at 60° C. for 72 h. The reaction mixture was concentrated to dryness and suspended in water (50 mL) and the pH adjusted to pH 1 using 6 M HCl. The aqueous was extracted into EtOAc (3×), dried (MgSO₄) and concentrated to give the desired product. The product was used with no further purification. Tr(METCR1410)=0.97 min, m/z (ES⁺) (M+H)⁺ 275.8, 50%.

Step 4: 3-{7-Fluoro-4-oxo-4H,5H-pyrazolo[1,5-a]quinoxalin-5-yl}-N-(5-methoxypyridin-2-yl)propanamide 3-(7-Fluoro-4-oxo-pyrazolo[1,5-a]quinoxalin-5-yl)propanoic acid (100 mg, 0.182 mmol) was dissolved in DMF (1.5 mL), then 5-methoxypyridin-2-amine (34 mg, 0.272 mmol), HATU (104 mg, 0.272 mmol) and DIPEA (0.10 mL, 0.545 mmol) were added and the reaction stirred at rt for 7 h. The reaction mixture was purified by basic preparative HPLC to give the title compound. ¹H NMR (500 MHz, DMSO-d₆) δ 10.51 (s, 1H), 8.27 (dd, J=9.0, 5.7 Hz, 1H), 8.09 (d, J=2.1 Hz, 1H), 8.04-7.98 (m, 2H), 7.73 (dd, J=11.2, 2.5 Hz, 1H), 7.43 (dd, J=9.1, 3.0 Hz, 1H), 7.31-7.24 (m, 1H), 7.19 (d, J=2.1 Hz, 1H), 4.58-4.52 (m, 2H), 3.80 (s, 3H), 2.79 (t, J=7.3 Hz, 2H). ¹⁹F NMR (471 MHz, DMSO-d₆) −113.24. Tr(MET-uHPLC-AB-101)=2.67 m7 m/z (ES⁺) (M+H)⁺ 382.2, 97%.

Also prepared by this route

| Ex. | Structure | LCMS data | NMR data |
|---|---|---|---|
| 8-2 | 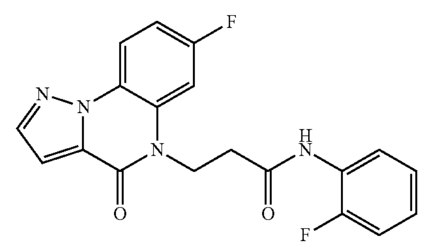 [SMILES: O=C(CCn1c(=O)c2ccnn2c2ccc(F)cc21)Nc1ccccc1F] | Tr(MET-uHPLC-AB-101) = 3.05 min m/z (ES⁺) (M + Na)+ 391.2, 99% | 1H NMR (500 MHz, DMSO-d6) 9.87 (s, 1H), 8.28 (dd, J = 9.0, 5.7 Hz, 1H), 8.11-8.06 (m, 1H), 7.86-7.82 (m, 1H), 7.71 (dd, J = 11.2, 2.4 Hz, 1H), 7.31-7.26 (m, 1H), 7.26-7.19 (m, 2H), 7.18-7.13 (m, 2H), 4.56 (t, J = 7.2 Hz, 2H), 2.83 (t, J = 7.2 Hz, 2H). 19F NMR (376 MHz, DMSO-d6) −113.23, −124.75. |
| 8-3 | 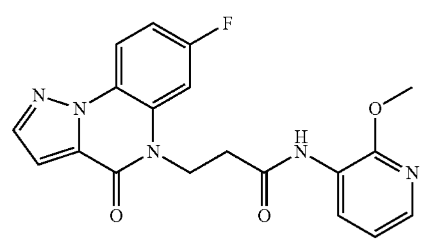 | Tr(MET-uHPLC-AB-101) = 2.82 min m/z (ES⁺) (M + H)⁺ 382.2, 98% | 1H NMR (500 MHz, DMSO-d6) 9.53 (s, 1H), 8.33-8.19 (m, 2H), 8.09 (d, J = 2.1 Hz, 1H), 7.86 (dd, J = 4.9, 1.7 Hz, 1H), 7.69 (dd, J = 11.2, 2.4 Hz, 1H), 7.36-7.22 (m, 1H), 7.19 (d, J = 2.1 Hz, 1H), 6.96 (dd, J = 7.7, 5.0 Hz, 1H), 4.54 (t, J = 7.2 Hz, 2H), 3.85 (s, 3H), 2.85 (t, J = 7.1 Hz, 2H). 19F NMR (376 MHz, DMSO-d6) −113.27. |
| 8-4 | 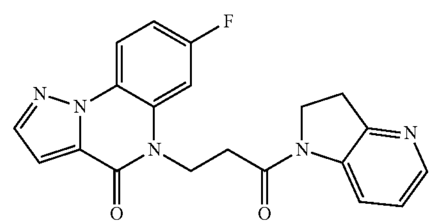 | Tr(MET-uHPLC-AB-101) = 2.29 min m/z (ES⁺) (M + H)⁺ 378.2, 100% | 1H NMR (400 MHz, DMSO-d6) 8.31-8.23 (m, 2H), 8.11 (dd, J = 5.0, 1.3 Hz, 1H), 8.08 (d, J = 2.1 Hz, 1H), 7.74 (dd, J = 11.2, 2.5 Hz, 1H), 7.34-7.20 (m, 1H), 7.20-7.09 (m, 2H), 4.58-4.50 (m, 2H), 4.10 (t, J = 8.6 Hz, 2H), 3.24-3.14 (m, 2H), 2.97-2.89 (m,2H). 19F NMR (376 MHz, DMSO-d6) −112.67. |

| Ex. | Structure | LCMS data | NMR data |
|---|---|---|---|
| 8-5 | 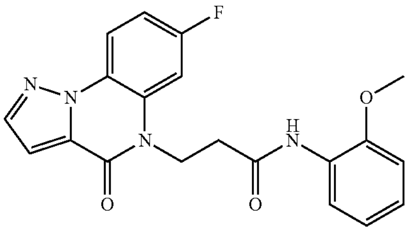 [SMILES: COc1ccccc1NC(=O)CCn1c(=O)c2ccnn2c2ccc(F)cc21] | Tr(MET-uHPLC-AB-101) = 3.10 min m/z (ES+) (M + H)+ 381.2, 100% | 1H NMR (400 MHz, DMSO-d6) 9.29 (s, 1H), 8.27 (dd, J = 9.0, 5.7 Hz, 1H), 8.09 (d, J = 2.1 Hz, 1H), 7.87 (d, J = 7.9 Hz, 1H), 7.73-7.65 (m, 1H), 7.31-7.22 (m, 1H), 7.19 (d, J = 2.1 Hz, 1H), 7.10-7.03 (m, 1H), 7.00 (dd, J = 8.2, 1.4 Hz, 1H), 6.93-6.84 (m, 1H), 4.54 (t, J = 7.1 Hz, 2H), 3.75 (s, 3H), 2.83 (t, J = 7.1 Hz, 2H). 19F NMR (376 MHz, DMSO-d6) −113.21. |
| 8-6 | 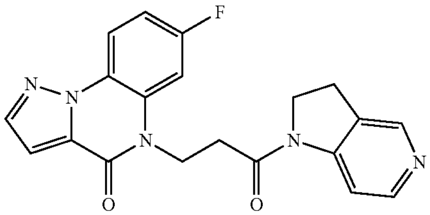 | Tr(MET-uHPLC-AB-101) = 1.59 min m/z (ES+) (M + H)+ 378.2, 99% | 1H NMR (400 MHz, DMSO-d6) 8.37 (s, 1H), 8.33 (d, J = 4.8 Hz, 1H), 8.28 (dd, J = 9.0, 5.7 Hz, 1H), 8.09 (d, J = 2.1 Hz, 1H), 7.92 (d, J = 5.1 Hz, 1H), 7.75 (dd, J = 11.2, 2.2 Hz, 1H), 7.33-7.23 (m, 1H), 7.19 (d, J = 2.1 Hz, 1H), 4.58-4.50 (m, 2H), 4.14-4.05 (m, 2H), 3.17-3.14 (m, 2H), 2.99-2.90 (m, 2H). 19F NMR (376 MHz, DMSO-d6) −113.09. |
| 8-7 | 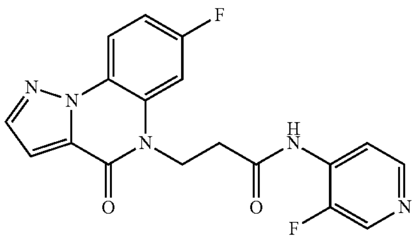 [SMILES: O=C(CCn1c(=O)c2ccnn2c2ccc(F)cc21)Nc1ccncc1F] | Tr(MET-uHPLC-AB-101), 2.11 min m/z (ES+) (M + H)+ 370.2, 99% | 1H NMR (400 MHz, DMSO-d6) 10.32 (s, 1H), 8.51 (d, J = 2.9 Hz, 1H), 8.31 (d, J = 5.4 Hz, 1H), 8.26 (dd, J = 9.0, 5.7 Hz, 1H), 8.16 (dd, J = 6.8, 5.5 Hz, 1H), 8.08 (d, J = 2.1 Hz, 1H), 7.72 (dd, J = 11.2, 2.5 Hz, 1H), 7.32-7.22 (m, 1H), 7.18 (d, J = 2.1 Hz, 1H), 4.56 (t, J = 7.2 Hz, 2H), 2.91 (t, J = 7.2 Hz, 2H). 19F NMR (376 MHz, DMSO-d6) −113.24, −141.52. |
| 8-8 | 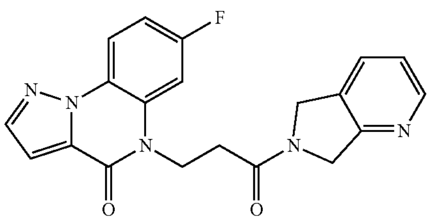 | Tr(MET-uHPLC-AB-101) = 2.28 min m/z (ES+) (M + H)+ 378.3, 98% | 1H NMR (500 MHz, DMSO-d6) 8.49-8.43 (m, 1H), 8.28 (dd, J = 9.0, 5.7 Hz, 1H), 8.09 (d, J = 2.1 Hz, 1H), 7.84-7.78 (m, 1H), 7.77-7.66 (m, 1H), 7.34-7.25 (m, 2H), 7.20 (d, J = 2.1 Hz, 1H), 4.89-4.81 (m, 2H), 4.72-4.63 (m, 2H), 4.58-4.51 (m, 2H), 2.85 (appt. q, J = 8.0 Hz, 2H). |
| 8-9 | 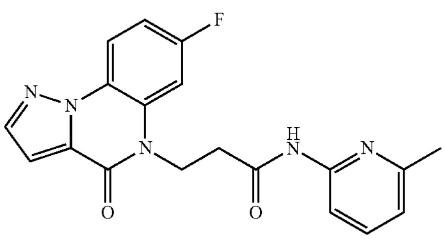 [SMILES: Cc1cccc(NC(=O)CCn2c(=O)c3ccnn3c3ccc(F)cc32)n1] | Tr(MET-uHPLC-AB-101) = 2.46 min m/z (ES+) (M + H)+ 366.2, 100% | 1H NMR (400 MHz, DMSO-d6) 10.59 (s, 1H), 8.26 (dd, J = 9.0, 5.7 Hz, 1H), 8.08 (d, J = 2.0 Hz, 1H), 7.88 (d, J = 8.2 Hz, 1H), 7.73 (dd, J = 11.2, 2.4 Hz, 1H), 7.70-7.60 (m, 1H), 7.31-7.22 (m, 1H), 7.18 (d, J = 2.0 Hz, 1H), 6.95 (d, J = 7.4 Hz, 1H), 4.54 (t, J = 7.4 Hz, 2H), 2.81 (t, J = 7.4 Hz, 2H), 2.38 (s, 3H). 19F NMR (376 MHz, DMSO-d6) −113.23. |
| 8-10 | 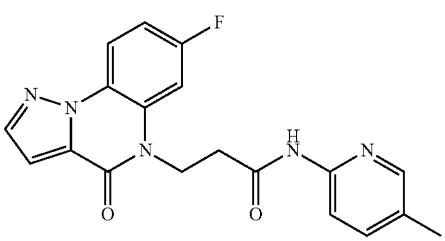 | Tr(MET-uHPLC-AB-101) = 2.39 min m/z (ES+) (M + H)+ 221, 306, 98% | 1H NMR (400 MHz, DMSO-d6) 10.54 (s, 1H), 8.27 (dd, J = 9.0, 5.7 Hz, 1H), 8.12 (s, 1H), 8.09 (d, J = 2.1 Hz, 1H), 7.97 (d, J = 8.9 Hz, 1H), 7.74 (dd, J = 11.3, 2.5 Hz, 1H), 7.60 (d, J = 8.6 Hz, 1H), 7.32-7.23 (m, 1H), 7.19 (d, J = 2.1 Hz, 1H), 4.59-4.51 (m, 2H), 2.81 (t, J = 7.4 Hz, 2H), 2.25 (s, 3H). 19F NMR (376 MHz, DMSO-d6) −113.23. |

| Ex. | Structure | LCMS data | NMR data |
|---|---|---|---|
| 8-11 | 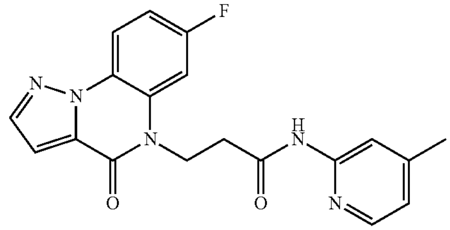 [SMILES: Cc1ccnc(NC(=O)CCn2c(=O)c3ccnn3c3ccc(F)cc32)c1] | Tr(MET-uHPLC-AB-101) = 2.09 min m/z (ES+) (M + H)+ 366.2, 99% | 1H NMR (400 MHz, DMSO-d6) 10.55 (s, 1H), 8.27 (dd, J = 9.0, 5.7 Hz, 1H), 8.14 (d, J = 5.0 Hz, 1H), 8.09 (d, J = 2.1 Hz, 1H), 7.92 (s, 1H), 7.73 (dd, J = 11.2, 2.5 Hz, 1H), 7.33-7.23 (m, 1H), 7.19 (d, J = 2.1 Hz, 1H), 6.94 (dd, J = 5.0, 0.8 Hz, 1H), 4.59-4.44 (m, 2H), 2.82 (t, J = 7.3 Hz, 2H), 2.38-2.25 (m, 3H). 19F NMR (376 MHz, DMSO-d6) −113.24. |
| 8-12 | 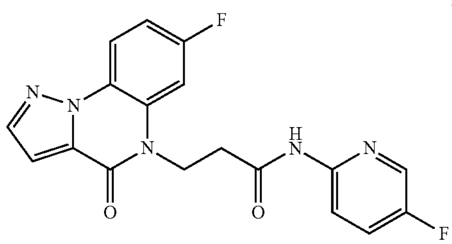 | Tr(MET-uHPLC-AB-101) = 2.89 min m/z (ES+) (M + H)+ 370.2, 97% | 1H NMR (400 MHz, DMSO-d6) 10.74 (s, 1H), 8.30 (d, J = 3.0 Hz, 1H), 8.27 (dd, J = 9.0, 5.7 Hz, 1H), 8.12-8.07 (m, 2H), 7.79-7.70 (m, 2H), 7.32-7.23 (m, 1H), 7.19 (d, J = 2.1 Hz, 1H), 4.60-4.52 (m, 2H), 2.82 (t, J = 7.4 Hz, 2H). 19F NMR (376 MHz, DMSO-d6) −113.26, −133.46. |
| 8-13 | 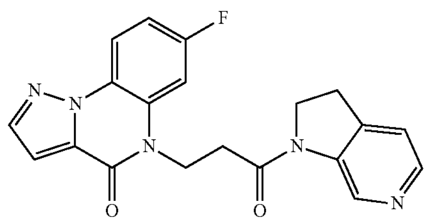 | Tr(MET-uHPLC-AB-101) = 1.57 min m/z (ES+) (M + H)+ 378.3, 96% | 1H NMR (400 MHz, DMSO-d6) 9.23 (s, 1H), 8.28 (dd, J = 9.0, 5.7 Hz, 1H), 8.23 (d, J = 4.7 Hz, 1H), 8.10 (d, J = 2.1 Hz, 1H), 7.75 (dd, J = 11.2, 2.5 Hz, 1H), 7.36-7.24 (m, 2H), 7.20 (d, J = 2.0 Hz, 1H), 4.61-4.52 (m, 2H), 4.08 (t, J = 8.6 Hz, 2H), 3.19 (t, J = 8.6 Hz, 2H), 2.97-2.89 (m, 2H). 19F NMR (376 MHz, DMSO-d6) −113.10. |

Scheme for Method 9

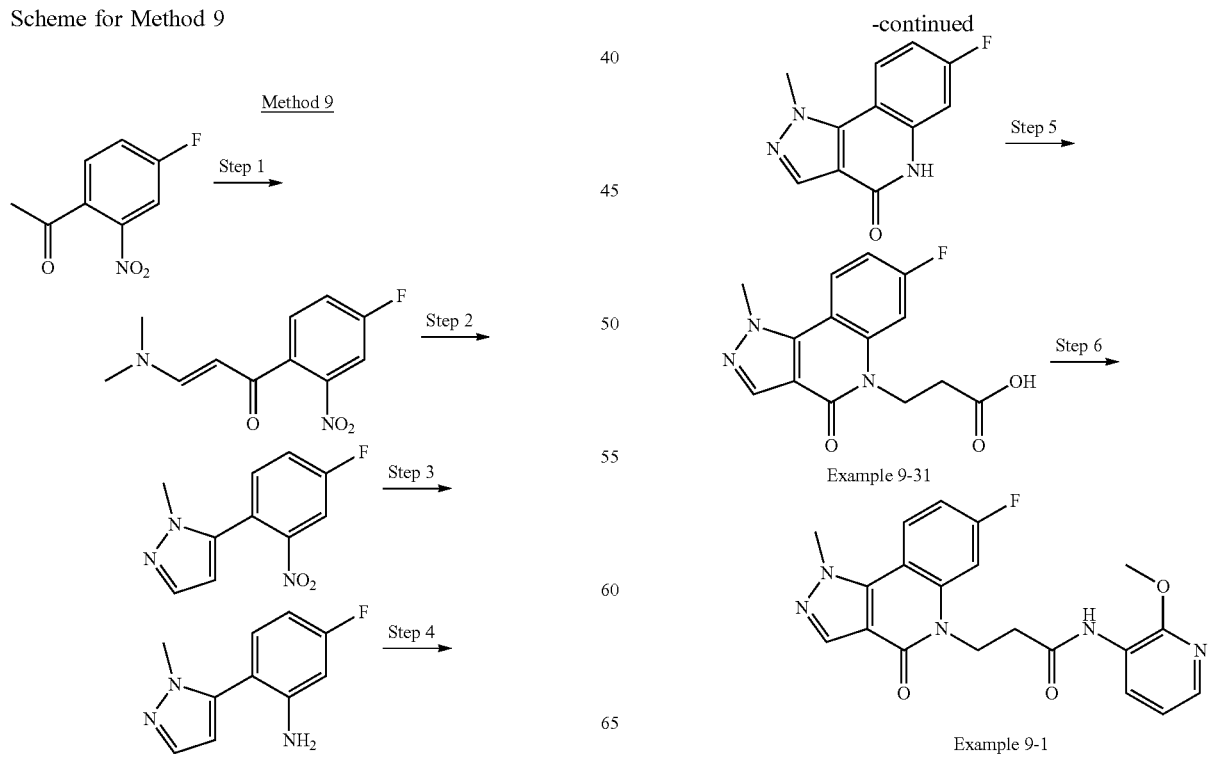

Example 9-1

Step 1: (E)-3-(Dimethylamino)-1-(4-fluoro-2-nitrophenyl)prop-2-en-1-one 1-(4-Fluoro-2-nitro-phenyl)ethanone (300 mg, 1.64 mmol) was dissolved in 1,1-dimethoxy-N,N-dimethylmethanamine (2.2 mL, 16.4 mmol) in a sealed tube and the reaction mixture was heated to 90° C. for 3 h. The reaction mixture was concentrated in vacuo to give the title compound. $^1$H NMR (500 MHz, DMSO-$d_6$) δ 7.91 (d, J=7.3 Hz, 1H), 7.78-7.18 (m, 3H), 5.38 (s, 1H), 3.11 (d, J=11.8 Hz, 3H), 2.88 (s, 3H). Tr(METCR1410)=0.91 min, m/z (ES$^+$) (M+H)$^+$ 238.9, 92%.

Step 2: 5-(4-Fluoro-2-nitro-phenyl)-1-methyl-pyrazole

Under a nitrogen atmosphere, methylhydrazine (0.19 mL, 3.58 mmol) was added to a solution of (E)-3-(dimethylamino)-1-(4-fluoro-2-nitro-phenyl)prop-2-en-1-one (310 mg, 1.30 mmol) in acetic acid (3.1 mL) in a pressure tube. The mixture was stirred at rt for 4 h. The reaction liquid was poured into a mixture of water/ethyl acetate. The aqueous layer was separated, and then the organic layer was washed with water and brine, then dried (MgSO$_4$). The solvent was evaporated under reduced pressure, and then the residue was purified by column chromatography (silica, n-hexane/ethyl acetate) to give the title compound $^1$H NMR (500 MHz, DMSO-$d_6$) δ 8.16 (dd, J=8.6, 2.6 Hz, 1H), 7.81-7.64 (m, 2H), 7.49 (d, J=1.9 Hz, 1H), 6.30 (d, J=1.9 Hz, 1H), 3.64 (s, 3H). Tr(METCR1410)=0.73 min, m/z (ES$^+$) (M+H)$^+$ 222.1, 95% and 3-(4-fluoro-2-nitro-phenyl)-1-methyl-pyrazole $^1$H NMR (500 MHz, DMSO-$d_6$) δ 7.89 (dd, J=8.4, 2.7 Hz, 1H), 7.83 (dd, J=8.7, 5.6 Hz, 1H), 7.78 (d, J=2.3 Hz, 1H), 7.60 (td, J=8.5, 2.7 Hz, 1H), 6.51 (d, J=2.3 Hz, 1H), 3.85 (s, 3H). Tr(METCR1410)=0.77 min, m/z (ES$^+$) (M+H)$^+$ 222.1, 100%.

Step 3: 5-Fluoro-2-(2-methylpyrazol-3-yl)aniline 5-(4-Fluoro-2-nitro-phenyl)-1-methyl-pyrazole (160 mg, 0.723 mmol) was dissolved in acetic acid (3.9 mL) before the addition of iron (162 mg, 2.89 mmol). The mixture was heated to 60° C. for 5 h in a sealed tube. The crude mixture was concentrated in vacuo, then this residue stirred in a mixture of 1 M Na$_2$CO$_3$ (100 ml) and EtOAc (100 ml) for 1 h. This mixture was then filtered through glass fibre filter paper. The filtrate was separated and the aqueous layer was extracted with EtOAc (2×50 mL). Combined organics were dried (MgSO$_4$) and concentrated to give the title compound. 1H NMR (500 MHz, DMSO-$d_6$) δ 7.49 (d, J=1.8 Hz, 1H), 7.01 (dd, J=8.4, 6.8 Hz, 1H), 6.55 (dd, J=11.7, 2.6 Hz, 1H), 6.41 (td, J=8.5, 2.6 Hz, 1H), 6.25 (d, J=1.8 Hz, 1H), 5.19 (s, 2H), 3.63 (s, 3H). Tr(METCR1410)=0.68 min, m/z (ES$^+$) (M+H)$^+$ 192.1, 194%.

Step 4: 7-Fluoro-1-methyl-5H-pyrazolo[4,3-c]quinolin-4-one

CDI (153 mg, 0.941 mmol) was added to a solution of 5-fluoro-2-(2-methylpyrazol-3-yl)aniline (90 mg, 0.471 mmol) in NMP (2 mL). The mixture was stirred at 150° C. for 30 min under microwave irradiation, and then cooled to rt. The reaction mixture was diluted with water and extracted with DCM. Combined organics were dried (MgSO$_4$) and concentrated to give the title compound. Tr (METCR1410)=0.88 min, m/z (ES$^+$) (M+H)$^+$ 218.0, 96%.

Steps 5-6: Performed as for Method 3, Steps 3-4
Prepared by this route:

| Ex. | Structure | LCMS data | NMR data |
|---|---|---|---|
| 9-1 | 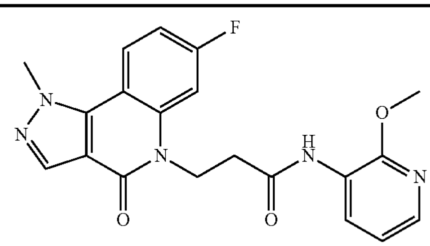 | Tr(MET-uHPLC-AB-101) = 2.50 min m/z (ES$^+$) (M + H)$^+$ 396.3, 100% | 1H NMR (400 MHz, DMSO-d6) 9.51 (s, 1H), 8.34 (dd, J = 9.0, 6.3 Hz, 1H), 8.27 (d, J = 7.7 Hz, 1H), 8.13 (s, 1H), 7.87 (dd, J = 5.0, 1.7 Hz, 1H), 7.65 (dd, J = 12.2, 2.4 Hz, 1H), 7.46-7.13 (m, 1H), 6.96 (dd, J = 7.7, 5.0 Hz, 1H), 4.65-4.47 (m, 2H), 4.36 (s, 3H), 3.88 (s, 3H), 2.82 (t, J = 7.3 Hz, 2H). 19F NMR (376 MHz, DMSO-d6) −108.73. |
| 9-2 | 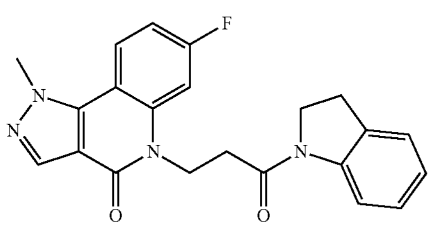 [SMILES: Cn1ncc2c(=O)n(CCC(=O)N3CCc4ccccc43)c3cc(F)ccc3c21] | Tr(MET-uHPLC-AB-101) = 3.05 min m/z (ES$^+$) (M + H)$^+$ 391.2, 100% | 1H NMR (500 MHz, DMSO-d6) 8.36 (dd, J = 9.0, 6.2 Hz, 1H), 8.14 (s, 1H), 8.13 (d, J = 8.1 Hz, 1H), 7.68 (dd, J = 12.2, 2.3 Hz, 1H), 7.32-7.26 (m, 1H), 7.24 (d, J = 7.3 Hz, 1H), 7.18 (t, J = 7.6 Hz, 1H), 7.01 (t, J = 7.4 Hz, 1H), 4.64-4.53 (m, 2H), 4.37 (s, 3H), 4.05 (t, J = 8.5 Hz, 2H), 3.11 (t, J = 8.5 Hz, 2H), 2.89-2.81 (m, 2H); 19F NMR (471 MHz, DMSO-d6) −108.53 |

| Ex. | Structure | LCMS data | NMR data |
|---|---|---|---|
| 9-3 | 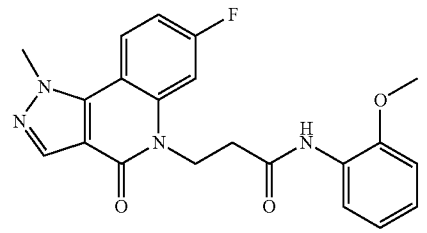 [SMILES: COc1ccccc1NC(=O)CCn1c(=O)c2cnn(C)c2c2ccc(F)cc21] | Tr(MET-uHPLC-AB-101) = 2.77 min m/z (ES⁺) (M + H)⁺ 395.3, 100% | 1H NMR (500 MHz, DMSO-d6) 9.23 (s, 1H), 8.27 (dd, J = 9.0, 6.3 Hz, 1H), 8.07 (s, 1H), 7.84 (d, J = 7.2 Hz, 1H), 7.59 (dd, J = 12.2, 1.9 Hz, 1H), 7.20 (td, J = 8.8, 2.4 Hz, 1H), 7.04-6.98 (m, 1H), 6.95 (dd, J = 8.2, 1.3 Hz, 1H), 6.88-6.77 (m, 1H), 4.50 (t, J = 7.4 Hz, 2H), 4.29 (s, 3H), 3.71 (s, 3H), 2.72 (t, J = 7.4 Hz, 2H); 19F NMR (471 MHz, DMSO-d6) −108.67. |
| 9-4 | 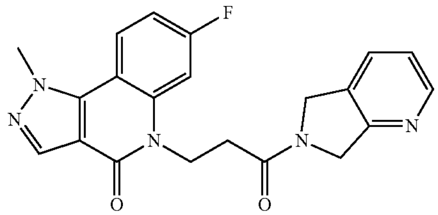 | Tr(MET-uHPLC-AB-101) = 1.99 min m/z (ES⁺) (M + H)⁺ 392.2, 99% | 1H NMR (500 MHz, DMSO-d6) 8.47 (dd, J = 11.1, 4.5 Hz, 1H), 8.36 (dd, J = 8.8, 6.3 Hz, 1H), 8.15 (s, 1H), 7.78 (m, 1H), 7.64 (t, J = 11.5 Hz, 1H), 7.36-7.25 (m, 2H), 4.89-4.79 (m, 2H), 4.73-4.63 (m, 2H), 4.60-4.53 (m, 2H), 4.37 (s, 3H), 2.79 (m, 2H); 19F NMR (471 MHz, DMSO-d6) −108.55. |
| 9-5 | 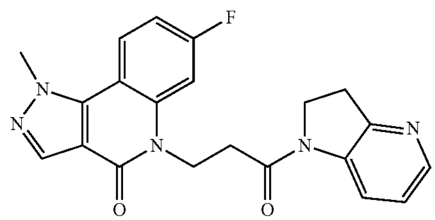 | Tr(MET-uHPLC-AB-101) = 1.98 min m/z (ES⁺) (M + H)⁺ 392.2, 97% | 1H NMR (500 MHz, DMSO-d6) 8.39-8.33 (m, 1H), 8.28 (d, J = 7.6 Hz, 1H), 8.19-8.09 (m, 2H), 7.68 (d, J = 11.3 Hz, 1H), 7.32-7.24 (m, 1H), 7.21-7.14 (m, 1H), 4.58 (s, 2H), 4.37 (s, 3H), 4.10 (t, J = 8.3 Hz, 2H), 3.24-3.14 (m, 2H), 2.87 (s, 2H).; 19F NMR (471 MHz, DMSO-d6) −108.55. |
| 9-6 | 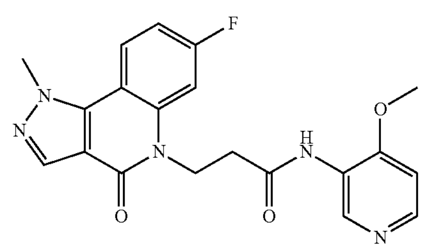 [SMILES: COc1ccncc1NC(=O)CCn1c(=O)c2cnn(C)c2c2ccc(F)cc21] | Tr(MET-uHPLC-AB-101) = 1.32 min m/z (ES⁺) (M + H)⁺ 396.3, 100% | 1H NMR (400 MHz, DMSO-d6) 9.50 (s, 1H), 8.83 (s, 1H), 8.34 (dd, J = 9.0, 6.3 Hz, 1H), 8.23 (d, J = 5.6 Hz, 1H), 8.13 (s, 1H), 7.65 (dd, J = 12.2, 2.1 Hz, 1H), 7.42-7.21 (m, 1H), 7.09 (d, J = 5.6 Hz, 1H), 4.57 (t, J = 7.3 Hz, 2H), 4.36 (s, 3H), 3.84 (s, 3H), 2.79 (t, J = 7.3 Hz, 2H). 19F NMR (376 MHz, DMSO-d6) −108.30. |
| 9-7 | 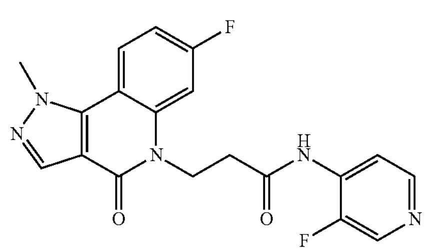 [SMILES: Cn1ncc2c(=O)n(CCC(=O)Nc3ccncc3F)c3cc(F)ccc3c21] | Tr(MET-uHPLC-AB-101) = 1.84 min m/z (ES⁺) (M + H)⁺ 384.2, 98% | 1H NMR (400 MHz, DMSO-d6) 10.31 (s, 1H), 8.51 (d, J = 2.9 Hz, 1H), 8.42-8.27 (m, 2H), 8.17 (dd, J = 6.9, 5.4 Hz, 1H), 8.13 (s, 1H), 7.68 (dd, J = 12.2, 2.4 Hz, 1H), 7.27 (m, 1H), 4.79-4.48 (m, 2H), 4.36 (s, 3H), 3.03-2.79 (m, 2H). 19F NMR (376 MHz, DMSO-d6) −108.71, −141.57. |

-continued

| Ex. | Structure | LCMS data | NMR data |
|---|---|---|---|
| 9-8 | 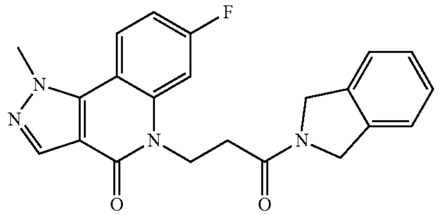 | Tr(MET-uHPLC-AB-101) = 2.75 min m/z (ES+) (M + H)+ 391.2, 100% | 1H NMR (400 MHz, DMSO-d6) 8.34 (dd, J = 9.0, 6.2 Hz, 1H), 8.13 (s, 1H), 7.64 (dd, J = 12.2, 2.4 Hz, 1H), 7.37 (d, J = 4.7 Hz, 1H), 7.28 (m, 4H), 4.81 (s, 2H), 4.67 (s, 2H), 4.62-4.47 (m, 2H), 4.36 (s, 3H), 2.84-2.73 (m, 2H). 19F NMR (376 MHz, DMSO-d6) −108.57. |
| 9-9 | 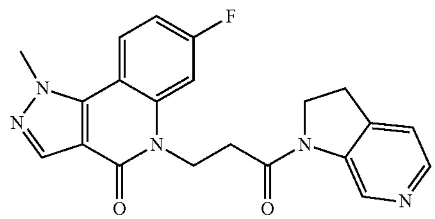 | Tr(MET-uHPLC-AB-101) = 1.39 min m/z (ES+) (M + H)+ 392.3, 96% | 1H NMR (500 MHz, DMSO-d6) 9.23 (s, 1H), 8.35 (dd, J = 8.9, 6.3 Hz, 1H), 8.22 (d, J = 4.7 Hz, 1H), 8.14 (s, 1H), 7.67 (dd, J = 12.1, 2.2 Hz, 1H), 7.43-7.30 (m, 1H), 7.31-7.08 (m, 1H), 4.81-4.45 (m, 2H), 4.37 (s, 3H), 4.07 (t, J = 8.6 Hz, 2H), 3.17 (t, J = 8.5 Hz, 2H), 3.00-2.77 (m, 2H). 19F NMR (471 MHz, DMSO-d6) −98.48- −113.39 (m). |
| 9-10 | 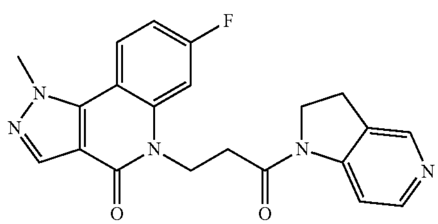 [SMILES: Cn1ncc2c(=O)n(CCC(=O)N3CCc4cnccc43)c3cc(F)ccc3c21] | Tr(MET-uHPLC-AB-101) = 1.43 min m/z (ES+) (M + H)+ 392.3, 100% | 1H NMR (400 MHz, DMSO-d6) ? 8.58-8.24 (m, 3H), 8.13 (s, 1H), 7.92 (d, J = 5.0 Hz, 1H), 7.67 (dd, J = 12.1, 2.3 Hz, 1H), 7.42-6.96 (m, 1H), 4.81-4.49 (m, 2H), 4.36 (s, 3H), 4.09 (t, J = 8.6 Hz, 2H), 3.15 (t, J = 8.6 Hz, 2H), 2.92-2.78 (m, 2H). 19F NMR (376 MHz, DMSO-d6) −108.56. |
| 9-11 | 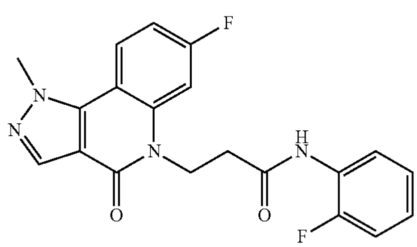 [SMILES: Cn1ncc2c(=O)n(CCC(=O)Nc3ccccc3F)c3cc(F)ccc3c21] | Tr(MET-uHPLC-AB-101) = 2.72 min m/z (ES+) (M + H)+ 383.2, 99% | 1H NMR (500 MHz, DMSO-d6) 9.86 (s, 1H), 8.35 (dd, J = 9.0, 6.3 Hz, 1H), 8.14 (s, 1H), 7.87 (t, J = 8.8 Hz, 1H), 7.74-7.60 (m, 1H), 7.39-7.19 (m, 2H), 7.19-6.99 (m, 2H), 4.58 (t, J = 7.3 Hz, 2H), 4.36 (s, 3H), 2.79 (t, J = 7.4 Hz, 2H). 19F NMR (471 MHz, DMSO-d6) −108.67 (dd, J = 12.2, 6.5 Hz), −120.56- −126.88 (m). |
| 9-12 | 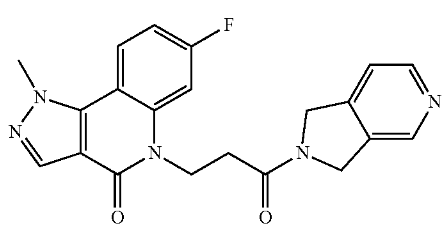 [SMILES: Cn1ncc2c(=O)n(CCC(=O)N3Cc4ccncc4C3)c3cc(F)ccc3c21] | Tr(MET-uHPLC-AB-101) = 1.34 min m/z (ES+) (M + H)+ 392.2, 98% | 1H NMR (500 MHz, DMSO-d6) 8.63-8.51 (m, 1H), 8.48 (dd, J = 7.2, 5.1 Hz, 1H), 8.35 (dd, J = 9.0, 6.2 Hz, 1H), 8.14 (s, 1H), 7.64 (dd, J = 12.1, 1.8 Hz, 1H), 7.46-7.33 (m, 1H), 7.28 (appt. td, J = 8.6, 2.3 Hz, 1H), 4.90-4.82 (m, 2H), 4.76-4.68 (m, 2H), 4.61-4.51 (m, 2H), 4.37 (s, 3H), 2.82-2.73 (m, 2H). 19F NMR (471 MHz, DMSO-d6) −106.72- −110.69 (m). |

| Ex. | Structure | LCMS data | NMR data |
|---|---|---|---|
| 9-13 | 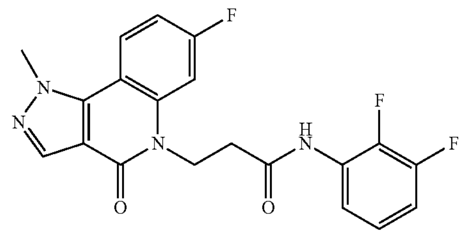 [SMILES: Cn1ncc2c(=O)n(CCC(=O)Nc3cccc(F)c3F)c3cc(F)ccc3c21] | Tr(MET-uHPLC-AB-101) = 2.86 min m/z (ES+) (M + H)+ 401.1, 95% | 1H NMR (500 MHz, DMSO-d6) 10.06 (s, 1H), 8.34 (dd, J = 9.0, 6.2 Hz, 1H), 8.13 (s, 1H), 7.85-7.55 (m, 2H), 7.42-7.21 (m, 1H), 7.22-7.07 (m, 2H), 4.58 (t, J = 7.4 Hz, 2H), 4.36 (s, 3H), 2.80 (t, J = 7.4 Hz, 2H). 19F NMR (471 MHz, DMSO-d6) −108.70, −138.72, −149.35. |
| 9-14 | 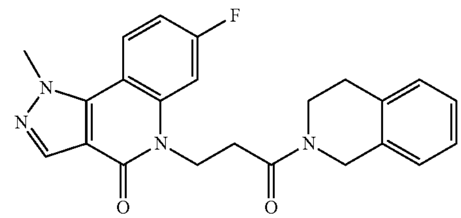 [SMILES: Cn1ncc2c(=O)n(CCC(=O)N3CCc4ccccc4C3)c3cc(F)ccc3c21] | Tr(MET-uHPLC-AB-101) = 2.7 min m/z (ES+) (M + H)+ 405.2, 99% | 1H NMR (400 MHz, 358 K, DMSO-d6) 8.54-8.20 (m, 1H), 8.07 (s, 1H), 7.51 (d, J = 11.8 Hz, 1H), 7.36-6.67 (m, 5H), 4.89-4.41 (m, 4H), 4.43-4.23 (m, 3H), 3.66 (t, J = 5.5 Hz, 2H), 2.98-2.64 (m, 4H). 19F NMR (471 MHz, DMSO-d6) −108.59. |
| 9-15 | 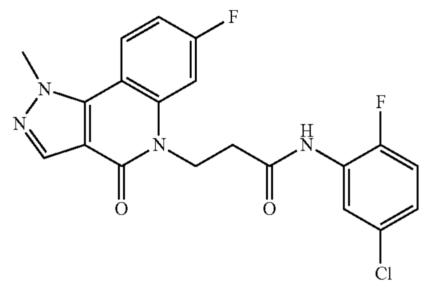 [SMILES: Cn1ncc2c(=O)n(CCC(=O)Nc3cc(Cl)ccc3F)c3cc(F)ccc3c21] | Tr(MET-uHPLC-AB-101) = 3.13 min m/z (ES+) (M + H)+ 417.1, 99% | 1H NMR (500 MHz, DMSO-d6) 10.04 (s, 1H), 8.34 (dd, J = 9.0, 6.3 Hz, 1H), 8.13 (s, 1H), 8.04 (dd, J = 6.7, 2.5 Hz, 1H), 7.65 (dd, J = 12.2, 2.3 Hz, 1H), 7.43-7.23 (m, 2H), 7.22-7.06 (m, 1H), 4.58 (t, J = 7.3 Hz, 2H), 4.36(s, 3H), 2.80 (t, J = 7.3 Hz, 2H). 19F NMR (471 MHz, DMSO-d6) −108.71, −127.18. |
| 9-16 | 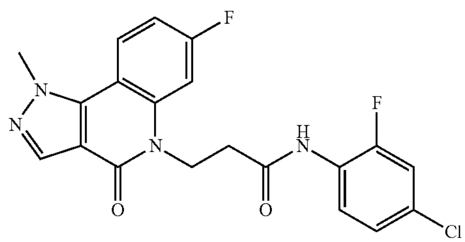 [SMILES: Cn1ncc2c(=O)n(CCC(=O)Nc3ccc(Cl)cc3F)c3cc(F)ccc3c21] | Tr(MET-uHPLC-AB-101) = 3.12 min m/z (ES+) (M + H)+ 417.1, 96% | 1H NMR (500 MHz, DMSO-d6) 9.96 (s, 1H), 8.34 (dd, J = 9.0, 6.3 Hz, 1H), 8.13 (s, 1H), 8.05-7.85 (m, 1H), 7.65 (dd, J = 12.2, 2.2 Hz, 1H), 7.47 (dd, J = 10.7, 2.4 Hz, 1H), 7.37-6.92 (m, 2H), 4.57 (t, J = 7.4 Hz, 2H), 4.36(s, 3H), 2.79 (t, J = 7.4 Hz, 2H). 19F NMR (471 MHz, DMSO-d6) −108.67, −121.62 |
| 9-17 | 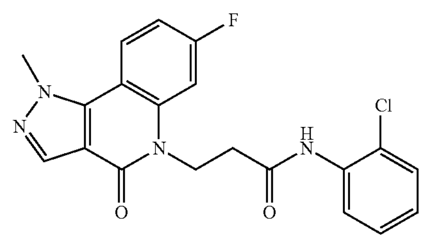 [SMILES: Cn1ncc2c(=O)n(CCC(=O)Nc3ccccc3Cl)c3cc(F)ccc3c21] | Tr(MET-uHPLC-AB-101) = 2.87 min m/z (ES+) (M + Na)+ 421.1, 95% | 1H NMR (500 MHz, DMSO-d6) 9.66 (s, 1H), 8.34 (dd, J = 9.0, 6.2 Hz, 1H), 8.14 (s, 1H), 7.79-7.59 (m, 2H), 7.47 (dd, J = 8.0, 1.4 Hz, 1H), 7.41-7.23 (m, 2H), 7.22-6.90 (m, 1H), 4.59 (t, J = 7.3 Hz, 2H), 4.36 (s, 3H), 2.79(t, J = 7.1 Hz, 2H). 19F NMR (471 MHz, DMSO-d6) −108.68. |
| 9-18 | 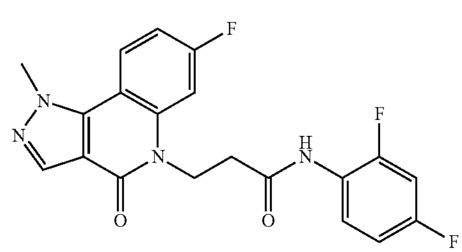 [SMILES: Cn1ncc2c(=O)n(CCC(=O)Nc3ccc(F)cc3F)c3cc(F)ccc3c21] | Tr(MET-uHPLC-AB-101) = 2.79 min m/z (ES+) (M + H)+ 401.1, 98% | 1H NMR (500 MHz, DMSO-d6) 9.86 (s, 1H), 8.34 (dd, J = 9.0, 6.3 Hz, 1H), 8.13 (s, 1H), 7.93-7.73 (m, 1H), 7.65 (dd, J = 12.2, 2.3 Hz, 1H), 7.41-7.20 (m, 2H), 7.16-6.92 (m, 1H), 4.57 (t, J = 7.4 Hz, 2H), 4.36 (s, 3H),2.76 (t, J = 7.4 Hz, 2H). 19F NMR (471 MHz, DMSO-d6) |

| Ex. | Structure | LCMS data | NMR data |
|---|---|---|---|
| | | | −108.68, −114.85, −119.60. |
| 9-19 | 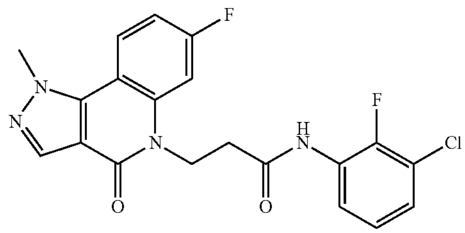 [SMILES: Cn1ncc2c(=O)n(CCC(=O)Nc3cccc(Cl)c3F)c3cc(F)ccc3c21] | Tr(MET-uHPLC-AB-101) = 3.08 min m/z (ES⁺) (M + H)⁺ 417.1, 98% | 1H NMR (400 MHz, DMSO-d6) 10.02 (s, 1H), 8.33 (dd, J = 9.0, 6.3 Hz, 1H), 8.13 (s, 1H), 7.92-7.75 (m, 1H), 7.65 (dd, J = 12.2, 2.4 Hz, 1H), 7.42-6.94 (m, 3H), 4.80-4.44 (m, 2H), 4.36 (s, 3H), 2.80 (t, J = 7.4 Hz, 2H). 19F NMR (376 MHz, DMSO-d6) −108.70, −126.41. |
| 9-20 | 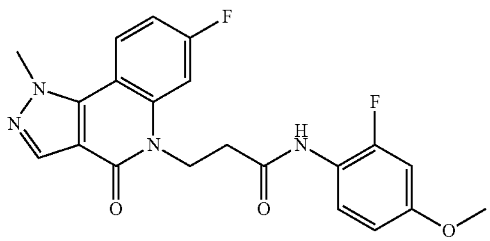 [SMILES: COc1ccc(NC(=O)CCn2c(=O)c3cnn(C)c3c3ccc(F)cc32)c(F)c1] | Tr(MET-uHPLC-AB-101) = 2.70 min m/z (ES⁺) (M + H)⁺ 413.1, 95% | 1H NMR (400 MHz, DMSO-d6) 9.67 (s, 1H), 8.34 (dd, J = 9.0, 6.3 Hz, 1H), 8.14 (s, 1H), 7.65 (dd, J = 12.2, 2.4 Hz, 1H), 7.61-7.56 (m, 1H), 7.30-7.25 (m, 1H), 6.87 (dd, J = 12.6, 2.8 Hz, 1H), 6.75 (dd, J = 8.7, 2.2 Hz, 1H), 4.58-4.54 (m, 2H), 4.36 (s, 3H), 3.75 (s, 3H), 2.75-2.71 (m, 2H).19F NMR (376 MHz, DMSO-d6) −108.68, −121.42. |
| 9-21 | 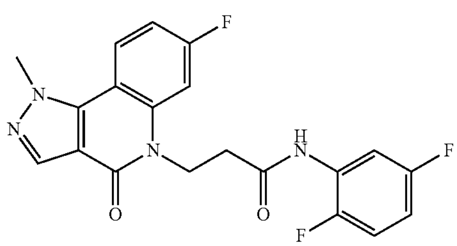 [SMILES: Cn1ncc2c(=O)n(CCC(=O)Nc3cc(F)ccc3F)c3cc(F)ccc3c21] | Tr(MET-uHPLC-AB-101) = 2.92 min m/z (ES⁺) (M + H)⁺ 401.3, 100% | 1H NMR (400 MHz, DMSO-d6) 10.06 (s, 1H), 8.55 (s, 1H), 8.35 (dd, J = 9.0, 6.3 Hz, 1H), 8.14 (s, 1H, formate salt), 7.89-7.82 (m, 1H), 7.66 (dd, J = 12.2, 2.3 Hz, 1H), 7.36-7.23 (m, 2H), 7.02-6.92 (m, 1H), 4.63-4.55 (m, 2H), 4.37 (s, 3H), 2.86-2.78 (m, 2H). 19F NMR (376 MHz, DMSO-d6) −108.73, −117.32 (d, J = 16.1 Hz), −130.81 (d, J = 16.1 Hz). |
| 9-22 | 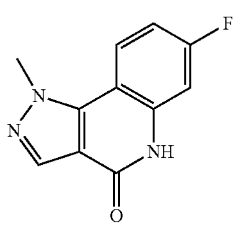 [SMILES: Cn1ncc2c(=O)[nH]c3cc(F)ccc3c21] | Tr(MET-uHPLC-AB-101) = 1.72 min m/z (ES⁺) (M + H)⁺ 218.1, 99% | 1H NMR (500 MHz, DMSO-d6) 11.50 (s, 1H), 8.24 (dd, J = 8.9, 5.9 Hz, 1H), 8.08 (s, 1H), 7.21 (dd, J = 10.4, 2.6 Hz, 1H), 7.18-7.09 (m, 1H), 4.34 (s, 3H). 19F NMR (471 MHz, DMSO-d6) −110.26 (d, J = 6.1 Hz). |
| 9-23 | 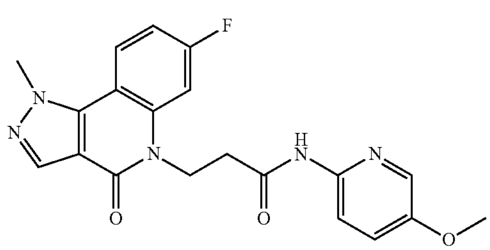 [SMILES: COc1ccc(NC(=O)CCn2c(=O)c3cnn(C)c3c3ccc(F)cc32)nc1] | Tr(MET-uHPLC-AB-101) = 2.35 min m/z (ES⁺) (M + H)⁺ 396.2, 92% | 1H NMR (400 MHz, DMSO-d6) 10.49 (s, 1H), 8.33 (dd, J = 9.0, 6.3 Hz, 1H), 8.13 (s, 1H), 8.07-7.92 (m, 2H), 7.68 (dd, J = 12.3, 2.4 Hz, 1H), 7.43 (dd, J = 9.0, 3.1 Hz, 1H), 7.33-7.18 (m, 1H), 4.77-4.50 (m, 2H), 4.36 (s, 3H), 3.80 (s, 3H), 2.85-2.66 (m, 2H). 19F NMR (376 MHz, DMSO-d6) −108.69. |

| Ex. | Structure | LCMS data | NMR data |
|---|---|---|---|
| 9-24 | 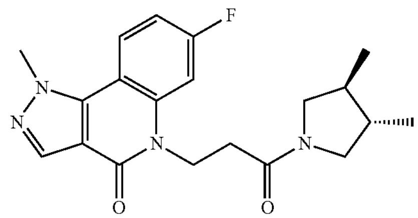 [SMILES: C[C@@H]1CN(C(=O)CCn2c(=O)c3cnn(C)c3c3ccc(F)cc32)C[C@H]1C] | Tr(MET-uHPLC-AB-101) = 2.71 min m/z (ES+) (M + H)+ 371.1, 100% | 1H NMR (400 MHz, DMSO-d6) 8.34 (dd, J = 9.0, 6.3 Hz, 1H), 8.13 (s, 1H), 7.57 (dd, J = 12.2, 2.4 Hz, 1H), 7.33-7.17 (m, 1H), 4.55-4.43 (m, 2H), 4.36 (s, 3H), 3.72-3.54 (m, 2H), 3.06-2.82 (m, 1H), 2.84-2.70 (m, 1H), 2.61-2.57 (m, 2H), 1.72-1.60 (m, 2H), 0.98 (d, J = 6.4 Hz, 3H), 0.93 (d, J = 6.4 Hz, 3H). 19F NMR (376 MHz, DMSO-d6) −108.62. |
| 9-25 | 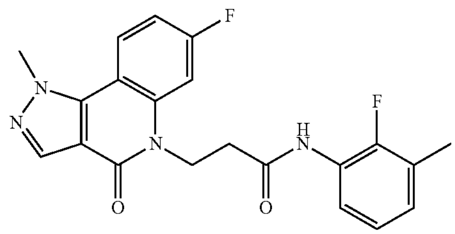 [SMILES: Cc1cccc(NC(=O)CCn2c(=O)c3cnn(C)c3c3ccc(F)cc32)c1F] | Tr(MET-uHPLC-AB-101) = 2.95 min m/z (ES+) (M + H)+ 397.3, 98% | 1H NMR (500 MHz, DMSO-d6) 9.78 (s, 1H), 8.34 (dd, J = 9.0, 6.2 Hz, 1H), 8.14 (s, 1H), 7.74-7.60 (m, 2H), 7.27 (td, J = 8.8, 2.4 Hz, 1H), 7.03 (t, J = 6.7 Hz, 2H), 4.64-4.50 (m, 2H), 4.36 (s, 3H), 2.83-2.74 (m, 2H), 2.23 (d, J = 1.8 Hz, 3H). 19F NMR (471 MHz, DMSO-d6) −108.67 (dt, J = 14.2, 7.3 Hz), −129.37. |
| 9-26 | 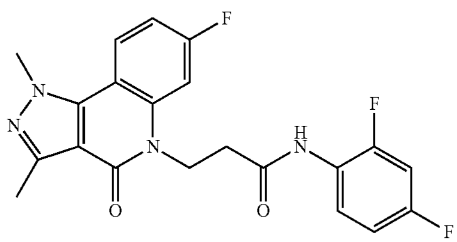 [SMILES: Cc1nn(C)c2c1c(=O)n(CCC(=O)Nc1ccc(F)cc1F)c1cc(F)ccc21] | Tr(MET-uHPLC-AB-101) = 2.99 min m/z (ES+) (M + H)+ 415.2, 98% | 1H NMR (500 MHz, DMSO-d6) 9.85 (s, 1H), 8.29 (dd, J = 9.0, 6.3 Hz, 1H), 7.80 (td, J = 9.0, 6.3 Hz, 1H), 7.60 (dd, J = 12.2, 2.4 Hz, 1H), 7.35-7.18 (m, 2H), 7.11-7.01 (m, 1H), 4.54 (t, J = 7.3 Hz, 2H), 4.26 (s, 3H), 2.75 (t, J = 7.4 Hz, 2H). C-Me signal under DMSO solvent peak. 19F NMR (471 MHz, DMSO-d6) −107.86−−109.61 (m), −114.02−−115.54 (m), −118.74−−120.49 (m). |
| 9-27 | 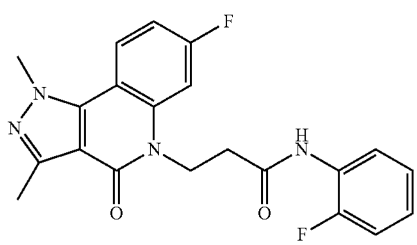 [SMILES: Cc1nn(C)c2c1c(=O)n(CCC(=O)Nc1ccccc1F)c1cc(F)ccc21] | Tr(MET-uHPLC-AB-101) = 2.91 min m/z (ES+) (M + H)+ 397.2, 95% | 1H NMR (500 MHz, DMSO-d6) 9.89 (s, 1H), 8.29 (dd, J = 9.0, 6.3 Hz, 1H), 7.89-7.80 (m, 1H), 7.65-7.58 (m, 1H), 7.27-7.19 (m, 2H), 7.18-7.12 (m, 2H), 4.55 (t, J = 7.5 Hz, 2H), 4.26 (s, 3H), 2.77 (t, J = 7.5 Hz, 2H). C-Me signal under DMSO solvent peak. 19F NMR (471 MHz, DMSO-d6) −108.89 (dt, J = 14.0, 7.2 Hz), −124.58 (m). |
| 9-28 | 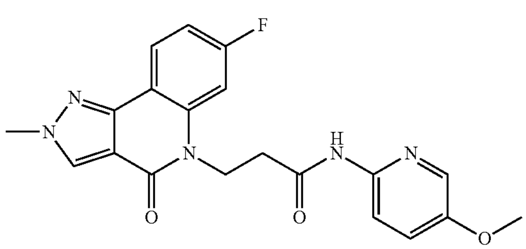 | Tr(MET-uHPLC-AB-101) = 2.39 min m/z (ES+) (M + H)+ 396.3, 99% | 1H NMR (400 MHz, DMSO-d6) 10.48 (s, 1H), 8.61 (s, 1H), 8.12 (dd, J = 8.7, 6.6 Hz, 1H), 8.08-7.86 (m, 2H), 7.56 (dd, J = 12.3, 2.3 Hz, 1H), 7.43 (dd, J = 9.0, 3.1 Hz, 1H), 7.27-6.96 (m, 1H), 4.80-4.36 (m, 2H), 4.08 (s, 3H), 3.80 (s, 3H), 2.88-2.69 (m, 2H). 19F NMR (376 MHz, DMSO-d6) −110.03. |

| Ex. | Structure | LCMS data | NMR data |
|---|---|---|---|
| 9-29 | 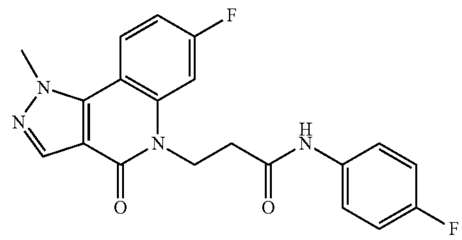 [SMILES: Cn1ncc2c(=O)n(CCC(=O)Nc3ccc(F)cc3)c3cc(F)ccc3c21] | Tr(MET-uHPLC-AB-101) = 2.82 min m/z (ES+)(M + H)+ 383.2, 98% | 1H NMR (500 MHz, DMSO-d6) δ 10.09 (s, 1H), 8.34 (dd, J = 9.0, 6.3 Hz, 1H), 8.14 (s, 1H), 7.67 (dd, J = 12.1, 2.3 Hz, 1H), 7.62-7.51 (m, 2H), 7.27 (m, 1H), 7.20-7.10 (m, 2H), 4.62-4.54 (m, 2H), 4.36 (s, 3H), 2.74-2.67 (m, 2H). 19F NMR (376 MHz, DMSO-d6) δ −108.67, −119.41. |
| 9-30 | 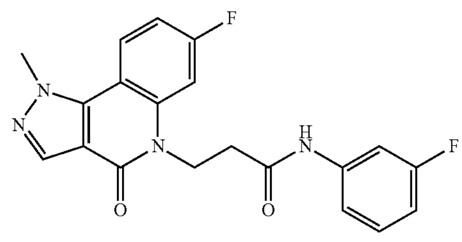 [SMILES: Cn1ncc2c(=O)n(CCC(=O)Nc3cccc(F)c3)c3cc(F)ccc3c21] | Tr(MET-uHPLC-AB-101) = 2.91 min m/z (ES+)(M + H)+ 383.2, 100% | 1H NMR (400 MHz, DMSO-d6) δ 10.24 (s, 1H), 8.35 (dd, J = 9.0, 6.3 Hz, 1H), 8.14 (s, 1H), 7.68 (dd, J = 12.2, 2.4 Hz, 1H), 7.58 (m, 1H), 7.38-7.21 (m, 3H), 6.93-6.82 (m, 1H), 4.66-4.53 (m, 2H), 4.37 (s, 3H), 2.77-2.69 (m, 2H). 19F NMR (376 MHz, DMSO-d6) δ −108.69, −112.13. |
| 9-31 | 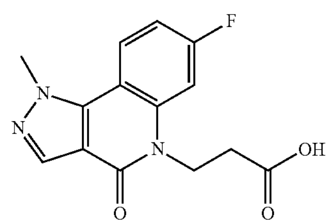 [SMILES: Cn1ncc2c(=O)n(CCC(=O)O)c3cc(F)ccc3c21] | Tr(MET-uHPLC-AB-101) = 1.89 min m/z (ES+)(M + H)+ 290.0, 99% | 1H NMR (400 MHz, DMSO-d6) δ 12.35 (s, 1H), 8.33 (dd, J = 9.0, 6.3 Hz, 1H), 8.11 (s, 1H), 7.61 (dd, J = 12.2, 2.4 Hz, 1H), 7.26 (m, 1H), 4.55-4.44 (m, 2H), 4.35 (s, 3H), 2.61-2.53 (m, 2H). 19F NMR (376 MHz, DMSO-d6) δ −108.64. |

Scheme for Method 10

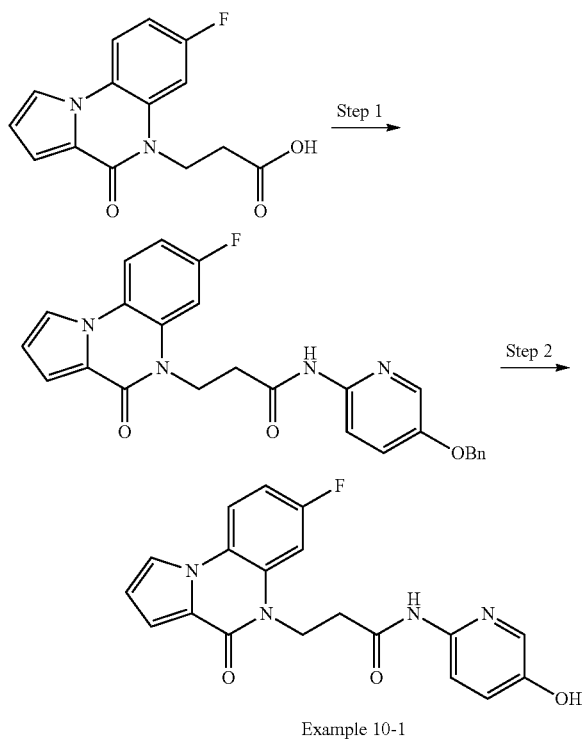

Example 10-1

Step 1: N-(5-Benzyloxy-2-pyridyl)-3-(7-fluoro-4-oxo-pyrrolo[1,2-a]quinoxalin-5-yl)propanamide 3-(7-fluoro-4-oxo-pyrrolo[1,2-a]quinoxalin-5-yl)propanoic acid (prepared according to Method 3, 100 mg, 0.365 mmol) was dissolved in DMF (3 mL) before the addition of 5-(benzyloxy)pyridin-2-amine (110 mg, 0.547 mmol), HATU (208 mg, 0.547 mmol) and DIPEA (0.19 mL, 1.09 mmol). The reaction mixture was stirred at rt for 1 h. The reaction mixture was poured into water, extracted with EtOAc (3×), dried (MgSO4), and concentrated to dryness. The residue was triturated with DCM/MeOH to give the title compound. 1H NMR (500 MHz, DMSO-d6) δ 10.50 (s, 1H), 8.21-8.19 (m, 1H), 8.18-8.15 (m, 1H), 8.07 (d, J=3.0 Hz, 1H), 8.01 (d, J=8.9 Hz, 1H), 7.57 (dd, J=11.3, 2.6 Hz, 1H), 7.50 (dd, J=9.1, 3.1 Hz, 1H), 7.45 (d, J=7.0 Hz, 2H), 7.40 (t, J=7.4 Hz, 2H), 7.37-7.31 (m, 1H), 7.20-7.13 (m, 1H), 7.06 (dd, J=3.9, 1.4 Hz, 1H), 6.70 (dd, J=3.8, 2.8 Hz, 1H), 5.15 (s, 2H), 4.52-4.42 (m, 2H), 2.75 (t, J=7.4 Hz, 2H). Tr(METCR1410)=1.19 min m/z (ES+) (M+H)+ 457.1, 95%.

Step 2: 3-{7-Fluoro-4-oxo-4H,5H-pyrrolo[1,2-a]quinoxalin-5-yl}-N-(5-hydroxypyridin-2-yl)propanamide N-[5-(Benzyloxy)pyridin-2-yl]-3-{7-fluoro-4-oxo-4H,5H-pyrrolo[1,2-a]quinoxalin-5-yl}propanamide (90 mg, 0.197 mmol) was dissolved in methanol (5 mL) and THF (5 mL) and placed under an inert atmosphere. Pd/C (10%, 10 mg, 0.197 mmol) was added and the reaction placed under a hydrogen atmosphere and stirred at rt for 3 h. The reaction mixture was filtered through Celite, washed with MeOH, and the filtrate concentrated to dryness to give the title compound. $^1$H NMR (400 MHz, DMSO-d$_6$) δ 10.35 (s, 1H), 9.63 (br. s, 1H), 8.22-8.13 (m, 2H), 7.90 (d, J=8.9 Hz, 1H), 7.82 (d, J=2.9 Hz, 1H), 7.56 (dd, J=11.3, 2.6 Hz, 1H), 7.21-7.12 (m, 2H), 7.06 (dd, J=3.9, 1.4 Hz, 1H), 6.69 (dd, J=3.8, 2.8 Hz, 1H), 4.54-4.36 (m, 2H), 2.82-2.64 (m, 2H). Tr(MET-uHPLC-AB-101)=2.16 min m/z (ES$^+$) (M+H)$^+$ 367.2, 100%.

Scheme for Method 11

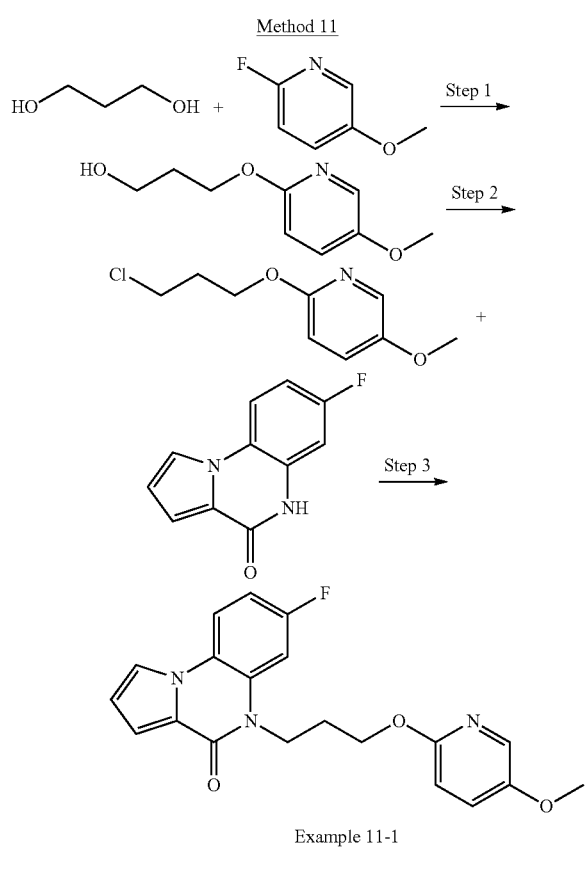

Example 11-1

Step 1: 3-[(5-Methoxy-2-pyridyl)oxy]propan-1-ol

Sodium hydride (60%, 0.17 g, 4.33 mmol) and propane-1,3-diol (269 mg, 3.54 mmol) were dissolved in DMF (5 mL) and 2-fluoro-5-methoxypyridine (0.50 g, 3.93 mmol) was added. The reaction mixture was stirred at rt for 2 h. The reaction mixture was concentrated. The residue was partitioned between DCM (10 mL) and water (10 mL) and extracted with DCM (2×5 mL). Combined organic extracts were dried and concentrated. Further purification by column chromatography (silica, EtOAc-heptane mixtures) gave the title compound. $^1$H NMR (500 MHz, DMSO-d$_6$) δ 7.83 (d, J=3.1 Hz, 1H), 7.37 (dd, J=8.9, 3.1 Hz, 1H), 6.74 (d, J=8.9 Hz, 1H), 4.50 (t, J=5.1 Hz, 1H), 4.23 (t, J=6.5 Hz, 2H), 3.76 (s, 3H), 3.53 (q, J=6.2 Hz, 2H), 2.00-1.51 (m, 2H). Tr(METCR1410)=0.78 min, (ES)$^+$ [M+H]$^+$=184.1, 99%.

Step 2: 2-(3-Chloropropoxy)-5-methoxy-pyridine

3-[(5-Methoxy-2-pyridyl)oxy]propan-1-ol (100 mg, 0.546 mmol) was dissolved in DCM (5 mL) and thionyl chloride (0.080 mL, 1.09 mmol) was added dropwise. The reaction mixture was stirred at rt for 1 h. The reaction mixture was concentrated in vacuo to give the title compound. Tr(METCR1410)=1.10 min, (ES)$^+$ [M+H]$^+$=202.1/204.1, 100%.

Step 3: 7-Fluoro-5-{3-[(5-methoxypyridin-2-yl)oxy]propyl}-4H,5H-pyrrolo[1,2-a]quinoxalin-4-one 7-Fluoro-5H-pyrrolo[1,2-a]quinoxalin-4-one (50 mg, 0.248 mmol), K$_2$CO$_3$ (137 mg, 0.992 mmol) and potassium iodide (165 mg, 0.992 mmol) were dissolved in DMF (5 mL) and 2-(3-chloropropoxy)-5-methoxy-pyridine (100 mg, 0.496 mmol) was added. The reaction mixture was stirred at rt for 17 h. The reaction mixture was heated at 60° C. for 4 h. The reaction mixture was concentrated in vacuo and triturated with water (5 mL). Further purification by column chromatography (silica, EtOAc-heptane mixtures) gave the title compound. $^1$H NMR (500 MHz, DMSO-d$_6$) δ 8.30-8.05 (m, 2H), 7.45-7.32 (m, 2H), 7.28 (dd, J=9.8, 3.3 Hz, 1H), 7.23-7.12 (m, 1H), 7.05 (dd, J=3.9, 1.4 Hz, 1H), 6.70 (dd, J=3.8, 2.8 Hz, 1H), 6.34 (d, J=9.8 Hz, 1H), 4.24 (t, J=7.3 Hz, 2H), 4.12-3.84 (m, 2H), 3.64 (s, 3H), 2.13-1.89 (m, 2H). $^{19}$F NMR (376 MHz, DMSO-d$_6$) −115.09. Tr(METCR1603)=3.53 min m/z (ES$^+$) (M+H)$^+$ 368.1, 97%.

Scheme for Method 12

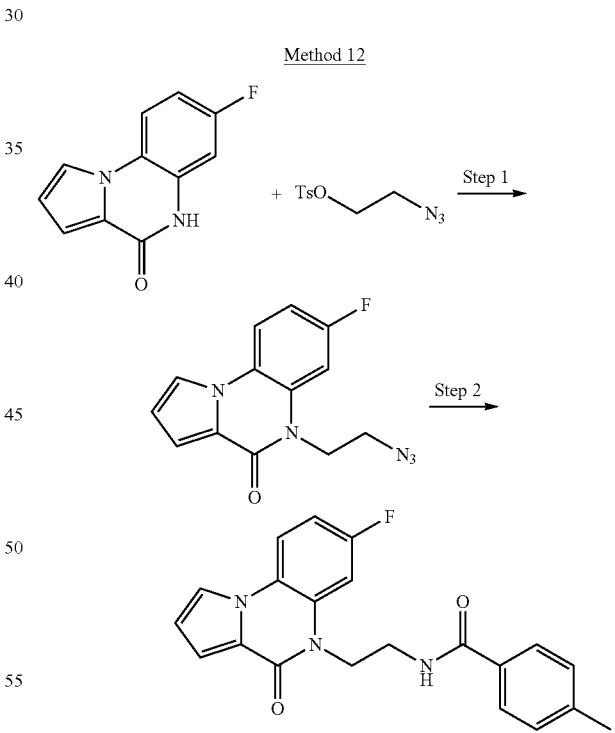

Example 12-1

Step 1: 5-(2-Azidoethyl)-7-fluoro-pyrrolo[1,2-a]quinoxalin-4-one

7-Fluoro-5H-pyrrolo[1,2-a]quinoxalin-4-one (300 mg, 1.48 mmol) was added to a suspension of sodium hydride (60%, 59 mg, 1.48 mmol) in DMF (3.5 mL) stirred at rt. After 30 min a solution of 2-azidoethyl 4-methylbenzenesulfonate (358 mg, 1.48 mmol) in DMF (0.5 mL) was added dropwise. The reaction was stirred at 80° C. under nitrogen for 24 h. After this time, more 2-azidoethyl 4-methylbenzenesulfonate (120 mg, 0.48 mmol) was added and the reaction stirred at 80° C. for another 24 h. The reaction was diluted with water and triturated for 30 min. The solid was filtered, dried and purified by column chromatography (silica, 0 to 50% EtOAc in heptane) to give the title compound. $^1$H NMR (500 MHz, Chloroform-d) δ 7.67 (dd, J=9.0, 5.2 Hz, 1H), 7.61 (dd, J=2.8, 1.5 Hz, 1H), 7.26-7.23 (m, 1H), 7.15 (dd, J=10.5, 2.6 Hz, 1H), 6.98 (ddd, J=9.0, 7.5, 2.6 Hz, 1H), 6.68 (dd, J=3.9, 2.8 Hz, 1H), 4.39 (t, J=6.4 Hz, 2H), 3.73 (t, J=6.4 Hz, 2H). Tr(METCR0990)=1.56 min, (ES$^+$) [M+H]+ 272.1, 100%.

Step 2: N-[2-(7-Fluoro-4-oxo-pyrrolo[1,2-a]quinoxalin-5-yl)ethyl]-4-methyl-benzamide Triphenylphosphine (235 mg, 0.896 mmol) was added to a solution of 5-(2-azidoethyl)-7-fluoro-pyrrolo[1,2-a]quinoxalin-4-one (81 mg, 0.299 mmol) in THF (2 mL) and water (0.2 mL) and the mixture stirred at rt for 2 h. The reaction was evaporated to dryness then dissolved in pyridine (2 mL). 4-Methylbenzoyl chloride (51 mg, 0.328 mmol) and DMAP (7.3 mg, 0.0597 mmol) were added and the mixture was stirred at rt for 1.5 h. The reaction was concentrated to dryness and purified by preparative HPLC (MeCN-water, 0.1% formic acid) to give the title compound. $^1$H NMR (400 MHz, DMSO-d6) δ 8.69 (t, J=5.8 Hz, 1H), 8.20 (dd, J=2.8, 1.5 Hz, 1H), 8.17 (dd, J=9.1, 5.5 Hz, 1H), 7.72 (dd, J=11.4, 2.6 Hz, 1H), 7.68 (d, J=8.2 Hz, 2H), 7.25 (d, J=7.9 Hz, 2H), 7.18-7.12 (m, 1H), 7.06 (dd, J=3.9, 1.5 Hz, 1H), 6.70 (dd, J=3.9, 2.8 Hz, 1H), 4.32 (t, J=6.9 Hz, 2H), 3.54 (q, J=6.5 Hz, 2H), 2.34 (s, 3H). 19F NMR (376 MHz, DMSO-d6) δ -115.19. Tr(MET-uPLC-AB-101)=3.17 min, (ES$^+$) [M+H]$^+$ 364.2, 100%.

Also prepared by this route:

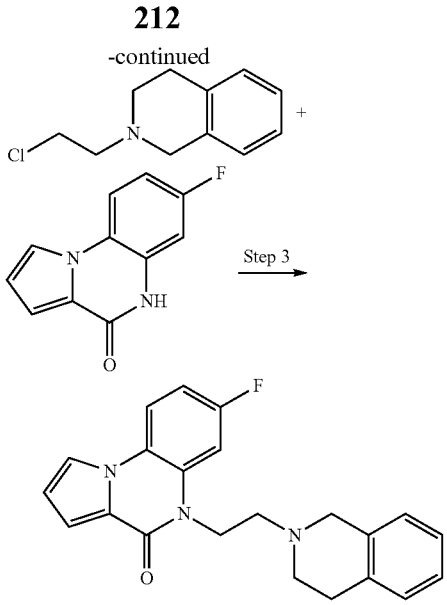

Example 13-1

Example 13-1

Step 1: 2-(3,4-Dihydro-1H-isoquinolin-2-yl)ethanol 1,2,3,4-Tetrahydroisoquinoline (500 mg, 3.68 mmol), $K_2CO_3$ (508 mg, 3.68 mmol) and 2-bromoethanol (460 mg, 3.68 mmol) were dissolved in acetonitrile (50 mL) and heated to 60° C. for 4 h. The reaction mixture was concentrated to dryness and partitioned between DCM (25 mL) and water (25 mL). The organic extracts were dried (MgSO$_4$), filtered and concentrated to give the title compound. $^1$H NMR (500 MHz, DMSO-d$_6$) δ 7.52 (d, J=8.5 Hz, 2H), 7.20 (d, J=8.5 Hz, 2H), 3.94-3.79 (m, 2H), 3.75 (t, J=8.8 Hz, 1H), 3.70 (s, 3H), 2.41-2.31 (m, 2H), 2.29 (s, 3H)

| Ex. | Structure | LCMS data | NMR Data |
|---|---|---|---|
| 12-2 | ![structure] | Tr(METCR1603) = 4.25 min m/z (ES$^+$) (M + H)$^+$ 378.2, 100% | 1H NMR (400 MHz, DMSO-d6) 8.44 (t, J = 5.6 Hz, 1H), 8.32 - 8.12 (m, 2H), 7.74 (d, J = 8.2 Hz, 2H), 7.46 (dd, J = 11.2, 2.6 Hz, 1H), 7.26 (d, J = 7.9 Hz, 2H), 7.22-7.10 (m, 1H), 7.06 (dd, J = 3.9, 1.5 Hz, 1H), 6.70 (dd, J = 3.9, 2.8 Hz, 1H), 4.43-4.00 (m, 2H), 3.61-3.34 (m, 2H), 2.33 (s, 3H), 2.12-1.70 (m, 2H). 19F NMR (376 MHz, DMSO-d6) -115.11. |

Scheme for Method 13

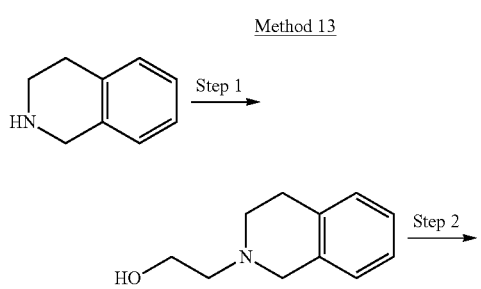

Step 2: 2-(2-Chloroethyl)-3,4-dihydro-1H-isoquinoline 2-(3,4-Dihydro-1H-isoquinolin-2-yl)ethanol (50 mg, 0.282 mmol) was dissolved in DCM (5 mL) and thionyl chloride (0.041 mL, 0.564 mmol) was added. The reaction mixture was stirred at rt for 2 h. A further portion of thionyl chloride (0.041 mL, 0.564 mmol) was added and the reaction mixture was stirred at rt for another 3 h. The reaction mixture was concentrated to dryness to give the title compound. The product was carried forward without further purification.

Step 3: 7-Fluoro-5-[2-(1,2,3,4-tetrahydroisoquinolin-2-yl)ethyl]-4H,5H-pyrrolo[1,2-a]quinoxalin-4-one 7-Fluoro-5H-pyrrolo[1,2-a]quinoxalin-4-one (100 mg, 0.495 mmol), $K_2CO_3$ (273 mg, 1.98 mmol) and potassium iodide (328 mg, 1.98 mmol) were dissolved in DMF (5 mL) and 2-(2-chloroethyl)-3,4-dihydro-1H-isoquinoline (194 mg, 0.989 mmol) was added. The reaction mixture was heated at 60° C. for 4 h. The reaction mixture was concentrated in vacuo and triturated with water (5 mL). Further purification by basic preparative HPLC gave the title compound. $^1$H NMR (400 MHz, DMSO-$d_6$) δ 8.32-8.08 (m, 2H), 7.50 (dd, J=11.3, 2.6 Hz, 1H), 7.32-6.92 (m, 6H), 6.68 (dd, J=3.8, 2.8 Hz, 1H), 4.43 (t, J=6.7 Hz, 2H), 3.66 (s, 2H), 2.92-2.63 (m, 6H). $^{19}$F NMR (376 MHz, DMSO-$d_6$) −115.14. Tr(MET-uHPLC-AB-101)=1.78 min m/z (ES$^+$) (M+H)$^+$ 362.2, 100%.

Also prepared by this route:

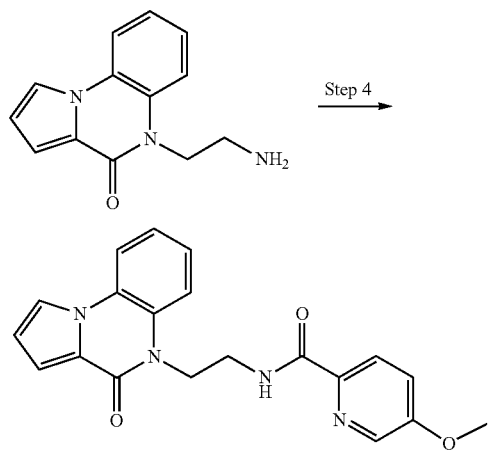

Example 14-1

| Ex. | Structure | LCMS data | NMR Data |
|---|---|---|---|
| 13-2 | (structure shown) | Tr(MET-uHPLC-AB-101) = 1.87 min m/z (ES$^+$) (M + H)$^+$ 376.3, 97% | 1H NMR (400 MHz, DMSO-d6) 8.40-7.87 (m, 2H), 7.54 (dd, J = 11.3, 2.6 Hz, 1H), 7.28-6.88 (m, 6H), 6.68 (dd, J = 3.8, 2.8 Hz, 1H), 4.45-4.18 (m, 2H), 3.57 (s, 2H), 2.82 (t, J = 5.8 Hz, 2H), 2.76-2.61 (m, 2H), 2.56 (t, J = 6.7 Hz, 2H), 1.97-1.79 (m, 2H). 19F NMR (376 MHz, DMSO-d6) −115.14. |

Scheme for Method 14

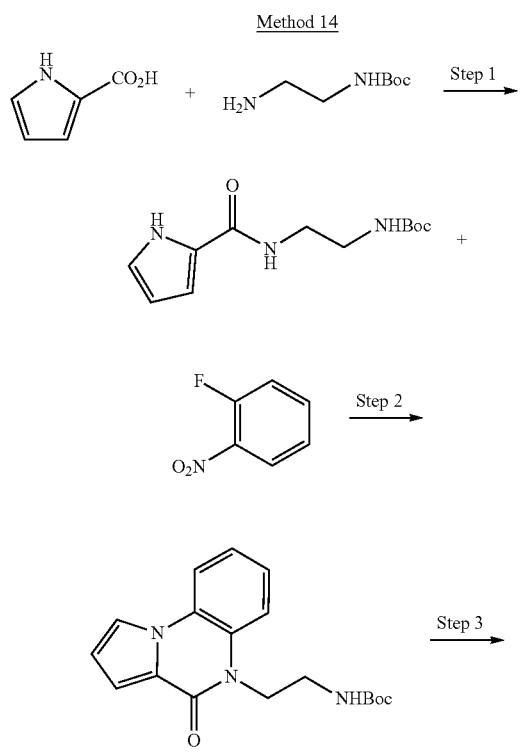

Method 14

Example 14-1

Step 1: tert-Butyl N-[2-(1H-pyrrole-2-carbonylamino)ethyl]carbamate

1H-Pyrrole-2-carboxylic acid (1.00 g, 9.00 mmol) was dissolved in DMF (25 mL), purged with nitrogen and stirred at rt. DIPEA (1.6 mL, 9.00 mmol) and HATU (5.13 g, 13.5 mmol) were added to the reaction mixture and stirred for 10 min. tert-Butyl N-(2-aminoethyl)carbamate (2.94 g, 18.0 mmol) was then added to the reaction mixture and stirred for 1 h. The solvent was removed under reduced pressure. The residue was suspended in water and washed with DCM (3×25 mL). The aqueous was concentrated and purified by column chromatography (silica, EtOAc-heptane mixtures) to give the title compound. $^1$H NMR (500 MHz, DMSO-$d_6$) δ 11.42 (s, 1H), 7.99 (t, J=5.6 Hz, 1H), 7.03-6.53 (m, 3H), 6.07 (dt, J=3.5, 2.4 Hz, 1H), 3.23 (q, J=6.4 Hz, 2H), 3.06 (q, J=6.3 Hz, 2H), 1.38 (s, 9H). Tr(METCR1410)=0.93 min, (ES)$^+$ [M+H]$^+$=275.9, 100%.

Step 2: tert-Butyl N-[2-(4-oxopyrrolo[1,2-a]quinoxalin-5-yl)ethyl]carbamate $Cs_2CO_3$ (1.49 g, 4.56 mmol) and 1-fluoro-2-nitro-benzene (225 mg, 1.56 mmol) were dissolved in Acetonitrile (5 mL) and tert-butyl N-[2-(1H-pyrrole-2-carbonylamino)ethyl]carbamate (330 mg, 1.30 mmol) was added. The reaction mixture was heated to 60° C. overnight. The reaction mixture was concentrated. The residue was partitioned between water (5 mL) and EtOAc (5 mL) and extracted with EtOAc (2×5 mL). The combined organics were dried ($MgSO_4$) and concentrated in vacuo. The residue was purified by column chromatography (silica, EtOAc-heptane mixtures) to give the title compound. ¹H NMR (400 MHz, DMSO-d₆) δ 8.21 (d, J=1.2 Hz, 1H), 8.13 (d, J=7.0 Hz, 1H), 7.66 (d, J=8.4 Hz, 1H), 7.39 (t, J=7.7 Hz, 1H), 7.33-7.13 (m, 1H), 7.11-6.82 (m, 2H), 6.70 (dd, J=3.8, 2.8 Hz, 1H), 4.25 (t, J=6.6 Hz, 2H), 3.24 (d, J=6.8 Hz, 2H), 1.33 (s, 9H). Tr(METCR1410)=1.10 min, (ES)⁺[M+Na]⁺=350.0, 91%.

Step 3: 5-(2-Aminoethyl)pyrrolo[1,2-a]quinoxalin-4-one hydrochloride tert-Butyl N-[2-(4-oxopyrrolo[1,2-a]quinoxalin-5-yl)ethyl]carbamate (100 mg, 0.305 mmol) was dissolved in 4 M HCl in dioxane (10 mL) and stirred at room temperature for 2 h. The reaction mixture was filtered to give the title compound. ¹H NMR (400 MHz, DMSO-d₆) δ 8.26 (dd, J=2.8, 1.5 Hz, 1H), 8.17 (dd, J=8.1, 1.4 Hz, 1H), 7.99 (s, 3H), 7.79-7.57 (m, 1H), 7.42 (td, J=8.4, 7.9, 1.4 Hz, 1H), 7.37-7.18 (m, 1H), 7.09 (dd, J=3.9, 1.5 Hz, 1H), 6.73 (dd, J=3.8, 2.8 Hz, 1H), 4.51 (t, J=6.6 Hz, 2H), 3.11 (q, J=6.1 Hz, 2H). Tr(METCR1410)=0.93 min, (ES)⁺ [M+H]⁺=275.9, 100%.

Step 4: 5-Methoxy-N-(2-{4-oxo-4H,5H-pyrrolo[1,2-a]quinoxalin-5-yl}ethyl)pyridine-2-carboxamide 5-Methoxypyridine-2-carboxylic acid (0.023 mL, 0.0948 mmol) was dissolved in DMF (1 mL) and HATU (54 mg, 0.142 mmol) and DIPEA (0.050 mL, 0.284 mmol) were added followed by 5-(2-aminoethyl)pyrrolo[1,2-a]quinoxalin-4-one hydrochloride (25 mg, 0.095 mmol). The reaction mixture was stirred at rt for 30 min. Purification by basic preparative HPLC gave the title compound. ¹H NMR (400 MHz, DMSO-d₆) δ 8.99 (t, J=6.0 Hz, 1H), 8.29 (d, J=2.8 Hz, 1H), 8.23-8.17 (m, 1H), 8.12 (d, J=7.1 Hz, 1H), 7.99 (d, J=8.7 Hz, 1H), 7.88 (d, J=8.1 Hz, 1H), 7.53 (dd, J=8.7, 2.9 Hz, 1H), 7.43-7.31 (m, 1H), 7.32-7.15 (m, 1H), 7.05 (dd, J=3.8, 1.3 Hz, 1H), 6.84-6.49 (m, 1H), 4.38 (t, J=6.9 Hz, 2H), 3.90 (s, 3H), 3.70-3.47 (m, 2H). Tr(MET-uHPLC-AB-101)=2.79 min m/z (ES⁺) (M+H)⁺ 363.2, 100%.

Also prepared by this route:

Scheme for Method 15

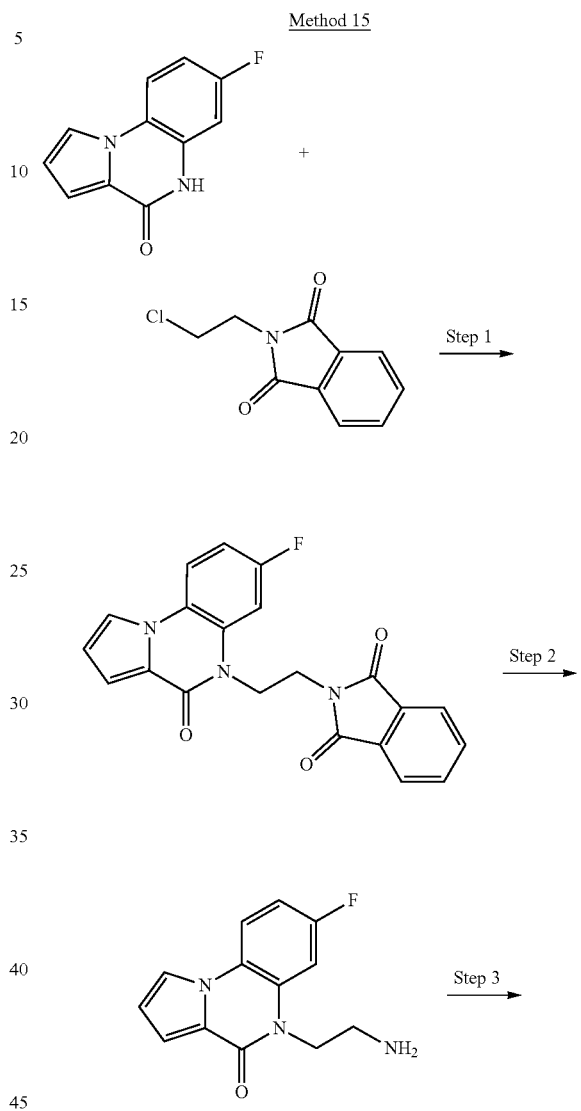

| Ex. | Structure | LCMS data | NMR Data |
|---|---|---|---|
| 14-2 | 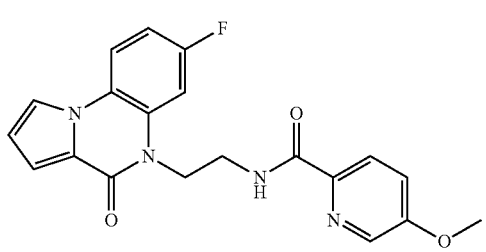 [SMILES: COc1ccc(C(=O)NCCn2c(=O)c3cccn3c3ccc(F)cc32)nc1] | Tr(MET-uHPLC-AB-101) = 2.98 min m/z (ES⁺) (M + H)⁺ 381.1, 97% | 1H NMR (400 MHz, DMSO-d6) 9.02 (t, J = 6.1 Hz, 1H), 8.28 (dd, J = 2.9, 0.4 Hz, 1H), 8.24-8.16 (m, 1H), 8.15 (dd, J = 9.1, 5.5 Hz, 1H), 8.05-7.89 (m, 1H), 7.81 (dd, J = 11.5, 2.6 Hz, 1H), 7.52 (dd, J = 8.7, 2.9 Hz, 1H), 7.13 (ddd, J = 9.0, 8.0, 2.6 Hz, 1H), 7.05 (dd, J = 3.9, 1.5 Hz, 1H), 6.69 (dd, J = 3.9, 2.8 Hz, 1H), 4.32 (t, J = 7.0 Hz, 2H), 3.90 (s, 3H), 3.69-3.49 (m, 2H). 19F NMR (376 MHz, DMSO-d6) −115.34. |

Scheme for Method 16

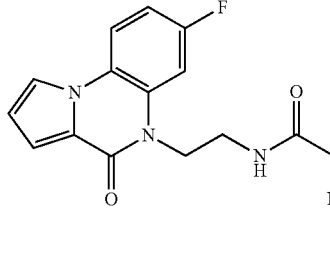

Example 15-1

Method 16

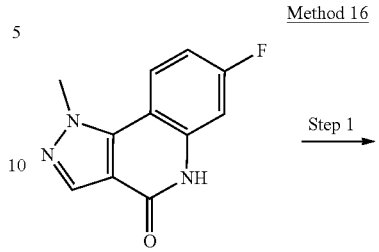

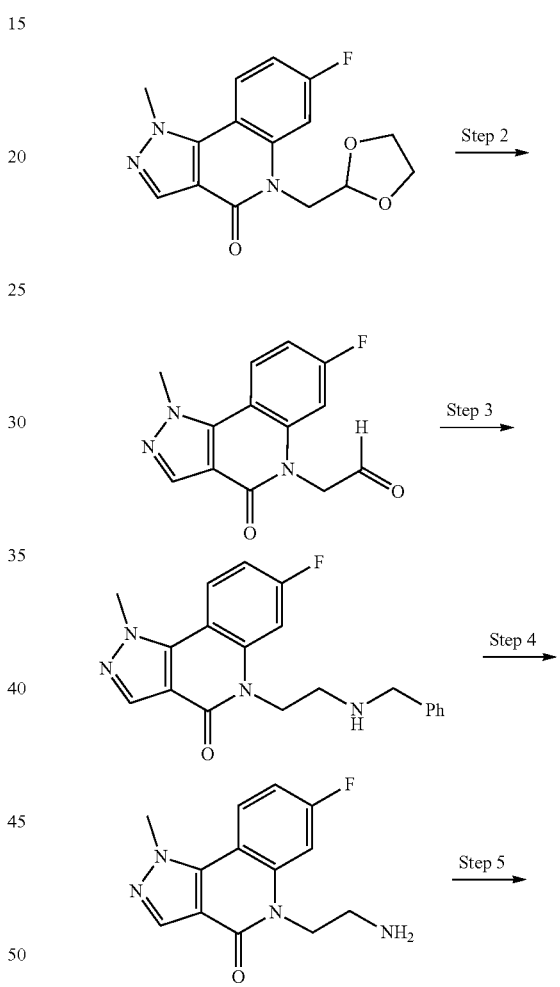

Example 15-1

Step 1: 2-[2-(7-Fluoro-4-oxo-pyrrolo[1,2-a]quinoxalin-5-yl)ethyl]isoindoline-1,3-dione 7-Fluoro-5H-pyrrolo[1,2-a]quinoxalin-4-one (500 mg, 2.47 mmol) was suspended in DMF (25 mL). $K_2CO_3$ (410 mg, 2.97 mmol) and potassium iodide (493 mg, 2.97 mmol) were added followed by 2-(2-chloroethyl)-1H-isoindole-1,3 (2H)-dione (622 mg, 2.97 mmol). The reaction mixture was heated to 60° C. overnight, then heated to 80° C. for 2 days. The reaction mixture was concentrated to dryness. The residue was partitioned between water (25 mL) and DCM (25 mL) and extracted with DCM (2×10 mL). The combined organics were dried ($MgSO_4$), filtered and concentrated. Purification by column chromatography (silica, EtOAc-heptane mixtures) gave the title compound. Tr(METCR1410)=1.18 min, m/z (ES$^+$) (M+H)$^+$ 376.0, 25%.

Step 2: 5-(2-Aminoethyl)-7-fluoro-pyrrolo[1,2-a]quinoxalin-4-one

2-[2-(7-fluoro-4-oxo-pyrrolo[1,2-a]quinoxalin-5-yl)ethyl]isoindoline-1,3-dione (510 mg, 0.340 mmol) was dissolved in dry EtOH (1.4167 mL). Hydrazine hydrate (0.039 mL, 0.679 mmol) was added, and the solution was heated at 50° C. for 30 min. The mixture was quenched with concentrated HCl (2 mL) and stirred for 10 min. The white solid was filtered off and washed with EtOH (2×10 mL). The filtrate was concentrated under reduced pressure and remaining aqueous solution was adjusted to pH>7 by 2 M NaOH. After extraction with EtOAc (2×30 mL), the combined organic layer was dried ($MgSO_4$) and concentrated under reduced pressure to give the title compound. Tr(METCR1410)=0.78 min, m/z (ES$^+$) (M+H)$^+$ 246.0, 43%.

Step 3: Performed as for Method 14, Step 4

Prepared by this route:

| Ex. | Structure | LCMS data | NMR data |
|---|---|---|---|
| 15-1 | 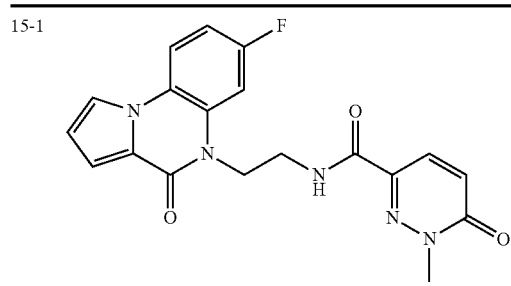 | Tr(MET-uHPLC-AB-101) = 2.34 min m/z (ES$^+$) (M + H)$^+$ 382.1, 97% | 1H NMR (400 MHz, DMSO-d6) 8.85 (t, J = 6.0 Hz, 1H), 8.40-7.97 (m, 2H), 7.82 (d, J = 9.6 Hz, 1H), 7.72 (dd, J = 11.4, 2.6 Hz, 1H), 7.29-7.11 (m, 1H), 7.06 (dd, J = 3.9, 1.5 Hz, 1H), 7.00 (d, J = 9.6 Hz, 1H), 6.69 (dd, J = 3.9, 2.8 Hz, 1H), 4.31 (t, J = 7.0 Hz, 2H), 3.71 (s, 3H), 3.62-3.44 (m, 2H). 19F NMR (376 MHz, DMSO-d6) −115.39. |

-continued

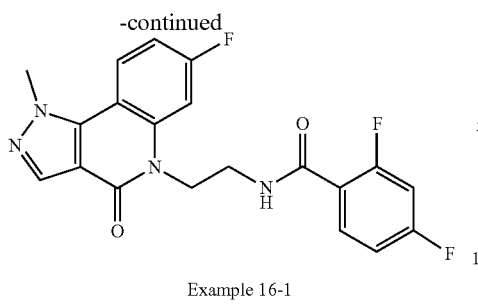

Example 16-1

Example 16-1

Step 1: 5-(1,3-Dioxolan-2-ylmethyl)-7-fluoro-1-methyl-pyrazolo[4,3-c]quinolin-4-one 7-Fluoro-1-methyl-5H-pyrazolo[4,3-c]quinolin-4-one (Prepared according to Method 9, 500 mg, 2.30 mmol) and $K_2CO_3$ (445 mg, 3.22 mmol) were dissolved in DMF (50 mL) and 2-(bromomethyl)-1,3-dioxolane (436 mg, 2.53 mmol) was added. The reaction mixture was heated at 60° C. for 24 h. $K_2CO_3$ (445 mg, 3.22 mmol) and 2-(bromomethyl)-1,3-dioxolane (436 mg, 2.53 mmol) were added and the reaction mixture was heated to 60° C. for a further 3 days. The reaction mixture was concentrated in vacuo and partitioned between DCM (50 mL) and water (50 mL). The organic phase was separated, dried (MgSO$_4$), filtered and concentrated in vacuo. Further purification by column chromatography (silica, EtOAc-heptane mixtures) gave the title compound. $^1$H NMR (400 MHz, DMSO-d$_6$) δ 8.32 (dd, J=9.0, 6.3 Hz, 1H), 8.13 (s, 1H), 7.67 (dd, J=12.4, 2.4 Hz, 1H), 7.26 (m, 1H), 5.13 (t, J=4.5 Hz, 1H), 4.51 (d, J=4.5 Hz, 2H), 4.36 (s, 2H), 4.05-3.90 (m, 2H), 3.86-3.76 (m, 2H). Tr(METCR1410)=1.01 min, m/z (ES$^+$) (M+H)$^+$ 304.0, 100%.

Step 2: 2-(7-Fluoro-1-methyl-4-oxo-pyrazolo[4,3-c]quinolin-5-yl)acetaldehyde 5-(1,3-dioxolan-2-ylmethyl)-7-fluoro-1-methyl-pyrazolo[4,3-c]quinolin-4-one (140 mg, 0.462 mmol) was dissolved in THF (4 mL) and 2 M hydrogen chloride (2.3 mL, 4.62 mmol) was added. The mixture was heated to 60° C. overnight. The solvent was removed in vacuo and the residue was partitioned between DCM and water. The organic phase was dried (MgSO$_4$), filtered and concentrated to give the title compound. $^1$H NMR (400 MHz, DMSO-d$_6$) δ 9.72 (s, 1H), 8.35 (dd, J=9.0, 6.2 Hz, 1H), 8.16-8.08 (m, 1H), 7.48 (dd, J=12.1, 2.4 Hz, 1H), 7.29-7.24 (m, 1H), 5.34 (s, 2H), 4.38 (s, 3H).

Step 3: 5-[2-(Benzylamino)ethyl]-7-fluoro-1-methyl-pyrazolo[4,3-c]quinolin-4-one A solution of 2-(7-fluoro-1-methyl-4-oxo-pyrazolo[4,3-c]quinolin-5-yl)acetaldehyde (120 mg, 0.463 mmol) and 1-phenylmethanamine (55 mg, 0.509 mmol) in DCM (4 mL) was treated with acetic acid (0.11 mL) and stirred for 1 h before portionwise addition of STAB (157 mg, 0.741 mmol) and stirring for a further 4 h. The reaction mixture was concentrated in vacuo and the residue was partitioned between DCM and water. The organic layer was dried (MgSO$_4$), filtered and concentrated in vacuo. Further purification by SCX cartridge gave the title compound. Tr(METCR1410)=0.89 min, m/z (ES$^+$) (M+H)$^+$ 351.4, 93%.

Step 4: 5-(2-Aminoethyl)-7-fluoro-1-methyl-pyrazolo[4,3-c]quinolin-4-one

5-[2-(benzylamino)ethyl]-7-fluoro-1-methyl-pyrazolo[4,3-c]quinolin-4-one (90 mg, 0.257 mmol) was dissolved in ethanol (9 mL) and palladium on carbon (10%, 27 mg, 0.0257 mmol) was added. The mixture was stirred under H$_2$ gas at rt for 4 h. The mixture was filtered, and the filtrate was concentrated in vacuo to give the title compound. Tr(METCR1410)=0.71 min, m/z (ES$^+$) (M+H)$^+$ 260.8, 93%.

Step 5: Performed as for Method 14, Step 4

Prepared by this route:

| Ex. | Structure | LCMS data | NMR data |
|---|---|---|---|
| 16-1 | 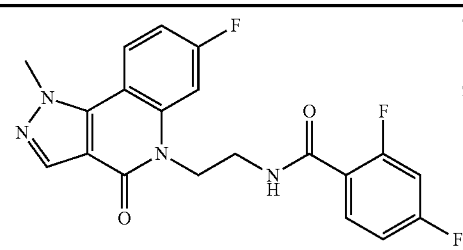 | Tr(MET-uHPLC-AB-101) = 2.74 min m/z (ES$^+$) (M + H)$^+$ 401.2, 96% | 1H NMR (400 MHz, DMSO-d6) 8.70-8.52 (m, 1H), 8.34 (dd, J = 9.0, 6.3 Hz, 1H), 8.14 (s, 1H), 7.85 (dd, J = 12.4, 2.4 Hz, 1H), 7.76-7.59 (m, 1H), 7.41-7.30 (m, 1H), 7.31-7.20 (m, 1H), 7.22-7.10 (m, 1H), 4.43 (t, J = 6.8 Hz, 2H), 4.36 (s, 3H), 3.64-3.48 (m, 2H). 19F NMR (376 MHz, DMSO-d6) −106.21 (d, J = 9.7 Hz), −108.76, −109.19 (d, J = 9.7 Hz). |
| 16-2 | 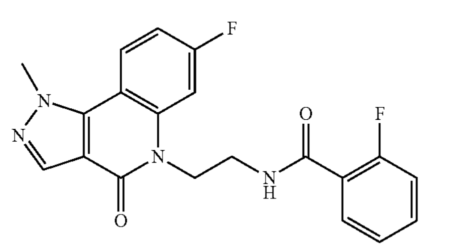 [SMILES: Cn1ncc2c(=O)n(CCNC(=O)c3ccccc3F)c3cc(F)ccc3c21] | Tr(MET-uHPLC-AB-101) = 2.61 min m/z (ES$^+$) (M + H)$^+$ 383.2, 97% | 1H NMR (400 MHz, DMSO-d6) 8.72-8.53 (m, 1H), 8.33 (dd, J = 9.0, 6.3 Hz, 1H), 8.14 (s, 1H), 7.86 (dd, J = 12.4, 2.4 Hz, 1H), 7.63-7.56 (m, 1H), 7.56-7.47 (m, 1H), 7.46-6.86 (m, 3H), 4.43 (t, J = 6.9 Hz, 2H), 4.36 (s, 3H), 3.75-3.48 (m, 2H). 19F NMR (376 MHz, DMSO-d6) −108.32, −113.64. |

Scheme for Method 17

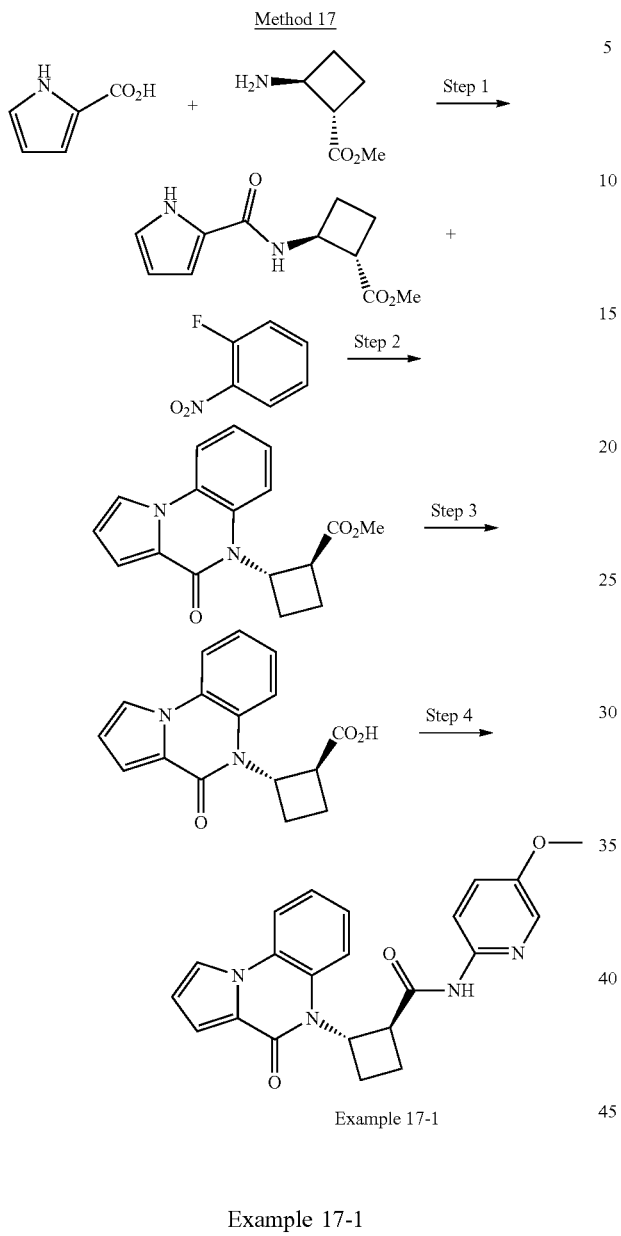

Example 17-1

Scheme for Method 18

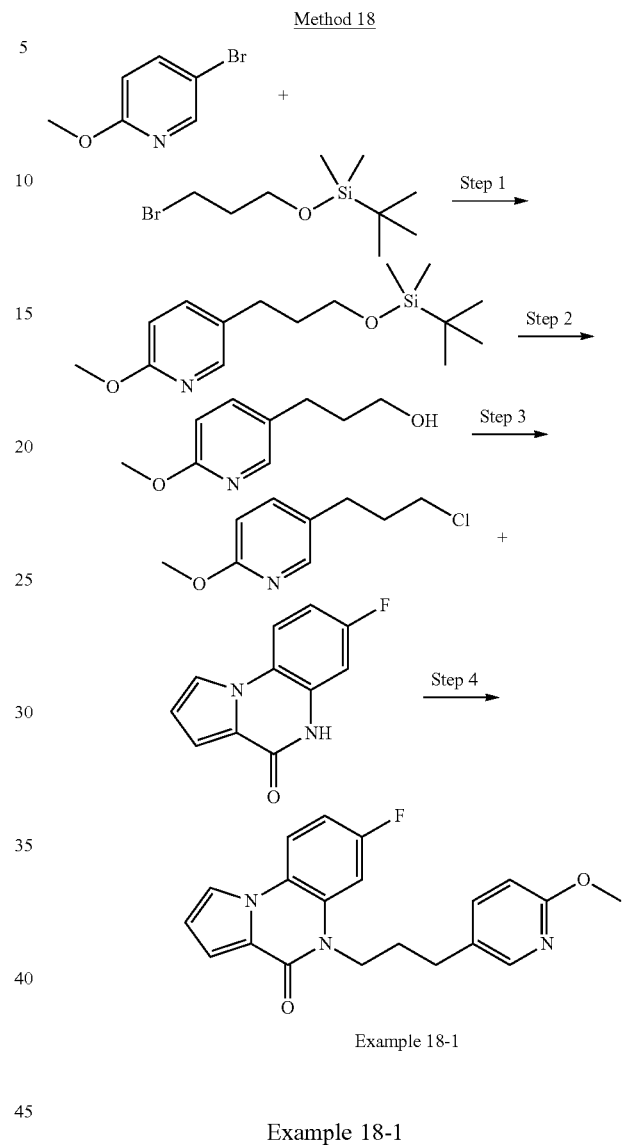

Example 18-1

Example 17-1

Steps 1-2: Performed as for Method 14, Steps 1-2
Steps 3-4: Performed as for Method 2, Steps 4-5
Prepared by this method:

(1SR,2SR)—N-(5-Methoxypyridin-2-yl)-2-{4-oxo-4H,5H-pyrrolo[1,2-a]quinoxalin-5-yl}cyclobutane-1-carboxamide $^1$H NMR (400 MHz, DMSO-$d_6$) δ 10.32 (s, 1H), 8.16 (dd, J=2.8, 1.5 Hz, 1H), 8.12-8.03 (m, 2H), 7.98 (d, J=2.8 Hz, 1H), 7.69 (d, J=7.8 Hz, 1H), 7.49-7.31 (m, 2H), 7.32-7.18 (m, 1H), 7.02 (dd, J=3.8, 1.5 Hz, 1H), 6.68 (dd, J=3.8, 2.8 Hz, 1H), 5.50-5.08 (m, 1H), 4.81-4.31 (m, 1H), 3.78 (s, 3H), 2.82-2.68 (m, 1H), 2.43-2.27 (m, 1H), 2.30-2.08 (m, 1H), 2.02-1.82 (m, 1H). Tr(MET-uHPLC-AB-101)=3.02 min m/z (ES$^+$) (M+H)$^+$ 389.2, 100%.

Example 18-1

Step 1: tert-Butyl-[3-(6-methoxy-3-pyridyl) propoxy]-dimethyl-silane

A mixture of 1,2-dimethoxyethane—dibromonickel (1:1) (40 mg, 0.13 mmol), 4,4'-dimethoxy-2,2'-bipyridine (28 mg, 0.13 mmol) and sodium iodide (155 mg, 1.03 mmol) in DMA (5 mL) was degassed with $N_2$ under sonication for 5 minutes. The solution was transferred to a 10 mL Electrasyn vial equipped with a RVC cathode and a Zinc anode. 5-Bromo-2-methoxypyridine (240 mg, 1.28 mmol) was added, followed by 3-bromopropoxy-tert-butyl-dimethyl-silane (438 mg, 1.66 mmol). A constant current of 10 mA was passed through the solution for 20 h. The reaction was diluted with EtOAc (40 mL) and washed with water (50 mL). The aqueous layer was further extracted with EtOAc (2×40 mL). The combined organic layers were washed with brine, dried (MgSO$_4$), filtered and concentrated. The crude was adsorbed on silica and purified by column chromatography (silica, 0-20% EtOAc in heptane) to give the title compound. $^1$H NMR (400 MHz, DMSO-$d_6$) δ 7.94 (d, J=1.9 Hz, 1H), 7.52 (dd, J=8.5, 2.5 Hz, 1H), 6.71 (d, J=8.5 Hz, 1H), 3.78 (s, 3H), 3.60-3.48 (m, 2H), 2.60-2.49 (m, 2H), 1.81-1.63 (m, 2H), 0.85 (s, 9H), −0.01 (s, 6H). Tr(METCR1410)=1.55 min, (ES⁺) [M+H]⁺ 282, 92%.

Step 2: 3-(6-Methoxy-3-pyridyl)propan-1-ol

4 M Hydrogen chloride in dioxane (0.77 mL, 3.06 mmol) was added to a solution of tert-butyl-[3-(6-methoxy-3-pyridyl)propoxy]-dimethyl-silane (224 mg, 0.56 mmol) in THF (5 mL) and stirred at rt. The reaction was diluted with saturated aqueous NaHCO₃ and extracted with EtOAc (3×10 mL). The combined organic layers were washed with brine, dried (MgSO₄), filtered and concentrated. The crude was purified by column chromatography (silica, 10-100% EtOAc in heptane) to give the title compound. ¹H NMR (500 MHz, Chloroform-d) δ 7.99 (d, J=2.3 Hz, 1H), 7.42 (dd, J=8.5, 2.5 Hz, 1H), 6.68 (d, J=8.4 Hz, 1H), 3.91 (s, 3H), 3.68 (t, J=5.8 Hz, 2H), 2.70-2.57 (m, 2H), 1.96-1.73 (m, 2H), 1.35 (s, 1H). Tr(METCR1410)=0.67 min, (ES⁺) [M+H]⁺ 168, 100%.

Step 3: 5-(3-Chloropropyl)-2-methoxy-pyridine

Thionyl chloride (68 µL, 0.957 mmol) was added to a solution of 3-(6-methoxy-3-pyridyl)propan-1-ol (20 mg, 0.120 mmol) in DCM (1 mL) cooled to 0° C. The mixture was allowed to warm to rt over 6 h. The reaction mixture was concentrated to give the title compound which was used in the next step without further purification. Tr(METCR1410)=1.11 min, (ES⁺) [M+H]⁺ 186, 100%.

Step 4: 7-Fluoro-5-[3-(6-methoxy-3-pyridyl)propyl]pyrrolo[1,2-a]quinoxalin-4-one 7-Fluoro-5H-pyrrolo[1,2-a]quinoxalin-4-one (12 mg, 0.059 mmol), K₂CO₃ (33 mg, 0.237 mmol) and potassium iodide (39 mg, 0.237 mmol) were dissolved in DMF (1 mL) and 5-(3-chloropropyl)-2-methoxy-pyridine (22 mg, 0.119 mmol) was added. The reaction mixture was stirred at 60° C. overnight. The reaction was partitioned between DCM and water and extracted through a Telos phase separator. The aqueous layer was extracted twice more and the combined organic layers were concentrated. The crude was purified by acidic preparative HPLC to give the title compound. ¹H NMR (500 MHz, DMSO-d₆) δ 8.22-8.10 (m, 2H), 8.02 (d, J=2.2 Hz, 1H), 7.59 (dd, J=8.5, 2.5 Hz, 1H), 7.37 (dd, J=11.2, 2.6 Hz, 1H), 7.21-7.10 (m, 1H), 7.03 (dd, J=3.9, 1.4 Hz, 1H), 6.71 (d, J=8.4 Hz, 1H), 6.68 (dd, J=3.8, 2.8 Hz, 1H), 4.26-4.14 (m, 2H), 3.80 (s, 3H), 2.66 (t, J=7.6 Hz, 2H), 1.89 (p, J=7.7 Hz, 2H). ¹⁹F NMR (471 MHz, DMSO-d₆) δ −104.51--121.69 (m). Tr(MET-uHPLC-AB-101)=3.24 min m/z (ES⁺) (M+H)⁺ 352.1, 100%.

Scheme for Method 19

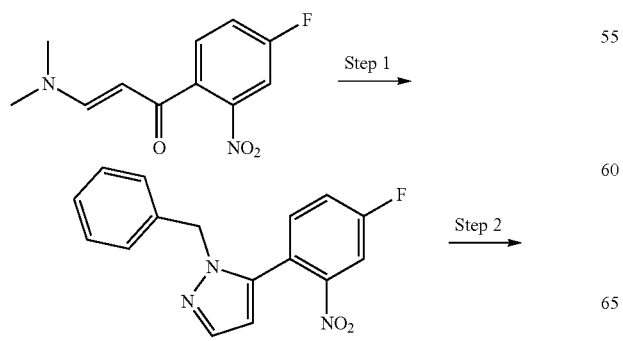

Method 19

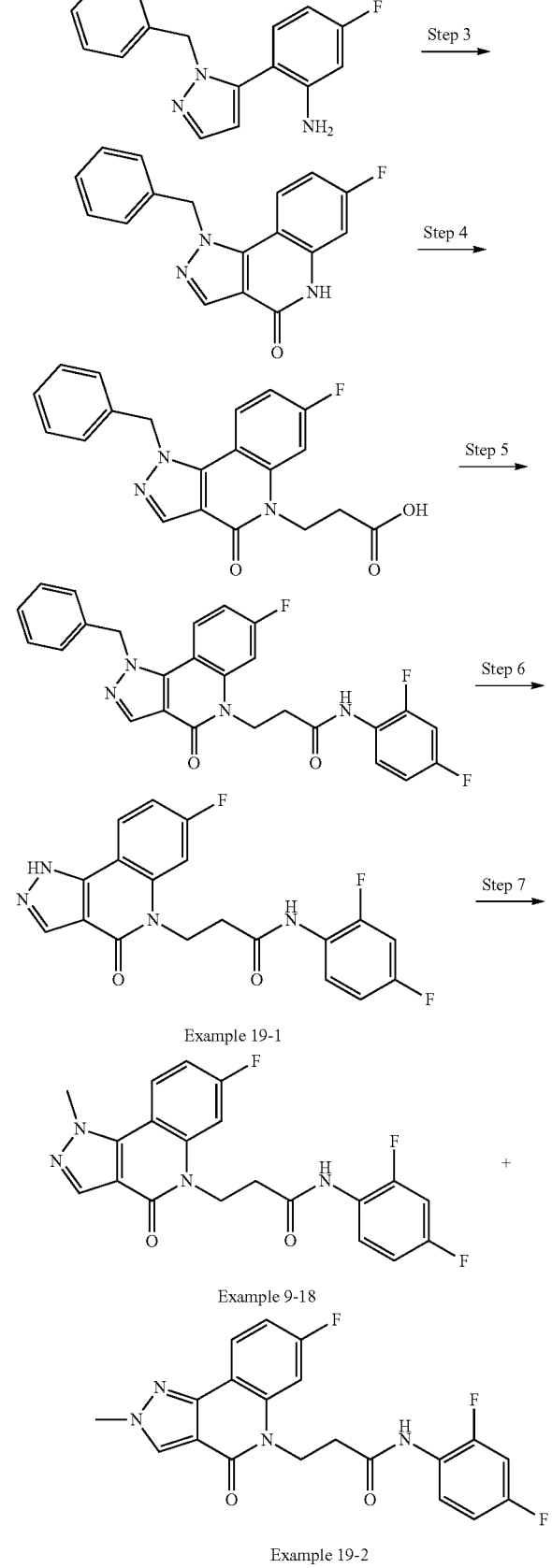

Examples 19-1 and 19-2

Steps 1-5: Performed as for Method 9, Steps 2-6

Step 6: N-(2,4-Difluorophenyl)-3-(7-fluoro-4-oxo-1H-pyrazolo[4,3-c]quinolin-5-yl)propanamide Ammonium formate (89 mg, 1.44 mmol) and palladium (II) hydroxide (20%, 26 mg, 0.0374 mmol) were added to a solution of 3-(1-benzyl-7-fluoro-4-oxo-pyrazolo[4,3-c]quinolin-5-yl)-N-(2,4-difluorophenyl)propanamide (137 mg, 0.288 mmol) in formic acid (10 mL). The reaction was stirred at 60° C. for 2 h in a sealed tube. The reaction was allowed to cool to rt, diluted with MeOH (130 mL), filtered through Celite, and concentrated in vacuo. The residue was triturated in the minimum volume of MeOH to give the title compound. $^1$H NMR (500 MHz, DMSO-$d_6$) δ 14.15 (s, 1H), 9.86 (s, 1H), 8.87-8.03 (m, 2H), 7.79 (m, 1H), 7.69-7.46 (m, 1H), 7.38-7.12 (m, 2H), 7.06 (t, J=7.9 Hz, 1H), 4.54 (t, J=7.0 Hz, 2H), 2.76 (t, J=7.3 Hz, 2H). $^{19}$F NMR (376 MHz, DMSO-$d_6$) δ −108.47 (s), −114.82 (d, J=5.0 Hz), −119.55 (d, J=5.1 Hz). Tr(MET-uHPLC-AB-101)=2.59 min, m/z (ES$^+$) (M+H)$^+$ 387.1, 99%.

Step 7: N-(2,4-Difluorophenyl)-3-(7-fluoro-2-methyl-4-oxo-pyrazolo[4,3-c]quinolin-5-yl)propanamide A solution of iodomethane (2.4 μL, 0.039 mmol) in anhydrous DMSO (0.5 mL) was added to a stirred mixture of N-(2,4-difluorophenyl)-3-(7-fluoro-4-oxo-1H-pyrazolo[4,3-c]quinolin-5-yl)propanamide (5.0 mg, 0.013 mmol) and Cs$_2$CO$_3$ (6.3 mg, 0.020 mmol) in anhydrous DMSO (0.5 mL). The reaction was stirred at rt for 1.5 h. The reaction was concentrated and purified by acidic preparative HPLC to afford each of the regioisomeric title compounds. Example 19-2: $^1$H NMR (500 MHz, DMSO-$d_6$) δ 9.91 (s, 1H), 8.61 (s, 1H), 8.13 (dd, J=8.6, 6.6 Hz, 1H), 7.79 (td, J=9.0, 6.3 Hz, 1H), 7.53 (dd, J=12.3, 2.2 Hz, 1H), 7.29 (ddd, J=11.6, 9.0, 2.9 Hz, 1H), 7.16 (td, J=8.5, 2.3 Hz, 1H), 7.11-6.97 (m, 1H), 4.52 (t, J=7.4 Hz, 2H), 4.08 (s, 3H), 2.76 (s, 2H). $^{19}$F NMR (376 MHz, DMSO-d6) δ −110.01 (s), −114.84 (d, J=5.0 Hz), −119.49 (d, J=5.1 Hz). Tr(MET-uHPLC-AB-101)=2.85 min, m/z (ES$^+$) (M+H)$^+$ 401.2, 100%. Characterization data for Example 9-18 has been previously provided.

Also prepared by this route:

| Ex. | Structure | LCMS data | NMR Data |
|---|---|---|---|
| 19-3 | ![structure] | Tr(MET-uHPLC-AB-101) = 2.82 min (ES$^+$)(M + H)$^+$ 404.2, 100% | 1H NMR (400 MHz, DMSO-$d_6$) δ 9.95 (s, 1H), 8.52 (s, 1H, formate salt), 8.38-8.29 (m, 1H), 8.13 (s, 1H), 7.86-7.74 (m, 1H), 7.65 (dd, J = 12.2, 2.3 Hz, 1H), 7.35-7.21 (m, 2H), 7.12-7.01 (m, 1H), 4.57 (t, J = 7.3 Hz, 2H), 2.76 (t, J = 7.4 Hz, 2H). 19F NMR (376 MHz, DMSO-$d_6$) δ −108.69, −114.86 (d, J = 5.1 Hz), −119.44 (d, J = 5.1 Hz). |
| 19-4 | ![structure] | Tr(MET-uHPLC-AB-101) = 2.84 min m/z (ES $^+$)(M + H)$^+$ 404.2, 99% | 1H NMR (400 MHz, DMSO-$d_6$) δ 9.90 (s, 1H), 8.61 (s, 1H), 8.53 (s, 1H, formate salt), 8.18-8.09 (m, 1H), 7.86-7.74 (m, 1H), 7.53 (dd, J = 12.3, 2.1 Hz, 1H), 7.29 (ddd, J = 11.7, 9.1, 2.9 Hz, 1H), 7.20-7.11 (m, 1H), 7.11-7.00 (m, 1H), 4.52 (t, J = 7.3 Hz, 2H), 2.75 (t, J = 7.4 Hz, 2H). 19F NMR (376 MHz, DMSO-$d_6$) δ −110.04, −114.88 (d, J = 5.1 Hz), −119.51 (d, J = 5.0 Hz). |

Scheme for Method 20

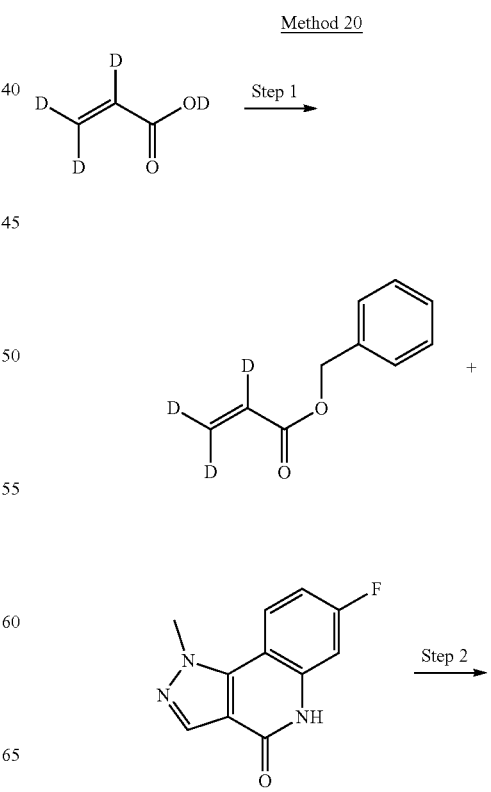

227
-continued

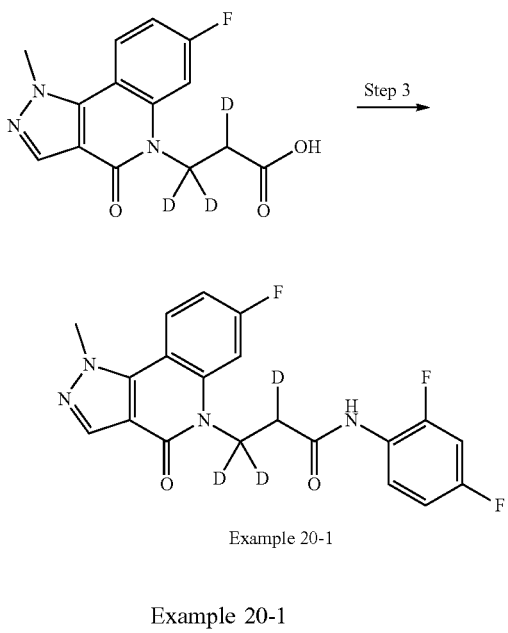

Example 20-1

Example 20-1

Step 1: Benzyl 2,3,3-trideuterioprop-2-enoate

K₂CO₃ (999 mg, 7.23 mmol) was added to a solution of acrylic acid-d₄ (500 mg, 6.57 mmol) in DMF (5 mL). Benzyl bromide (0.78 mL, 6.57 mmol) in DMF (1 mL) was added dropwise at rt. The reaction was stirred at rt for 6 h. The reaction was diluted with EtOAc (10 mL) and washed with water (3×2 mL). The organic layer was dried over Na₂SO₄, filtered, and concentrated in vacuo. The crude residue was purified by column chromatography to give the title compound. ¹H NMR (500 MHz, DMSO-d₆) δ 7.41-7.30 (m, 5H), 5.19 (s, 2H). Tr(METCR1704)=0.87 min, m/z (ES)⁺ no mass ion observed, 95%.

Step 2: 2,3,3-Trideuterio-3-(7-fluoro-1-methyl-4-oxo-pyrazolo[4,3-c]quinolin-5-yl)propanoic acid 7-Fluoro-1-methyl-5H-pyrazolo[4,3-c]quinolin-4-one (100 mg, 0.460 mmol), 2 M sodium hydroxide (0.23 mL, 0.460 mmol), benzyl 2,3,3-trideuterioprop-2-enoate (114 mg, 0.691 mmol), tetrabutylammonium bromide (74 mg, 0.230 mmol) and THF (5 mL) were combined in a pressure tube and stirred at 50° C. for 1 h. The reaction mixture was diluted with water (3 mL) and extracted with EtOAc (10 mL). The organic fraction was concentrated in vacuo. K₂CO₃ (64 mg, 0.460 mmol), THF (2 mL) and methanol (2 mL) were added to the residue. The reaction was stirred at rt for 0.5 h and concentrated in vacuo. The residue was acidified to pH 3 using 2 M HCl and the resulting precipitate was collected and dried by vacuum filtration to afford the title compound. The filtrate was extracted with chloroform: IPA (3:1, 3×5 mL). The combined organics were dried using a separator cartridge and concentrated in vacuo with the original precipitate to afford the title compound. Tr(MET-uHPLC-AB-101)=3.00 min, m/z (ES⁺)(M+H)⁺ 293.1, 17%.

Step 3: (N-(2,4-difluorophenyl)-3-{7-fluoro-1-methyl-4-oxo-1H,4H,5H-pyrazolo[4,3-c]quinolin-5-yl}(2,3,3-²H3)propanamide A solution of 2,3,3-trideuterio-3-(7-fluoro-1-methyl-4-oxo-pyrazolo[4,3-c]quinolin-5-yl)propanoic acid (17%, 140

228 mg, 0.07 mmol), 2,4-difluoroaniline (10 mg, 0.08 mmol) and EDC.HCl (21 mg, 0.11 mmol) in pyridine (3 mL) was stirred overnight at rt. The solvents were removed in vacuo and the residue purified by column chromatography. The product-containing fractions were concentrated in vacuo and the residue was further purified by trituration with ethanol to afford the title compound. ¹H NMR (500 MHz, DMSO-d₆) δ 9.86 (s, 1H), 8.34 (dd, J=9.0, 6.2 Hz, 1H), 8.14 (s, 1H), 7.86-7.76 (m, 1H), 7.65 (dd, J=12.2, 2.4 Hz, 1H), 7.36-7.23 (m, 2H), 7.11-7.02 (m, 1H), 4.36 (s, 3H), 2.73 (s, 1H). ¹⁹F NMR (471 MHz, DMSO-d₆) δ −108.57--108.87 (m), −114.85 (ddd, J=14.3, 8.6, 6.0 Hz), −119.60 (td, J=9.8, 5.5 Hz). Tr(MET-uHPLC-AB-101)=2.82 min, m/z (ES⁺)(M+H)⁺ 404.2, 87%.

Scheme for Method 21

Method 21

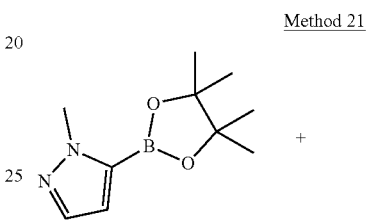

+

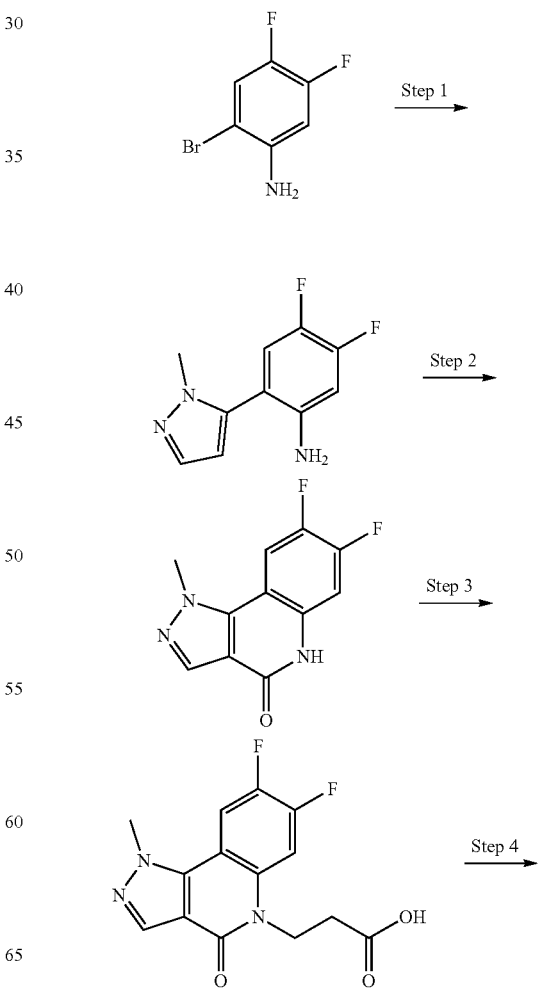

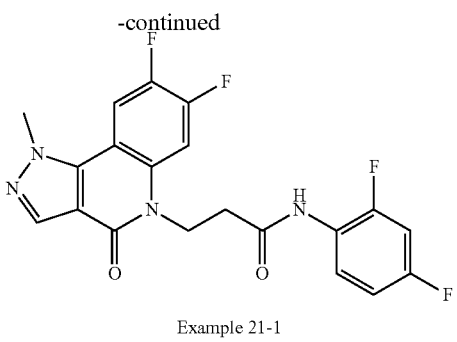

Example 21-1

Example 21-1

Step 1: 4,5-Difluoro-2-(2-methylpyrazol-3-yl)aniline

The reaction was carried out as 2×250 mg reactions in separate reaction tubes. The reactions were carried out in parallel and under identical conditions as below. Once the reactions were complete, they were combined and purified together. 2-Bromo-4,5-difluoro-aniline (0.30 mL, 2.40 mmol) was dissolved in 1,4-dioxane (22.838 mL) and water (2.2838 mL), and 1-methyl-5-(4,4,5,5-tetramethyl-1,3,2-dioxaborolan-2-yl)-1H-pyrazole (750 mg, 3.61 mmol) was added. The mixture was degassed for 5 min before the addition of Pd(PPh$_3$)$_4$(278 mg, 0.240 mmol). The reaction was heated in a sealed tube at 85° C. for 18 h. The mixture was allowed to cool to rt and then concentrated in vacuo onto silica. Purification by flash column chromatography gave the title compound. $^1$H NMR (400 MHz, DMSO-d$_6$) δ 7.47 (d, J=1.8 Hz, 1H), 7.09 (dd, J=11.3, 9.1 Hz, 1H), 6.71 (dd, J=13.2, 7.5 Hz, 1H), 6.27 (d, J=1.9 Hz, 1H), 5.03 (s, 2H), 3.63 (s, 3H). Tr(METCR1410)=0.72 min, m/z (ES)$^+$ [M+H]$^+$=210.1, 87%.

Step 2: Performed as for Method 9, Step 4

Step 3: 3-(7,8-Difluoro-1-methyl-4-oxo-pyrazolo[4,3-c]quinolin-5-yl)propanoic acid 7,8-Difluoro-1-methyl-5H-pyrazolo[4,3-c]quinolin-4-one (276 mg, 1.17 mmol), tetrabutylammonium bromide (189 mg, 0.59 mmol), ethyl acrylate (0.25 mL, 2.35 mmol) and K$_2$CO$_3$ (162 mg, 1.17 mmol) were combined in THF (2 mL) and the reaction was heated to 80° C. for 4 h. The reaction was allowed to cool to rt and further THF (2 mL) was added, followed by 2 M NaOH (0.59 mL, 1.17 mmol). The reaction was stirred vigorously for 18 h at rt. The volatiles were removed in vacuo and the aqueous phase was acidified using 2 M HCl. The resulting precipitate was filtered to afford the title compound. Tr(METCR1410)=0.62 min, m/z (ES)$^+$ [M+H]$^+$=308.1, 68%.

Step 4: (3-{7,8-Difluoro-1-methyl-4-oxo-1H,4H,5H-pyrazolo[4,3-c]quinolin-5-yl}-N-(2,4-difluorophenyl)propanamide 3-(7,8-Difluoro-1-methyl-4-oxo-pyrazolo[4,3-c]quinolin-5-yl)propanoic acid (357 mg, 1.16 mmol), 2,4-difluoroaniline (0.12 mL, 1.16 mmol) and DIPEA (0.61 mL, 3.49 mmol) were combined in DMF (17.62 mL), and T3P (50% in EtOAc) (0.85 mL, 1.74 mmol) was added. The reaction was stirred at rt for 18 h. Further 2,4-difluoroaniline (0.12 mL, 1.16 mmol), DIPEA (0.61 mL, 3.49 mmol) and 3-(7,8-difluoro-1-methyl-4-oxo-pyrazolo[4,3-c]quinolin-5-yl)propanoic acid (357 mg, 1.16 mmol) were added, and the reaction mixture was stirred at rt for another 3 h. Water was added and a solid precipitated which was filtered. The precipitate was washed with water, EtOAc, and EtOH. Purification by basic preparative HPLC gave the title compound. $^1$H NMR (400 MHz, DMSO-d$_6$) δ 9.84 (s, 1H), 8.29 (dd, J=11.4, 8.6 Hz, 1H), 8.15 (s, 1H), 7.92 (dd, J=13.6, 7.2 Hz, 1H), 7.80 (td, J=9.0, 6.3 Hz, 1H), 7.34-7.24 (m, 1H), 7.11-7.01 (m, 1H), 4.57 (t, J=7.3 Hz, 2H), 4.37 (s, 3H), 2.76 (t, J=7.4 Hz, 2H). $^{19}$F NMR (376 MHz, DMSO-d$_6$) δ -112.17--116.63 (m), -117.81--121.79 (m), -133.63 (ddd, J=22.5, 13.6, 8.6 Hz), -144.95 (ddd, J=24.1, 11.3, 7.2 Hz). Tr(MET-uHPLC-AB-101)=2.95 min, m/z (ES$^+$)(M+H)$^+$ 419.2, 98%.

Also prepared by this route:

| Ex. | Structure | LCMS data | NMR Data |
|---|---|---|---|
| 21-2 | 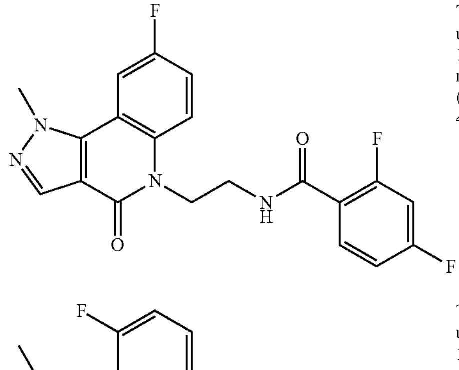 | Tr(MET-uHPLC-AB-101) = 2.80 min m/z (ES$^+$)(M + H)$^+$ 401.2, 100% | $^1$H NMR (400 MHz, DMSO-d$_6$) δ 9.85 (s, 1H), 8.14 (s, 1H), 8.05 (dd, J = 9.6, 2.9 Hz, 1H), 7.78 (td, J = 9.3, 5.4 Hz, 2H), 7.55 (td, J = 9.4, 2.9 Hz, 1H), 7.28 (ddd, J = 11.7, 9.0, 2.9 Hz, 1H), 7.09-6.99 (m, 1H), 4.62-4.53 (m, 2H), 4.37 (s, 3H), 2.79-2.70 (m, 2H). $^{19}$F NMR (376 MHz, DMSO-d$_6$) δ -114.79 (d, J = 5.1 Hz), -119.48 (d, J = 5.1 Hz), 120.37. |
| 21-3 | 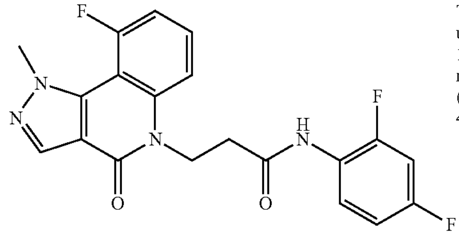 | Tr(MET-uHPLC-AB-101) = 2.92 min m/z (ES$^+$)(M + H)$^+$ 401.2, 100% | $^1$H NMR (400 MHz, DMSO-d$_6$) δ 9.87 (s, 1H), 8.22 (s, 1H), 7.85-7.76 (m, 1H), 7.74-7.65 (m, 1H), 7.60 (d, J = 8.6 Hz, 1H), 7.34-7.21 (m, 2H), 7.11-7.01 (m, 1H), 4.67-4.55 (m, 2H), 4.30 (d, J = 11.6 Hz, 3H), 2.82-2.72 (m, 2H). $^{19}$F NMR (376 MHz, DMSO-d$_6$) δ -104.81, -114.78 (d, J = 5.1 Hz), -119.50 (d, J = 5.1 Hz). |

Scheme for Method 22

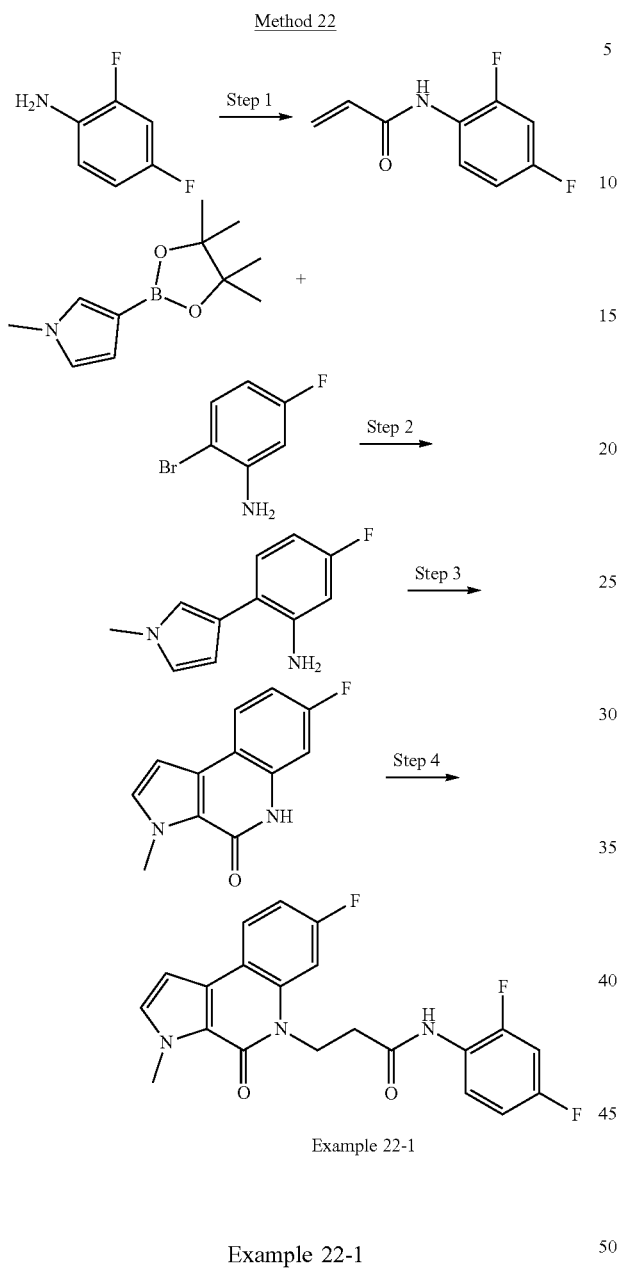

Example 22-1

Example 22-1

Step 1: N-(2,4-Difluorophenyl)prop-2-enamide

K$_2$CO$_3$ (4.28 mg, 31.0 mmol) was added to a solution of 2,4-difluoroaniline (1 g, 7.75 mmol) in acetone (30 mL) at rt under N$_2$. Acryloyl chloride (1.9 mL, 23.2 mmol) was added dropwise over 5 minutes. The suspension was stirred at rt overnight, filtered, and concentrated to give a solid. The solid was triturated with heptane and dried in vacuo to give the title compound. $^1$H NMR (500 MHz, DMSO-d$_6$) δ 9.95 (s, 1H), 7.97-7.88 (m, 1H), 7.33 (ddd, J=11.6, 9.0, 2.9 Hz, 1H), 7.12-7.03 (m, 1H), 6.57 (dd, J=17.0, 10.2 Hz, 1H), 6.27 (dd, J=17.0, 1.9 Hz, 1H), 5.78 (dd, J=10.2, 1.9 Hz, 1H). Tr(METCR1704)=0.63 min, m/z (ES)$^+$ [M+H]$^+$=184.0, 99%.

Step 2: Performed as for Method 21, Step 1

Step 3: Performed as for Method 9, Step 4

Step 4: N-(2,4-Difluorophenyl)-3-{7-fluoro-3-methyl-4-oxo-3H,4H,5H-pyrrolo[2,3-c]quinolin-5-yl}propanamide 7-Fluoro-3-methyl-5H-pyrrolo[2,3-c]quinolin-4-one (50 mg, 0.231 mmol), K$_2$CO$_3$ (45 mg, 0.324 mmol), and N-(2,4-difluorophenyl)prop-2-enamide (0.10 mL, 0.463 mmol) were combined in DMF (1 mL) in a pressure tube, and the reaction was heated to 80° C. for 3 h. After cooling to rt, DMSO (1.5 mL) was added, and the mixture was purified by high pH preparative HPLC. The resultant residue was suspended in methanol (3 mL), heated, and sonicated until almost complete dissolution, then cooled to 4° C. for 1.5 h and filtered. The collected solid was dried in the oven to give the title compound. $^1$H NMR (400 MHz, DMSO-d$_6$) δ 9.86 (s, 1H), 8.04 (dd, J=8.7, 6.5 Hz, 1H), 7.81 (ddd, J=9.0, 6.3 Hz, 1H), 7.49 (dd, J=12.3, 2.2 Hz, 1H), 7.41 (d, J=2.8 Hz, 1H), 7.30 (ddd, J=11.7, 9.0, 2.9 Hz, 1H), 7.13 (ddd, J=8.5, 2.3 Hz, 1H), 7.10-7.03 (m, 1H), 6.84 (d, J=2.8 Hz, 1H), 4.63-4.45 (m, 2H), 4.09 (s, 3H), 2.82-2.71 (m, 2H). $^{19}$F NMR (376 MHz, DMSO-d$_6$) δ -113.55, -114.84, -119.54. Tr(MET-uHPLC-AB-101)=3.46 min, m/z (ES$^+$)(M+H)$^+$ 400, 100%.

Scheme for Method 23

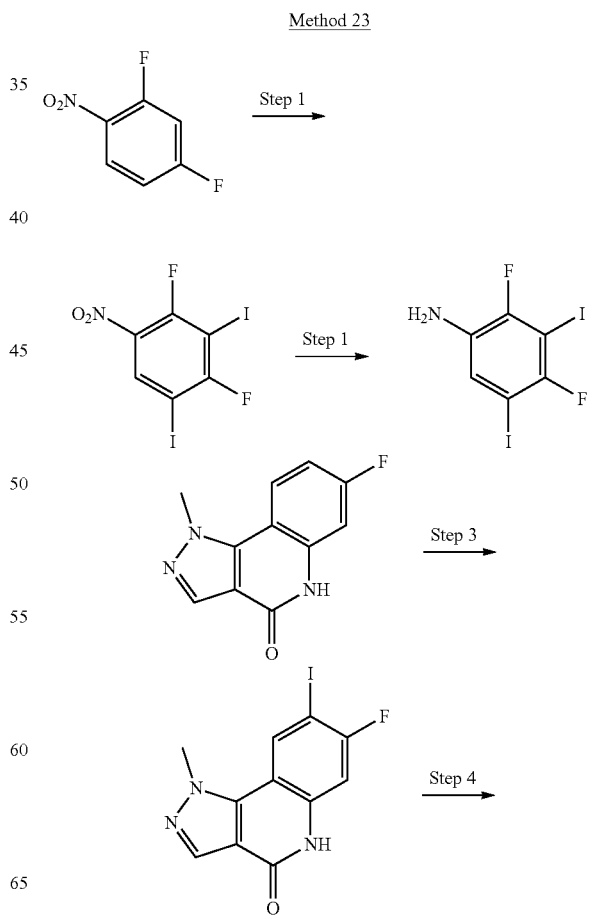

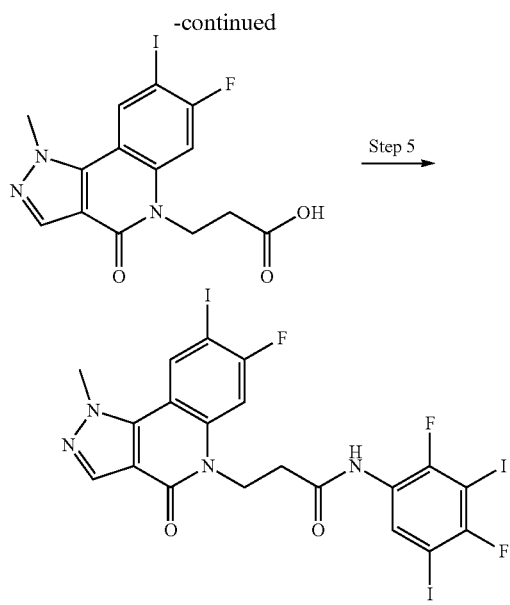

Example 23-1

Example 23-1

Step 1: 2,4-Difluoro-1,3-diiodo-5-nitro-benzene

Periodic acid (312 mg, 1.37 mmol) was added to concentrated sulfuric acid (10 mL, 1.37 mmol) and the mixture was cooled to 0° C. before slow addition of potassium iodide (681 mg, 4.10 mmol). After stirring for 15 min, 2,4-difluoro-1-nitrobenzene (0.15 mL, 1.37 mmol) was added dropwise and the solution was stirred at 0° C. for 30 min. The reaction was warmed to 50° C. and stirred for 2 h. The reaction was allowed to cool and then was poured onto ice (50 mL) and extracted with TBME. The combined organics were washed with sodium thiosulfate solution (10%), dried over $Na_2SO_4$, filtered, and concentrated in vacuo. The crude residue was purified by column chromatography to give the title compound. $^1$H NMR (500 MHz, DMSO-$d_6$) δ 8.64 (dd, J=8.3, 6.4 Hz, 1H). $^{19}$F NMR (471 MHz, DMSO-$d_6$) δ −62.38 (dd, J=10.1, 6.0 Hz), −94.13 (d, J=1.8 Hz).

Step 2: 2,4-Difluoro-3,5-diiodo-aniline 2,4-Difluoro-1,3-diiodo-5-nitro-benzene (200 mg, 0.487 mmol) was added to a solution of iron (109 mg, 1.95 mmol) in acetic acid (5 mL), and the reaction mixture was stirred at 80° C. for 1 h. The crude mixture was cooled to rt, filtered, and washed with ethanol. The filtrate was concentrated in vacuo and the residue was partitioned between DCM and 1 M aqueous $Na_2CO_3$. The organic phase was dried (hydrophobic frit) and concentrated to give the title compound. $^1$H NMR (500 MHz, DMSO-$d_6$) δ 7.19 (dd, J=9.5, 6.5 Hz, 1H), 5.33 (s, 2H). Tr(METCR1410)=1.25 min, m/z (ES$^+$) (M+H)$^+$ 381.7, 95%.

Step 3: 7-Fluoro-8-iodo-1-methyl-5H-pyrazolo[4,3-c]quinolin-4-one

7-Fluoro-1-methyl-5H-pyrazolo[4,3-c]quinolin-4-one (250 mg, 1.15 mmol), N-iodosuccinimide (388 mg, 1.73 mmol), and hydrogen tetrafluoroborate (in water) (50%, 0.72 mL, 5.76 mmol) were combined in acetonitrile (20 mL) in a pressure tube and stirred at 60° C. for 2 h. The cooled reaction mixture was poured into a solution of saturated $NaHCO_3$ (20 mL). The resulting precipitate was filtered, washed with 10% aqueous sodium thiosulfate solution (10 mL) and water (10 mL), and dried overnight under vacuum at 40° C. to afford the title compound. $^1$H NMR (500 MHz, DMSO-$d_6$) δ 11.58 (s, 1H), 8.47 (d, J=6.5 Hz, 1H), 8.09 (s, 1H), 7.27 (d, J=9.3 Hz, 1H), 4.35 (s, 3H). Tr(METCR1410)=1.07 min, m/z (ES$^+$) (M+H)$^+$ 343.9, 94%.

Steps 4-5: Performed as for Method 21, Steps 3-4

Prepared by this route:

| Ex. | Structure | LCMS data | NMR data |
|---|---|---|---|
| 23-1 | (structure) | Tr(MET-uHPLC-AB-101) = 4.04 min m/z (ES$^+$) (M + H)$^+$ 778.9, 73%. | $^1$H NMR (500 MHz, DMSO-$d_6$) δ 9.98 (s, 1H), 8.52 (d, J = 6.8 Hz, 1H), 8.30-8.22 (m, 1H), 8.13 (s, 1H), 7.70 (d, J = 11.1 Hz, 1H), 4.55 (t, J = 7.1 Hz, 2H), 4.37 (s, 3H), 2.74 (t, J = 6.9 Hz, 2H). $^{19}$F NMR (471 MHz, DMSO-$d_6$) δ −78.60−−78.95 (m), −91.31 (dd, J = 11.0, 6.8 Hz), −101.25 (d, J = 8.0 Hz). |

Scheme for Method 24

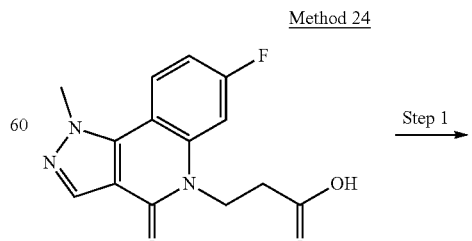

Example 9-31

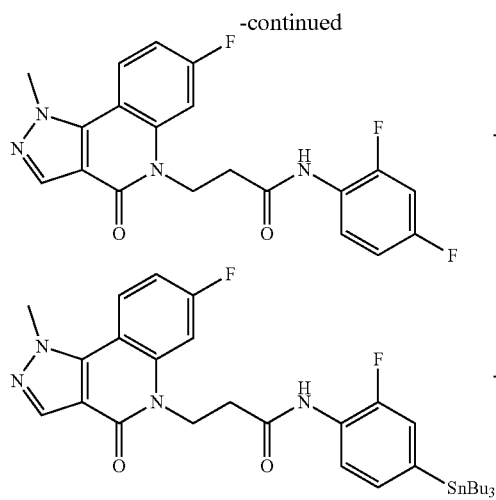

Example 24-1

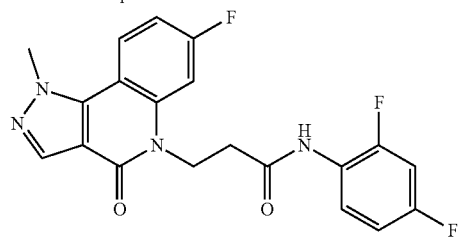

Example 9-18

Example 24-1

Step 1: Performed as for Method 9, Step 6

Step 2: 3-{7-Fluoro-1-methyl-4-oxo-1H,4H,5H-pyrazolo[4,3-c]quinolin-5-yl}-N-[2-fluoro-4-(tributylstannyl)phenyl]propanamide A suspension of hexabutyldistannane (0.60 mL, 1.18 mmol) and N-(2-fluoro-4-iodo-phenyl)-3-(7-fluoro-1-methyl-4-oxo-pyrazolo[4,3-c]quinolin-5-yl)propanamide (300 mg, 0.590 mmol) in anhydrous toluene (30 mL) was degassed for 5 minutes with N2 in a pressure tube. Pd(PPh$_3$)$_4$ (136 mg, 0.118 mmol) was added, the vial was sealed, and the reaction was stirred at 90° C. for 6 h. The cooled reaction mixture was filtered through Celite (eluting with toluene). The filtrate was partitioned with brine and the organic fraction was extracted with toluene. The combined organics were dried over Na$_2$SO$_4$, filtered, and concentrated in vacuo. The crude residue was purified by column chromatography to give the title compound. $^1$H NMR (400 MHz, DMSO-d$_6$) δ 9.83 (s, 1H), 8.34 (dd, J=9.0, 6.2 Hz, 1H), 8.13 (s, 1H), 7.87-7.79 (m, 1H), 7.65 (dd, J=12.3, 2.5 Hz, 1H), 7.31-7.11 (m, 3H), 4.57 (t, J=7.4 Hz, 2H), 4.36 (s, 3H), 2.78 (t, J=7.5 Hz, 2H), 1.62-1.38 (m, 6H), 1.33-1.24 (m, 6H), 1.16-0.95 (m, 6H), 0.85 (t, J=7.3 Hz, 9H). 19F NMR (376 MHz, DMSO-d6) δ -108.66, -125.74. Tr(METCR1503)=4.67 min, m/z (ES$^+$) (M+H)$^+$ 671.2, 673.2, 96%.

Step 3: N-(2,4-Difluorophenyl)-3-(7-fluoro-1-methyl-4-oxo-pyrazolo[4,3-c]quinolin-5-yl)propanamide DMA (3 mL) was added to a vial containing 3-(7-fluoro-1-methyl-4-oxo-pyrazolo[4,3-c]quinolin-5-yl)-N-(2-fluoro-4-tributylstannyl-phenyl)propanamide (10 mg, 0.015 mmol), pyridine (0.018 mL, 0.223 mmol), copper (II) triflate (11 mg, 0.030 mmol), 18-crown-6 (2.0 mg, 7.45 µmol), and potassium fluoride (3.5 mg, 0.060 mmol) under nitrogen. The reaction mixture was stirred at 100° C. for 0.5 h. The reaction mixture was concentrated in vacuo and partitioned between DCM and water. The organic phase was extracted, dried (phase separator cartridge), and concentrated in vacuo. The resulting residue was dissolved in acetonitrile and methanol for purification by acidic phase preparative HPLC to give the title compound. $^1$H NMR (500 MHz, DMSO-d$_6$) δ 9.88 (s, 1H), 8.34 (dd, J=9.0, 6.2 Hz, 1H), 8.14 (s, 1H), 7.80 (td, J=9.0, 6.3 Hz, 1H), 7.65 (dd, J=12.3, 2.3 Hz, 1H), 7.35-7.23 (m, 2H), 7.10-7.02 (m, 1H), 4.57 (t, J=7.5 Hz, 2H), 4.36 (s, 3H), 2.76 (t, J=7.4 Hz, 2H). Tr(MET-uHPLC-AB-101)=2.81 min, m/z (ES$^+$)(M+H)$^+$ 401.2, 98%.

Scheme for Method 25

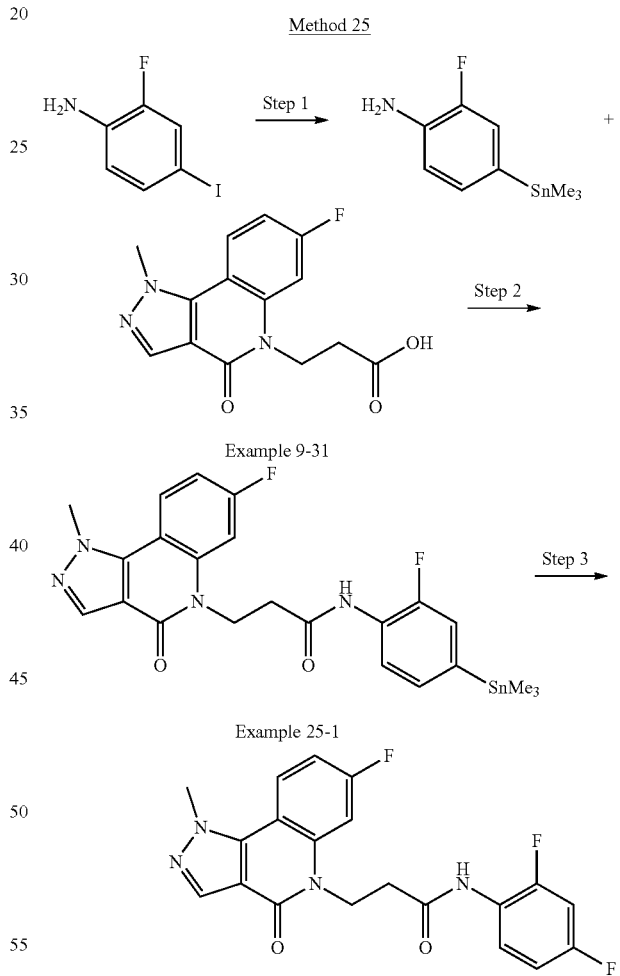

Method 25

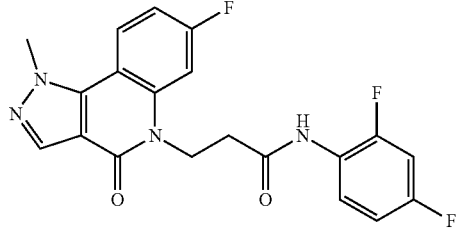

Example 25-1

Example 25-1

Step 1: 2-Fluoro-4-trimethylstannyl-aniline

A suspension of hexamethyldistannane (8.29 g, 25.3 mmol) and 2-fluoro-4-iodoaniline (3.00 g, 12.7 mmol) in anhydrous 1,4-dioxane (75 mL) was degassed for 5 minutes with N₂. Pd(PPh₃)₄(731 mg, 0.63 mmol) was added under nitrogen. The reaction was then stirred at 80° C. for 20 h. The cooled reaction mixture was filtered, and DCM (25 mL) was added to the filtrate, which was then concentrated onto silica in vacuo. Purification by flash column chromatography and concentration of the fractions under a flow of nitrogen afforded the title compound. Tr(METCR1906) =0.92 min, m/z (ES)⁺ [M+H]⁺=274.0, 275.9, 463.0, 89%.

Step 2: 3-(7-Fluoro-1-methyl-4-oxo-pyrazolo[4,3-c]quinolin-5-yl)-N-(2-fluoro-4-trimethylstannyl-phenyl)propanamide A solution of 3-(7-fluoro-1-methyl-4-oxo-pyrazolo[4,3-c]quinolin-5-yl)propanoic acid (300 mg, 1.04 mmol), 2-fluoro-4-trimethylstannyl-aniline (341 mg, 1.24 mmol), and EDC.HCl (298 mg, 1.56 mmol) in pyridine (9 mL) was stirred at rt for 3 h. The solvents were removed in vacuo and DCM and water were added. The organic phase was separated, dried (hydrophobic frit), and concentrated in vacuo. The crude residue was purified by flash column chromatography to afford the title compound. #H NMR (400 MHz, DMSO-d₆) δ 9.83 (s, 1H), 8.34 (dd, J=9.0, 6.3 Hz, 1H), 8.13 (s, 1H), 7.88-7.79 (m, 1H), 7.66 (dd, J=12.2, 2.5 Hz, 1H), 7.39-7.15 (m, 3H), 4.57 (t, J=7.5 Hz, 2H), 4.36 (s, 3H), 2.78 (t, J=7.5 Hz, 2H), 0.27 (s, 9H). ¹⁹F NMR (376 MHz, DMSO-d₆) δ −108.67, −125.92. Tr(MET-CR-AB106)=3.68 min, m/z (ES)⁺ [M+H]⁺=545.0, 546.9, 97%.

Step 3: N-(2,4-Difluorophenyl)-3-(7-fluoro-1-methyl-4-oxo-pyrazolo[4,3-c]quinolin-5-yl)propanamide DMA (5 mL) was added to a vial containing 3-(7-fluoro-1-methyl-4-oxo-pyrazolo[4,3-c]quinolin-5-yl)-N-(2-fluoro-4-trimethylstannyl-phenyl)propanamide (20 mg, 0.032 mmol), pyridine (0.039 mL, 0.484 mmol), copper (II) triflate (23 mg, 0.065 mmol), 18-crown-6 (4.3 mg, 0.016 mmol), and potassium fluoride (7.5 mg, 0.129 mmol) under nitrogen, and the vessel was stirred at 100° C. for 3 h. The reaction mixture was concentrated in vacuo and partitioned between DCM and water. The organic phase was extracted, washed with water (×3), dried (phase separator cartridge), and concentrated in vacuo. The reaction was repeated on 60 mg scale, and the crude residues were combined and dissolved in acetonitrile and methanol for purification by acidic preparative HPLC, which gave the title compound. ¹H NMR (400 MHz, DMSO-d₆) δ 9.86 (s, 1H), 8.34 (dd, J=8.9, 6.2 Hz, 1H), 8.13 (s, 1H), 7.89-7.76 (m, 1H), 7.65 (dd, J=12.2, 2.3 Hz, 1H), 7.37-7.22 (m, 2H), 7.11-7.02 (m, 1H), 4.65-4.52 (m, 2H), 4.36 (s, 3H), 2.82-2.70 (m, 2H). Tr(MET-uHPLC-AB-101)=2.84 min, m/z (ES)⁺[M+H]⁺=401.1, 95%.

Scheme for Method 26

Method 26

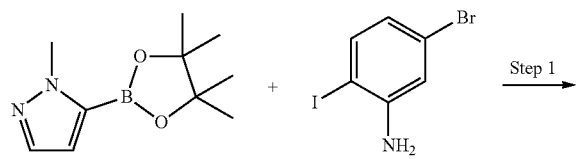

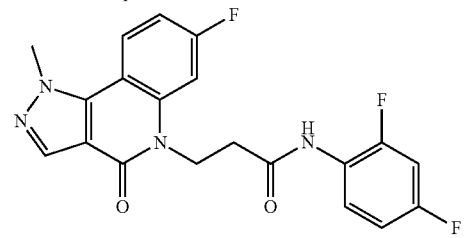

Example 26-1

Example 9-18

Example 26-1

Step 1: 5-Bromo-2-(2-methylpyrazol-3-yl)aniline

Split over 8 pressure vials: 5-Bromo-2-iodo-aniline (5.00 g, 16.8 mmol) was dissolved in 1,4-dioxane (160 mL). Water (16 mL), 1-methyl-5-(4,4,5,5-tetramethyl-1,3,2-dioxaborolan-2-yl)pyrazole (5.24 g, 25.2 mmol), and K₂CO₃ (6.96 g, 50.3 mmol) were added. The vials were degassed with N₂ for 5 minutes before Pd(PPh₃)₄(1.94 g, 1.68 mmol) was added, and then degassed for a further 5 min. The reaction mixture was stirred at 85° C. for 18 h. The cooled combined reaction mixtures were diluted with water and extracted with EtOAc. The combined organic extracts were dried over $Na_2SO_4$ and concentrated in vacuo. The residue was purified by flash column chromatography to afford the title compound. $^1H$ NMR (500 MHz, DMSO-$d_6$) δ 7.50 (d, J=1.8 Hz, 1H), 6.98 (d, J=2.0 Hz, 1H), 6.93 (d, J=8.1 Hz, 1H), 6.75 (dd, J=8.1, 2.0 Hz, 1H), 6.27 (d, J=1.8 Hz, 1H), 5.20 (s, 2H), 3.64 (s, 3H). Tr(METCR1704)=0.79 min, m/z (ES$^+$) [M+H]$^+$=252.1, 254.1, 99%.

Step 2: 7-Bromo-1-methyl-5H-pyrazolo[4,3-c]quinolin-4-one

CDI (4.01 g, 24.8 mmol) was added to a solution of 5-bromo-2-(2-methylpyrazol-3-yl)aniline (3.12 g, 12.4 mmol) in anhydrous NMP (40 mL) and the reaction mixture was stirred at 150° C. under microwave irradiation for 30 min. The reaction mixture was diluted with water (20 mL) and then stirred at 0° C. for 2 h. The resulting precipitate was filtered under vacuum, washing with water, to afford the title compound. $^1H$ NMR (500 MHz, DMSO-$d_6$) δ 11.50 (s, 1H), 8.14 (d, J=8.7 Hz, 1H), 8.10 (s, 1H), 7.64 (d, J=2.0 Hz, 1H), 7.46 (dd, J=8.6, 2.0 Hz, 1H), 4.35 (s, 3H). Tr(METCR1704) =0.64 min, m/z (ES$^+$) [M+H]$^+$=278.0, 280.0, 100%.

Step 3: 3-(7-Bromo-1-methyl-4-oxo-pyrazolo[4,3-c]quinolin-5-yl)propanoic acid

A suspension of 7-bromo-1-methyl-5H-pyrazolo[4,3-c]quinolin-4-one (2.35 g, 8.45 mmol), $K_2CO_3$ (1.17 g, 8.45 mmol), tetrabutylammonium bromide (1.36 g, 4.23 mmol), and ethyl acrylate (1.8 mL, 16.9 mmol) was stirred without solvent at 80° C. for 3 h. The reaction mixture was allowed to cool to rt and was concentrated in vacuo. The residue was dissolved in THF (25 mL), then 2 M NaOH (13 mL, 25.4 mmol) was added and the reaction was stirred at rt for 45 min. The reaction mixture was concentrated in vacuo to remove the THF, acidified to pH 2-3 using 6 M aqueous HCl, and the resultant aqueous solution was extracted with EtOAc. The combined organic extracts were dried over $Na_2SO_4$ and concentrated in vacuo. Purification by trituration using EtOAc afforded the title compound. $^1H$ NMR (400 MHz, DMSO-$d_6$) δ 12.42 (s, 1H), 8.22 (d, J=8.6 Hz, 1H), 8.14 (s, 1H), 7.93 (d, J=1.4 Hz, 1H), 7.57 (dd, J=8.6, 1.5 Hz, 1H), 4.57-4.45 (m, 2H), 4.36 (s, 3H), 2.64-2.54 (m, 2H). Tr(METCR1704)=0.65 min, m/z (ES$^+$) [M+H]$^+$=350.1, 352.1, 99%.

Step 4: 3-(7-Bromo-1-methyl-4-oxo-pyrazolo[4,3-c]quinolin-5-yl)-N-(2,4-difluorophenyl)propanamide HATU (1.50 g, 3.94 mmol), 3-(7-bromo-1-methyl-4-oxo-pyrazolo[4,3-c]quinolin-5-yl)propanoic acid (920 mg, 2.63 mmol), 2,4-difluoroaniline (356 mg, 2.76 mmol), and DIPEA (1.4 mL, 7.88 mmol) were combined in DMF (25 mL), and the reaction mixture was stirred at rt for 2.5 h. The reaction mixture was concentrated in vacuo and partitioned between water and DCM. The organic fraction was separated and the aqueous phase re-extracted with further DCM. The combined organic extracts were washed with water and brine, dried (hydrophobic frit), and concentrated in vacuo. The crude residue was triturated with EtOH to afford the title compound. $^1H$ NMR (400 MHz, DMSO-$d_6$) δ 9.86 (s, 1H), 8.22 (d, J=8.7 Hz, 1H), 8.15 (s, 1H), 7.95 (d, J=1.5 Hz, 1H), 7.80 (ddd, J=9.1, 6.4 Hz, 1H), 7.56 (dd, J=8.6, 1.7 Hz, 1H), 7.29 (ddd, J=11.7, 9.0, 2.9 Hz, 1H), 7.11-7.01 (m, 1H), 4.59 (t, J=7.2 Hz, 2H), 4.36 (s, 3H), 2.76 (t, J=7.2 Hz, 2H). Tr(METCR1704)=0.82 min, m/z (ES)$^+$[M+H]$^+$=461.0, 463.0, 92%.

Step 5: N-(2,4-difluorophenyl)-3-[1-methyl-4-oxo-7-(trimethylstannyl)-1H,4H,5H-pyrazolo [4,3-c]quinolin-5-yl]propanamide A suspension of hexamethyldistannane (355 mg, 1.08 mmol) and 3-(7-bromo-1-methyl-4-oxo-pyrazolo[4,3-c]quinolin-5-yl)-N-(2,4-difluorophenyl)propanamide (250 mg, 0.54 mmol) in anhydrous toluene (25 mL) was sonicated and degassed with $N_2$ for 5 minutes in a pressure tube, before adding Pd(PPh$_3$)$_4$(125 mg, 0.108 mmol) under nitrogen. The reaction vessel was sealed and stirred at 90° C. for 2.5 h. The cooled reaction mixture was filtered through Celite, washing with further toluene. The filtrate was partitioned with brine and the organic fraction was separated. The combined organics were dried over $Na_2SO_4$, filtered, and concentrated in vacuo. The crude residue was purified by flash column chromatography to afford the title compound. $^1H$ NMR (400 MHz, DMSO-$d_6$) δ 9.85 (s, 1H), 8.30-8.19 (m, 1H), 8.13 (s, 1H), 7.84-7.67 (m, 2H), 7.49 (d, J=7.7 Hz, 1H), 7.28 (ddd, J=11.1, 9.0, 2.9 Hz, 1H), 7.06-7.02 (m, 1H), 4.63 (t, J=7.2 Hz, 2H), 4.37 (s, 3H), 2.77 (t, J=7.2 Hz, 2H), 0.32 (s, 9H). $^{19}F$ NMR (376 MHz, DMSO-$d_6$) δ −114.80 (d, J=5.3 Hz), −119.42 (d, J=5.3 Hz). Tr(MET-uHPLC-AB-101)=3.88 min, m/z (ES$^+$)(M+H)$^+$ 545.0, 546.9, 100%.

Step 6: N-(2,4-Difluorophenyl)-3-(7-fluoro-1-methyl-4-oxo-pyrazolo[4,3-c]quinolin-5-yl)propanamide DMA (4 mL) was added to a vial containing N-(2,4-difluorophenyl)-3-(1-methyl-4-oxo-7-trimethylstannyl-pyrazolo[4,3-c]quinolin-5-yl)propanamide (20 mg, 0.037 mmol), pyridine (0.044 mL, 0.550 mmol), copper (II) triflate (27 mg, 0.074 mmol), 18-crown-6 (4.8 mg, 0.018 mmol), and potassium fluoride (8.5 mg, 0.147 mmol) under nitrogen. The reaction mixture was stirred at 100° C. for 1.5 h. Product observed in LCMS trace by comparison of retention time to reference sample. Tr(MET-uHPLC-AB-101)=2.82 min, m/z (ES$^+$)(M+Na)$^+$ 423.1, 10%.

Scheme for Method 27

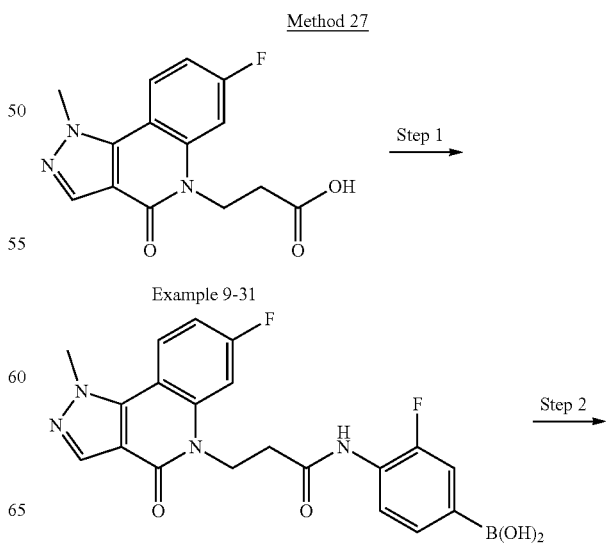

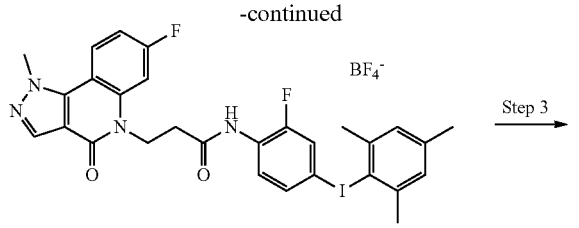

Example 27-1

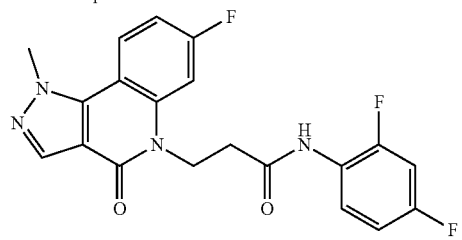

Example 9-18

Example 27-1

Step 1: [3-Fluoro-4-[3-(7-fluoro-1-methyl-4-oxo-pyrazolo[4,3-c]quinolin-5-yl)propanoylamino]phenyl]boronic acid DIPEA (1.0 mL, 5.70 mmol) was added to a solution of T3P (50% in EtOAc, 1.4 mL, 2.85 mmol), 3-(7-fluoro-1-methyl-4-oxo-pyrazolo[4,3-c]quinolin-5-yl)propanoic acid (550 mg, 1.90 mmol), and 2-fluoro-4-(4,4,5,5-tetramethyl-1,3,2-dioxaborolan-2-yl)aniline (451 mg, 1.90 mmol) in DMF (25 mL). The reaction mixture was stirred at rt for 24 h. The reaction mixture was concentrated in vacuo and triturated with water. Further purification by trituration from acetonitrile (4 mL) gave the title compound. $^1$H NMR (400 MHz, DMSO-d6) δ 9.88 (s, 1H), 8.34 (dd, J=9.0, 6.3 Hz, 1H), 8.13 (d, J=1.7 Hz, 1H), 7.92 (t, J=7.8 Hz, 1H), 7.66 (dd, J=12.2, 2.2 Hz, 1H), 7.60-7.50 (m, 2H), 7.27 (td, J=8.8, 2.4 Hz, 1H), 4.65-4.53 (m, 2H), 4.36 (s, 3H), 2.80 (t, J=7.3 Hz, 2H). Tr(METCR1410)=1.00 min, $(ES)^+[M+H]^+$=427.0, 77%.

Step 2: [3-Fluoro-4-[3-(7-fluoro-1-methyl-4-oxo-pyrazolo[4,3-c]quinolin-5-yl)propanoylamino]phenyl]-(2,4,6-trimethylphenyl)iodonium tetrafluoroborate A solution of finely ground [3-fluoro-4-[3-(7-fluoro-1-methyl-4-oxo-pyrazolo[4,3-c]quinolin-5-yl)propanoylamino]phenyl]boronic acid (77%, 154 mg, 0.361 mmol) in anhydrous DCM (100 mL) under nitrogen was sonicated until a fine suspension was achieved. The suspension was cooled to 0° C. and boron trifluoride diethyl etherate (0.13 mL, 1.08 mmol) was added. The reaction mixture was stirred for 10 min. A solution of iodomesitylene diacetate (145 mg, 0.397 mmol) in DCM (3 mL) was added at 0° C. The reaction was allowed to warm to rt and stirred for 1.5 h. The reaction mixture was re-treated with a solution of iodomesitylene diacetate (145 mg, 0.397 mmol) in DCM (3 mL) at 0° C. and stirred overnight at rt. After 22 h, the reaction mixture was re-treated with a solution of iodomesitylene diacetate (145 mg, 0.397 mmol) in DCM (3 mL) at 0° C. and stirred for a further 24 h after sonication. The reaction mixture was cooled to 0° C. and treated with boron trifluoride diethyl etherate (0.13 mL, 1.08 mmol) and stirred for 10 min before the addition of iodomesitylene diacetate (145 mg, 0.397 mmol) in DCM (3 mL). The reaction was allowed to warm to rt and stirred overnight. A saturated solution of NaBF$_4$ (50 mL) was added to the reaction mixture. The mixture was stirred for 10 min and then filtered. The precipitate was discarded (mixture of starting material and product). The layers for the filtrate were separated and the aqueous layer was extracted with DCM (2×50 mL). The combined organic extracts were dried (Na$_2$SO$_4$), filtered, and concentrated. The crude product was triturated in DCM (2×3 mL) to give the title compound. $^1$H NMR (400 MHz, DMSO-d$_6$) δ 10.16 (s, 1H), 8.34 (dd, J=9.0, 6.3 Hz, 1H), 8.17-8.09 (m, 2H), 8.04 (dd, J=9.8, 2.0 Hz, 1H), 7.85-7.75 (m, 1H), 7.63 (dd, J=12.2, 2.4 Hz, 1H), 7.30-7.19 (m, 3H), 4.57 (t, J=7.2 Hz, 2H), 4.36 (s, 3H), 2.82 (t, J=7.2 Hz, 2H), 2.62 (s, 6H), 2.31 (s, 3H). $^{19}$F NMR (376 MHz, DMSO-d$_6$) δ −108.71, −119.89, −148.25, −148.31. Tr(MET-uHPLC-AB-101)=2.00 min, m/z (ES$^+$) (M+H)$^+$ 627.2, 97%.

Step 3: N-(2,4-Difluorophenyl)-3-(7-fluoro-1-methyl-4-oxo-pyrazolo[4,3-c]quinolin-5-yl)propanamide A mixture of copper (II) triflate (2.5 mg, 7.00 μmol), 18-crown-6 (3.7 mg, 0.014 mmol), [3-fluoro-4-[3-(7-fluoro-1-methyl-4-oxo-pyrazolo[4,3-c]quinolin-5-yl)propanoylamino]phenyl]-(2,4,6-trimethylphenyl)iodonium;tetrafluoroborate (5.0 mg, 7.00 μmol), and potassium fluoride (0.61 mg, 0.0105 mmol) in anhydrous DMF (1 mL, de-gassed with N$_2$ for 5 minutes prior to reaction) under N$_2$, in a pressure vial, was stirred at 85° C. for 30 min. The reaction was quenched with water (1 mL) and concentrated in vacuo. The residue was purified by acidic preparative HPLC to give the title compound. Tr(MET-uHPLC-AB-101)=2.81 min, m/z (ES$^+$) (M+H)$^+$ 401.1, 93%.

Scheme for Method 28

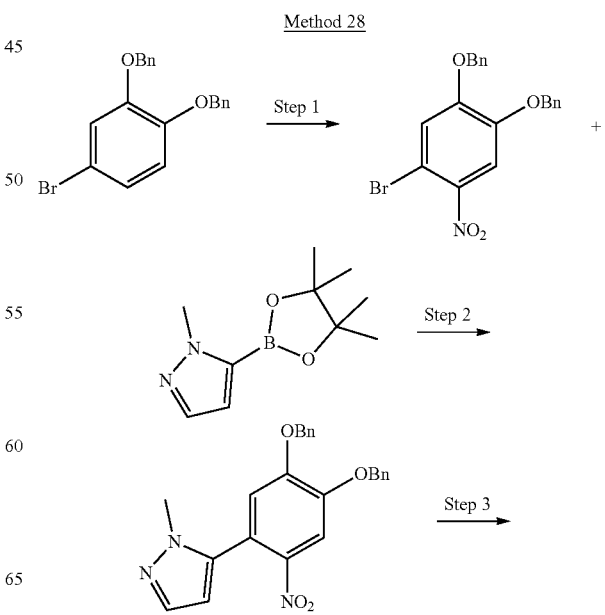

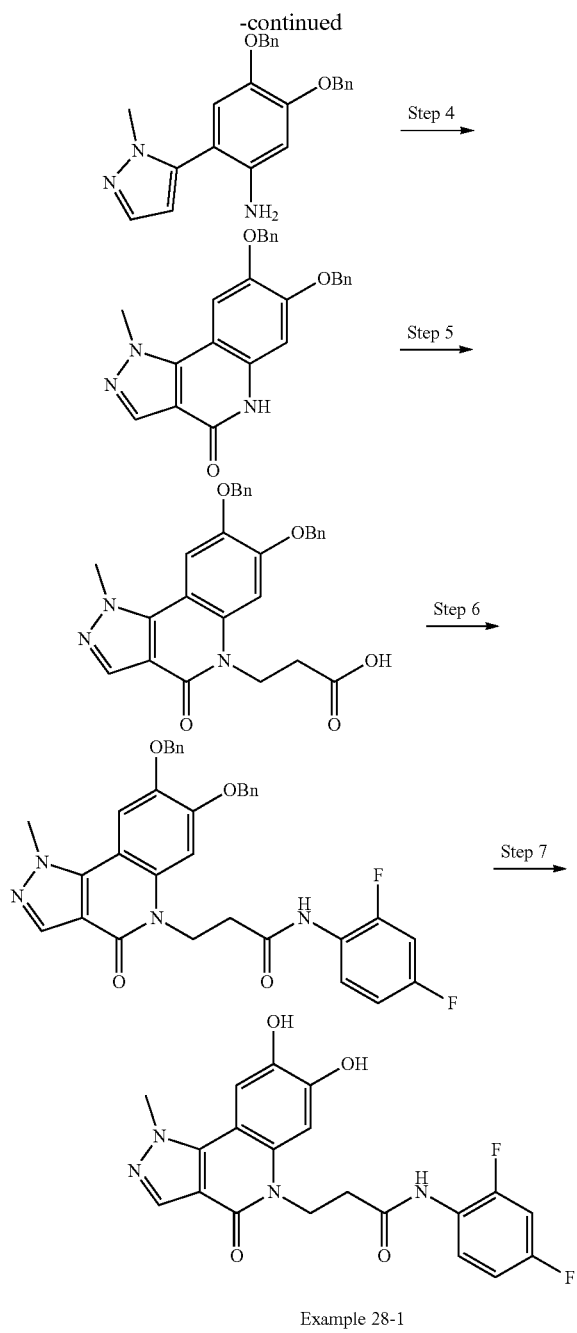

Example 28-1

Step 1: 1,2-Dibenzyloxy-4-bromo-5-nitro-benzene 1,2-Dibenzyloxy-4-bromo-benzene (1.00 g, 2.71 mmol) was suspended in acetic acid (15 mL), and the mixture was warmed to 50° C. until the mixture was in solution. The solution was then allowed to cool to rt, and nitric acid (70%, 0.78 mL, 12.2 mmol) was added dropwise slowly. The reaction was stirred at room temperature for 20 h, by which time a solid had precipitated. The mixture was poured carefully over ice and then the precipitate was filtered. The solid was dissolved in DCM and washed with saturated aqueous NaHCO$_3$ solution, until the aqueous phase remained basic. The organics were dried (hydrophobic frit) and concentrated in vacuo to afford the title compound. $^1$H NMR (500 MHz, CDCl$_3$) δ 7.63 (s, 1H), 7.45-7.31 (m, 10H), 7.19 (s, 1H), 5.21 (s, 2H), 5.18 (s, 2H). Tr(METCR1704)=1.13 min, m/z (ES)$^+$ [M+H]$^+$=mass ion not observed, 96%.

Step 2: Performed as for Method 21, Step 1

Step 3: 4,5-Dibenzyloxy-2-(2-methylpyrazol-3-yl)aniline

Ammonium chloride (722 mg, 13.5 mmol) was added to a suspension of 5-(4,5-dibenzyloxy-2-nitro-phenyl)-1-methyl-pyrazole (676 mg, 1.63 mmol) in a mixture of water (4 mL) and ethanol (6 mL), followed by the portion-wise addition of iron powder (454 mg, 8.14 mmol). The reaction was then stirred at 70° C. for 75 minutes, allowed to cool, and filtered through Celite, washing with EtOAc. The filtrate was washed with brine. The organic layer was dried over Na$_2$SO$_4$, filtered, and concentrated in vacuo to give the title compound. $^1$H NMR (500 MHz, CDCl$_3$) δ 7.51 (d, J=1.8 Hz, 1H), 7.49-7.45 (m, 2H), 7.42-7.36 (m, 4H), 7.36-7.27 (m, 4H), 6.65 (s, 1H), 6.44 (s, 1H), 6.24 (d, J=1.9 Hz, 1H), 5.17 (s, 2H), 5.07 (s, 2H), 3.59 (s, 3H). Tr(METCR1704)=0.94 min, m/z (ES)$^+$[M+H]$^+$=386.2, 94%.

Step 4: 7,8-Dibenzyloxy-1-methyl-5H-pyrazolo[4,3-c]quinolin-4-one 4,5-Dibenzyloxy-2-(2-methylpyrazol-3-yl)aniline (0.30 mL, 1.64 mmol) was dissolved in anhydrous DMF (10 mL), and CDI (796 mg, 4.91 mmol) was added. The mixture was heated to 120° C. under microwave irradiation for 20 minutes. The reaction mixture was carefully poured over water. The precipitate was collected by filtration, washing with further water to afford the title compound. $^1$H NMR (400 MHz, DMSO-d$_6$) δ 11.18 (s, 1H), 7.99 (s, 1H), 7.64 (s, 1H), 7.49 (t, J=6.8 Hz, 2H), 7.46-7.27 (m, 8H), 7.16 (s, 1H), 5.27 (s, 2H), 5.20 (s, 2H), 4.26 (s, 3H). Tr(METCR1704)=0.88 min, m/z (ES)$^+$ [M+H]$^+$=412.3, 74%.

Step 5: Performed as for Method 21, Step 3

Step 6: 3-(7,8-Dibenzyloxy-1-methyl-4-oxo-pyrazolo[4,3-c]quinolin-5-yl)-N-(2,4-difluorophenyl)propanamide 3-(7,8-Dibenzyloxy-1-methyl-4-oxo-pyrazolo[4,3-c]quinolin-5-yl)propanoic acid (84 mg, 0.17 mmol) was dissolved in pyridine (6.3 mL), and 2,4-difluoroaniline (0.02 mL, 0.21 mmol) was added, followed by EDC.HCl (50 mg, 0.26 mmol). The mixture was stirred at rt for 18 h and then concentrated in vacuo. Water was added, as well as a small amount of EtOAc, and the resulting precipitate was filtered. The solid was washed with further EtOAc and the organic phase from the filtrate was separated from the aqueous phase, dried (hydrophobic frit), and concentrated in vacuo to afford the title compound. $^1$H NMR (400 MHz, DMSO-d$_6$) δ 9.86 (s, 1H), 8.05 (s, 1H), 7.85-7.75 (m, 1H), 7.71 (s, 1H), 7.49 (t, J=7.0 Hz, 4H), 7.44-7.36 (m, 4H), 7.36-7.25 (m, 4H), 7.06 (t, J=9.2 Hz, 1H), 5.32 (s, 4H), 4.55 (t, J=7.2 Hz, 2H), 4.27 (s, 3H), 2.71-2.66 (m, 2H). Tr(METCR1704)=1.02 min, m/z (ES)$^+$ [M+H]$^+$=595.1, 92%.

Step 7: 2,4-Difluorophenyl)-3-{7,8-dihydroxy-1-methyl-4-oxo-1H,4H,5H-pyrazolo[4,3-c]quinolin-5-yl}propanamide 3-(7,8-Dibenzyloxy-1-methyl-4-oxo-pyrazolo[4,3-c]quinolin-5-yl)-N-(2,4-difluorophenyl)propanamide (52 mg, 0.0875 mmol) was dissolved in ethanol (6 mL) and EtOAc (6 mL) under a $N_2$ atmosphere, and $Pd(OH)_2$ (5.0%, 37 mg, 0.01 mmol) was added. The reaction mixture was stirred at rt under an atmosphere of hydrogen (balloon) for 18 h. The reaction mixture was filtered through Celite, washing with EtOAc, ethanol, and DCM. The filtrate was concentrated in vacuo and purified by column chromatography to give the title compound. $^1$H NMR (400 MHz, DMSO-$d_6$) δ 9.88 (s, 1H), 8.00 (s, 1H), 7.89-7.78 (m, 1H), 7.62 (s, 1H), 7.31 (ddd, J=11.7, 9.1, 2.9 Hz, 1H), 7.16-7.02 (m, 2H), 4.51-4.40 (m, 2H), 4.27 (s, 3H), 2.79-2.69 (m, 2H). $^{19}$F NMR (376 MHz, DMSO-$d_6$) δ −114.77 (d, J=5.1 Hz), −119.34 (d, J=5.1 Hz). Tr(MET-uHPLC-AB-101)=2.08 min, m/z $(ES^+)(M+H)^+$ 415.2, 100%.

Biological Assays

Exon1-Q46 Radioligand Binding Assay

For radioligand binding assays (RBA) MBP-HTT(1-89)Q46-His(6×) ("Exon1-Q46") protein was generated based on a previous publication (Scherzinger et al. Cell, Vol. 90, 549-558, Aug. 8, 1997). For experiments 30 μM MBP-Exon1-Q46 was incubated with 150 μg/mL thrombin in assay buffer (150 mM NaCl, 50 mM Tris pH 8.0) and 2 mM $CaCl_2$ for 16 hours at 37° C. Aggregated Exon1-Q46 was pelleted by centrifugation for 5 minutes at 13,000 rpm in a bench top centrifuge and re-dissolved in the same volume of assay buffer. Test compounds were prepared by titration in DMSO at 11 concentrations from 63 μM to 2 nM. For the RBA, Q46 protein aggregates and test compounds were pre-incubated in assay buffer for 20 minutes at room temperature, in 100 μL/well in a 96-well plate (pp, round bottom). Then, ligand was added in 50 μL/well and incubated for 60 minutes at 37° C. Final assay concentrations were 1 μM to 30 μM test compound, 1 μM Exon1-Q46 protein (equivalent monomer concentration) and 0.3 nM ligand [$^3H_3$-methyl]-5-((5-methoxypyridin-2-yl)methoxy)-2-(pyrazin-2-yl)benzo[d]oxazole. Samples were transferred onto GF/B filter plates and washed 2× with 200 μL PBS using a Filtermate Harvester. After drying filter plates for 1 hour at 55° C., the back of the plates were sealed with foil and 30 μL/well scintillation fluid (Packard MicroScint 40) added, incubated for 15 minutes in the dark and counted in a MicroBeta reader. For analysis, replicate data from independent assay plates were normalized towards 0% and 100% inhibition using control wells of vehicle (0% inhibition) and 1 μM unlabeled [$^3H_3$-methyl]-5-((5-methoxypyridin-2-yl)methoxy)-2-(pyrazin-2-yl)benzo[d]oxazole (100% inhibition). $IC_{50}$ values were determined with a sigmoidal inhibition model with four variables (top, bottom, slope, $IC_{50}$) in a global fit using the normalized replicate data.

The results for various example compounds were as provided in the table below (+++<100 nM; ++100-500; +500-10000; ND: not determined):

| Compound No. | Potency Range |
| --- | --- |
| 1-1 | +++ |
| 1-2 | +++ |
| 1-3 | +++ |
| 1-4 | +++ |
| 1-5 | +++ |
| 1-6 | +++ |
| 1-7 | ++ |
| 1-8 | +++ |
| 1-9 | +++ |
| 1-10 | +++ |
| 1-11 | +++ |
| 1-12 | +++ |
| 1-13 | +++ |
| 1-14 | +++ |
| 1-15 | +++ |
| 1-16 | +++ |
| 1-17 | +++ |
| 1-18 | +++ |
| 1-19 | +++ |
| 1-20 | +++ |
| 1-21 | +++ |
| 1-22 | +++ |
| 1-23 | +++ |
| 1-24 | +++ |
| 1-25 | +++ |
| 1-26 | +++ |
| 1-27 | ++ |
| 1-28 | ++ |
| 1-29 | ++ |
| 1-30 | + |
| 1-31 | ++ |
| 1-32 | ++ |
| 1-33 | ++ |
| 1-34 | ++ |
| 1-35 | ++ |
| 1-36 | +++ |
| 1-37 | +++ |
| 1-38 | +++ |
| 1-39 | +++ |
| 1-40 | +++ |
| 1-41 | +++ |
| 1-42 | +++ |
| 1-43 | +++ |
| 1-44 | +++ |
| 1-45 | +++ |
| 1-46 | +++ |
| 1-47 | +++ |
| 1-48 | +++ |
| 1-49 | +++ |
| 2-1 | +++ |
| 2-2 | +++ |
| 2-3 | +++ |
| 2-4 | +++ |
| 2-5 | +++ |
| 3-1 | +++ |
| 3-2 | +++ |
| 3-3 | +++ |
| 3-4 | +++ |
| 3-5 | +++ |
| 3-6 | +++ |
| 3-7 | +++ |
| 3-8 | +++ |
| 3-9 | +++ |
| 3-10 | +++ |
| 3-11 | +++ |
| 3-12 | +++ |
| 3-13 | +++ |
| 3-14 | +++ |
| 3-15 | +++ |
| 3-16 | +++ |
| 3-17 | +++ |
| 3-18 | +++ |
| 3-19 | +++ |
| 3-20 | +++ |
| 3-21 | +++ |
| 3-22 | +++ |
| 3-23 | +++ |
| 3-24 | +++ |
| 3-25 | +++ |
| 3-26 | +++ |
| 3-27 | +++ |
| 3-28 | +++ |
| 3-29 | +++ |
| 3-30 | +++ |
| 3-31 | +++ |
| 3-32 | +++ |
| 3-33 | +++ |

-continued

| Compound No. | Potency Range |
|---|---|
| 3-34 | +++ |
| 3-35 | +++ |
| 3-36 | +++ |
| 3-37 | +++ |
| 3-38 | +++ |
| 3-39 | ++ |
| 3-40 | +++ |
| 3-41 | +++ |
| 3-42 | +++ |
| 3-43 | +++ |
| 3-44 | +++ |
| 3-45 | +++ |
| 3-46 | +++ |
| 3-47 | +++ |
| 3-48 | +++ |
| 3-49 | +++ |
| 3-50 | +++ |
| 3-51 | +++ |
| 3-52 | +++ |
| 3-53 | +++ |
| 3-54 | +++ |
| 3-55 | +++ |
| 3-56 | +++ |
| 3-57 | +++ |
| 3-58 | +++ |
| 3-59 | +++ |
| 3-60 | +++ |
| 3-61 | +++ |
| 3-62 | +++ |
| 3-63 | +++ |
| 3-64 | +++ |
| 3-65 | +++ |
| 3-66 | +++ |
| 3-67 | +++ |
| 3-68 | +++ |
| 3-69 | ++ |
| 4-1 | +++ |
| 4-2 | +++ |
| 4-3 | +++ |
| 4-4 | +++ |
| 4-5 | +++ |
| 4-6 | +++ |
| 4-7 | +++ |
| 4-8 | +++ |
| 4-9 | +++ |
| 4-10 | +++ |
| 5-1 | +++ |
| 5-2 | +++ |
| 5-3 | +++ |
| 5-4 | +++ |
| 5-5 | +++ |
| 5-6 | +++ |
| 5-7 | +++ |
| 5-8 | +++ |
| 5-9 | +++ |
| 5-10 | +++ |
| 5-11 | +++ |
| 5-12 | +++ |
| 5-13 | ++ |
| 5-14 | +++ |
| 5-15 | ++ |
| 5-16 | ND |
| 5-17 | ND |
| 5-18 | +++ |
| 6-1 | +++ |
| 6-2 | +++ |
| 6-3 | +++ |
| 6-4 | +++ |
| 6-5 | +++ |
| 7-1 | +++ |
| 8-1 | +++ |
| 8-2 | +++ |
| 8-3 | +++ |
| 8-4 | +++ |
| 8-5 | +++ |
| 8-6 | +++ |
| 8-7 | +++ |
| 8-8 | +++ |
| 8-9 | +++ |
| 8-10 | +++ |
| 8-11 | +++ |
| 8-12 | +++ |
| 8-13 | +++ |
| 9-1 | +++ |
| 9-2 | +++ |
| 9-3 | +++ |
| 9-4 | +++ |
| 9-5 | +++ |
| 9-6 | +++ |
| 9-7 | +++ |
| 9-8 | +++ |
| 9-9 | +++ |
| 9-10 | +++ |
| 9-11 | +++ |
| 9-12 | +++ |
| 9-13 | +++ |
| 9-14 | +++ |
| 9-15 | +++ |
| 9-16 | +++ |
| 9-17 | +++ |
| 9-18 | +++ |
| 9-19 | +++ |
| 9-20 | +++ |
| 9-21 | +++ |
| 9-22 | +++ |
| 9-23 | +++ |
| 9-24 | +++ |
| 9-25 | +++ |
| 9-26 | +++ |
| 9-27 | +++ |
| 9-28 | +++ |
| 9-29 | +++ |
| 9-30 | +++ |
| 9-31 | + |
| 10-1 | +++ |
| 11-1 | +++ |
| 12-1 | +++ |
| 12-2 | +++ |
| 13-1 | +++ |
| 13-2 | +++ |
| 14-1 | +++ |
| 14-2 | +++ |
| 15-1 | +++ |
| 16-1 | +++ |
| 16-2 | +++ |
| 17-1 | +++ |
| 18-1 | +++ |
| 19-1 | +++ |
| 19-2 | ND |
| 19-3 | +++ |
| 19-4 | +++ |
| 20-1 | +++ |
| 21-1 | +++ |
| 21-2 | +++ |
| 21-3 | +++ |
| 22-1 | +++ |
| 23-1 | ND |
| 24-1 | +++ |
| 25-1 | ND |
| 26-1 | +++ |
| 27-1 | ND |
| 28-1 | ND |
| 29-1 | +++ |
| 29-2 | +++ |
| 29-3 | +++ |
| 29-4 | +++ |
| 29-5 | +++ |

PET Imaging Example

The following example provides an illustrative, non-limiting, procedure that may be utilized when performing PET imaging studies on an individual in a clinical setting.

The individual is either unmedicated or pre-medicated with an unlabeled compound. The individual may undergo fasting, allowing water intake ad libitum, prior to PET imaging. A 20 G two inch venous catheter is inserted into the contralateral ulnar vein for administration of the imaging agent.

The human subject is positioned in the PET camera and a tracer dose of imaging agent is administered via i.v. catheter. Either arterial or venous blood samples are taken at appropriate time intervals throughout the PET scan in order to analyze and quantitate the fraction of umetabolized compound in plasma. Images are acquired for up to 120 minutes. Within ten minutes of the injection of radiotracer and at the end of the imaging session, 1 ml blood samples are obtained for determining the plasma concentration of any unlabeled imaging agent compound (or other compound of intervention) which may have been administered before the PET tracer.

Tomographic images are obtained through image reconstruction. For example, for determining the distribution of imaging agent, regions of interest (ROIs) are drawn on the reconstructed image. Regions of interest in a brain image may include, for example, the striatum, cerebellum, or basal ganglia. Imaging agent uptake over time in these regions may be used to generate time activity curves (TAC). Data may be expressed as radioactivity per unit time per unit volume (e.g., µCi/cc/mCi injected dose), or as radioactivity per unit volume. TAC data may be processed with various methods known in the field to yield quantitative parameters, an example of which is Binding Potential (BP). For further description of imaging procedure, see, for example, Waxman A. D., et al., Society of Nuclear Medicine Procedure Guideline for FDG PET Brain Imaging, ver. 1.0, (Feb. 8, 2009).

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A compound of formula:

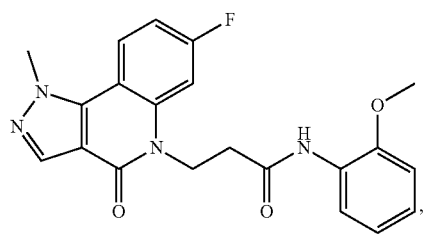

-continued

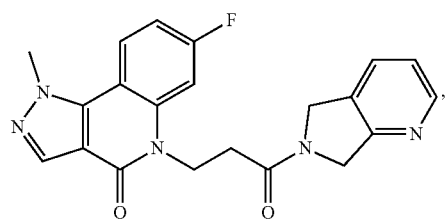

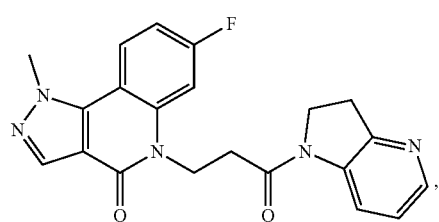

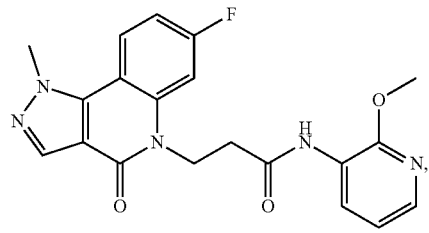

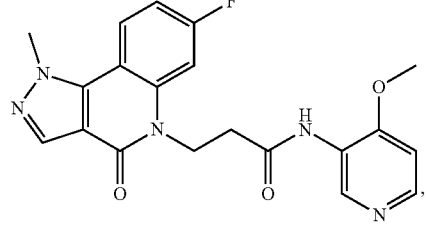

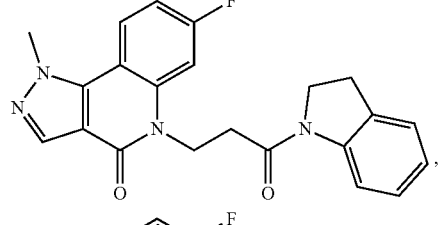

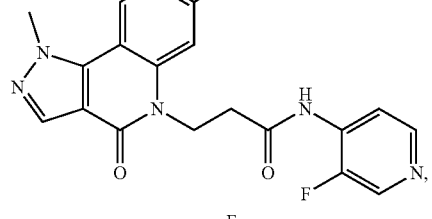

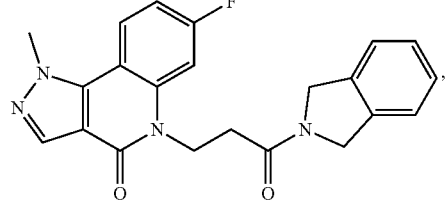

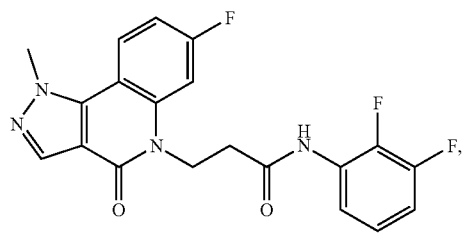
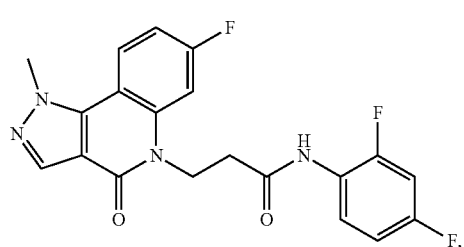
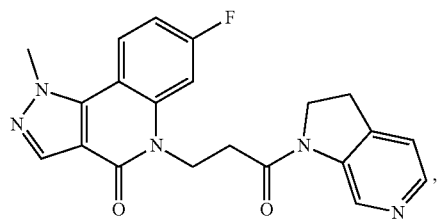
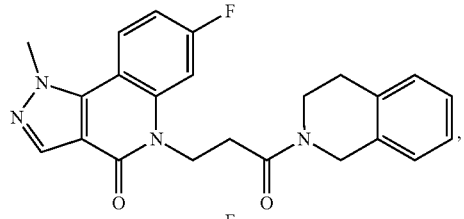
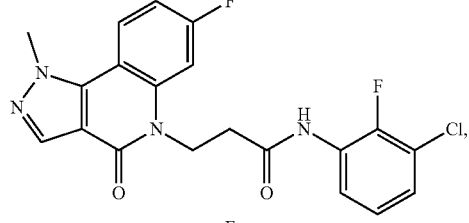
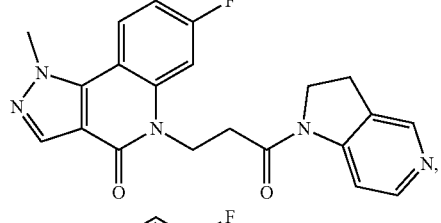
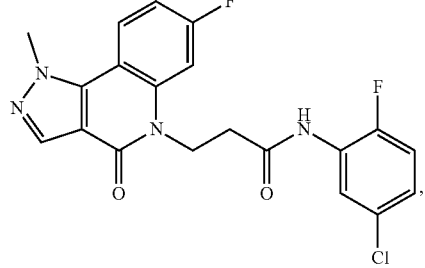
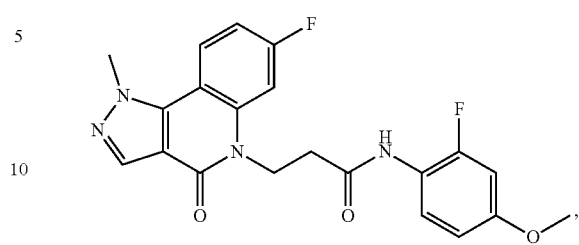
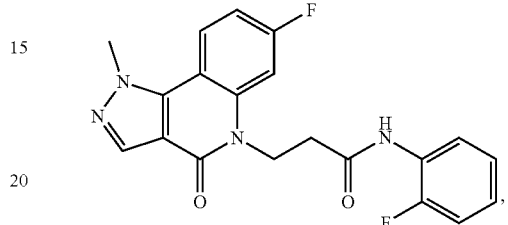
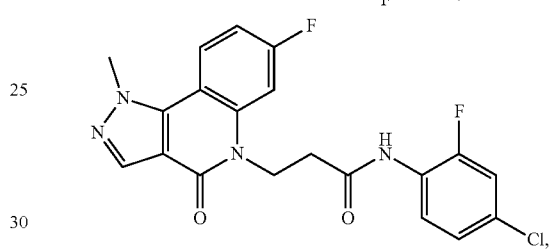
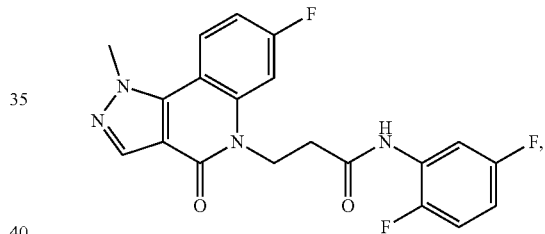
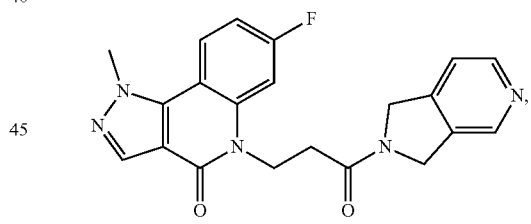
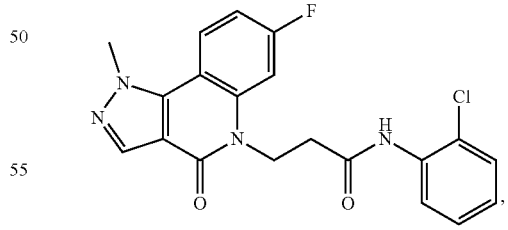
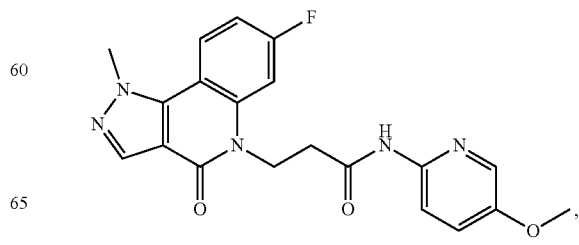

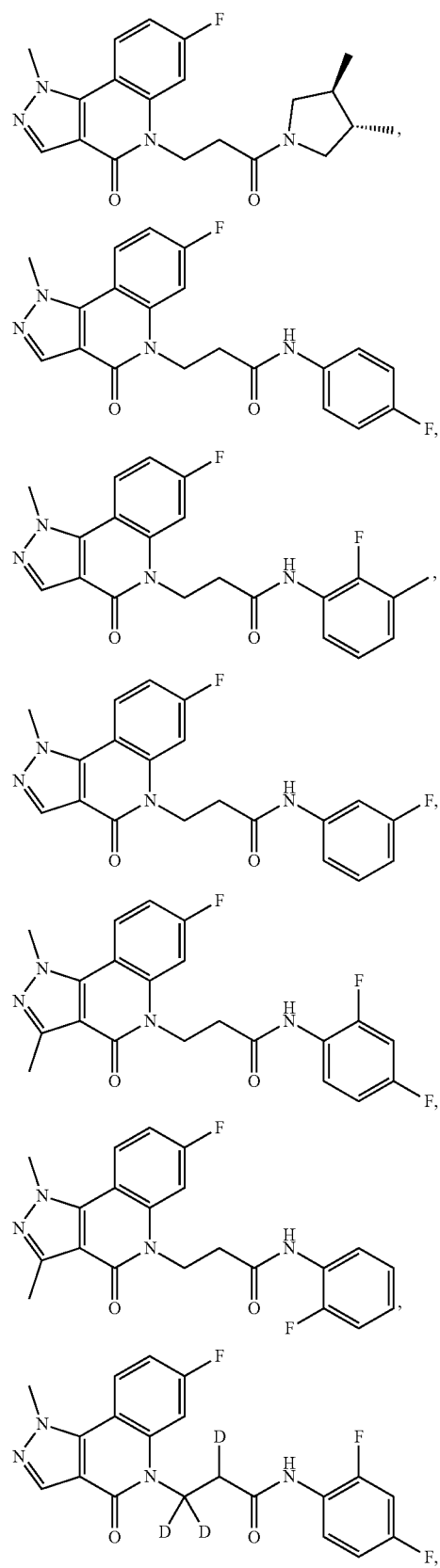
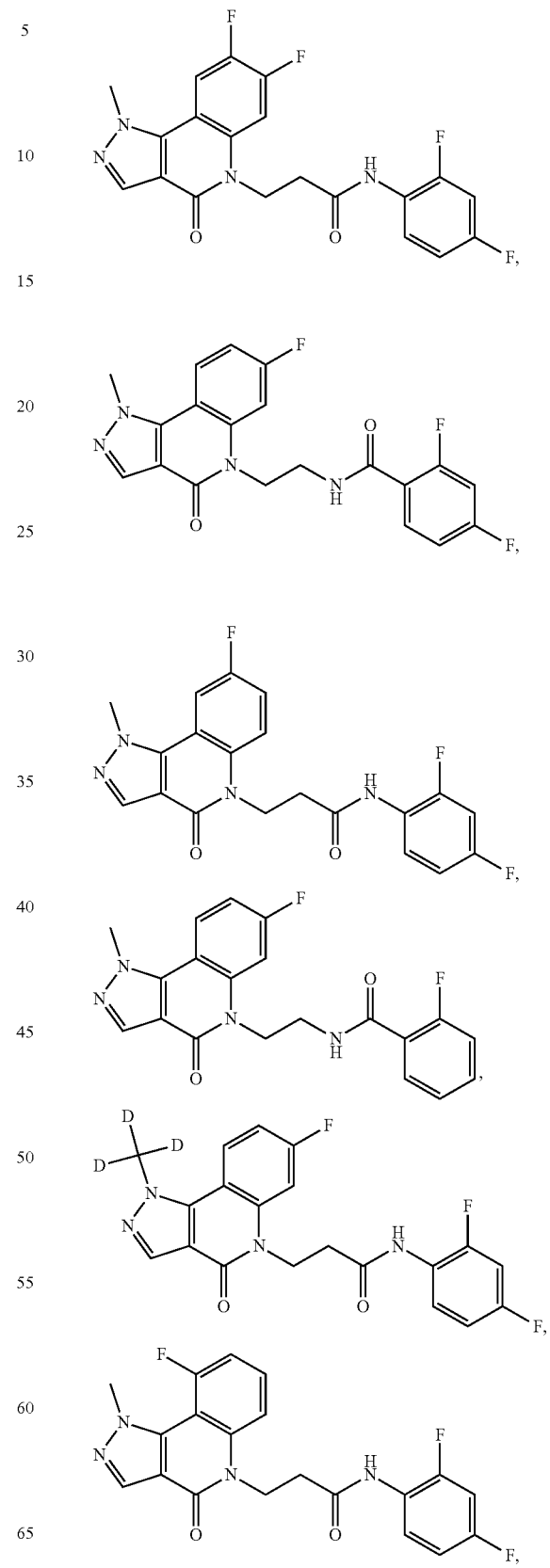

-continued

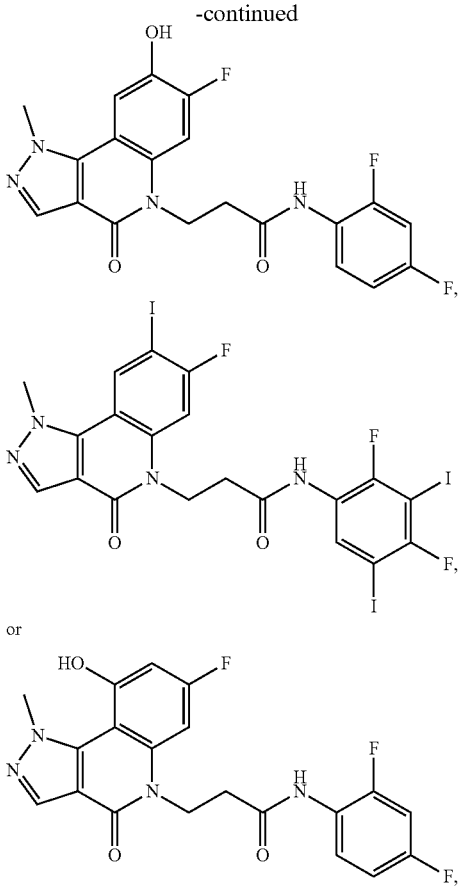

or an isotopically enriched analog, pharmaceutically acceptable salt, tautomer, stereoisomer, or a mixture of stereoisomers thereof, wherein the compound is labeled with one or more positron-emitting radioactive isotopes selected from $^{11}C$, $^{13}N$, $^{15}O$, and $^{18}F$.

2. A method of generating diagnostic images in an individual comprising administering an effective amount of a compound of claim 1 to an individual, and generating an image of a body part or body area of the individual.

3. The method of claim 2, wherein generating an image of a body part or body area of the individual comprises generating an image to detect the presence or absence of a protein susceptible to aggregation in the image.

4. The method of claim 3, wherein the protein susceptible to aggregation is huntingtin protein (HTT protein).

5. The method of claim 3, wherein the presence or absence of a protein aggregate corresponds to the presence or absence of a neurodegenerative disease.

6. The method of claim 5, wherein the neurodegenerative disease is selected from Alzheimer's disease, amyotrophic lateral sclerosis, Huntington's disease, Parkinson's disease, Prion disease and spinocerebellar ataxias.

7. The method of claim 6, wherein the neurodegenerative disease is Huntington's disease (HD).

8. The method of claim 2, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

* * * * *